US012426568B2

(12) United States Patent
Sayre et al.

(10) Patent No.: US 12,426,568 B2
(45) Date of Patent: Sep. 30, 2025

(54) SYSTEM AND METHODS FOR THE BIOCONTROL OF PLANT PATHOGENS

(71) Applicant: Pebble Labs Inc., Los Alamos, NM (US)

(72) Inventors: Richard Sayre, Los Alamos, NM (US); Karen Yin, Los Alamos, NM (US); Pedro Costa Nunes, Albuquerque, NM (US)

(73) Assignee: Pebble Labs Inc., Los Alamos, NM (US)

( * ) Notice: Subject to any disclaimer, the term of this patent is extended or adjusted under 35 U.S.C. 154(b) by 1357 days.

(21) Appl. No.: 16/467,010

(22) PCT Filed: Dec. 6, 2017

(86) PCT No.: PCT/US2017/064977
§ 371 (c)(1),
(2) Date: Jun. 5, 2019

(87) PCT Pub. No.: WO2018/106847
PCT Pub. Date: Jun. 14, 2018

(65) Prior Publication Data

US 2020/0071713 A1 Mar. 5, 2020

Related U.S. Application Data

(60) Provisional application No. 62/430,671, filed on Dec. 6, 2016.

(51) Int. Cl.
*A01H 17/00* (2006.01)
*A01N 63/60* (2020.01)
*C12N 15/82* (2006.01)

(52) U.S. Cl.
CPC ............ *A01H 17/00* (2013.01); *A01N 63/60* (2020.01); *C12N 15/8218* (2013.01); *C12N 15/8283* (2013.01); *C12N 2310/14* (2013.01); *C12N 2310/531* (2013.01)

(58) Field of Classification Search
CPC .................................................... A01H 17/00
USPC ........................................................ 800/279
See application file for complete search history.

(56) References Cited

U.S. PATENT DOCUMENTS

| | | | | |
|---|---|---|---|---|
| 2009/0304594 | A1 | 12/2009 | Fantin et al. | |
| 2012/0164205 | A1 | 6/2012 | Baum et al. | |
| 2013/0337302 | A1* | 12/2013 | Inagaki ................ | C01G 23/005 252/182.1 |
| 2015/0337302 | A1* | 11/2015 | Donohue ............... | A01N 57/16 435/320.1 |
| 2016/0108096 | A1 | 4/2016 | Thompson et al. | |

FOREIGN PATENT DOCUMENTS

| | | | | |
|---|---|---|---|---|
| WO | 2007074405 A2 | 7/2007 | | |
| WO | 2016105696 | 6/2016 | | |
| WO | WO-2016096923 A1 * | 6/2016 | .......... | C12N 15/113 |

OTHER PUBLICATIONS

Tenllado et al. BMC Biotechnology 3:1-10 (Year: 2003).*
Tenllado et al. BMC Biotechnology 3:1-11 (Year: 2003).*
Haywood et al. The Plant Journal 42:49-68 (Year: 2005).*
Gilet et al. Mol. Microbiol. 95:270-282 (Year: 2015).*
Germaine, et al.; Engineering of Microbes for Plant and Soil Systems. Applications of Microbial Engineering. (2013), pp. 229-250.
Ryan, et al., Bacterial endophytes: recent developments and applications. (c) 2007, Federation of European Microbiological Societies, 9 pages.
Mitter, et al., Advances in Elucidating Beneficial Interactions between plants, soil and bacteria. (c) 2013, Elsevier Inc., pp. 381-445.
Ding, et al., Symplasmic protein and RNA traffic: regulatory points and regulatory factors., 2003, 6:596-602.
Arguel, et al., siRNAs Trigger Efficient Silencing of a Parasitism Gene in Plant Parasitic Root-Knot Nematodes, Genes 2012, 3, 391-408.
Huang, et al., Efficient and specific gene knockdown by small interfering RNAs produced in bacteria, Nat Biotechnol, Apr. 31, 2013(4), 350-356, 19 pages.
Australian Examination Report in Australian Application No. 2017370683 dated Sep. 16, 2020, 6 pages.
Knip, et al., Trans-kingdom Cross-Talk: Small RNAs on the Move. PLOS Genetics. vol. 10, Issue 9, Sep. 2014, 7 pages.
Kim, et al., Genomic-scale exchange of mRNA between a parsitic plant and its hosts. Plant Science, vol. 345, Issue 6198, Aug. 15, 2014, 5 pages.
Weiberg, et al., Small RNAs—the secret agents in the plant-pathogen interactions. Current Opinion in Plant Biology, 2015, 26:87-94.
Baulcombe, VIGS, HIGS, and FIGS: small RNA silencing in the interactions of viruses or filamentous organisms with their plant hosts. Current Opinion in Plant Biology, 2015, 26:141-146.
Kumar et al. MWJ 2013, 4:6 (GCE special issue). "Development of an RNAi based microalgal larvicide to control mosquitoes";https://malariaworld.org/sites/default/files/mwjournal/article/MWJ2013_4_6.pdf.

(Continued)

*Primary Examiner* — Li Zheng
(74) *Attorney, Agent, or Firm* — Hovey Williams LLP; Crissa A. Cook

(57) ABSTRACT

The inventive technology relates to novel systems, methods, and strategies for the control of plant pathogens and herbivores. The inventive technology may specifically include novel compositions, systems, and methods configured to deliver inhibitory RNA molecules to a pathogen-infected plant. In a preferred embodiment, the invention may include genetically engineered endophytic bacteria configured to deliver one or more inhibitory RNA molecules to a pathogen-infected plant. One preferred embodiment may include a novel trans-kingdom delivery of hairpin RNA targeting viral encoded proteins resulting in the reduction of viral protein accumulation levels.

20 Claims, 24 Drawing Sheets

Specification includes a Sequence Listing.

(56) References Cited

OTHER PUBLICATIONS

Qi et al. "Direct Role of a Viroid RNA Motif in Mediating Directional RNA Trafficking across a Specific Cellular Boundary" Plant Cell. Jul. 2004; 16(7): 1741-1752;https://www.ncbi.nlm.nih.gov/pmc/articles/PMC514158/.
Tenllado et al. "Crude extracts of bacterially expressed dsRNA can be used to protect plants against virus Infections," BMC Biotechnology, Mar. 20, 2003 (Mar. 20, 2003), vol. 3, pp. 1-11. entire document.
Hu et al. "Down-regulation of Fusarium oxysporum endogenous genes by Host-Delivered RNA Interference enhances disease resistance," Front. Chem., Jan. 20, 2015 (Jan. 20, 2015), vol. 3, Article 1, pp. 1-10. entire document.
Gilet et al. "Small stable RNA maturation and turnover in Bacillus subtilis." Mol Microbiol, Jan. 1, 2015 (Jan. 1, 2015), vol. 95, pp. 270-282. entire document.
Haywood et al. "Phloem long-distance trafficking of Gibberellic Acid-Insensitive RNA regulates leaf development," The Plant Journal, Apr. 1, 2005 (Apr. 1, 2005), vol. 42, pp. 49-68. entire document.
Cash et al. "Symbiotic Bacteria Direct Expression of an Intestinal Bactericidal Lectin," Science, Aug. 25, 2006 (Aug. 25, 2006), vol. 313, p. 1126-1130. entire document.
Chang et al. "The microbial metabolite butyrate regulates intestinal macrophage function via histone deacetylase inhibition," Proc Natl Acad Sci USA, Feb. 11, 2014 (Feb. 11, 2014), vol. 111, pp. 2247-2252. entire document.
International Search Report in International Application No. PCT/US2017/064977 mailed Apr. 30, 2018, 5 pages.
Written Opinion in International Application No. PCT/US2017/064977 mailed Apr. 30, 2018, 19 pages.
International Preliminary Report on Patentability in International Application No. PCT/US2017/064977 mailed Jun. 11, 2019, 20 pages.
F. Tenllado et al., "Double-Stranded RNA-Mediated Interference with Plant Virus Infection", Journal of Virology, US, (Dec. 15, 2001), vol. 75, No. 24, doi:10.1128/JVI.75.24.12288-12297.2001, ISSN 0022-538X, pp. 12288-12297.
Office Action in corresponding Mexican Patent Application Serial No. MX/a/2019/006510, dated Aug. 24, 2023.

* cited by examiner

M-JM109-GHY2 (RNaseIII mutant) + pAD-WRKY-GHY1 (hpRNA)

TMV-GFP TMV-GFP+hpRNA

Postive control:

Positive control:

SYSTEM AND METHODS FOR THE BIOCONTROL OF PLANT PATHOGENS

CROSS REFERENCE TO RELATED APPLICATION

This application is the United States National Stage of International Application No. PCT/US2017/064977, filed Dec. 6, 2017, which claims the benefit of and priority to U.S. Provisional Application No. 62/430,671, filed Dec. 6, 2016. The entire specification and figures of the above-referenced application are hereby incorporated, in their entirety by reference.

SEQUENCE LISTING

The instant application contains a Sequence Listing which has been submitted electronically in ASCII format and is hereby incorporated by reference in its entirety. Said ASCII copy, created on Nov. 5, 2020, is named 90115-00140-Sequence-Listing-2.txt and is 86 kb in size.

TECHNICAL FIELD

The field of the present invention relates generally to plant molecular biology and plant biotechnology. More specifically it relates to constructs and methods to suppress the expression of targeted genes or to down-regulate targeted genes. The inventive technology further relates to the biocontrol of plant pathogens, pests and/or herbivores. Specifically, the invention may relate to novel techniques, systems, and methods for the biocontrol of disease-transmitting plant pathogens through the delivery of inhibitory RNA molecules through genetically modified bacterium.

BACKGROUND OF THE INVENTION

Domestication of agricultural crops, estimated at 2,500+ species globally, has involved artificial selection of desirable traits that enhance yield and quality of the harvested product. While breeding for agronomic targets in high input environments has successfully increased global crop productivity, it has tended to produce modern crop varieties with relatively low levels of diversity. This reduced genetic diversity could limit the availability of varieties adapted for crop production under non-optimal conditions. Plant defensive traits can be lacking or expressed weakly in domesticated plants as a consequence of selection for other desirable traits. This poses a particular challenge for improving the sustainability of crop production as it suggests that modern varieties would perform poorly in low input systems with restricted pesticide use. While crop productivity has increased over the past century, combined global crop losses due to weeds, pests and diseases can be up to 40% (Oerke and Dehne, 2004). Across all vegetation systems, foliage, sap and root feeding herbivores remove >20% of net plant productivity (Agrawal, 2011). These losses occur despite increased pesticide use over recent decades (Oerke and Dehne, 2004), highlighting the need to develop sustainable approaches for pathogen and pest control with less reliance on chemical inputs.

Disease control is often achieved and/or enhanced by the use of plants that have been bred for good resistance to many diseases, and by plant cultivation approaches such as crop rotation, use of pathogen-free seed, appropriate planting date and plant density, control of field moisture, and pesticide use. Across large regions and many crop species, it is estimated that diseases typically reduce plant yields by 10% every year in more developed settings, but yield loss to diseases that often exceeds 20% in less developed settings. While traditional cultivation techniques have produced significant gains in agricultural output, such techniques cannot address all of the threats to plant populations. Such threats being especially acute with respect to cash and food stuff crops.

With these trends in mind, a growing concern involves the fact that plant pathogens are a direct threat to the quality and abundance of food, feed, and fiber produced by growers around the world. Different approaches may be used to prevent, mitigate or control plant diseases. Beyond traditional agronomic and horticultural practices, growers are often forced to rely on chemical fertilizers and pesticides. Such inputs to agriculture have contributed significantly to the spectacular improvements in crop productivity and quality over the past 100 years. However, the environmental pollution caused by excessive use and misuse of agrochemicals, as well as fear-mongering by some opponents of pesticides, has led to considerable changes in peoples' attitudes towards the use of pesticides in agriculture. Today, there are strict regulations on chemical pesticide use, and there is political pressure to remove reliable and effective chemicals from the market. Additionally, the spread of plant diseases in natural ecosystems may preclude successful application of chemicals, because of the scale to which such applications might have to be applied.

One way to address the use and/or overuse of pesticides and herbicides is through the development of transgenic plants. Transgenic plant DNA is modified using genetic engineering techniques. The aim is to introduce a new trait to the plant which does not occur naturally in the species. A transgenic plant may contain a gene or genes that have been artificially inserted. The inserted gene sequence is known as the transgene, it may come from an unrelated plant or from a completely different species. Example of such transgenic plants may include the insertion of genes that code for proteins such as anti-viral protein complexes, pesticides, or metabolic pathway enzymes that may convert precursors such as beta-carotene into vitamin A. The purpose of inserting a combination of genes in a plant is to make it as useful and productive as possible. However, such transgenic plant systems also have several scientific and practical drawbacks.

In one example, transgenic plants have been developed to control specific insect/pests through the expression of Bt-based toxins. Expression of Bt insecticidal proteins which help in the permeabilization of gut epithelial cell's membrane in susceptible insects have proven initially effective. However, this approach is limited for some specific crops to manage some specific pests, and there is also a threat that some insects can develop resistance against Bt. Additional limitations on transgenic plant systems may include the fact that they are difficult and time-consuming to select and generate. For example, the development of a transgenic strain may be limited by the ability to successfully reproduce seeds or allow the natural outgrowth and spread of the transgenic plant species in any given environment. In addition, significant social pressures have arisen in opposition to the use of transgenic plants. Movements in Western and European countries have sought to prevent the use of transgenic plants in food stuffs. Additionally, new markets for organic and non-transgenic products have concurrently arisen in the last decade which allows non-transgenic plants to be sold at a market premium. Finally, many transgenic plants are controlled by large agricultural conglomerates making supply of seeds for transgenic plants limited, and thereby inhibiting their widespread use in many third-world countries, as one example.

In an effort to address some of the limitations, plant-based microorganisms, such as endophytes and the like, may be utilized as delivery vectors for beneficial genes, as well as genetic inhibition of undesirable genes, such as those that cause plant diseases. Plants may harbor a number of beneficial bacteria intracellularly as well as on their surfaces, including roots, leaves, and stem tissues. Endophytic and ectopic bacteria that live in association with plants include those in the following subphyla: Acidobacteria, Actinobacteria, Alphaproteobacteria, Armatimonadetes, *Bacteroides*, Betaproteobacteria, Deltaproteobacteria, Firmicutes, Grammaproteobacteria, TM7, *Bacillus, Escherichia* among others.

Many of these bacteria can be quickly cultured in vitro and can be genetically engineered to express foreign RNA molecules that may be made available to the plant by trans-kingdom delivery systems that are currently poorly characterized (Baulcombe, 2015; Kim et al., 2014; Arguel et al., 2012). For example, it has been demonstrated that tomato pathogenic fungi can deliver sRNAs to plants and that the fungal sRNAs can be mobilized throughout the plant through the vasculature tissue (Baulcombe, 2015; Weiberg and Jin, 2015). Trans-kingdom delivery of siRNA from transgenic plants has also been successfully demonstrated and used to control nematodes that ingest the siRNA (Bakheti et al., 2005; Knip et al., 2014).

In addition, trans-kingdom delivery of siRNA and dsRNA produced in cytoplasm and chloroplasts of microalgae, respectively, that is targeted to inactivate an essential gene, HKT, involved in tryptophan metabolism in mosquitoes, has been shown to suppress 3-hydroxykynurenine transaminase ("HKT") expression and lead to elevated mosquito mortality (Kumar et al., 2015). In contrast to eukaryotes, however, bacteria do not have a Dicer/RISC complex capable of generating siRNAs from dsRNA precursors. However, as noted above, such systems are still poorly understood and inefficient in both their application and commercial viability. Thus, it is not surprising that bacterial delivery of inhibitory RNA molecules to plants to control pathogens, pests and herbivores that feed on plants has not been effectively demonstrated. For example, some have attempted to apply dsRNA or sRNA directly on plants to control gene expression but at great cost to produce the RNA and with limited lifetime for the RNA due to degradation. (See e.g., Nature Plants 3, Article number: 16207 (2017) doi:10.1038/nplants.2016.207) To the contrary, the novel system described here results in the continuous production of dsRNA or sRNA at no apparent cost as the inhibitory RNA are made by genetically modified bacteria.

The foregoing problems regarding the biocontrol of diseases endemic in plant and/or herbivore populations through effective bacterial delivery of inhibitory RNA molecules may represent a long-felt need for an effective—and economical—solution to the same. While implementing elements may have been available, actual attempts to meet this need may have been lacking to some degree. This may have been due to a failure of those having ordinary skill in the art to fully appreciate or understand the nature of the problems and challenges involved.

As a result of this lack of understanding, attempts to meet these long-felt needs may have failed to effectively solve one or more of the problems or challenges here identified. These attempts may even have led away from the technical directions taken by the present inventive technology and may even result in the achievements of the present inventive technology being considered to some degree an unexpected result of the approach taken by some in the field. As will be discussed in more detail below, the current inventive technology overcomes the limitations of traditional plant pathogen control systems, while meeting the objectives of a truly effective vector biocontrol strategy.

BRIEF SUMMARY OF THE INVENTION

Generally, the inventive technology relates to novel strategies for the control of plant pathogens and pests including plant pathogens, plant viruses, fungal pathogens, insect pests and the like. Specifically, the invention may comprise novel techniques, systems, and methods for the biocontrol of select plant pathogens and herbivores.

In some embodiments, the invention relates to a novel trans-kingdom delivery of inhibitory RNAs homologous to the viral genome efficiently down-regulates or eliminates viral replication and translation of viral proteins.

One preferred embodiment may include a novel trans-kingdom delivery of hairpin RNA/dsRNA molecules targeting pathogen coding RNAs for degradation, resulting in the reduction of the encoded protein accumulation levels. This novel trans-kingdom delivery may be accomplished through infection of the plant by genetically modified endophyte bacteria carrying a nucleotide construct encoding the regulatory dsRNA homologous to pathogen coding or regulatory RNA sequences.

Another preferred embodiment may include a novel trans-kingdom delivery of hairpin RNA targeting viral pathogen encoded proteins which results in the reduction of viral protein accumulation levels. This novel trans-kingdom delivery may be accomplished through infection of the plant by genetically modified endophyte bacteria carrying a nucleotide construct encoding a hairpin RNA that is homologous to the target pathogen protein.

Another preferred embodiment may include a novel trans-kingdom delivery of hairpin RNA targeting fungal pathogen encoded proteins which results in the reduction of fungal protein accumulation levels. This novel trans-kingdom delivery may be accomplished through infection of the plant by genetically modified endophyte bacteria carrying a nucleotide construct encoding a hairpin RNA that is homologous to the target pathogen protein.

One preferred embodiment may include a novel trans-kingdom delivery of hairpin RNA targeting pest encoded proteins which results in the reduction of viral protein accumulation levels. This novel trans-kingdom delivery may be accomplished through infection of the plant by genetically modified endophyte bacteria carrying a nucleotide construct encoding a hairpin RNA that is homologous, or directed to the target pathogen protein.

In one preferred embodiment, the invention may include innovative systems and strategies to control plant-borne disease agents using a novel, cross-kingdom mechanism to incapacitate, potentially kill and/or prevent replication of plant pathogens by introducing genetically engineered microorganisms that may target inactivation of unique targeted genes in the pathogen involved in reproduction, pathogenicity, and/or general metabolism using inhibitory RNA molecules such as hpRNA, dsRNA, shRNA, siRNA or microRNAs, whose expression may lead to the turnover of the targeted mRNA for the gene of interest. Examples of unique targeted genes of interest include viral coat proteins, fungal cell wall genes, insect exoskeleton component genes and species-specific unique mRNA targets for metabolic genes in fungi and insects.

Additional embodiments include the expression of inhibitory RNA molecules, such as hpRNA, dsRNA, shRNA, siRNA and micro RNAs, in engineered endophytic bacteria that may be found in plant roots, stems, leaves and reproductive organs. In this embodiment, the inventive technology may include various cross-kingdom mechanisms for the knock-down of essential or other targeted plant pathogen and/or herbivore genes. In certain embodiments, this may be accomplished through the introduction of engineered micro-organisms into plants that express specific inhibitory RNA molecules that may down-regulate targeted plant, pathogen and/or herbivore genes needed or essential to pathogenicity or reproduction and the like. Additional embodiments of the inventive technology encompass genetic constructs, such as plasmids and the like, having various promoter and other genetic elements to allow targeted levels of expression of specific inhibitory RNA molecules, and other proteins, in endophytic bacteria, plant and/or herbivore systems.

According to one aspect, the present invention provides a method of down-regulating a pathogen gene(s) by sequence homology targeting in a plant cell and a nucleic acid construct for use in this method, as well as an inhibitory RNA polynucleotide, such as a hpRNA or annealed dsRNA, for use in the nucleic acid construct. The method comprises introducing into the cell a nucleic acid construct capable of producing inhibitory RNA and expressing the nucleic acid construct for a time sufficient to produce siRNAs (small interfering RNAs) or microRNA (miRNA), wherein the siRNA/miRNA inhibits expression of the target pathogen gene or sequence. miRNA constructs comprise a polynucleotide encoding a modified RNA precursor capable of forming a double-stranded RNA (dsRNA) or a hairpin (hpRNA), wherein the modified RNA precursor comprises a modified miRNA and a sequence complementary to the modified miRNA, wherein the modified miRNA is a miRNA modified to be (i) fully or partially complementary to the target sequence. As is well known in the art, the pre-miRNA forms a hairpin which in some cases the double-stranded region may be very short, e.g., not exceeding 21-25 bp in length. The nucleic acid construct may further comprise a promoter operably linked to the polynucleotide.

In some embodiment, as described in more detail below, the cell may be a plant cell, either monocot or dicot, including, but not limited to, corn, wheat, rice, barley, oats, sorghum, millet, sunflower, safflower, cotton, soy, canola, alfalfa, *Arabidopsis*. Some embodiments may include plants described herein can also be specific dicot crops, such as apple, grape, citrus, pear, peach, plum, orange, lemon, lime, grapefruit, pomegranate, olive, peanut, tobacco, etc. Also, the plants can be horticultural plants such as rose, marigold, primrose, dogwood, pansy, geranium, etc. In other embodiments, the plants are tobacco, such as *N. benthamiana, N. tabacum*. Additional examples are provided below. The promoter may be a pathogen-inducible promoter or other inducible promoters. The binding of the modified miRNA to the target RNA leads to cleavage of the target RNA. The target sequence of a target RNA may be a non-coding untranslated region of a gene, a coding sequence, an intron or a splice site.

According to another aspect, the present invention provides an isolated polynucleotide encoding a modified plant miRNA or siRNA precursor, the modified precursor is capable of forming a dsRNA or a hairpin and comprises a modified miRNA and a sequence complementary to the modified miRNA, wherein the modified miRNA is an miRNA modified to be (i) fully or partially complementary to the target sequence. Expression of the polynucleotide produces an miRNA precursor which is processed in a host cell to provide a mature miRNA which inhibits expression of the target sequence. The inhibitory RNA polynucleotide(s) may formed from a nucleic acid construct, such as a plasmid, that may be delivered to the plant through a genetically modified micro-organism, such as an endophytic bacteria, or a neutralized pathogenic bacteria. The nucleic acid construct may further comprise a promoter operably linked to the polynucleotide. The promoter may be a pathogen-inducible promoter or other inducible promoter. The binding of the modified miRNA to the target RNA leads to cleavage of the target RNA. The target sequence of a target RNA may be a non-coding untranslated region of a gene, a coding sequence, a non-coding sequence or a splice site.

According to another aspect, the present invention provides an inhibitory RNA nucleic acid construct for suppressing a multiple number of target sequences. The nucleic acid construct comprises at least two and up to 45 or more polynucleotides, each of which encodes an miRNA precursor capable of forming a dsRNA or a hairpin. Each miRNA is substantially complementary to a target or is modified to be complementary to a target as described herein. In some embodiments, each of the polynucleotides encoding precursor miRNAs in the construct is individually placed under control of a single promoter. In some embodiments, the multiple polynucleotides encoding precursor miRNAs are operably linked together such that they can be placed under the control of a single promoter. The promoter may be operably linked to the construct of multiple miRNAs or it may be operably linked to a single promoter. The promoter may be a pathogen-inducible promoter or other inducible promoter. In some embodiments, the multiple polynucleotides are linked one to another so as to form a single transcript when expressed. Expression of the polynucleotides in the nucleic acid construct produces multiple miRNA precursors which are processed in a host cell to provide multiple mature miRNAs, each of which inhibits expression of a target sequence. In one embodiment, the binding of each of the mature miRNA to each of the target RNA leads to cleavage of each of the target RNA. The target sequence of a target RNA may be a non-coding untranslated region of a gene, a coding sequence, non-coding untranslated region of a gene, a non-coding sequence or a splice site. The inhibitory RNA polynucleotide(s) may formed from a nucleic acid construct, such as a plasmid, that may be delivered to the plant through a genetically modified micro-organism, such as an endophytic bacteria, or a neutralized pathogenic bacteria.

According to another aspect, the invention provides methods and compositions useful for delivering inhibitory RNA molecules to a plant cell through genetically modified bacteria. Such genetically modified bacteria may include genetic modifications to efficiently and stably produce inhibitory RNA molecules, such as dsRNA and hpRNA. In some embodiment, such genetically modified bacteria may have been modified to have reduced, or no RNAaseIII activity, which may degrade dsRNA present in a bacteria. In some embodiments, such genetically modified bacteria may have been modified to include a knock-out of the RNAase III, or express a mutant-type RNAase III having reduced or no enzymatic activity.

In certain embodiment, the compositions selectively suppress the target gene expression by encoding an inhibitory RNA having substantial complementarity to a region of the target sequence. The miRNA/siRNA is provided in a nucleic acid construct which, when transcribed into RNA, is predicted to form a hairpin structure which is processed by the cell to generate the mature siRNAs/miRNAs, which then suppresses expression of the target gene or sequence as generally described below.

In additional embodiments, a nucleic acid construct is provided to encode the inhibitory RNA for any specific target pathogen gene. This may be encoded on, for example, a plasmid that may be expressed by a genetically modified bacteria capable of colonizing in or around a plant cell and expressing and transmitting the inhibitory RNA to the plant cell for miRNA processing, resulting in suppression of the target pathogen gene as generally described herein. Any inhibitory RNA can be inserted into the construct, such that the encoded inhibitory RNA selectively targets and suppresses the target pathogen gene.

In additional embodiments, a method for suppressing a target sequence is provided. The method employs the constructs above, in which an inhibitory RNA molecule is designed to a region of the target sequence, and inserted into a construct, such as a bacterial plasmid. Upon introduction into a cell through an endophytic bacteria for example, the miRNA produced within the bacteria is produced and transmitted to the plant cell and suppresses expression of the targeted sequence as generally described herein. In some embodiments, the genetically modified bacteria may exhibit, whether through selection or genetic manipulation hypervesiculation. In a certain embodiment, this hypervesiculation may aid in the efficient transport of inhibitory RNA molecules produced by the bacterial plasmid into the surrounding cell, or cell surface, or other cellular plant structure.

In a certain embodiment, the target gene or sequence can be an endogenous plant gene, or a heterologous gene. The target gene may also be a gene from a plant pathogen, such as a pathogenic bacteria or virus, nematode, herbivore, insect, or mold or fungus. A plant, cell, and seed comprising the construct and/or the miRNA is provided. Typically, the cell will be a cell from a plant, but other eukaryotic cells are also contemplated, including but not limited to yeast, insect, nematode, or animal cells. Plant cells include cells from monocots and dicots. The invention also provides plants and seeds comprising the construct and/or the miRNA. Viruses and prokaryotic cells comprising the construct are also provided.

In some embodiments, the target gene or sequence, (the terms being generally interchangeable) is selected from a plant pathogen. Plants or cells comprising a inhibitory RNA molecules directed to the target gene or of the pathogen are expected to have decreased sensitivity and/or increased resistance to the pathogen. In some embodiments, the inhibitory RNA molecule is encoded by a nucleic acid construct, such as a bacterial plasmid being expressed in an endophytic bacteria further and comprising an operably linked promoter. In some embodiments, the promoter is a pathogen-inducible promoter.

One aim of the current invention includes development of bacterial dsRNA stabilization and delivery systems to block targeted gene expression and viral replication in plants. As shown understood, dsRNA production and delivery to plants is a multi-component process involving dsRNA biogenesis, export, stabilization, import into the host and regulation of inactivation of pathogen replication.

One aim of the current invention includes systems and methods for enhancing transfer of dsRNA from bacteria to plant host cells. In certain embodiments, this may include the use of bacteria strains and helper genes that enhance dsRNA production, stabilization, export and/or delivery. For example, certain classes of bacteria have developed a variety of molecular secretion systems to enable various molecules including toxins and proteins to gain access to the host organism. Six different bacterial secretion systems have been described below. These six secretion systems have common as well as unique modes of action. The Type II and Type V secretion systems are two-step processes in which proteins are transported first through the inner membrane (IM) and then through the outer membrane (OM) of the bacterium. For secretion via the Type I, Type III, and Type IV secretion systems, the material is transferred directly into the extracellular milieu or into the host cell. The Type III system is specific for the transport of factors by pathogenic bacteria and involves a direct injection into the host cell. The distinct Type VI secretion system enables bacteria to secrete a large complex group of proteins and lipids into the extracellular milieu in extra-cellular vesicles formed from the bacterial outer membrane. These vesicles then fuse with the host cell to deliver their cargo.

Objects, advantages and novel features, and further scope of applicability of the present invention will be set forth in part in the detailed description to follow, taken in conjunction with the accompanying drawing, and in part will become apparent to those skilled in the art upon examination of the following, or may be learned by practice of the invention. The objects and advantages of the invention may be realized and attained by means of the instrumentalities and combinations particularly pointed out in the appended claims.

Figure 1:
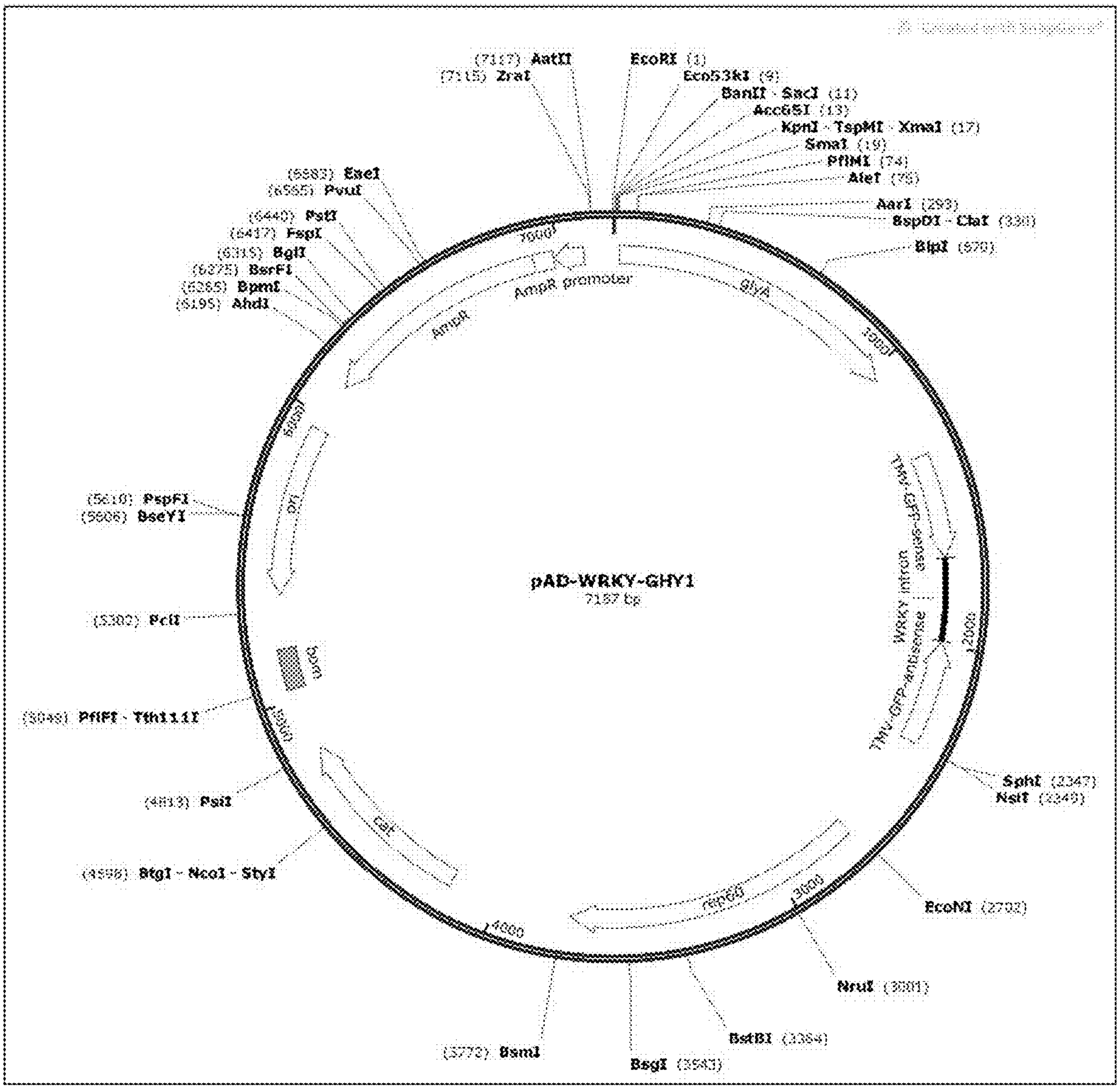
FIG. 1: Map of the hpRNA vector pAD-WRKY-GHY1.

Tables and sequence listings also are provided herein and are part of the specification.

MODE(S) FOR CARRYING OUT THE INVENTION(S)

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and with any and all various permutations and combinations of all elements in this or any subsequent application.

Disclosed herein are methods and compositions for genetic control of plant pathogens, pest infestations, and herbivores all generally being collectively described as plant pathogen(s). Methods for identifying one or more gene(s) essential to the lifecycle of a plant pathogen, pest and/or herbivore for use as a target gene for enhanced siRNA-mediated interference are also provided. DNA plasmid vectors encoding inhibitory RNA molecules may be designed to suppress one or more target gene(s) essential for growth, survival, development, and/or reproduction of a plant pathogen. Genetically modified endophytic bacteria, or other microorganisms, that may be engineered to efficiently infect, produce, and deliver such inhibitory RNA molecules is also described in the present invention.

In some embodiments, the present invention provides methods for post-transcriptional repression of expression or inhibition of a target gene via nucleic acid molecules that are complementary to a coding or non-coding sequence of the target gene in a plant pathogen. In these and further embodiments, a pest or herbivore may ingest one or more dsRNA, siRNA, miRNA, and/or hpRNA molecules transcribed from all or a portion of a nucleic acid molecule that is complementary to a coding or non-coding sequence of a target gene, thereby providing a plant-protective effect.

One embodiment of the present inventive technology may include systems and methods for introducing inhibitory RNA molecules into a target plant cell through infection by genetically engineered microorganisms. In one embodiment, the invention may provide for genetically engineered microorganisms such as bacteria, fungi or even viruses that may express one or more inhibitory RNA molecules within plant cells. In certain embodiments such inhibitory RNA molecules may initiate biological process in which the inhibitory RNA molecules inhibit or knock-down gene expression, typically by causing the destruction of specific targeted mRNA molecules within the cell. Additional embodiments may introduce inhibitory RNA molecules into plant systems that inhibit genes necessary for plant pathogenesis. Such embodiments may include introduction of inhibitory RNA molecules into plant systems that may target viral coat proteins, fungal cell wall genes, unique, species-specific gene sequences targeting suppression of genes involved in the replication and production of DNA and RNA, insect exoskeleton component genes, species-specific metabolic genes and herbivores.

Additional preferred embodiments may include improved delivery systems for inhibitory RNA molecules, for example through the use of stabilizing factors, such as stabilizing proteins and the like. Another preferred embodiment of the inventive technology may include improved systems to facilitate the transmission of inhibitory RNA molecules within the plant cell, either by co-delivery of smRNA or dsRNA precursor stabilizing proteins or hpRNA/dsRNA intra-cellular transport proteins. In one embodiment, specific RNA motifs may be incorporated into dsRNA that may facilitate its transmission through, for example the plant phloem, or direct smRNA loading to a specific effector complex. Yet further embodiments may include genetically modified microorganisms that may include genetic constructs that may further co-express certain protein having processing enzymatic activity.

Other similar embodiments may include the introduction of microorganisms into plant systems that may express, or even over-express various genes that may enhance mobilization of inhibitory RNA molecules and/or genes that may activate secondary downstream host genes that may target pathogenic pathways.

One preferred embodiment of the present invention may be to provide leaf and root endophytic and ectophytic bacteria that may further be genetically engineered to express inhibitory RNA molecules, such as dsRNA, shRNA, hpRNA (that may, in some embodiments, contain an intron from a targeted organism located at the hairpin loop of the dsRNA), siRNA, and microRNAs that are homologous to the pathogen genome, and again target critical or essential genes responsible for growth, reproduction, metabolism or pathogenicity. These inhibitory RNA molecules may inactivate and/or knock-down expression of these essential targeted genes in plant viral, fungal, and insect pathogens and pests through generation of ~21-22 nucleotide siRNAs mediated by the host Dicer/RISC complex. This process may generally be referred to as RNA interference or RNAi.

As used herein, RNA interference (RNAi) is a biological mechanism which leads to post transcriptional gene silencing (PTGS) triggered by double-stranded RNA (dsRNA) molecules, for example provided by hpRNA, to prevent the expression of specific genes. For example, in one preferred embodiment, RNA interference may be accomplished as short hpRNA molecules may be imported directly into the cytoplasm, anneal together to form a dsRNA, and then cleaved to short fragments by the Dicer enzyme. This enzyme Dicer may processes the dsRNA into ~21-22-nucleotide fragment with a 2-nucleotide overhang at the 3' end, small interfering RNAs (siRNAs). The antisense strand of siRNA become specific to endonuclease-protein complex, RNA-induced silencing complex (RISC), which then targets the homologous RNA and degrades it at specific site that results in the knock-down of protein expression.

Endophytic bacteria that may transmit hpRNA, dsRNA, shRNA, siRNA and microRNA species to plants include those in the subphyla: Acidobacteria, Actinobacteria, Alphaproteobacteria, Armatimonadetes, *Bacteroides*, Betaproteobacteria, Deltaproteobacteria, Firmicutes, Grammaproteobacteria, TM7, *Bacillus, Escherichia* and the like. In one preferred embodiment, endophytic, entophytic, or any bacteria that may infect or otherwise colonize a plant or live in its surface leaf, stem or root, may be transformed with artificially created genetic constructs, such as plasmids that may generate the inhibitory RNA molecules. Such plasmids may be constructed to be transferrable to other bacteria through conjugation which may allow for widespread environmental inoculation in some instances, as well as vertical transmission among offspring of the plant and any pest or herbivore that ingests the plant matter as an example.

In this embodiment, such constructs may include transcription regulation portions, such as promoters, terminators, co-activators and co-repressors and similar control elements that may be regulated in prokaryotic, as well as eukaryotic systems. Such systems may allow for control of the type, timing, and amount of inhibitory RNA molecules expressed within the systems. Additional embodiments may include genetic constructs that may be induced through outside factors, such as the presence of a specific protein or compound within the plant cell, such as stress-related proteins generated in response to plant pathogens or even the proteins and other precursor compounds generated by plant pathogens and the like.

In another preferred embodiment, the present inventive technology may include systems and methods whereby genetically transformed leaf and root endophytic and ectophytic bacteria that generate one or more inhibitory RNA molecules may be delivered to targeted plant phyla and/or species where the inhibitory RNA molecules may inactivate and/or knock-down expression of target viral, fungal as well as insect pathogens and herbivores. In certain embodiments, a selection of microorganisms, such as bacteria that are known to be specific to one phyla or even a certain species may be utilized. In another embodiment, transcriptional activation and promotion of inhibitory RNA molecules may be dependent on the presence of certain factors that may be specific to one phyla, or even a certain plant or herbivore species. Additional embodiments may include increased virulence factors, such as the expression or inhibition of surface protein and importation factors for specific plant phyla or even specific plant species, as well as the possible inhibition of bacterial factors, such as surface or other by-product proteins that may be recognized by, for example, intracellular host receptors that may cause the host plant cell to mount an immune-type defense.

In another preferred embodiment, the inventive technology may include systems and methods for the trans-kingdom delivery of pathogen as well as species-specific inhibitory RNA molecules that may further be stabilized by one or more proteins or protein complexes. In certain embodiments, such stabilizing proteins may include the P19 protein selected from plant RNA virus, tombusvirus which may contribute to the suppression of a plant's RNA silencing response. In certain embodiments, for example the P19 protein may recognize and bind siRNA, typically as a dimer. In the manner, the P19 protein may sequester the siRNA, whether exogenous or endogenous, and as a consequence prevent its loading into Argonaute proteins and formation of RISC(RNA-induced silencing complex).

In another preferred embodiment, the inventive technology may include the incorporation of RNA mobilization motifs into inhibitory RNA molecules, such as dsRNA, to facilitate transmission of the bacterial synthesized RNA through the plant phloem and may be co-expressed in the bacteria with the RNA species targeting inactivation of pathogen and herbivore essential genes. For example, plasmodesmata and phloem form a simplistic network that mediates direct cell-cell communication and transport throughout a plant. Selected endogenous RNAs, viral RNAs, avoid traffic between specific cells or organs via this network. As noted above, in one preferred embodiment, inhibitory RNA molecules may be generated to contain sequence/structural motifs that interact with cellular factors to facilitate trafficking across cellular boundaries.

In certain embodiments multiple inhibitory RNA molecules, expressing different sequence/structural motifs may be concurrently expressed. In this embodiment, the differing sequence/structural motifs may allow recognition of specific motifs allowing multi-direction trafficking of inhibitory RNA molecules across multiple specific cellular boundaries and/or cell types. Such motifs may further be configured to exhibit specific activity, or inactivity within certain phyla and/or species.

Yet another embodiment of the inventive technology may include development of novel bacterial strains that have decreased RNase III expression, or inactivated RNase III function or activity, generally referred to as suppresses activity. This decrease or inactivation in RNAase III expression and/or activity may inhibit or decrease RNase III-mediated processing of dsRNA species into smaller RNA species.

Additional embodiments may include novel bacterial strains that overexpress RNase III such that processing of dsRNA species to smaller RNA species is enhanced. The inventive technology may also include development of systems and methods to bacterially express dsRNAs encoding viral siRNA to trigger secondary host (plant) RNA-dependent RNA Polymerase-dependent expression of secondary siRNAs to target viral and fungal inactivation. Each of the aforementioned systems may be embodied in genetic constructs that may include transcription regulation elements such as promoters, terminators, co-activators and co-repressors and other control elements that may be regulated in prokaryotic as well as eukaryotic systems. Such systems may allow for control of the type, timing and amount of, for example RNAase III or other proteins, expressed within the system. Additional embodiments may include genetic constructs that may be induced through outside factors, such as the presence of a specific protein or compound within the plant cell, such as stress-related proteins generated in response to plant pathogens or even proteins and other precursor compounds generated by plant pathogens and the like.

Another embodiment of the inventive technology may include systems and methods to facilitate the overexpression of plant host, exogenous or genetically-modified strains of bacteria having genes known to enhance siRNA mobilization. For example, as shown in Tables 5-8 and below, overexpression of certain proteins identified in column one below may enhance siRNA mobilization throughout the subject plant or other system.

In one preferred embodiment, additional embodiments of the inventive technology may include a novel system of trans-kingdom delivery and expression of hpRNAs homologous to a pathogen's genome/gene and efficiently down-regulates or eliminates viral replication and translation of essential proteins necessary for pathogen growth, metabolism, or pathogenicity etc.

Additional embodiments of the inventive technology may include a novel system of trans-kingdom delivery and expression of inhibitory RNA molecules, such as dsRNA, shRNA, siRNA and micro RNAs, in engineered endophytic bacteria that may be found in plant roots, stems, leaves and reproductive organs. In this embodiment, the inventive technology may include various cross-kingdom mechanisms for the knock-down of targeted genes that may, for example, allow for enhanced cold, heat, salt, drought, and abiotic stress tolerance as well as integrating novel traits in various plant species including insect/pest/pathogen resistance and enhanced nutritional output, to name a few.

In another preferred embodiment, RNase III mutants of endophytic bacteria harboring plasmids encoding hairpin dsRNAs targeting suppression of pathogen proteins will suppress said proteins in plants infected with said pathogen expressing a pathogen genome encoded pathogen gene.

One preferred embodiment includes an endophytic bacterial delivery of dsRNA, processing to siRNA in plants and suppressing one or more pathogen encoded genes. In another preferred embodiment, an endophytic bacterial delivery of dsRNA, may include RNase III mutants of bacteria having no, or suppressed RNase III, harboring plasmids encoding hairpin dsRNAs, targeting suppression of pathogen proteins that may suppress said proteins in plants infected with said pathogen.

One embodiment of the present invention provides for a method of enhancing a plant's resistance to plant pathogens, such as viral and fungal diseases by introducing one or more genetically modified bacteria that may naturally colonize said target plant, encoding or interfering RNA molecules described herein such that the plant containing the heterologous DNA produces the interfering RNA molecule, such as hpRNA, and the interfering RNA molecule kills target plant pathogen, or suppresses expression of one or more of the target plant's pathogenic or critical genes.

Another embodiment provides for a method of enhancing a plant's resistance to viral diseases wherein the plant's resistance to the target viral diseases is greater than said wild-type plant's resistance to the target viral diseases. Another embodiment provides for a method of enhancing a plant's resistance to pests, wherein the plant's resistance to the target pest is greater than said wild-type plant's resistance to the target pest. Another embodiment provides for a method of enhancing a plant's resistance to herbivores, wherein the plant's resistance to the target herbivore is greater than said wild-type plant's resistance to the target herbivore.

Another embodiment demonstrated by the current inventors, may include the generation of pathogen resistant plant. In this preferred embodiment, targeting a pathogen's essential RNA transcripts by the host's RNAi machinery may result in essential pathogen RNA degradation and hence failure to translate pathogen's essential mRNAs into proteins. In this embodiment, boosting of the plant host's RNAi defenses, by a novel trans-kingdom delivery of an inhibitory RNA molecule, such as a hairpin RNA homologous to the pathogen encoded protein, may result in the loss or decrease in the pathogen's encoded protein accumulation by triggering smRNA biogenesis in the plant host, ultimately conferring resistance to pathogen infection.

Another embodiment demonstrated by the current inventors, may include the generation of a viral pathogen resistant plant. In this preferred embodiment, a plant may be infected with endophyte bacteria producing an hpRNA homologous to an essential viral encoded protein. These hpRNA transcripts may be processed by the host's RNAi machinery and result in essential viral RNA degradation and hence failure to translate the viral pathogen's essential mRNAs into proteins. In this embodiment, boosting of the plant host's RNAi defenses, by a novel trans-kingdom delivery of an inhibitory RNA molecule, such as a hairpin RNA homologous to the viral encoded protein, may result in the loss or decrease in viral encoded accumulation by triggering smRNA biogenesis in the plant host, ultimately conferring resistance to pathogen infection.

In one embodiment, the invention may include the use of *Bacillus cereus* as an endophytic bacteria expressing plasmids encoding hpRNAs targeting the suppression of pathogen proteins expressed in a plant cell. In one embodiment, this *Bacillus cereus* strain may be genetically modified to be RNase III deficient, where deficient may mean decreased RNase III expression, or inactivated RNase III function. In a preferred embodiment, this strain may include the strain 53522 as described herein.

In one embodiment, the invention may include the use of *Bacillus subtilis* as an endophytic bacteria expressing plasmids encoding hpRNAs targeting the suppression of pathogen proteins expressed in a plant cell. In one embodiment, this *Bacillus subtilis* strain may be genetically modified to be RNase III deficient, where deficient may mean decreased RNase III expression, or inactivated RNase III function. In a preferred embodiment, this strain may include the strain CCB422 as described herein.

In one embodiment, the invention may include the use of *E. coli* as an endophytic bacteria expressing plasmids encoding hpRNAs targeting the suppression of pathogen proteins expressed in a plant cell. In one embodiment, this strain may be genetically modified to be RNase deficient. In one embodiment, this strain may be naturally, or genetically modified to express a hypervesiculation genotype/phenotype. In a preferred embodiment, this strain may include the strain HT27 as described herein.

In one embodiment, the invention may include the use of a Bascillis as an endophytic bacteria expressing plasmids encoding hpRNAs targeting the suppression of pathogen proteins expressed in a plant cell. In one embodiment, this strain may be genetically modified to be RNase deficient. In one embodiment, this strain may be naturally, or genetically modified to express a hypervesiculation genotype/phenotype. In a preferred embodiment, this strain may include the strain HT27 as described herein.

In certain other embodiments, the hpRNA generated by one or more of these endophytic bacteria strains may migrate throughout the plant, leaf, root or stem from an original site of infection or introduction. In certain other embodiments, the hpRNA generated by one or more of these endophytic bacteria strains may migrate throughout the plant, leaf, root or stem from an original site of infection or introduction, as well as prevent the migration of plant pathogen migration/signal.

Further still, another embodiment comprises a composition comprising a genetically modified bacteria configured to colonize a target plant and deliver one or more inhibitory RNA molecules to inhibit one or more plant pathogens essential genes, as well as provide increased pathogen resistance, such method as disclosed herein as a topical treatment of plants at risk for infection or for plant that are already infected with a target pathogen.

In certain embodiments, this may include the use of bacteria strains and helper genes that enhance dsRNA production, stabilization, export and/or delivery into plant cells or locations where plant pathogens are located. As noted above, bacteria have developed a number of secretion systems including:

Type I secretion systems (TiSSs), exemplified by the haemolysin secretion system in *Escherichia coli*, are simple, tripartite systems facilitating the passage of proteins of various sizes across the cell envelope of Gram-negative bacteria. They consist of an ATP-binding cassette (ABC) transporter or a proton-antiporter, an adaptor protein that bridges the inner membrane (IM) and outer membrane (OM), and an outer membrane pore. They secrete substrates in a single step without a stable periplasmic intermediate. TiSSs are involved in the secretion of cytotoxins belonging to the RTX (repeats-in-toxin) protein family, cell surface layer proteins, proteases, lipases, bacteriocins, and haem-acquisition proteins.

Type II secretion systems (T2SSs) are multicomponent machines that use a two-step mechanism for translocation. During the first step, the precursor effector protein is translocated through the inner membrane by the Sec translocon or the Tat pathway. Once in the periplasm, the effector protein is translocated by the T2SS through the outer membrane. The T2SS translocon consists of 12-16 protein component that are found in both bacterial membranes, the cytoplasm and the periplasm. The T2SS shows an evolutionary relationship with the type IV pilus assembly machinery.

Type III secretion systems (T3SSs), also called injectisomes, mediate a single-step secretion mechanism and are used by many plant and animal pathogens, including *Salmonella* spp., *Shigella* spp., *Yersinia* spp., enteropathogenic and enterohaemorrhagic *Escherichia coli* and *Pseudomonas aeruginosa*. The T3SS is illustrated by the *Salmonella enterica* subsp. *enterica* serovar *Typhimurium* system, which uses the invasion (Inv) and Prg proteins (see lower figure). T3SSs deliver effector proteins into the eukaryotic host cell cytoplasm in a Sec-independent manner. T3SSs are genetically, structurally and functionally related to bacterial flagella. They are composed of more than 20 different proteins, which form a large supramolecular structure crossing the bacterial cell envelope.

Type IV secretion systems are versatile systems that are found in Gram-negative and Gram-positive bacteria and that secrete a wide range of substrates, from single proteins to protein-protein and protein-DNA complexes. These systems are exemplified by the *Agrobacterium tumefaciens* VirB/D system.

Type V secretion systems (T5SSs) include autotransporters and two-partner secretion systems. T5SSs translocate substrates in two steps. Autotransporter proteins, such as NalP from *Neisseria meningitidis*, are multidomain proteins that are secreted as precursor proteins across the inner membrane in a Sec-dependent process. Subsequently, the translocator domain of the protein inserts into the outer membrane and facilitates surface localization of the passenger domain. In two-partner secretion systems, a separate translocator protein (TpsB) mediates the secretion of the effector protein (TpsA) through the outer membrane. Over 700 proteins with functions that include auto-aggregation, adherence, invasion, cytotoxicity, serum resistance, cell-to-cell spread and proteolysis use these two secretion systems to cross both inner and outer membranes during a simple two-step process.

Type VI secretion systems (T6SSs) are recently discovered secretion systems that are found in several pathogens such as *P. aeruginosa*, enteroaggregative *E. coli*, S. *Typhimurium, Vibrio cholerae* and *Yersinia pestis*. T6SSs are multi-component systems that could be composed of 12 to 25 subunits.

One embodiment of the present invention may include exploiting bacterial secretion systems to enhance delivery of dsRNA to the plant host. In one preferred embodiment, the invention may include a system for enhancing bacterial Type IV secretion systems to deliver dsRNA to plant cells. For example, the plant pathogen *Agrobacterium tumefaciens* uses the type IV secretion system to deliver a VirD2-single stranded DNA complex as well as the virulence proteins VirD5, VirE2, VirE3, and VirF into host cells. One embodiment may include a fusion of dsRNA binding proteins to the Vir proteins could facilitate dsRNA delivery to insect cells.

In one embodiment, the invention may include a system for enhancing bacterial Type VI secretion systems for delivery of dsRNA to cells. In this preferred embodiment, overexpression of the bacterial gene yfgL may enhance phosphatidyl glycerol (membrane lipid) synthesis and vesicle production and budding. In another embodiment, mutation of the hns gene, a global regulatory factor that regulates many virulence factors, may cause an increase in *E. coli* vesicle production. In another embodiments, *Salmonella* and *P. aeruginosa* mutants missing the LPS O-antigen side chain also show increased vesicle formation.

In one embodiment, the invention may include a system for Enhancing dsRNA stabilization and mobilization into the plant cell. Some embodiments may include, but not be limited to:

- Co-expression, or over expression the nucleotidyltransferase (MUT2) is essential for mobilization of RNA between cells
- MicroRNAs derived from dsRNA having a motif that is bound by sumoylated hnRNPA2B1 have been found to be enriched in vesicles secreted from T cells, RNAs with a miR-1289 binding site and a sequence motif (CUGCC presented in a stem-loop structure), MicroRNAs with non-templated 3' uridylation ndogenous RNAs in cells can modulate the sorting of miRNAs into extracellular vesicles.

Co-expression, or over expression the Ago2 protein

Four *C. elegans* proteins with relatively well characterized roles in the import of RNA into cells were identified (Winston et al., 2002). Additional alleles of the same genes were identified in two other screens—the fed (feeding RNAi defective) screen (Timmons et al., 2003) and the rsd (RNAi spreading defective) screen.

Co-expression of the bromovirus P19 protein to facilitate stabilization and delivery of shRNA to cell Expression of fusion proteins between secretion effector proteins and dsRNA binding protein, e.g. Argonaut (Ago) protein involved in dsRNA processing, to facilitate stabilization and delivery of shRNAs into host cells.

Co-expression, or over expression any gene identified in Tables 5-8 below.

Employed, as part of the invention described herein, any of the strain identified in Table 7 below.

Further still, another embodiment comprises a composition comprising a genetically modified bacteria configured to colonize a target plant and deliver one or more inhibitory RNA molecules to inhibit one or more plant pathogen essential genes, as well as provide increased pathogen resistance, such method as disclosed herein as an aerial treatment of plants at risk for infection or for plants that are already infected with a target pathogen. In a preferred embodiment, this aerial treatment may include an aerosol, a liquid or desiccated bacteria or spore application.

In an embodiment, the plant is a monocot, or a cell of a monocot plant. For example, the monocot plant is in the gramineae and cereal groups. Non-limiting exemplary monocot species include grains, tropical fruits and flowers, bananas, maize, rice, barley, duckweed, gladiolus, sugar cane, pineapples, dates, onions, rice, sorghum, turfgrass and wheat.

In another embodiment, the plant is a dicot, or a cell of a monocot plant. For example, the dicot plant is selected from the group consisting of Anacardiaceae (e.g., cashews, pistachios), Asteraceae (e.g., asters and all the other composite flowers), Brassicaceae (e.g., cabbage, turnip, and other mustards), Cactaceae (e.g., cacti), Cucurbitaceae (e.g., watermelon, squashes), Euphorbiaceae (e.g., cassaya (manioc)), Fabaceae (e.g., beans and all the other legumes), Fagaceae (e.g., oaks), Geraniales (e.g., geraniums), Juglandaceae (e.g., pecans), Linaceae (e.g., flax), Malvaceae (e.g., cotton), Oleaceae (e.g., olives, ashes, lilacs), Rosaceae (e.g., roses, apples, peaches, strawberries, almonds), Rubiaceae (e.g., coffee), Rutaceae (e.g., oranges and other citrus fruits), Solanaceae (e.g., potatoes, tomatoes, tobacco), Theaceae (e.g., tea), and Vitaceae (e.g., grapes).

The term "plant" or "target plant" includes any plant sustainable to a pathogen. It further includes whole plants, plant organs, progeny of whole plants or plant organs, embryos, somatic embryos, embryo-like structures, protocorms, protocorm-like bodies (PLBs), and suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like). The class of plants that can be used in the method of the invention is generally as broad as the class of higher and lower plants amenable to the molecular biology and plant breeding techniques described herein, specifically angiosperms (monocotyledonous (monocots) and dicotyledonous (dicots) plants including eudicots. It includes plants of a variety of ploidy levels, including aneuploid, polyploid, diploid, haploid and hemizygous. The genetically altered plants described herein can be monocot crops, such as, sorghum, maize, wheat, rice, barley, oats, rye, millet, and triticale. The invention may also include Cannabaceae and other *Cannabis* strains, such as *C. sativa* generally.

Examples of additional plants species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), *papaya* (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley; vegetables, ornamentals, and conifers. Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis*, such as cucumbers (*C. sativus*), cantaloupe (*C. cantalupensis*), and musk melon (*C. melo*). Ornamentals include azalea (*Rhododendron* spp.), *hydrangea* (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnations (*Dianthus caryophyllus*), poinsettias (*Euphorbia pulcherrima*), and chrysanthemums. Conifers that may be employed in practicing the present invention include, for example, pines such as loblolly pine (*Pinus taeda*), slash pine (*Pinus elliotii*), *ponderosa* pine (*Pinus ponderosa*), lodgepole pine (*Pinus contorta*), and Monterey pine (*Pinus radiata*), Douglas-fir (*Pseudotsuga menziesii*), Western hemlock (*Tsuga canadensis*), Sitka spruce (*Picea glauca*), redwood (*Sequoia sempervirens*), true firs such as silver fir (*Abies amabilis*) and balsam fir (*Abies balsamea*), and cedars such as Western red cedar (*Thuja plicata*) and Alaska yellow-cedar (*Chamaecyparis nootkatensis*). In specific embodiments, plants of the present invention are crop plants (for example, as noted above, corn, alfalfa, sunflower, *Brassica*, soybean, cotton, safflower, peanut, sorghum, wheat, millet, tobacco, etc.).

A "plant pathogen" or "pathogen" refers to an organism (bacteria, virus, protist, algae or fungi) that infects plants or plant components. Examples include molds, fungi and rot that typically use spores to infect plants or plant components (e.g fruits, vegetables, grains, stems, roots). A "plant pathogen" also includes all genes necessary for the pathogenicity or pathogenic effects in the plant, or that by their suppression or elimination, such effects are reduced or eliminated.

In one preferred embodiment, the present invention may be applied to one or more of the following non-limiting group of plant viruses, including pathogen gene targets, generally referred to as gene targets, or essential genes, which would be recognized and available to those of ordinary skill in the art without undue experimentation:

| | Plant Pathogens | | |
|---|---|---|---|
| Virus diseases | hosts | Pathogenic genes | References |
| Tobacco mosaic virus (TMV) | Tobacco, tomato, and other solanaceous plants. It can infect well over 350 different species of plants. The typical symptoms are necrosis, mosaic, mottling, stunting, leaf curling, and yellowing of plant tissues, etc. | Replicase gene, movement protein, coat protein | (Scholthof, 2004) |
| Tomato spotted-wilt virus (TSWV) | Over 1,000 species in over 85 families, including many vegetables, peanut, and tobacco, are susceptible to TSWV. The Solanaceae and Compositae families contain the largest numbers of susceptible plant species. TSWV also replicates in its insect vector, thrips (Thysanoptera: Thripidae) | glycoproteins (GPs), NSm protein, NSs protein, virus RNA genomic segment L, M, and S. | (Adkins, 2000) |
| Tomato yellow leaf curl virus (TYLCV) | Plants are stunted or dwarfed, can infect about 50 different plant species | V1, V2, C1, C2, C3, and C4. V1 protein | (Czosnek, 2007) |
| Cucumber mosaic virus (CMV) | Over 1,200 species in over 100 families of monocots and dicots, including many vegetables, ornamentals and woody and semi-woody plants | 1a, 2a and 2b protein, 3a and coat protein | (Palukaitis & Garcia-Arenal, 2003) |
| Potato virus Y (PVY) | PVY mostly infects plants in the family Solanaceae. The Solanaceous plants include economically important ones like potato (Solanum tuberosum), as well as tomato, tomatillo, green pepper, chili pepper, eggplant, petunia and many weeds, such as the nightshades. Easily spread by aphids | P1, HC-Pro, P3, 6k1, CI, 6k2, NIa, Nib, and CP | (Jakab et al., 1997) |
| Cauliflower mosaic virus (CaMV) | CaMV infects mostly plants of the Brassicaceae family (such as cauliflower and turnip) but some CaMV strains (D4 and W260) are also able to infect Solanaceae species of the genera Datura and Nicotiana. | Movement protein, two aphid transmission factors (P2 and P3), the precursor of the capsid proteins (P4), and polyprotein precursor of proteinase, P5, and P6 protein. | (Hoh et al., 2010) |
| African cassava mosaic virus (ACMV) | Mosaic, leaf distortion and stunting | AV1, AV2, AC1, AC2, AC3, AC4, BC1, BVI | (Bock & Harrison, 1985, Fauquet & Fargette, 1990) |
| Plum pox virus (PPV) | Prunus species is widespread in most stone fruit-producing countries. Symptoms include chlorotic and necrotic ring patterns or blotches | P1, HC-Pro, P3, 6k1, CI, 6k2, NIa, Nib, and CP | (Cambra et al., 2006, Ilardi & Tavazza, 2015) |

-continued

| | Plant Pathogens | | |
|---|---|---|---|
| Virus diseases | hosts | Pathogenic genes | References |
| Brome mosaic virus (BMV) | BMV is cosmopolitan and found virtually wherever wheat is grown. | 1a, 2a, movement protein, coat protein | (Miller et al., 1985, Ahlquist & Janda, 1984) |
| Potato virus X (PVX) | PVX is found mainly in potatoes and is only transmitted mechanically, most infections are transmitted by farm machinery, can also be transmitted by vectors such as grasshoppers or biting insects | Replicase, TGB1, TGB2, TGB3, and coat protein | (Kaniewski et al., 1990, Kutnjak et al., 2014) |

Additional plant pathogens may include: *Citrus tristeza* virus, Barley yellow dwarf virus, Potato leafroll virus and Tomato and bushy stunt virus.

In one preferred embodiment, the present invention may be applied to one or more of the following non-limiting group of plant fungal pathogens, including pathogen gene targets, generally referred to as gene targets, or essential genes, which would be recognized and available to those of ordinary skill in the art without undue experimentation:

| Plant Pathogens | hosts | Pathogenic genes | References |
|---|---|---|---|
| *Magnaporthe oryzae* | Rice (*Oryza sativa*). | MoABC1, MoM4C1 and MoPMK1, pathogenicity-related genes, effectors Iug6, Iug9 and Iug18, secreted proteins: MoMpg1, MoEmp1, MoMhp1, MoMsp1, MC69, and Slp1, etc. | (Zhu et al., 2017, Dong et al., 2015) |
| *Botrytis cinerea* | It can infect over 200 plant species, causing grey mould, evident on the surface as grey fluffy mycelium. Worldwide, it causes annual losses of $10 billion to $100 billion. | pathogenicity-related genes Bcpg1 and BMP1 | (Williamson et al., 2007, Have et al., 1998, Zheng et al., 2000) |
| *Puccinia* spp. | Wheat and barley, common barberry (and some additional *Berberis*, *Mahoberberis*, and *Mahonia* spp.) | pathogenicity-related genes MAPK, cyclophilin, and calcineurin regulatory subunit, and secreted proteins etc. | (Stakman & Levine, 1944, Chen, 2005, Rampitsch et al., 2006, Panwar et al., 2013, Cantu et al., 2013) |
| *Fusarium graminearum* | Wheat (*Triticum aestivum*), Durum Wheat (*Triticum durum*), Barley (*Hordeum vulgare*) and Oat (*Avena saliva*). *F. graminearum* parasitizes roots, stems, leaves, and reproductive tissues of many species of cereals and grasses. | MAP1, and MAP kinase gpmk1 etc. | (Goswami & Kistler, 2004, Urban et al., 2003, Jenczmionka et al., 2003) |
| *Fusarium oxysporum* | It can infect many plants including potato, sugarcane, garden bean, cowpea, Prickly pear, cultivated zinnia, pansy, Assam rattlebox, Baby's breath, and *Musa* sp. | MAP kinase, pg1, pathogenicity-related genes, secreted proteins, etc. | (Di Pietro et al., 2001, Michielse & Rep, 2009, Di Pietro & Roncero, 1998) |

-continued

| Plant Pathogens | hosts | Pathogenic genes | References |
|---|---|---|---|
| *Blumeria graminis* | Causing powdery mildew on grasses, including cereals. | effector gene Avra10, pathogenicity-related genes, secreted proteins, etc. | (Nowara et al., 2010, Bindschedler et al., 2016) |
| *Mycosphaerella graminicola* | causing septoria leaf blotch, in most years is the second most important disease of wheat in the United States | pathogenicity-related genes, MgSlt2, ABC Transporter Genes MgAtr1 and MgAtr2, secreted proteins, etc. | (Goodwin et al., 2011, Brading et al., 2002, Mehrabi et al., 2006, Zwiers & De Waard, 2000) |
| *Colletotrichum* spp. | black spot disease in the common bean plant | CMK1, and clk1, pathogenesis-related protein 10, secreted proteins, etc. | (Cannon et al., 2012, Takano et al., 2000, Dufresne et al., 1998, Lo et al., 1999) |
| *Ustilago maydis* | causing smut on maize and teosinte | pathogenicity-related genes, Kpp2, ukc1, secreted proteins, etc. | (Kämper et al., 2006, Müller et al., 1999, Dürrenberger & Kronstad, 1999) |
| *Melampsoralini* | flax rust | pathogenicity-related genes, secreted proteins, etc. | (Flor, 1956, Lawrence et al., 1981, Nemri et al., 2014) |

Any gene being expressed in a cell (preferably a plant cell) can be targeted. A gene that is expressed in the cell is one that is transcribed to yield RNA (e.g., miRNA) and, optionally, a protein. The target gene can be an endogenous gene or an exogenous or foreign gene (i.e., a transgene or a pathogen gene). For example, a transgene that is present in the genome of a cell as a result of genomic integration of the viral delivery construct can be regulated using inhibitory RNA according to the invention. The foreign gene can be integrated into the host genome (preferably the chromosomal DNA), or it may be present on an extra-chromosomal genetic construct such as a plasmid or a cosmid. For example, the target gene may be present in the genome of the cell into which the interfering RNA is introduced through the novel trans-kingdom method described herein, or similarly in the genome of a pathogen, such as a virus, a bacterium, a fungus or a protozoan, which is capable of infecting such organism or cell.

Preferably the target gene is an endogenous gene of the cell or a heterologous gene relative to the genome of the cell, such as a pathogen gene. Preferably, the gene of a pathogen is from a pathogen capable of infecting an eukaryotic organism. Most preferably, said pathogen is selected from the group of virus, bacteria, fungi and nematodes as noted above. By expressing the inhibitory RNA of the invention in plants, not only plant genes can function as target genes for gene silencing, but also genes of organisms which infect plants or eat plants (as food or feed). Thus the target gene can also be a gene of an animal or plant pathogen. The target gene is preferably selected from the group consisting of genes in a plant or of a plant infecting pathogen. Preferably, the expression of the target gene (as measured by the expressed RNA or protein) is reduced, inhibited or attenuated by at least 10%, preferably at least 30% or 40%, preferably at least 50% or 60%, more preferably at least 80%, most preferably at least 90% or 95% or 100%.

The levels of target products such as transcripts or proteins may be decreased throughout an organism such as a plant, pest or herbivore, or such decrease in target products may be localized in one or more specific organs or tissues of the organism. For example, the levels of products may be decreased in one or more of the tissues and organs of a plant including without limitation: roots, tubers, stems, leaves, stalks, fruit, berries, nuts, bark, pods, seeds and flowers. A preferred organ is a seed of a plant. A broad variety of target genes can be modulated by using the method of the invention, including genes in a plant but also genes or plant infecting or eating pathogens, animals, or even human. Preferably, the target gene is selected from the group consisting of plant endogenous, transgenes, or genes from a plant infecting pathogen. More preferably the plant infecting pathogen is selected from the group consisting of viruses, fungi, bacteria, insects, and nematodes.

In the case of pathogens, the target or essential gene may, for example, be a house-keeping or other gene, which is essential for viability or proliferation of the pathogen. The attenuation or silencing of the target gene may have various effects (also depending on the nature of the target gene). Preferably, silencing or attenuating said target gene results in loss or reduction or the pathogen's harmful effects, i.e., pathogenicity, or an agronomic trait. Said agronomic trait may preferably be selected from the group consisting of disease resistance, herbicide resistance, resistance against biotic or abiotic stress, and improved nutritional value. In this context, the target gene may, for example, be preferably selected from the group consisting of genes involved in the synthesis and/or degradation of proteins, peptides, fatty acids, lipids, waxes, oils, starches, sugars, carbohydrates, flavors, odors, toxins, carotenoids, hormones, polymers, flavinoids, storage proteins, phenolic acids, alkaloids, lignins, tannins, celluloses, glycoproteins, and glycolipids. All these sequences are well known to the person skilled in the art and can be easily obtained from DNA data bases by those of ordinary skill in the art (e.g., GenBank).

In certain embodiments, the novel trans-kingdom delivery of inhibitory RNA molecules, namely the methods and means of the invention may be especially suited for obtaining pathogen (e.g., virus or nematode) resistance, in eukaryotic cells or organisms, particularly in plant cells and plants. It is expected that the inhibitory RNA molecules (or the dsRNA molecules derived therefrom) produced by transcription in a host organism (e.g., a plant), can spread systemically throughout the organism. Thus it is possible to reduce the phenotypic expression of a nucleic acid in cells of a non-transgenic scion of a plant grafted onto a transgenic stock comprising the genes of the invention (or vice versa) a method which may be important in horticulture, viticulture or in fruit production. A resistance to plant pathogens such as arachnids, fungi, insects, nematodes, protozoans, viruses, bacteria and diseases can be achieved by reducing the gene expression of genes which are essential for the growth, survival, certain developmental stages (for example pupation), or the multiplication of a certain pathogen. A suitable reduction can bring about a complete inhibition of the above steps, but also a delay of one or more steps. This may include plant genes which, for example, allow the pathogen to enter, but may also be pathogen-homologous genes. Preferably, the inhibitory RNA (such as hpRNA or the dsRNA derived therefrom) is directed against genes of the pathogen. For example, plants can be treated with suitable formulations of above mentioned agents, for example sprayed or dusted; the plants themselves, however, may also comprise the agents in the form of a transgenic organism and pass them on to the pathogens, for example in the form of a stomach poison. Various essential genes of a variety of pathogens are known to those of ordinary skill in the art (for example for nematode resistance: WO 93/10251, WO 94/17194).

Another aspect of methods of the novel trans-kingdom delivery of inhibitory RNA molecules described here provides a method where the target gene for suppression encodes a protein in a plant pathogen (e.g., an insect or nematode). In this aspect, a method comprises introducing into the genome of a pathogen-targeted plant a nucleic acid construct comprising DNA, such as a plasmid, which is transcribed into a inhibitory RNA, such as a hpRNA, that forms at least one dsRNA molecule which is effective for reducing expression of a target gene within the pathogen when the pathogen (e.g., insect or nematode) ingests or infects cells from said plant. In a preferred embodiment, the gene suppression is fatal to the pathogen. Most preferred as a pathogen are fungal pathogens, to the extent not already listed elsewhere, such as *Phytophthora infestans, Fusarium nivale, Fusarium graminearum, Fusarium culmorum, Fusarium oxysporum, Blumeria graminis, Magnaporthe grisea, Sclerotinia sclerotium, Septoria nodorum, Septoria tritici, Alternaria brassicae, Phoma lingam*, and nematodes such as *Globodera rostochiensis, G. pallida, Heterodera schachtii, Heterodera avenae, Ditylenchus dipsaci, Anguina tritici* and *Meloidogyne hapla.*

Resistance to pathogenic viruses can be obtained for example by reducing the expression of a viral coat protein, a viral replicase, a viral protease, a, a structural protein, a toxin and the like. A large number of plant viruses, and suitable target genes are known to those of ordinary skill in the art. The methods and compositions of the present invention are especially useful to obtain nematode resistant plants (for target genes see e.g., WO 92/21757, WO 93/10251, WO 94/17194).

Also provided by the invention is a method for obtaining pathogen resistant organisms, particularly plants, comprising the steps of providing cells of the organism with an inhibitory RNA molecule of the invention, said inhibitory RNA molecule capable to provide in an eukaryotic cell an at least partially double-stranded RNA molecule, said inhibitory RNA molecule comprising a) at least one first ribonucleotide sequence that is substantially identical to at least a part of a target nucleotide sequence of at least one gene of a pathogen, b) at least one second ribonucleotide sequence which is substantially complementary to said first nucleotide sequence and is capable to hybridize to said first nucleotide sequence to form a double-stranded RNA structure, and c) at least one third ribonucleotide sequence located between said first and said second ribonucleotide sequence comprising at least one removable RNA element, which can be removed by the RNA processing mechanism of an eukaryotic cell without subsequently covalently joining the resulting sequences comprising said first and said second ribonucleotide sequence, respectively. Preferably, said first ribonucleotide sequence has between 65 and 100% sequence identity, preferably between 75 and 100%, more preferably between 85 and 100%, most preferably between 95 and 100%, with at least part of the nucleotide sequence of the genome of a pathogen. More preferably the pathogen is selected from the group of virus, bacteria, fungi, and nematodes.

Because this invention involves production of genetically modified bacteria and involves recombinant DNA techniques, the following definitions are provided to assist in describing this invention. The terms “isolated,” “purified,” or “biologically pure” as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term “purified” denotes that a nucleic acid or protein that gives rise to essentially one band in an electrophoretic gel. Typically, isolated nucleic acids or proteins have a level of purity expressed as a range. The lower end of the range of purity for the component is about 60%, about 70%, or about 80%, and the upper end of the range of purity is about 70%, about 80%, about 90%, or more than about 90%.

The term “contact” (with an plant): As used herein, the term “contact with” or “uptake by” an organism (e.g., a plant or pest or herbivore), with regard to a nucleic acid molecule, includes internalization of the nucleic acid molecule into the organism, for example and without limitation: ingestion of the molecule by the organism (e.g., by feeding); contacting the organism with a composition comprising the nucleic acid molecule; soaking of organisms with a solution comprising the nucleic acid molecule; injecting the organism with a composition comprising the nucleic acid molecule; and spraying the organism with an aerosol composition comprising the nucleic acid molecule.

The term “expression,” as used herein, or “expression of a coding sequence” (for example, a gene or a transgene) refers to the process by which the coded information of a nucleic acid transcriptional unit (including, e.g., genomic DNA or cDNA) is converted into an operational, nonoperational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

The term “nucleic acid” or “nucleic acid molecules” include single- and double-stranded forms of DNA; single-stranded forms of RNA; and double-stranded forms of RNA (dsRNA). The term “nucleotide sequence” or “nucleic acid sequence” refers to both the sense and antisense strands of a nucleic acid as either individual single strands or in the duplex. The term “ribonucleic acid” (RNA) is inclusive of iRNA (inhibitory RNA), dsRNA (double stranded RNA), siRNA (small interfering RNA), mRNA (messenger RNA), miRNA (micro-RNA), hpRNA (hairpin RNA), tRNA (transfer RNA), whether charged or discharged with a corresponding acylated amino acid), and cRNA (complementary RNA). The term “deoxyribonucleic acid” (DNA) is inclusive of cDNA, genomic DNA, and DNA-RNA hybrids. The terms “nucleic acid segment” and “nucleotide sequence segment,” or more generally “segment,” will be understood by those in the art as a functional term that includes both genomic sequences, ribosomal RNA sequences, transfer RNA sequences, messenger RNA sequences, operon sequences, and smaller engineered nucleotide sequences that encoded or may be adapted to encode, peptides, polypeptides, or proteins.

As used herein “hairpin RNA” (hpRNA) refers to any self-annealing double-stranded RNA molecule. In its simplest representation, a hairpin RNA consists of a double stranded stem made up by the annealing RNA strands, connected by a single stranded RNA loop, and is also referred to as a, “pan-handle RNA.” However, the term “hairpin RNA” is also intended to encompass more complicated secondary RNA structures comprising self-annealing double stranded RNA sequences, but also internal bulges and loops. The specific secondary structure adapted will be determined by the free energy of the RNA molecule, and can be predicted for different situations using appropriate software such as FOLDRNA (Zuker and Stiegler (1981) Nucleic Acids Res 9(1):133-48; Zuker, M. (1989) Methods Enzymol. 180:262-288).

In still other embodiments of the invention, inhibition of the expression of one or more plant pathogen gene products by RNAi may be obtained by hairpin RNA (hpRNA) interference or intron-containing hairpin RNA (ihpRNA) interference. For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene product whose expression is to be inhibited, in this case, a cytochrome P450 polypeptide described herein, and an antisense sequence that is fully or partially complementary to the sense sequence. Alternatively, the base-paired stem region may correspond to a portion of a promoter sequence controlling expression of the gene encoding the target polypeptide to be inhibited. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz (2000) Proc. Natl. Acad. Sci. USA 97:4985-4990; Stoutjesdijk et al. (2002) Plant Physiol. 129:1723-1731; and Waterhouse and Helliwell (2003) Nat. Rev. Genet. 4:29-38. Methods for using hpRNA interference to inhibit or silence the expression of genes are described, for example, in Chuang and Meyerowitz (2000) Proc. Natl. Acad. Sci. USA 97:4985-4990; Stoutjesdijk et al. (2002) PlantPhysiol. 129:1723-1731; Waterhouse and Helliwell (2003) Nat. Rev. Genet. 4:29-38; Pandolfini et al. BMC Biotechnology 3:7, and U.S. Patent Publication No. 20030175965; each of which is herein incorporated by reference. A transient assay for the efficiency of hpRNA constructs to silence gene expression in vivo has been described by Panstruga et al. (2003) Mol. Biol. Rep. 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith et al. (2000) Nature 407:319-320. In fact, Smith et al. show 100% suppression of endogenous gene expression using ihpRNA-mediated interference. Methods for using ihpRNA interference to inhibit the expression of endogenous plant genes are described, for example, in Smith et al. (2000) Nature 407: 319-320; Wesley et al. (2001) Plant J 27:581-590; Wang and Waterhouse (2001) Curr. Opin. Plant Biol. 5:146-150; Waterhouse and Helliwell (2003) Nat. Rev. Genet. 4:29-38; Helliwell and Waterhouse (2003) Methods 30:289-295, and U.S. Patent Publication No. 20030180945, each of which is herein incorporated by reference.

As used herein, on oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of DNA and RNA (reverse transcribed into a cDNA) sequences. In PCR, the oligonucleotide is typically referred to as a “primer,” which allows a DNA polymerase to extend the oligonucleotide and replicate the complementary strand.

The term “gene” or “sequence” refers to a coding region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (down-stream) the coding region (open reading frame, ORF) as well as, where applicable, intervening sequences (i.e., introns) between individual coding regions (i.e., exons). The term “structural gene” as used herein is intended to mean a DNA sequence that is transcribed into mRNA which is then translated into a sequence of amino acids characteristic of a specific polypeptide.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hair-pinned, circular, and padlocked conformations.

As used herein with respect to DNA, the term "coding sequence," "structural nucleotide sequence," or "structural nucleic acid molecule" refers to a nucleotide sequence that is ultimately translated into a polypeptide, via transcription and mRNA, when placed under the control of appropriate regulatory sequences. With respect to RNA, the term "coding sequence" refers to a nucleotide sequence that is translated into a peptide, polypeptide, or protein. The boundaries of a coding sequence are determined by a translation start codon at the 5'-terminus and a translation stop codon at the 3'-terminus. Coding sequences include, but are not limited to: genomic DNA; cDNA; EST; and recombinant nucleotide sequences.

As used herein, the term "genome" refers to chromosomal DNA found within the nucleus of a cell, and also refers to organelle DNA found within subcellular components of the cell. The term "genome" as it applies to bacteria refers to both the chromosome and plasmids within the bacterial cell. In some embodiments of the invention, a DNA molecule may be introduced into a bacterium such that the DNA molecule is integrated into the genome of the bacterium. In these and further embodiments, the DNA molecule may be either chromosomally-integrated or located as or in a stable plasmid.

The term "sequence identity" or "identity," as used herein in the context of two nucleic acid or polypeptide sequences, refers to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10. The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acid sequences with even greater similarity to the reference sequences will show increasing percentage identity when assessed by this method.

As used herein, the terms "hybridizable" and "complementary" are terms that indicate a sufficient degree of complementarity such that stable and specific binding occurs between the nucleic acid molecule and a target nucleic acid molecule. Hybridization between two nucleic acid molecules involves the formation of an anti-parallel alignment between the nucleic acid sequences of the two nucleic acid molecules. The two molecules are then able to form hydrogen bonds with corresponding bases on the opposite strand to form a duplex molecule that, if it is sufficiently stable, is detectable using methods well known in the art. A nucleic acid molecule need not be 100% complementary to its target sequence to be specifically hybridizable. However, the amount of sequence complementarity that must exist for hybridization to be specific is a function of the hybridization conditions used, and may be between 50%-10$^{0}$%.

As used herein, the term "homologous" with regard to a contiguous nucleic acid sequence, refers to contiguous nucleotide sequences that hybridize under appropriate conditions to the reference nucleic acid sequence. For example, homologous sequences may have from about 70%-100, or more generally 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

The term, "operably linked," when used in reference to a regulatory sequence and a coding sequence, means that the regulatory sequence affects the expression of the linked coding sequence. “Regulatory sequences,” or “control elements,” refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

As used herein, the term “promoter” refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell. A “plant promoter” may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as “tissue-preferred.” Promoters which initiate transcription only in certain tissues are referred to as “tissue-specific.” A “cell type-specific” promoter primarily drives expression in certain cell types in one or more organs, for example, vascular cells in roots or leaves. An “inducible” promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of “non-constitutive” promoters. A “constitutive” promoter is a promoter which may be active under most environmental conditions or in most cell or tissue types.

Any inducible promoter can be used in some embodiments of the invention. See Ward et al. (1993) Plant Mol. Biol. 22:361-366. With an inducible promoter, the rate of transcription increases in response to an inducing agent. Exemplary inducible promoters include, but are not limited to: Promoters from the ACEI system that responds to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone are general examples (Schena et al. (1991) Proc. Natl. Acad. Sci. USA 88:0421).

As used herein, the term “transformation” or “genetically modified” refers to the transfer of one or more nucleic acid molecule(s) into a cell. A microorganism is “transformed” or “genetically modified” by a nucleic acid molecule transduced into the bacteria when the nucleic acid molecule becomes stably replicated by the bacteria. As used herein, the term “transformation” or “genetically modified” encompasses all techniques by which a nucleic acid molecule can be introduced into, such as a bacteria.

The term “vector” refers to some means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature, etc. There are various types of vectors including virus, plasmid, bacteriophages, cosmids, and bacteria.

An “expression vector” is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an “expression cassette.” In contrast, as described in the examples herein, a “cassette” is a polynucleotide containing a section of an expression vector of this invention. The use of the cassettes assists in the assembly of the expression vectors. An expression vector is a replicon, such as plasmid, phage, virus, chimeric virus, or cosmid, and which contains the desired polynucleotide sequence operably linked to the expression control sequence(s).

A polynucleotide sequence is operably linked to an expression control sequence(s) (e.g., a promoter and, optionally, an enhancer) when the expression control sequence controls and regulates the transcription and/or translation of that polynucleotide sequence.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). Because of the degeneracy of nucleic acid codons, one can use various different polynucleotides to encode identical polypeptides. Table 1a, infra, contains information about which nucleic acid codons encode which amino acids.

TABLE 1a

Amino acid Nucleic acid codons

| Amino Acid | Nucleic Acid Codons |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |

TABLE 1a-continued

| Amino acid Nucleic acid codons | |
|---|---|
| Amino Acid | Nucleic Acid Codons |
| Trp/W | TGG |
| Tyr/Y | TAT, TAC |
| Val/V | GTT, GTC, GTA, GTG |

Oligonucleotides and polynucleotides that are not commercially available can be chemically synthesized e.g., according to the solid phase phosphoramidite triester method first described by Beaucage and Caruthers, Tetrahedron Letts. 22:1859-1862 (1981), or using an automated synthesizer, as described in Van Devanter et al., Nucleic Acids Res. 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, J. Chrom. 255:137-149 (1983).

The term "recombinant" when used with reference, e.g., to a cell, or nucleic acid, protein, or vector, indicates that the cell, organism, nucleic acid, protein or vector, has been modified by the introduction of a heterologous nucleic acid or protein, or the alteration of a native nucleic acid or protein, or that the cell is derived from a cell so modified. Thus, for example, recombinant cells may express genes that are not found within the native (nonrecombinant or wild-type) form of the cell or express native genes that are otherwise abnormally expressed—over-expressed, under expressed or not expressed at all.

The terms "approximately" and "about" refer to a quantity, level, value or amount that varies by as much as 30%, or in another embodiment by as much as 20%, and in a third embodiment by as much as 10% to a reference quantity, level, value or amount. As used herein, the singular form "a," "an," and "the" include plural references unless the context clearly dictates otherwise. For example, the term "a bacterium" includes both a single bacterium and a plurality of bacteria.

As used here "suppression" or "silencing" or "inhibition" are used interchangeably to denote the down-regulation of the expression of the product of a target sequence relative to its normal expression level in a wild type organism. Suppression includes expression that is decreased by about 10%, 15%, 20%, 25%, 30%, 35%, 40%, 45%, 50%, 55%, 60%, 65%, 70%, 75%, 80%, 85%, 90%, 95%, or 100% relative to the wild type expression level. An "effective amount" is an amount of inhibitory RNA sufficient to result in suppression or inhibition of a plant pathogen.

As used herein, "heterologous" in reference to a nucleic acid is a nucleic acid that originates from a foreign species, or is synthetically designed, or, if from the same species, is substantially modified from its native form in composition and/or genomic locus by deliberate human intervention. A heterologous protein may originate from a foreign species or, if from the same species, is substantially modified from its original form by deliberate human intervention. By "host cell" is meant a cell which contains an introduced nucleic acid construct and supports the replication and/or expression of the construct. Host cells may be prokaryotic cells such as *E. coli*, or eukaryotic cells such as fungi, yeast, insect, amphibian, nematode, or mammalian cells. Alternatively, the host cells are monocotyledonous or dicotyledonous plant cells. An example of a monocotyledonous host cell is a maize host cell.

Polynucleotide sequences may have substantial identity, substantial homology, or substantial complementarity to the selected region of the target gene. As used herein "substantial identity" and "substantial homology" indicate sequences that have sequence identity or homology to each other. Generally, sequences that are substantially identical or substantially homologous will have about 75%, 80%, 85%, 90%, 91%, 92%, 93%, 94%, 95%, 96%, 97%, 98%, 99%, or 100% sequence identity wherein the percent sequence identity is based on the entire sequence and is determined by GAP alignment using existing default parameters (GCG, GAP version 10, Accelrys, San Diego, CA). GAP uses the algorithm of Needleman and Wunsch ((1970) J Mol Biol 48:443-453) to find the alignment of two complete sequences that maximizes the number of matches and minimizes the number of sequence gaps. Sequences which have 100% identity are identical. "Substantial complementarity" refers to sequences that are complementary to each other, and are able to base pair with each other. In describing complementary sequences, if all the nucleotides in the first sequence will base pair to the second sequence, these sequences are fully complementary.

EXAMPLES

Example 1: Demonstrates Construction of Bacterial Plasmids Encoding Hairpin (hp) RNA Constructs Encoding a Foldback RNA Targeting a Green Fluorescent Protein (GFP)

As demonstrated by the present inventors, hpRNAs encoding plasmid vectors were constructed using NEBuilder® HiFi DNA Assembly Cloning Kit from New England BioLabs Inc. Here, seven hpRNA vectors were constructed to target the green fluorescent protein (GFP) encoding mRNA expressed from pJL-TRBO-G (Lindbo 2007) as an exemplary embodiment.

Figure 2:
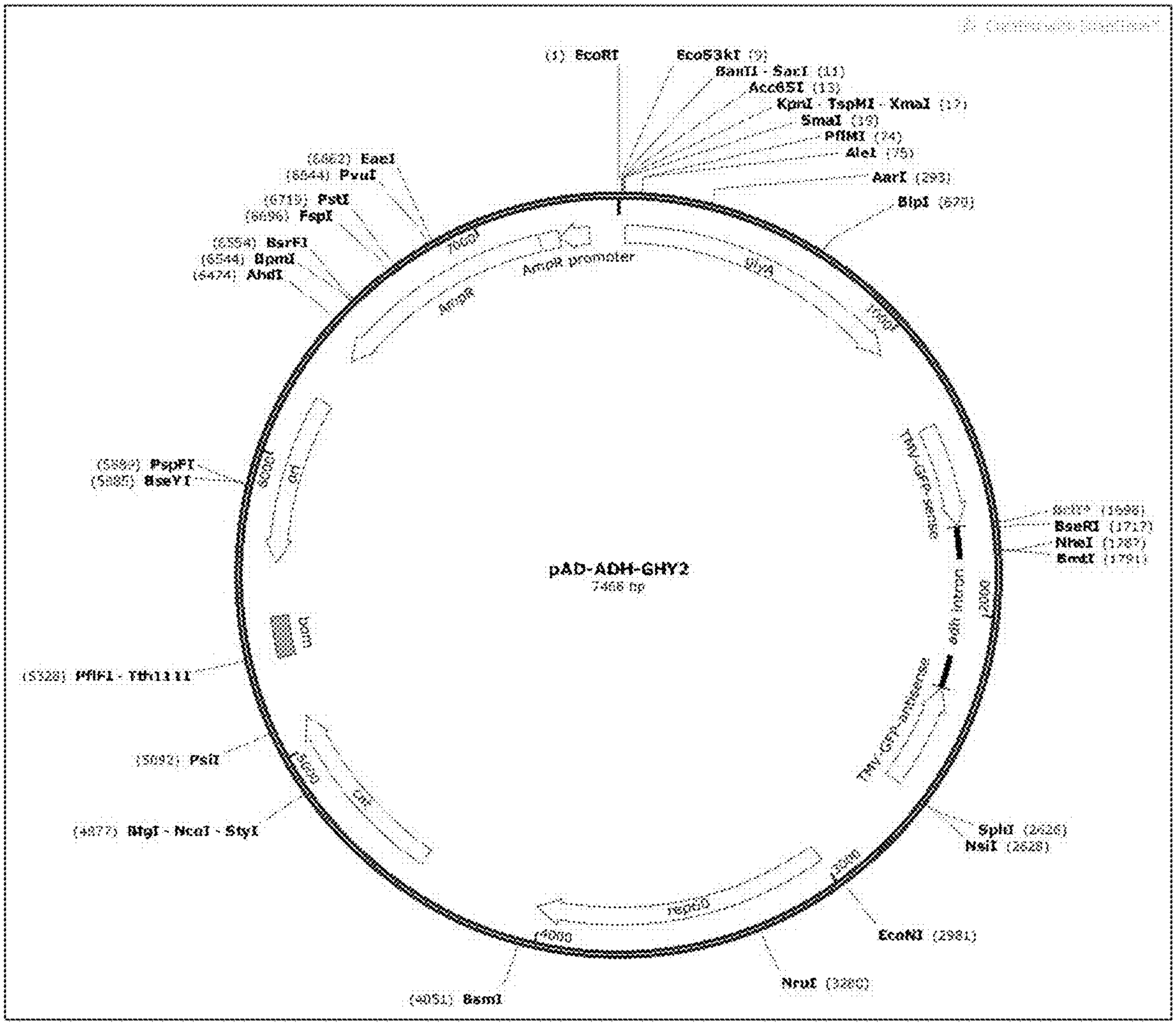
FIG. 2: Map of the hpRNA vector pAD-ADH-GHY2.
Figure 3:
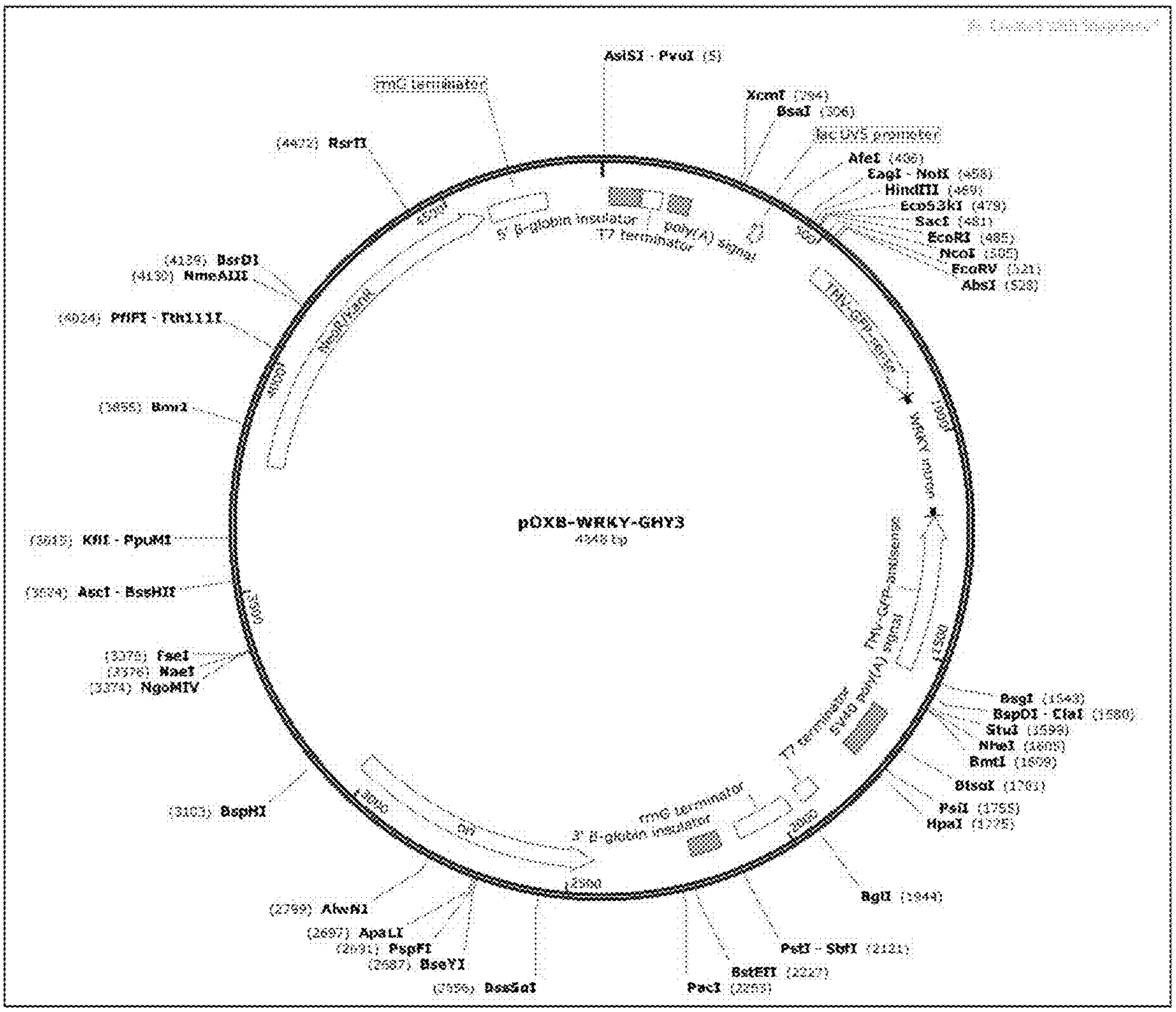
FIG. 3: Map of the hpRNA vector pOXB-WRKY-GHY3.
Figure 4:
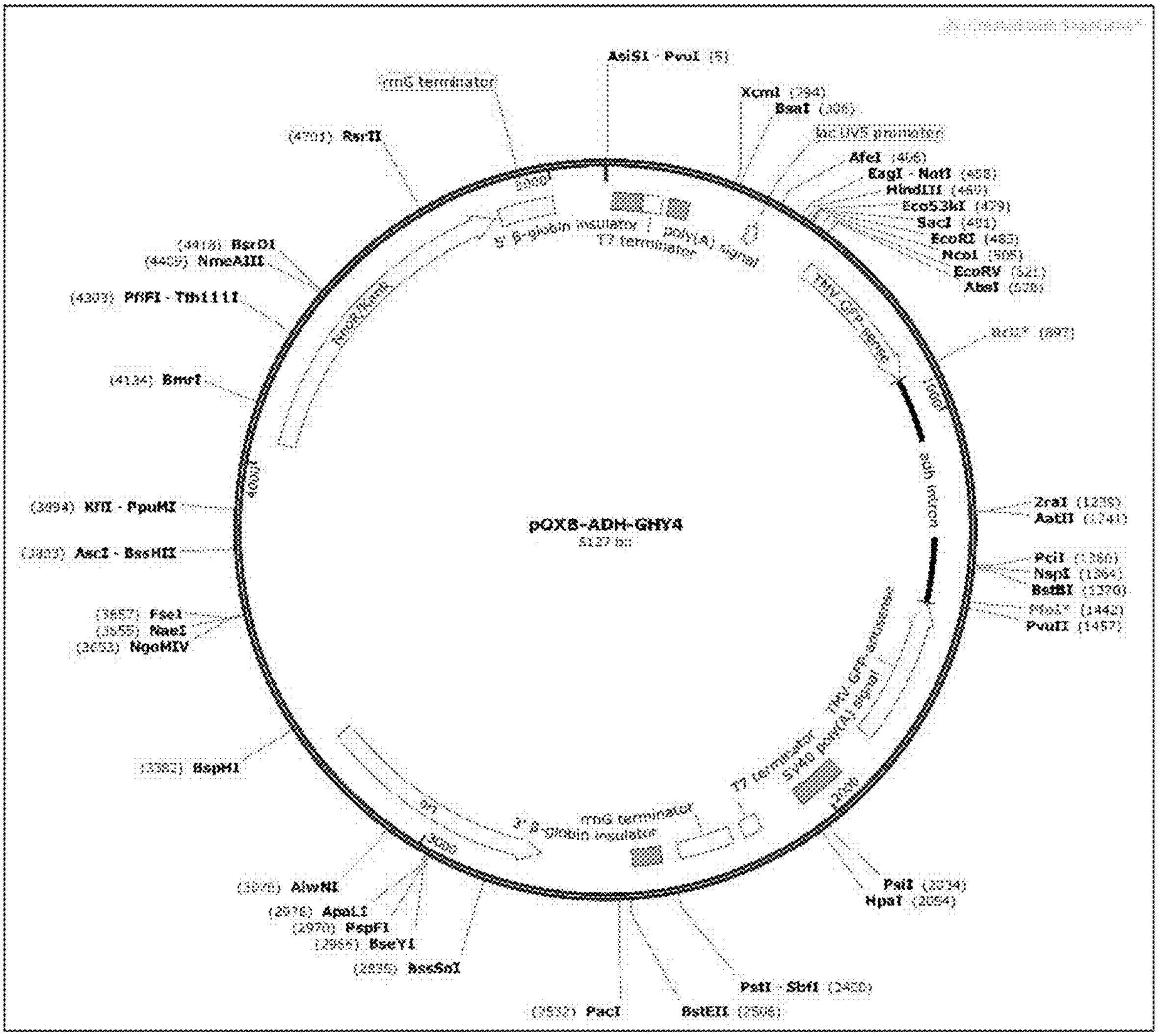
FIG. 4: Map of the hpRNA pOXB-ADH-GHY4.
Figure 5:
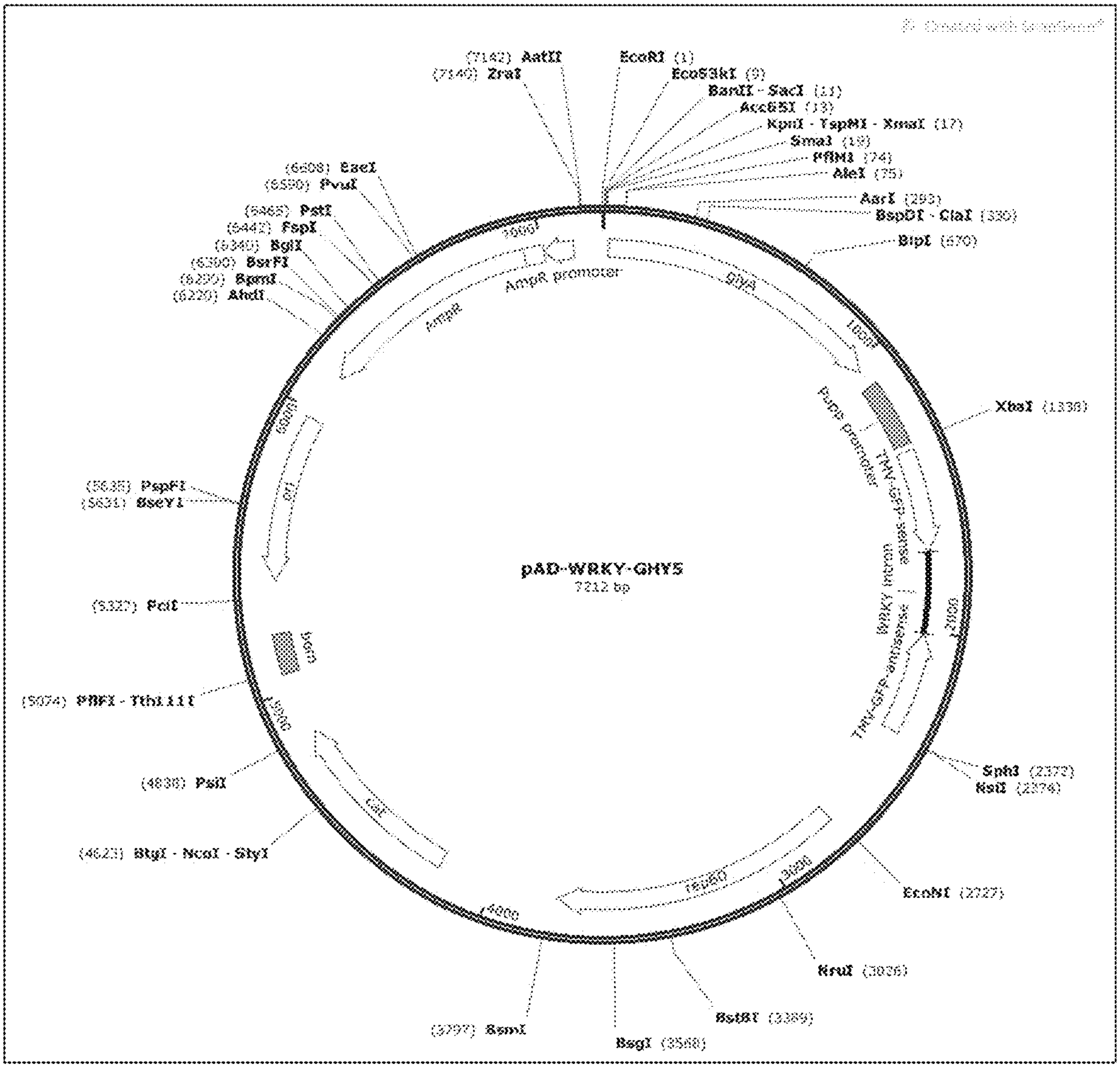
FIG. 5: Map of the hpRNA pAD-WRKY-GHY5.
Figure 6:
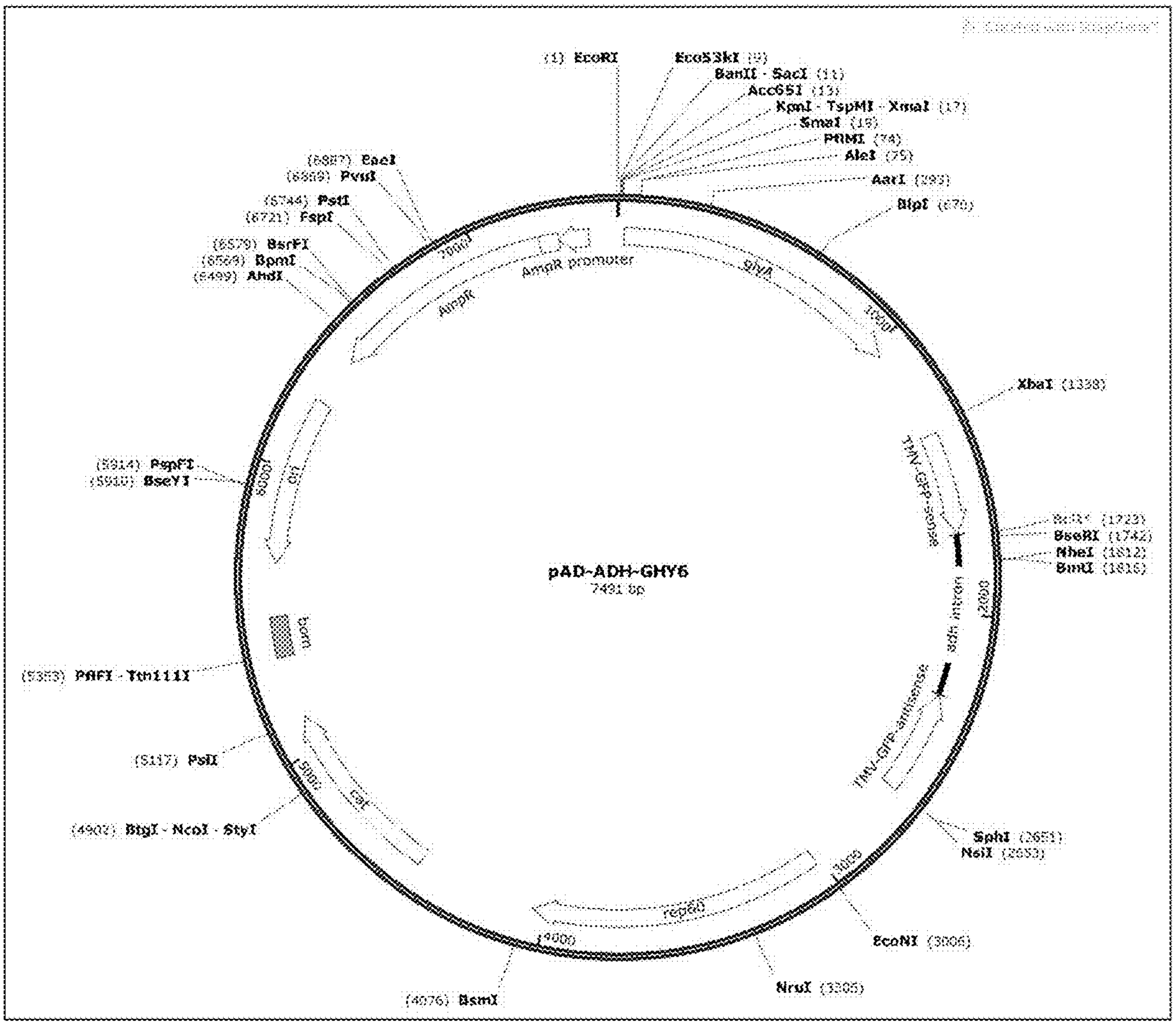
FIG. 6: Map of the hpRNA pAD-ADH-GHY6.
Figure 7:
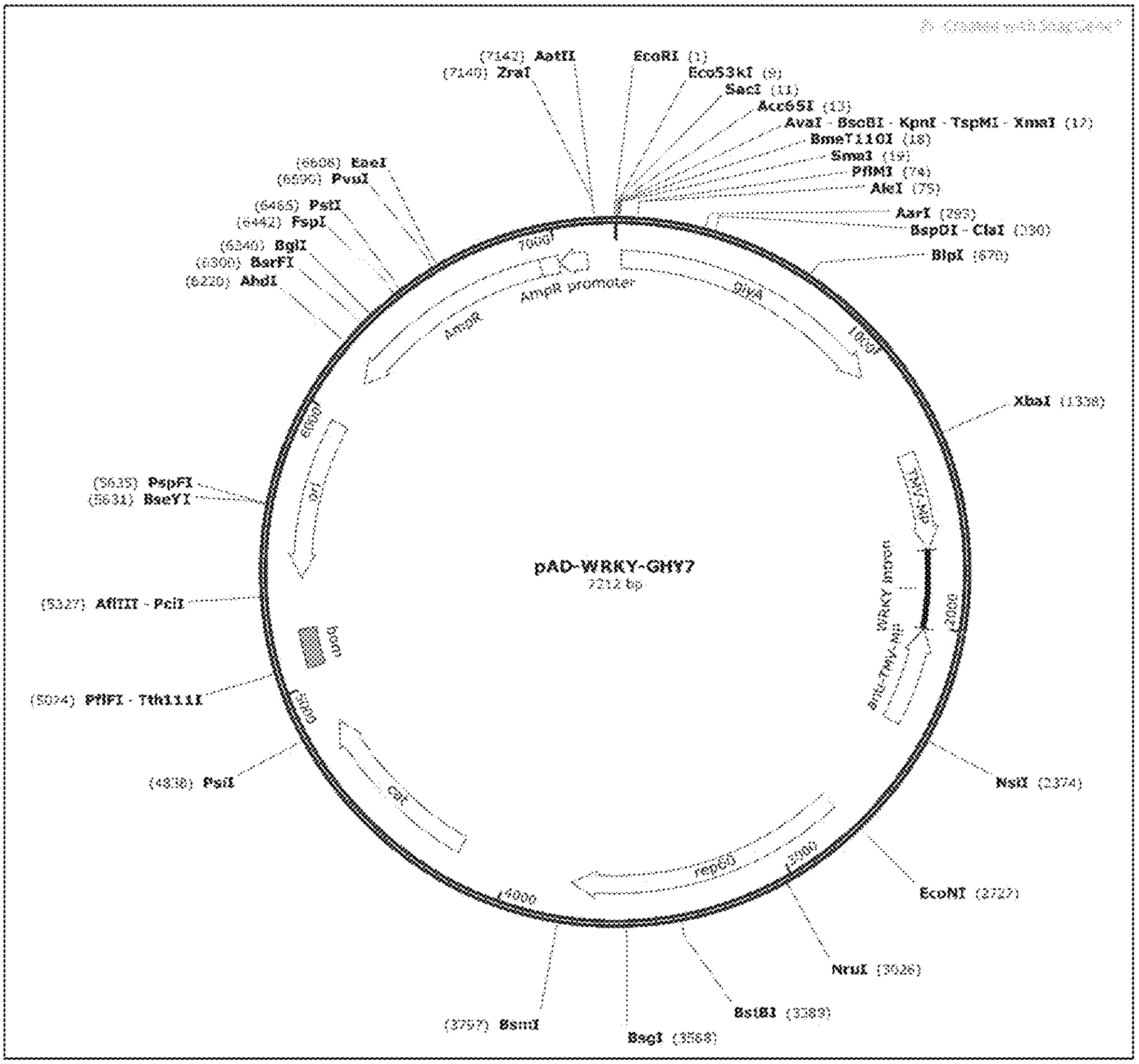
FIG. 7: Map of the hpRNA pAD-WRKY-GHY7.

The maps for these plasmids are shown in the following figures 1=7: pAD-WRKY-GHY1 (FIG. 1), pAD-ADH-GHY2 (FIG. 2), pOXB-WRKY-GHY3 (FIG. 3), pOXB-ADH-GHY4 (FIG. 4), pAD-WRKY-GHY5 (FIG. 5), pAD-ADH-GHY6 (FIG. 6). One hpRNA designed using TMV movement protein: pAD-WRKY-GHY7 (FIG. 7). were constructed to target both movement protein and GFP from PJL-TRBO-G Bold bases are overlapped sequences. Italicized bases are inserted sequences.

Among the above seven hpRNAs, five shuttle vectors pAD-WRKY-GHY1, pAD-ADH-GHY2, pAD-WRKY-GHY5, pAD-ADH-GHY6, and pAD-WRKY-GHY7 were constructed by the present inventors by ligating the GFP sense fragment, an intervening intron, and the GFP antisense fragment into the backbone plasmid pAD43-25 (Dunn and Handelsman 1999) digested with XbaI+NsiI. Two vectors pOXB-WRKY-GHY3 and pOXB-ADH-GHY4 were constructed using the backbone plasmid of pSF-OXB19 (Oxford Genetics Biology Engineered) digested with XbaI.

Exemplary primers used to construct the hpRNA insert in the plasmids and for DNA sequencing are shown in Table 1 below. All the maps of hpRNAs were made using SnapGene™ software.

Example 2: Demonstrates Construction of Bacterial Plasmids Encoding an Intervening Intron Between the Sense and Antisense Strands of the GFP Gene Target One intron was from the *Arabidopsis thaliana* putative WRKY-type DNA-binding protein, 287 bp in length, and cloning from plasmid pJawohl3-RNAi (Accession no. AF404854) (Table 9: SEQ ID NO. 26).

Another intron was generated by the current inventors from *Zea mays* alcohol dehydrogenase intron Adh1, 566 bp in length, and cloning from plasmid pMCG161 (Accession no. AY572837). (Table 9: SEQ ID NO. 27-29)

Example 3: Demonstrates Construction and Sequence Listing of Exemplary hpRNAs

In this embodiment, exemplary hpRNAs were constructed comprising SEQ ID NO. 30-36 presented in Table 10 below.

Example 4: Demonstrates Construction of RNaseIII Mutant Bacterial Strain for the Stable Expression of dsRNA Constructs In this embodiment, the present inventors used exemplary *E. coli* strain JM109(DE3) to construct an RNaseIII mutant (Genotype: endA1, recA1, gyrA96, thi, hsdR17 ($r_k^-$, $m_k^+$), relA1, supE44, λ-, Δ(lac-proAB), [F', traD36, proAB, $lacI^qZ\Delta M15$], 1DE3. Promega, USA). Two *E. coli* RNaseIII mutants were made by using Red-mediated homologous recombination system expressed from plasmid pSIJ8 (Jensen et al. 2015).

The design of RNaseIII mutant was performed using the DNA sequence for the mc gene of *Escherichia coli* str. K-12 substr. MG1655 (NCBI Reference Sequence: NC_000913.3). The primers RNaseIII50-5 and RNaseIII50-3 were used for amplifying the kanamycin resistance gene with 50-bp homologous sequences with the mc genes. The targeting PCR fragments with $Kan^R$ were amplified by using Q5® High-Fidelity DNA Polymerase. The plasmid pKD4 was used as template (Yin et al. 2009). The targeting PCR fragments with KanR were ligated to Pmini T2.0 vector to obtain Pmini4T plasmid and then Pmini-4T was used as template to amplify the targeting fragments by using phosphorothioated primers Ec_phos_50-5 and Ec_phos_50-3. The mutants were generated according to Jensen et al (Jensen et al. 2015). The mutant containing Kanamycin resistance marker was labelled as M-JM109-GHY1. The mutant eliminating Kanamycin resistance was labelled as M-JM109-GHY2 and may be used to deliver hpRNA to plants. Primers were listed in Table 2. PCR amplification analysis to verify the mutants is demonstrated in FIG. 1.

Figure 8:
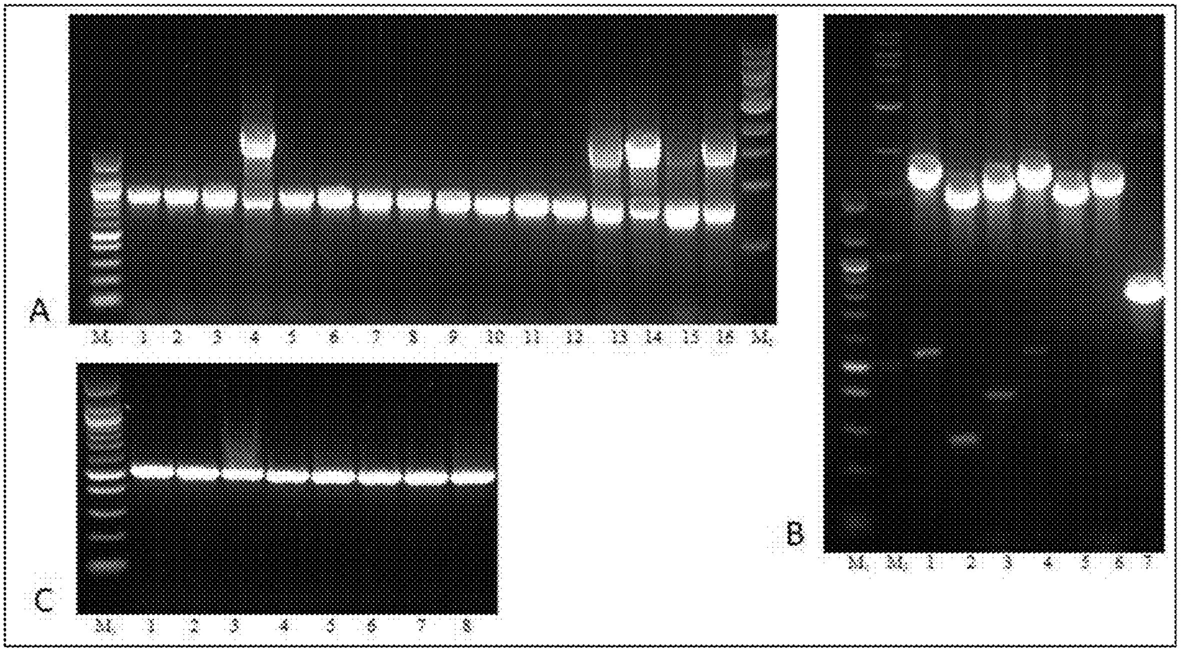
FIG. 8: PCR analysis to verify the successful construction of RNaseIII mutants.

Example 5: Demonstrates PCR Analysis to Confirm Construction of RNaseIII Mutant Bacterial Strain for the Stable Expression of hpRNA Constructs As shown in FIG. 8A-C, the present inventors conducted a PCR analysis to verify the successful construction of *E. coli* RNaseIII mutants. Again, as demonstrated in FIG. 8A, PCR analysis was generated to verify mutants M-JM109-GHY1. Lanes 1-16: Colony PCR performed with M-JM109-GHY1 with the primers JD-5 and JD-3, expected fragment size 1,936 bp; and the wide-type is 879 bp. Picking up the possible correct mutants 4, 13, 14, 15, and 16 and inoculated them in LB (Kanamycin, 50 μg/ml) media and cultivated overnight for further identification. Mutants 13 and 15 grew well. These two mutants were used for further identification by the present inventors.

As shown in FIG. 8B, further identification the purified mutants 13 and 15 was conducted. Two colonies were analyzed. Lanes 1-3: the first colony mutant was analyzed with primers JD-5 and JD-3, JD-5 and Cat-3, and Cat-5 and JD-3, respectively; lanes 4-6: the second colony mutant were analyzed with primers JD-5 and JD-3, JD-5 and Cat-3, and Cat-5 and JD-3, respectively; lane 7: The wild-type JM109(DE3) was amplified with JD-5 and JD-3. Correct mutant size PCR products were 1936 bp (amplified with primers JD-5 and JD-3), 1664 bp (amplified with primers JD-5 and Cat-3), and 1787 bp (amplified with primers Cat-5 and JD-3). All the DNA sequencing results were correct. The correct mutant containing Kanamycin resistant marker was labelled as M-JM109-GHY1.

As shown in Figure C, PCR performed on Kanamycin resistance gene eliminated mutant with the primers JD-5 and JD-3, expected fragment size 543 bp. Lanes 1-8: Eight individual mutants amplified with primers JD-5 and JD-3. The correct mutant without Kanamycin resistant marker was labelled as M-JM109-GHY2. (References Lanes=$M_1$: 100 bp DNA ladder; lane $M_2$: 1 Kb DNA ladder.) All the PCR products were sent for sequencing and all the sequencing results were confirmed and reproduced below in Table 11. (SEQ ID NO. 37-39)

Example 6: Demonstrates the Use of a Genetically Modified *E. coli* RNaseIII Mutants Containing Plasmids Encoding hpRNA Molecules to Infiltrate Plant Leaves, Express and Deliver dsRNA or hpRNAs to the Plant to be Processed into siRNAs to Inactivate TMV Encoded GFP as an Exemplary Embodiment of Bacterial dsRNA-Mediated Silencing of a Viral Encoded Gene Here the present inventors used two *E. coli* RNase III mutants (one *Bacillus subtilis* CCB422 RNaseIII mutant) containing the indicated plasmids to infiltrate leaves, express and deliver dsRNA or hpRNAs to the plants to be processed into siRNAs to inactivate Tobacco Mosaic Virus (TMV) encoded GFP, thereby demonstrating bacterial dsRNA-mediated silencing of a viral encoded gene.

Figure 11A:
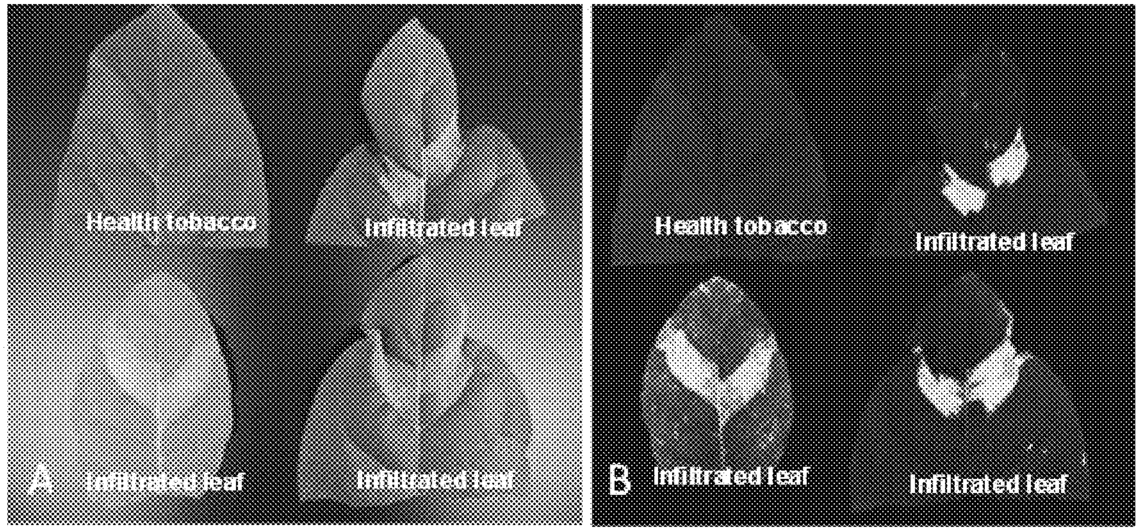
FIG. 11*a*: Symptoms and GFP signal detected under UV illumination of health and infiltrated leaves of *N. tabacum.*

The present inventors conducted tobacco infiltration assays with bacteria containing plasmids encoding hpRNA targeting the suppression of the GFP gene were performed according to Lindbo (Lindbo 2007). Symptoms were observed and GFP signal was detected under UV illumination after 5, 7, or 9 days post-infiltration (dpi). Two tobacco species: *Nicotiana tabacum* and *Nicotiana benthamiana* were used in this embodiment. For example, as an exemplary embodiment, in FIG. 11A, infiltration symptoms and GFP signal detected under UV illumination of healthy and infiltrated leaves of *N. tabacum* is demonstrated.

The present inventors further demonstrated TMV encoded GFP was expressed from vector pJL-TRBO-G (Lindbo 2007). The vector was transformed into *Agrobacterium tumefaciens* (At) and co-infiltrated with bacterial RNaseIII mutants containing different hpRNAs. The bacterial concentration was measured using a spectrometer and all the bacterial concentrations were adjusted to $OD_{600}$ between 0.9950~1.0050. The present inventors further demonstrate that the hpRNA inhibited the TMV-GFP signal, and confirmed by co-infiltration of the bacterial containing hpRNA with *Agrobacterium* GV3101 containing vector pJL-TRBO-G. The RNaseIII mutants and hpRNA used are listed in Table 3.

Figure 10:
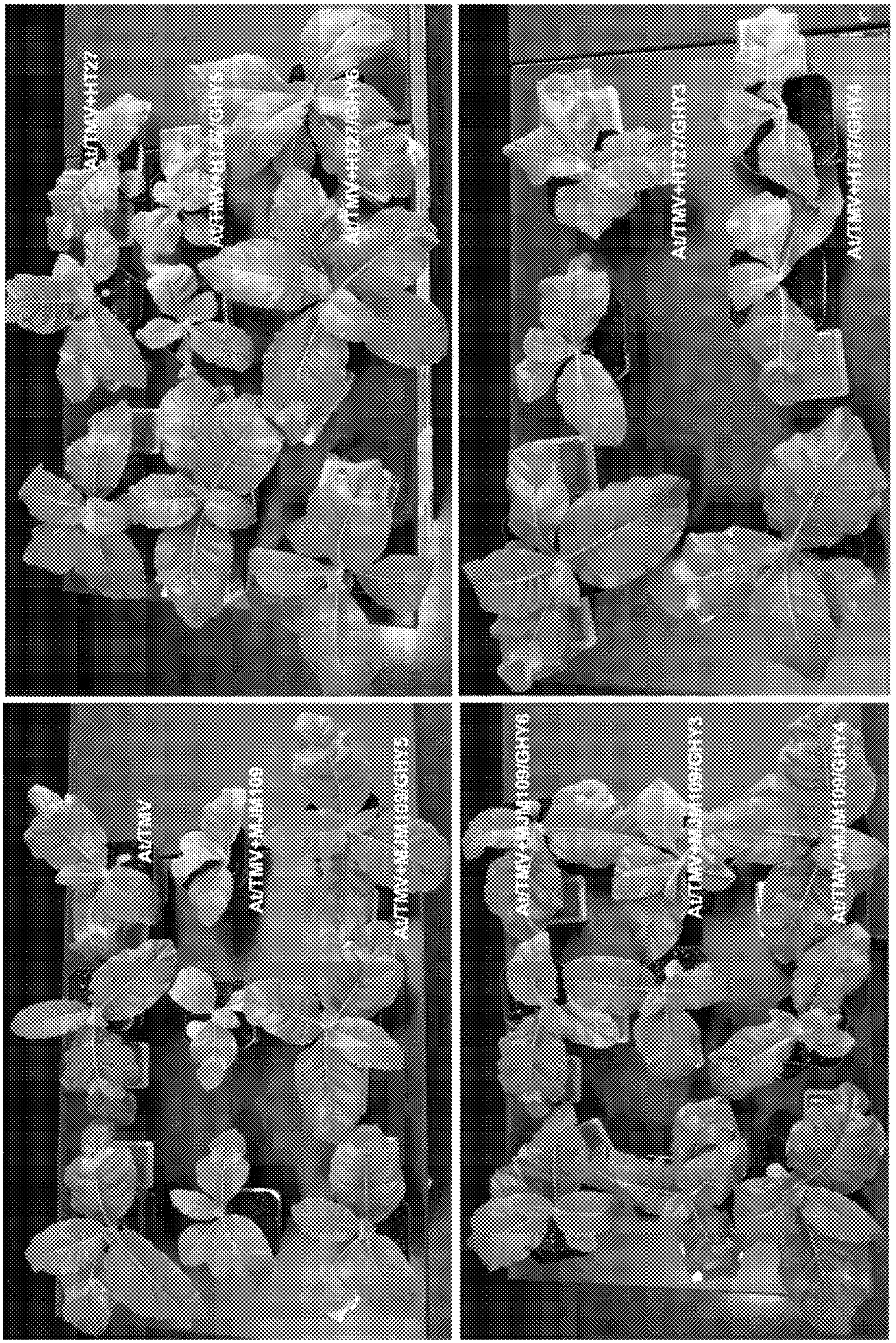
FIG. 10: Symptoms of infiltration in *N. tabacum* after 7 dpi. (At: *Agrobacterium tumefaciens*; TMV: pJL-TRBO-G; MJM109: M-JM109-GHY2 (RNaseIII mutant, no antibiotic); GHY5: pAD-WRKY-GHY5; GHY6: pAD-ADH-GHY6; GHY3: pOXB-WRKY-GHY3; GHY4: pOXB-ADH-GHY4)

As shown in FIGS. 10-111B, present inventors demonstrated that both MJM109 and HT27, each expressing different hpRNAs, show inhibition to the spreading of TMV-encoded GFP signal. The shuttle hpRNA vectors were shown by the inventors to produce better inhibition of GFP expression. MJM109 showed a better result compared to HT27 in this exemplary embodiment.

Figure 11B:
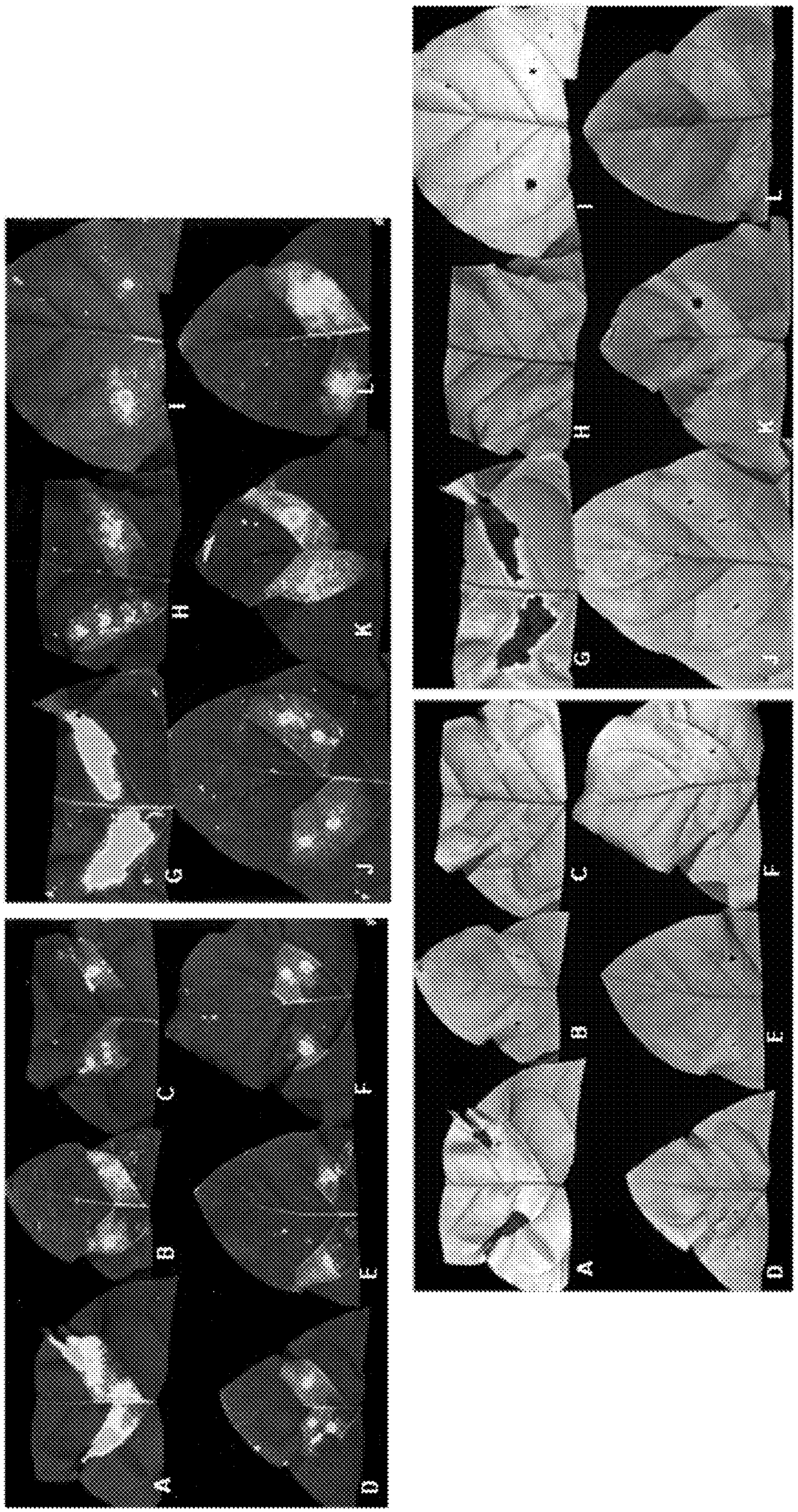
FIG. 11*b*: TMV-GFP signal of *N. tabacum* under UV illumination at 7 dpi.
Figure 11C:
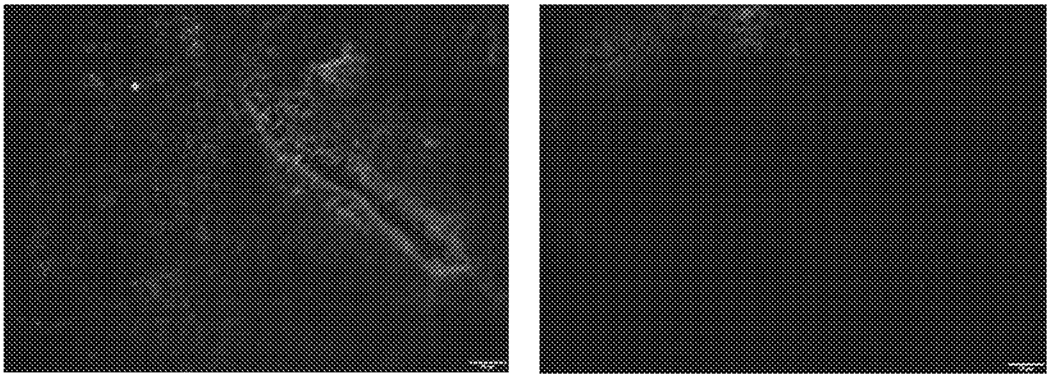
FIG. 11*c*: TMV-GFP signal of *N. tabacum* treated by M-JM109-GHY2/pAD-WRKY-GHY1 under UV illumination at 7 dpi.

As further shown in FIG. 11C, the present inventors have shown that both MJM109 and HT27 with different hpRNAs show different inhibition to the spreading of TMV-encoded GFP signal. The present inventors demonstrated that shuttle hpRNA vectors produce better inhibition of GFP expression. For example, MJM109 shows increased inhibition of TMV-GFP signal compared to HT27. The present inventors demonstrated that all the hpRNA can produce dsRNA structures that can generate RNAi effects in plants, which is consistent with disease symptoms show in FIG. 11B and elsewhere.

Legend FIG. 10:

At: *Agrobacterium tumefaciens*; TMV: pJL-TRBO-G; MJM109: M-JM109-GHY2 (RNaseIII mutant, no antibiotic); GHY5: pAD-WRKY-GHY5; GHY6: pAD-ADH-GHY6; GHY3: pOXB-WRKY-GHY3; and GHY4: pOXB-ADH-GHY4.

Legend FIG. 11:

At: *Agrobacterium tumefaciens*; TMV, TMVexpressing GFP: pJL-TRBO-G (TMV green fluorescence signal); MJM109: M-JM109-GHY2 (RNaseIII mutant, no antibiotic); HT27, RNaseIII mutant, Tetracycline resistance; GHY5: pAD-WRKY-GHY5; GHY6: pAD-ADH-GHY6; GHY3:pOXB-WRKY-GHY3; GHY4: pOXB-ADH-GHY4.

A and G: At/TMV;
B: At/TMV+MJM109;
H: At/TMV+HT27;
C: At/TMV+MJM109/GHY5;
D: At/TMV+MJM109/GHY6;
E: At/TMV+MJM109/GHY3;
F: At/TMV+MJM109/GHY4;
I At/TMV+HT27/GHY5;
J: At/TMV+HT27/GHY6;
K: At/TMV+HT27/GHY3; and
L: At/TMV+HT27/GHY4.

Example 7: Demonstrates that hpRNA Inhibits the Spread of TMV-Encoded GFP Signal in Model Tobacco Plant As demonstrated in FIGS. 12, the present inventors demonstrated that after At/TMV infection, tobacco plants were inoculated with hpRNAs over a course of 6 day. The present inventors demonstrated that within three days that the expression of hpRNAs could inhibit the spreading of the TMV-encoded GFP signal.

Figure 12:
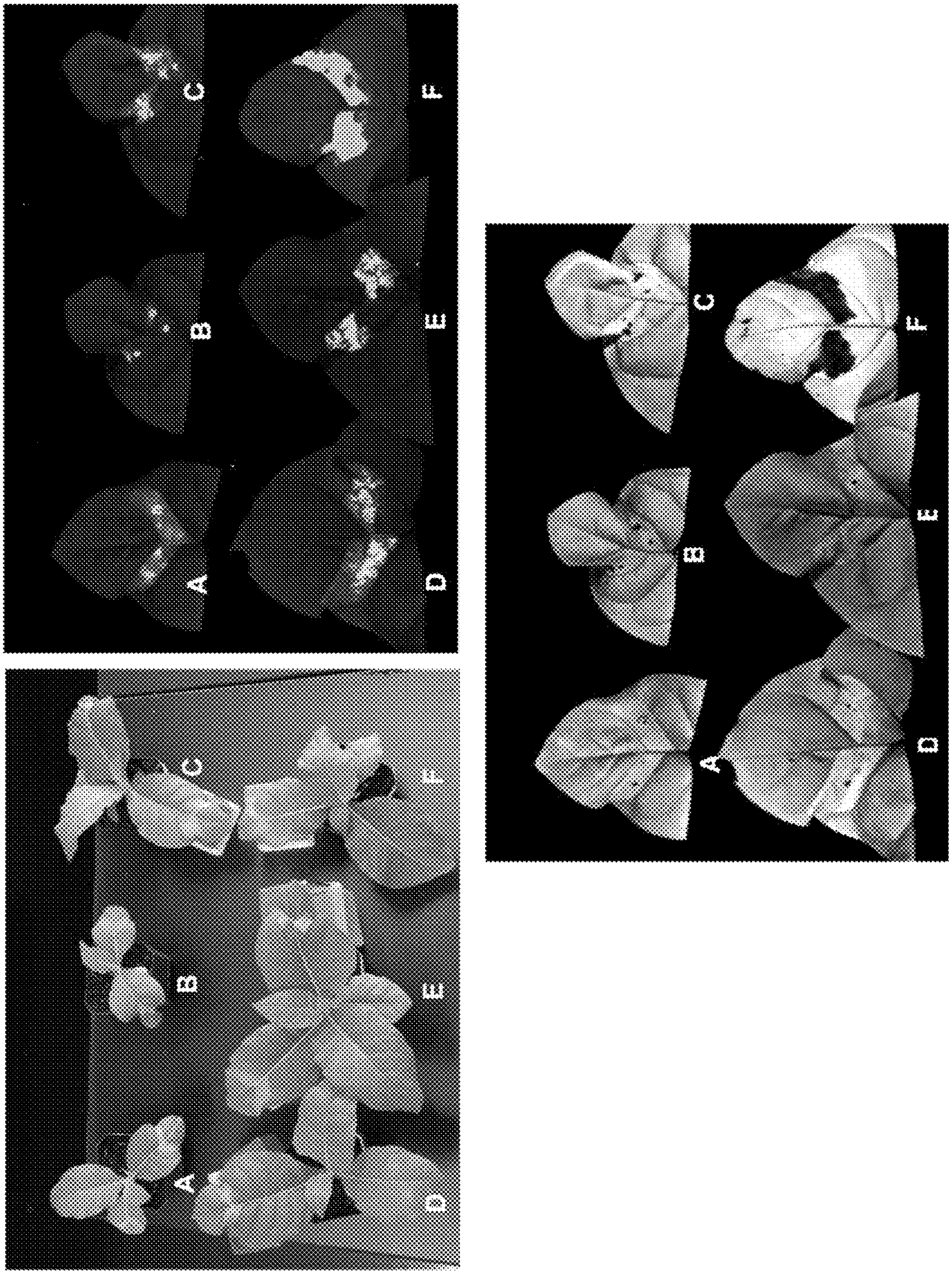
FIG. 12: Time-course images demonstrating the efficiency of hpRNA inhibiting the spread of TMV-encoded GFP signal in tobacco plant.

Legend FIG. 12:

A: hpRNAs inoculated 1 day later;
B: hpRNAs inoculated 2 days later;
C: hpRNAs inoculated 3 days later;
D: hpRNAs inoculated 4 days later;
E: hpRNAs inoculated 5 days later; and
F: hpRNAs inoculated 6 days later.

Example 8: Demonstrates Tobacco Plant Infiltration with *Bacillus subtilis* CCB422/pAD-WRKY-GHY5 in *N. tabacum*

Figure 13:
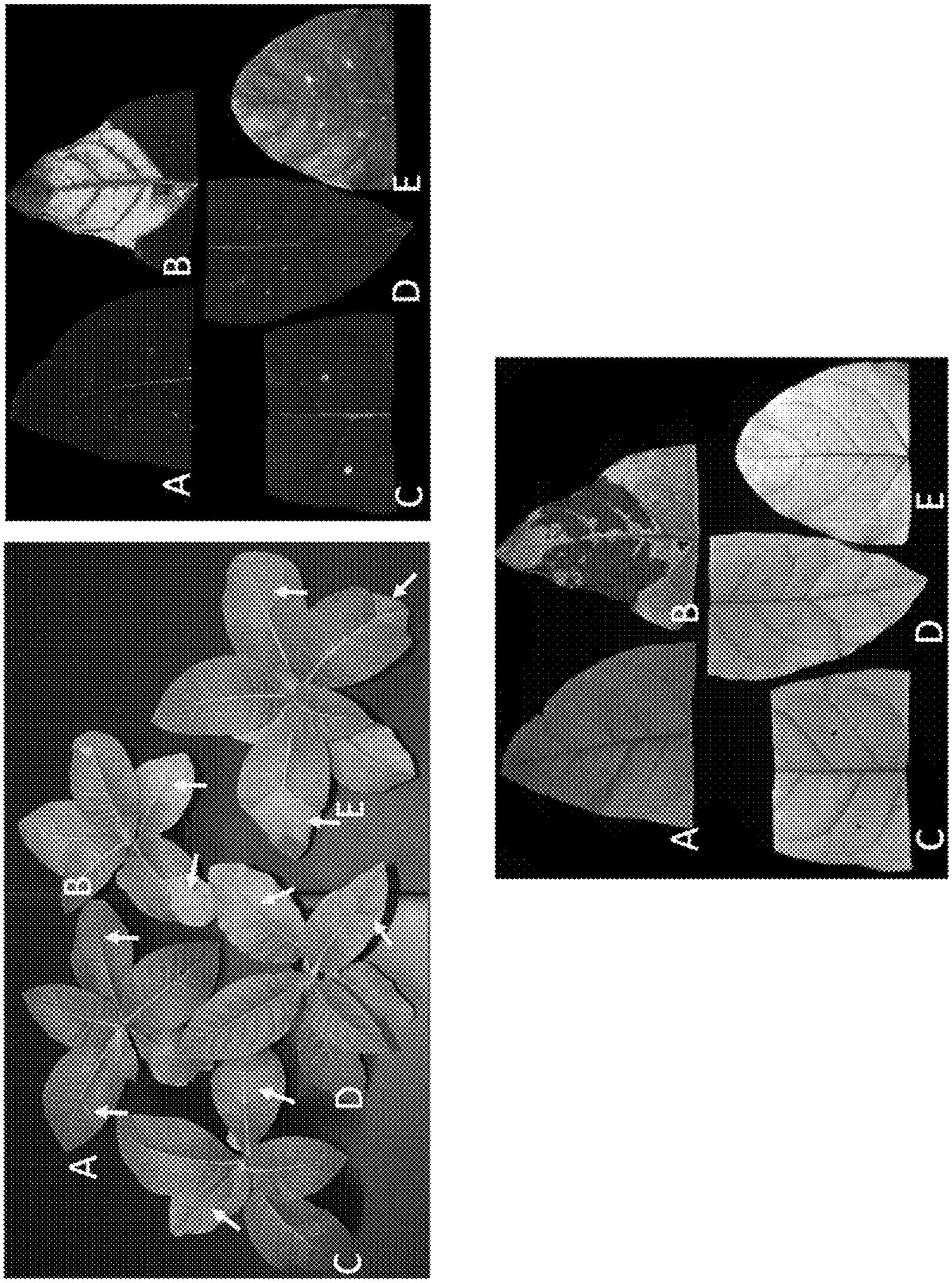
FIG. 13: Tobacco infiltration with *Bacillus subtilis* CCB422/pAD-WRKY-GHY5 in *N. tabacum.*

As demonstrated in FIG. 13, the present inventors demonstrated that a genetically modified *B. subtilis* expressing hpRNA could successfully infiltrate and inhibit the spreading of At/TMV signal in *N. tabacum*. In this embodiment, the present inventors demonstrated that CCB422 with hpRNA can significantly inhibit the spreading of At/TMV signal.

Legend FIG. 13:

At: *Agrobacterium tumefaciens*; TMV: pJL-TRBO-G (TMV green fluorescence signal); CCB422 (*Bacillus subtilis* RNaseIII mutant, Spectinomycin and Kanamycin resistance); GHY5: pAD-WRKY-GHY5, and each treatment repeated three times. Red arrows indicated infiltrated areas.

A: Blank Negative Control
B: At/TMV (TMV expressing GFP)
C: CCB422 (bacteria without plasmid only)
D: CCB422/GHY5 (bacteria with plasmid but no TMV)
E: TMV+CCB422/GHY5 (TMV and hpRNA)

Example 9: Hypervesiculating Bacteria Strains Show Increased Ability to Inhibit the Spreading of At/TMV Signal in *N. benthamiana*

Figure 14:
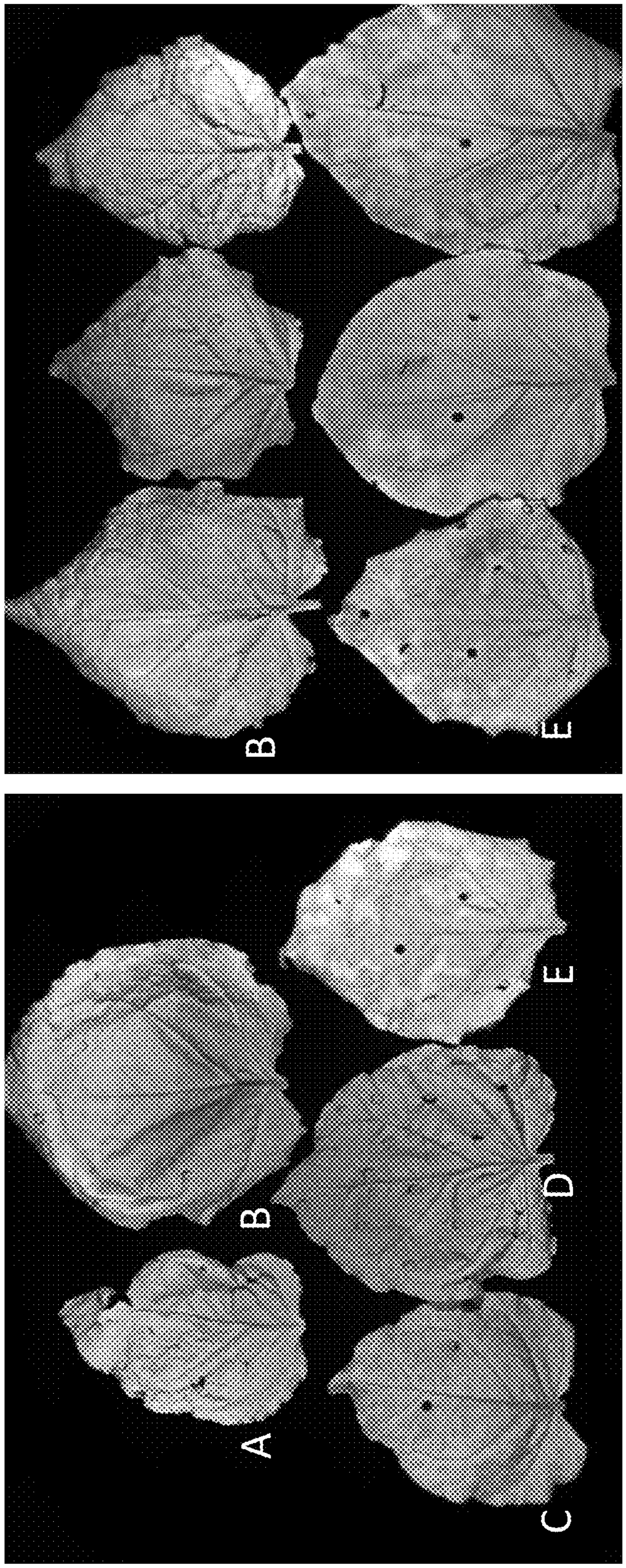
FIG. 14: Hypervesiculating *E. coli* strain HT27 with hpRNA in inhibiting the spreading of At/TMV signal in a whole leaf infiltration in *N. benthamiana.*

As demonstrated in FIG. 14, the present inventors demonstrated that a genetically modified *B. subtilis* expressing hpRNA could successfully infiltrate and inhibit the spreading of At/TMV signal in *N. benthamiana*. In this embodiment, the present inventors demonstrated that an hypervesiculating *E. coli* strain HT27 with hpRNA can significantly inhibit the spreading of At/TMV signal. In this embodiment, the present inventors demonstrated that, hypervesiculating strains may increase the ability of interfering RNAs, like hpRNA, inhibit target pathogen gene expression.

Legend FIG. 14:

Right panel: upper, three repeats of At/TMV treatment; lower, three repeats of TMV+HT27/GHY5

At: *Agrobacterium tumefaciens*; TMV: pJL-TRBO-G (TMV green fluorescence signal); HT27, RNaseIII mutant, Tetracycline resistance; GHY5: pAD-WRKY-GHY5, and each treatment repeated three times.

A: Blank Negative Control
B: At/TMV
C: HT27
D: HT27/GHY5
E: TMV+HT27/GHY5

Figure 15:
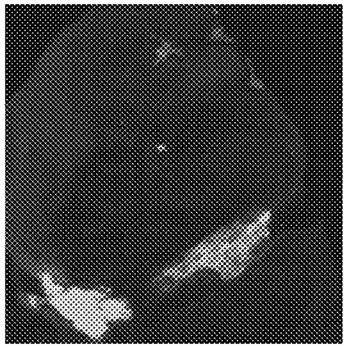
FIG. 15: Time-course demonstration of the efficiency of hpRNA mediated GFP signal suppression in model plant organism.
Figure 15:
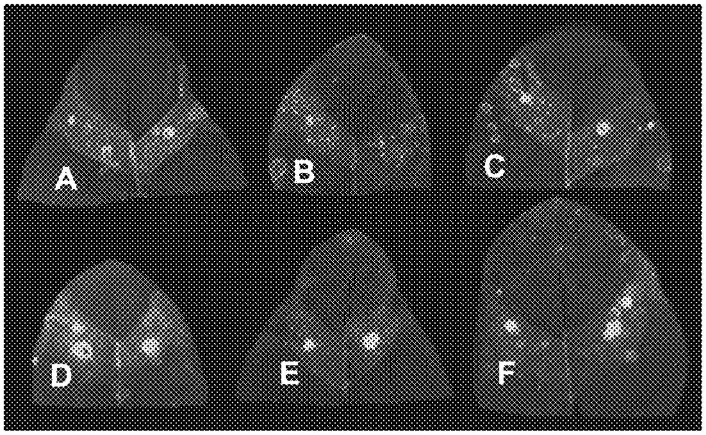
Figure 15:
Figure 15:
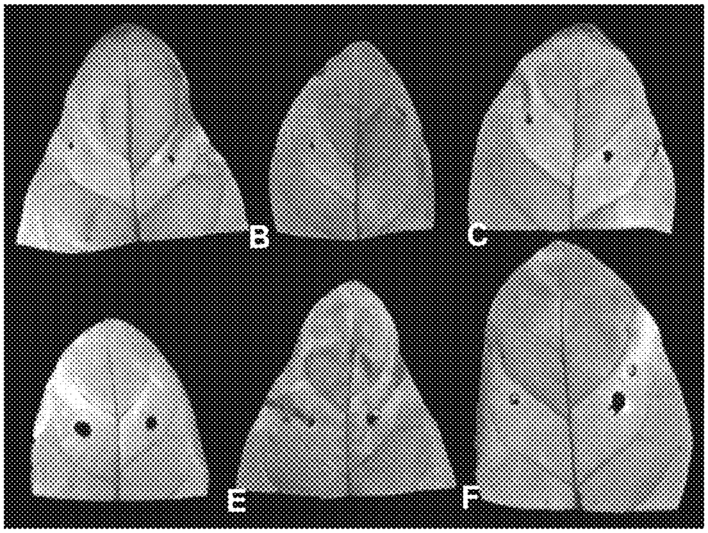
Figure 16:
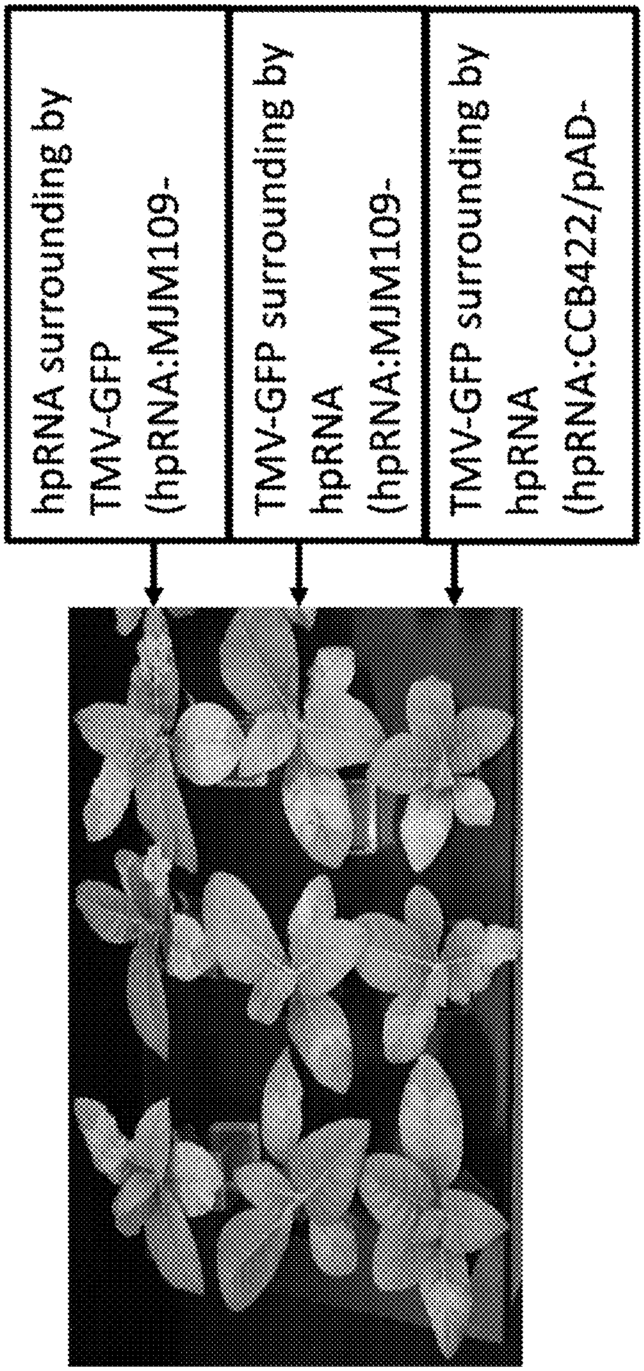
FIG. 16: Symptoms of siRNA migration limit the spreading of TMV-GFP through leaf structure at 7 dpi.

Example 10: Time-Course Demonstration of the Efficiency of hpRNA Mediated GFP Signal Suppression in Model Plant Organism The present inventors demonstrated the hpRNA mediated GFP signal suppression in a tobacco plant of over a prescribed time-course. Here, the present inventors a tobacco plant with inoculated hpRNA: MJM109-GHY2/pAD-WRKY-GHY5, then inoculated the same plant with At/TMV in different dates. As generally shown in FIG. 15, after hpRNA inoculation, the model tobacco plant was protected from the modified TMV virus infection up to at least 6 dpi. The present inventors further demonstrated in FIGS. 16-17, that hpRNA migrated to different parts of the infiltration area within a leaf 7 dpi. For example, in FIG. 16-17, TMV-GFP was shown to be surrounding by hpRNA at 7 dpi. This demonstrates the long-term and continuing nature of the inoculation and suppression of the target viral gene.

Legend FIG. 15:

A: At/TMV inoculated 1 day later
B: At/TMV inoculated 2 days later
C: At/TMV inoculated 3 days later
D: At/TMV inoculated 4 days later
E: At/TMV inoculated 5 days later
F: At/TMV inoculated 6 days later

Example 11: HpRNA can Effectively Produce siRNAs in Tobacco and Limit the Spreading of At/TMV Signal in *N. tabacum*

Figure 18:
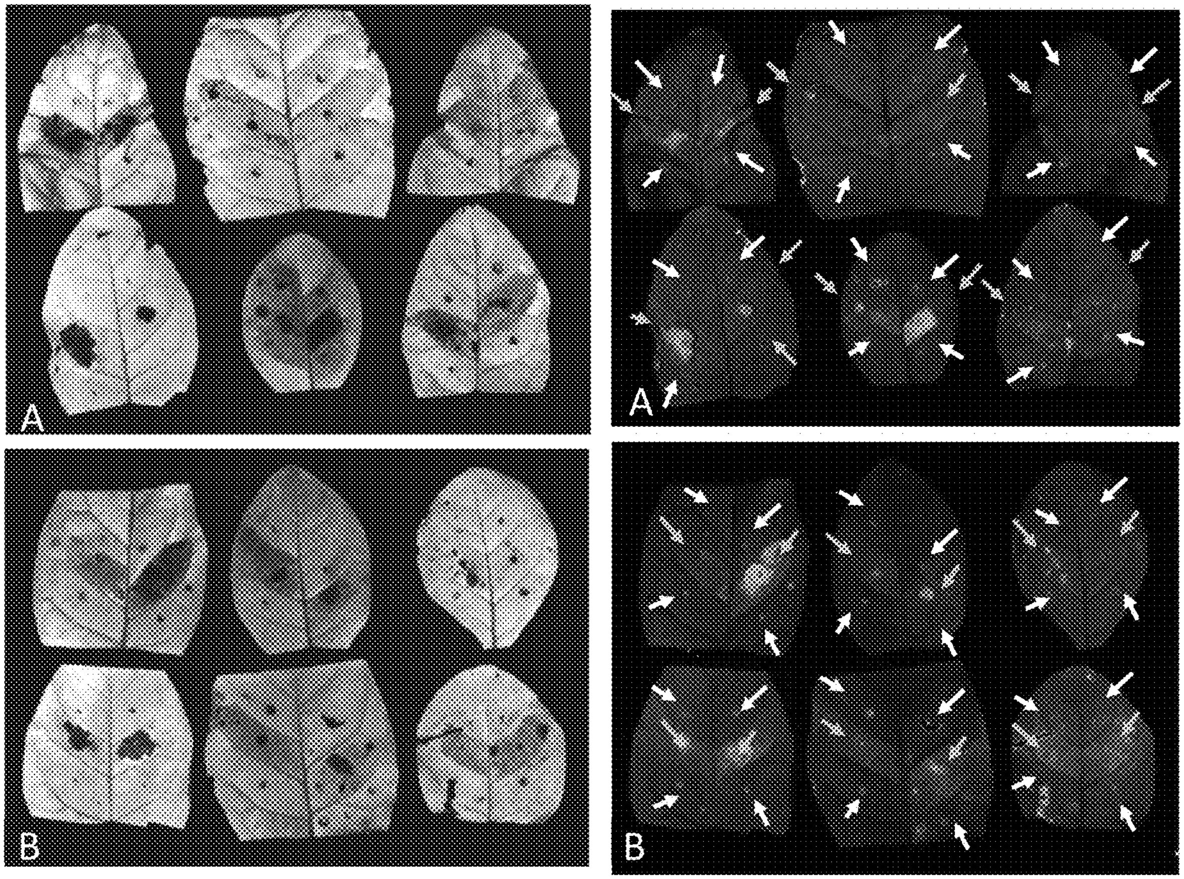
FIG. 18*a-b*: siRNA limiting the spreading of TMV-GFP signal in model tobacco plant.

The present inventors demonstrated that hpRNA can effectively produce siRNAs in plants and limit the spreading, and expression of At/TMV signal. In this embodiment, hpRNA derived from MJM109-GHY2/pAD-WRKY-GHY5 infiltrated *N. tabacum* and processed into siRNA as generally described above. As shown in FIG. 18, MJM109-GHY2/pAD-WRKY-GHY5 derived siRNA limited the spreading of TMV-GFP signal.

Figure 17:
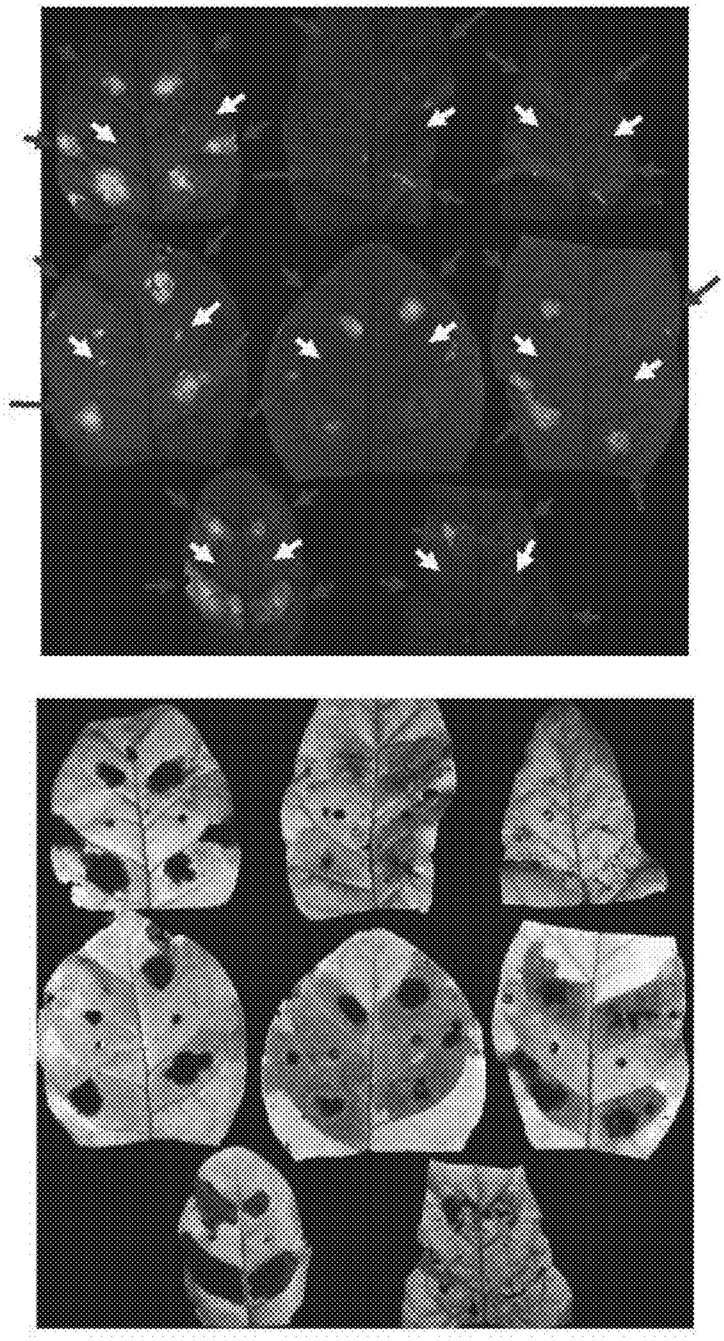
FIG. 17: MJM109-GHY2/pAD-WRKY-GHY5 derived siRNA limited the spreading of TMV-GFP signal in tobacco plant model.

Legend FIG. 17:

Dark arrows indicate At/TMV infiltration treatment.

White arrows indicate hpRNA (MJM109-GHY2/pAD-WRKY-GHY5) infiltration treatment.

At: *Agrobacterium tumefaciens;*

TMV: pJL-TRBO-G (TMV green fluorescence signal

Example 12: SiRNA can Effectively Limit the Spreading of TMV-GFP Signal in *N. tabacum*

The present inventors demonstrated that hpRNA can effectively produce siRNAs in plants and limit the spreading, and expression of TMV-GFP signal. In this embodiment, M-JM109-GHY2/pAD-WRKY-GHY7 derived siRNA limited the spreading of TMV-GFP signal. (FIG. 18A). In addition, the present inventors demonstrated that, CCB422/pAD-WRKY-GHY5 derived siRNA also limited the spreading of TMV-GFP signal. (FIG. 18B). In the embodiment, the present inventors demonstrated that hpRNA may induce more siRNAs production for RNAi in *N. tabacum* in a dose-dependent manner and limit the spreading of TMV-GFP signal.

Legend FIG. 18A-B:

Dark arrows indicate At/TMV infiltration treatment.

White arrows indicate hpRNA (MJM109-GHY2/pAD-WRKY-GHY5) infiltration treatment.

FIG. 18A: At: *Agrobacterium tumefaciens;*

FIG. 18B: TMV: pJL-TRBO-G (TMV green fluorescence signal)

Example 13: Demonstrates *Bacillus cereus* Identification and Colonization

As an exemplary embodiment, the present inventors demonstrate the endophytic bacteria *Bacillus cereus*, to express a shuttle vector pAD43-25 encoding green fluorescent protein can colonize the leaves of tobacco.

Figure 9:
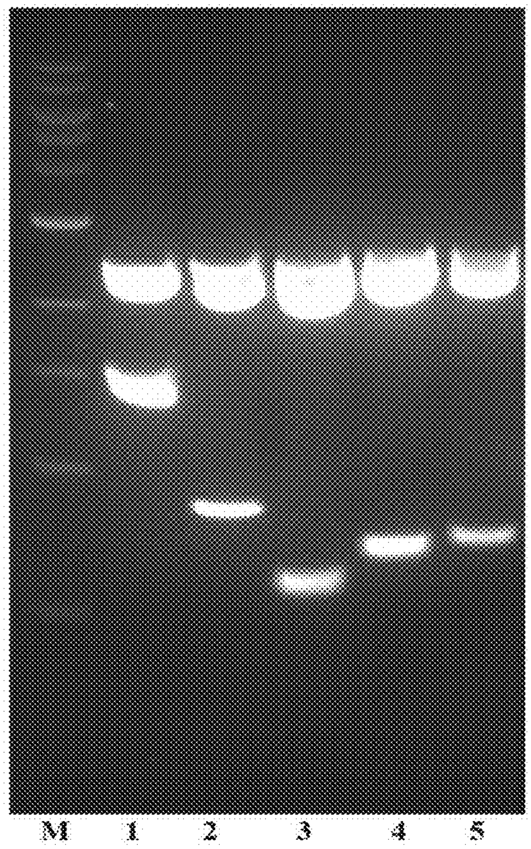
FIG. 9: Identification of *B. cereus* 53522 strain. Lane M: 1 kb DNA ladder. Lane 1: PminiT-16s rRNA was digested with XhoI. Lane 2: PminiT-23s rRNA was digested with XhoI. Lane 3: PminiT-motB was digested with XhoI. Lane 4: PminiT-endo-glucanase was digested with XhoI. Lane 5: PminiT-rncA was digested with XhoI.

In this exemplary embodiment, *B. cereus* 53522 was obtained from ATCC and primers used for identification were listed in Table 4. The correct PCR fragments were ligated to the vector of PminiT 2.0 vector and then digested with XhoI to inspect the correct sizes and then identify the correct clones by DNA sequence analysis to confirm the identity of the *B. cereus* strain (FIG. 9). Results of *B. cereus* 53522 (UW85) sequencing are provided in Table 12: 16S rRNA: 1514 bp; 23S rRNA: 855 bp; motB: 574 bp; endo-b-1,4-glucanase genes: 659 bp, me gene: 738 bp; SCAP: no PCR bands.

Figure 19:
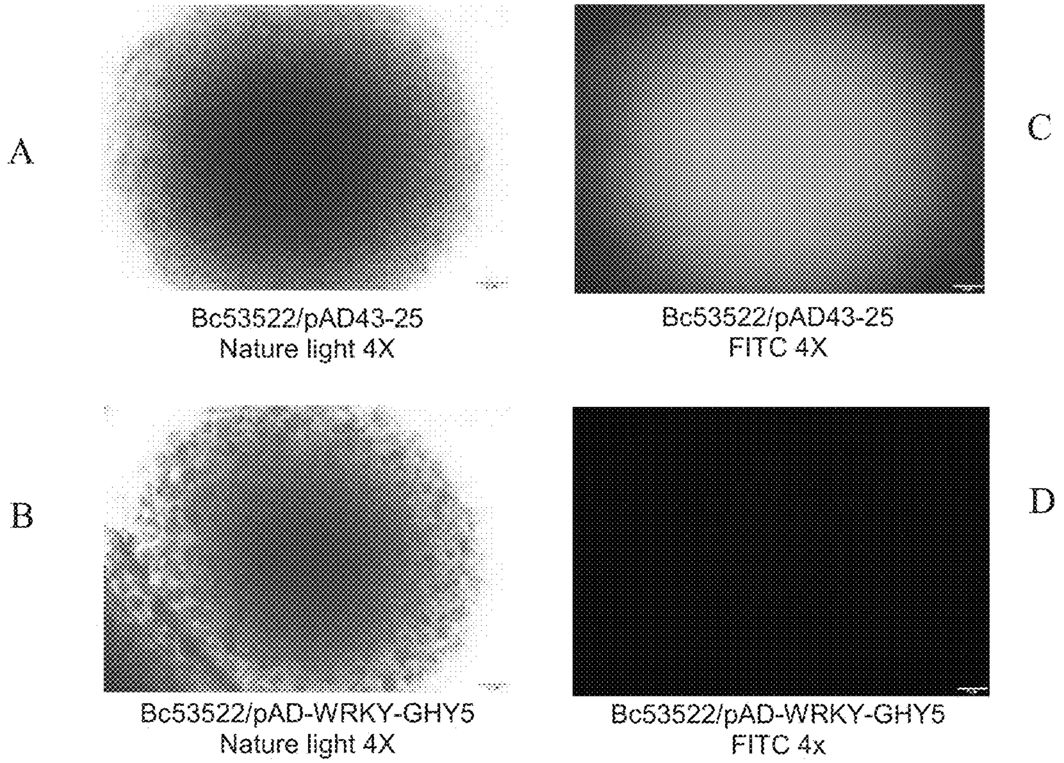
FIG. 19*a-c*: Colonies of Bc53522/pAD43-25 and Bc53522/pAD-WRKY-GHY5 under 4× magnification observed with natural light and with exposure to fluorescein isothiocyanate (FITC). A) demonstrates a colony of Bc53522/pAD43-25 viewed under nature light at 4× magnification; B) demonstrates a colony of Bc53522/pAD43-25 with exposure to FITC a 4× magnification showing a green signal; C) demonstrates a colony of Bc53522/pAD-WRKY-GHY5 viewed under nature light at 4× magnification; D) demonstrates a colony of Bc53522/pAD-WRKY-GHY5 with exposure to FITC a 4× magnification showing no signal.
Figure 20:
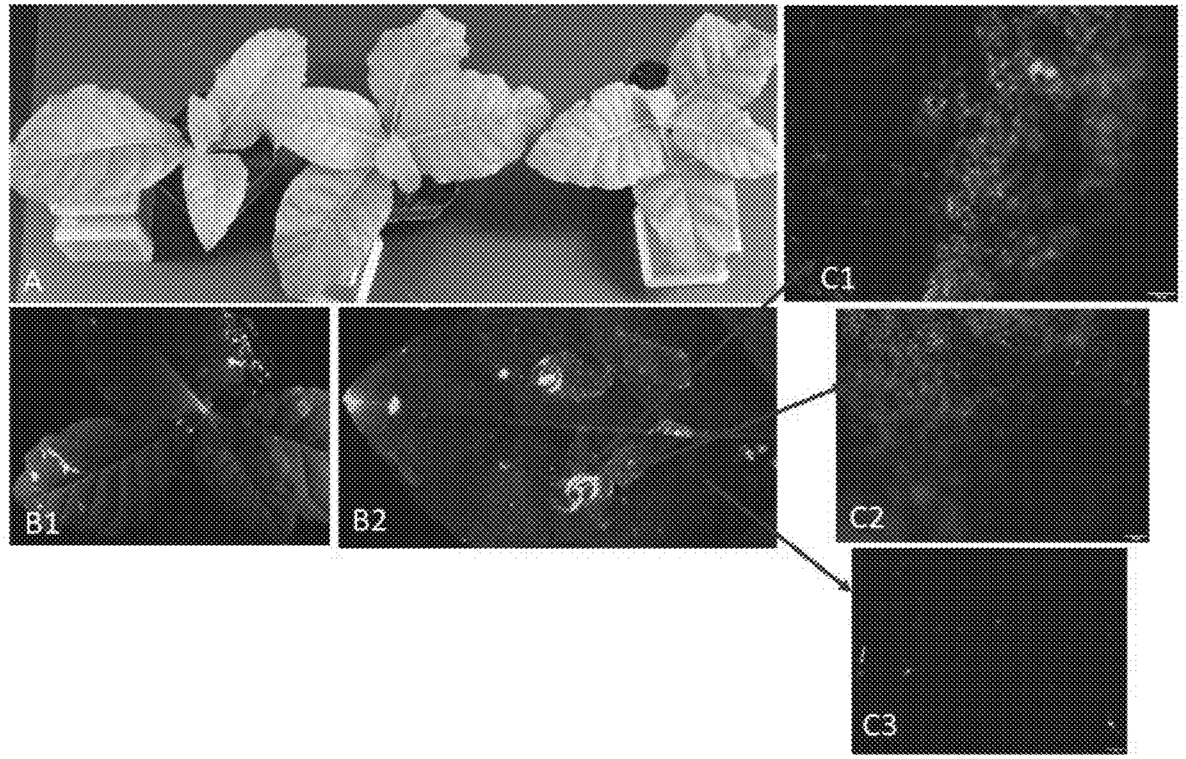
FIG. 20*a-c*: Colonization of *B. cereus* 53522 in an exemplary tobacco plant. A) Inoculated *B. cereus* to tobacco showed no harmful symptom to plants. B) GFP signal under UV. C) GFP signal of different areas of plant under fluorescence stereo microscope.

Example 14: Transformation and Expression of hpRNA in *Bacillus cereus* as Well as Inoculation and Colonization into Model Plant Organism The shuttle vector pAD43-25 and hpRNA vector of pAD-WRKY-GHY5 was transformed into *Bacillus cereus* 53522 strain by the present inventors, and then inoculated into an exemplary tobacco plant to confirm the expression of GFP signal under the constitutive promoter Pupp. This signal is demonstrated by the present inventors in FIG. 19, and the colonization of the transformed *B. cereus* in the model tobacco plant is further demonstrated in FIG. 20.

Example 15: Reduction in Viral Encoded GFP Protein Accumulation/Infection Severity Mediated by Hairpin RNA Endophyte Delivery As noted above, targeting of TMV-GFP RNA transcript by the host's RNAi machinery is expected to result in viral RNA degradation and hence failure to translate viral mRNAs into proteins. Boosting of the host's RNAi defenses, by trans-kingdom delivery of a hairpin RNA homologous to the viral encoded GFP, is therefore predicted to result in loss or decrease in viral encoded GFP accumulation by triggering siRNA biogenesis in the *N. tabacum* host, ultimately conferring resistance to viral infection.

Figure 21:
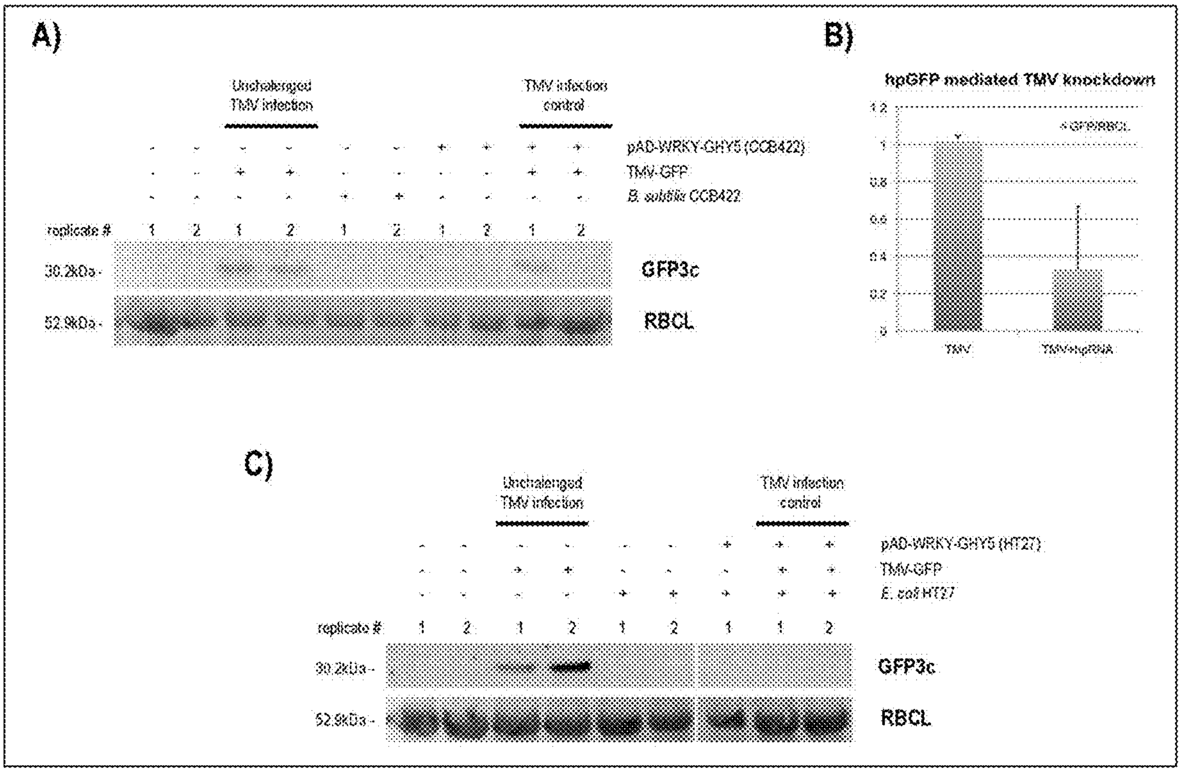
FIG. 21: Trans-kingdom delivery of hairpin RNA targeting viral encoded GFP results in the reduction of viral protein accumulation levels. A) *Bacillus subtilis* CCB422 mediated trans-kingdom delivery of hpRNA successfully triggers host's RNAi response leading to significant reduction Viral GFP accumulation in *N. tabacum* plants. B) Quantification of GFP protein levels in TMV-GFP infected and TMV-GFP+pAD-WRKY-GHY5 (CCB422) infiltrated samples. GFP signal normalized to RBCL. TMV-GFP replicate #1 used as reference. C) Viral GFP protein is undetectable in TMV samples co-infiltrated with HT27 encoding hpRNA trigger. GFP3c signal from immuno-detection. RBCL as loading control (Ponceau stain).

To evaluate this hypothesis, 2×0.4 mm leaf discs were collected from infiltrated areas (5 dpi) of *N. tabacum* plants infected with TMV-GFP, or co-infiltrated with TMV-GFP and bacterial strains carrying the pAD-WRKY-GHY5 construct—encoding the viral GFP homologous hairpin RNA, as well as experimental controls (see FIG. 21). Total protein extraction was performed with 100 μl of protein extraction buffer and insoluble material pelleted for 15 min; 16,000 g, 4° C. according to Baumberger and Baulcombe (2005). Samples were resolved by PAGE and blotted to a nitrocellulose membrane by semi-dry transfer. Membranes were stained with Ponceau S prior to western blotting to allow quantification of Rubisco largest subunit (RBCL). Viral GFP was detected by incubation with anti-GFP antibody (Millipore 3F8.2; 1:10,000) followed by incubation with goat anti-mouse HRP secondary antibody (Agrisera, 1:20,000). Signal detection and acquisition was performed with ECL western detection kit according to manufacturer's instructions (GE) and ChemiDoc MP imaging system (BioRad) respectively. GFP signal quantification was performed with Image Lab software (BioRad).

As demonstrated by the present inventors in FIG. 21, co-infiltration of TMV-GFP virus with the endophyte *Bacillus subtilis* CCB422 (Durand et al. 2012) (FIG. 21*a,b*) encoding the GFP-hpRNA resulted in a decrease in GFP accumulation in infected plants when compared to infiltration of TMV-GFP alone. Significantly, a replicate experiment using *E. coli* HT27 as vehicle for trans-kingdom delivery (FIG. 21*c*) failed to detect accumulation of any viral encoded GFP when co-infiltration was performed, strongly contrasting with the observed GFP accumulation in unchallenged TMV infections. Our results indicate that trans-kingdom delivery of hpRNAs homologous to the viral genome efficiently downregulates or eliminates viral replication and translation of viral proteins.

Example 16: QPCR to Monitor the TMV-GFP mRNA Suppression by HT27/pAD-WRKY-GHY5

Figure 22:
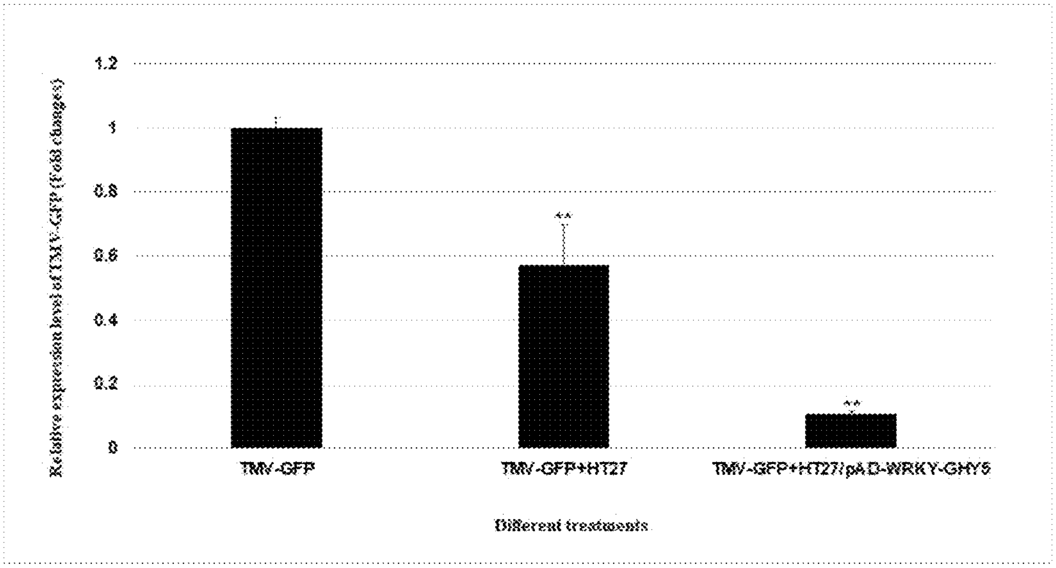
FIG. 22: qPCR to monitor the TMV-GFP mRNA suppression by HT27/pAD-WRKY-GHY5. qPCR data on GFP mRNA suppression in plants infected with bacteria expressing the hpRNA versus controls (TMV-GFP alone, TMV-GFP plus bacteria without hpRNA).

L25 ribosomal protein gene mRNA levels were used as the *N. tabacum* reference gene, and primers targeting amplification of TMV-GFP RNA were used in a quantitative PCR experiment (qPCR) for analysis of relative RNA levels in different biological treatments infected with TMV-GFP, TMV-GFP plus bacteria alone, and TMV plus bacteria expressing hpRNA-GFP. Total RNA was extracted from different treated tobacco leaves by using mirVana™ miRNA Isolation kit. The cDNA was synthesized using the EcoDry™ Premix kit. QRT-PCR was performed using iTaq™ Universal SYBR® Green Supermix. The results are generally shown in FIG. 22 and Table 6.

The present inventors demonstrated a reduction in TMV-GFP due to the presence of the bacteria (~43%). The present inventors demonstrated bacteria expressing hpDNA-GFP had nearly a 90% reduction in GFP RNA levels consistent with enhanced siRNA-mediated interference in TMV-GFP RNA levels.

TABLES

TABLE 1

Primers used for the construction of hpRNAs. Bold bases are overlapped sequences. Italicized bases are inserted sequences. (SEQ ID NO. 1-25)

| Primers | Sequences (5'→3') | SEQ ID No. |
|---|---|---|
| pAD-JL-F1 | **GGAAAACTGTATGTATTTGATCCT**TGCCCGAAGGTTATGTACAGG | SEQ ID No. 1 |
| pJL-WRKY-R1 | **GCAGAGGAGGAG**AAAGGGCAGATTGTGTCGACA | SEQ ID No. 2 |
| WRKY-F1 | **CAATCTGCCCTTT**CTCCTCCTCTGCTAACGTAAG | SEQ ID No. 3 |
| WRKY-R1 | **CAATCTGCCCTTT**CTGTGGTTGGAGAAGCTAG | SEQ ID No. 4 |
| pJL-WRKY-F1 | **CTCCAACCACAG**AAAGGGCAGATTGTGTCGACA | SEQ ID No. 5 |
| pAD-JL-R1 | **AAGTTAAGGGATGCAGTTTATGCA**TGCCCGAAGGTTATGTACAGG | SEQ ID No. 6 |
| pJL-adh-R2 | **TTGCACTTGATC**AAAGGGCAGATTGTGTCGACA | SEQ ID No. 7 |
| pJL-adh-F2 | **GTGCAGCTGCGG**AAAGGGCAGATTGTGTCGACA | SEQ ID No. 8 |
| adh-F1 | **CAATCTGCCCTTT**GATCAAGTGCAAAGGTCCGCCTTG | SEQ ID No. 9 |
| adh-R1 | **CAATCTGCCCTTT**CCGCAGCTGCACGGGTCC | SEQ ID No. 10 |
| OXB19-JL-F1 | **ACCGCGATATCTACCTCGAGGTTT**TGCCCGAAGGTTATGTACAGG | SEQ ID No. 11 |
| OXB19-JL-R1 | **AGTCAGTGCAGGAGGAGACAACTT**TGCCCGAAGGTTATGTACAGG | SEQ ID No. 12 |
| pAD-JL-F2 | **GGAAAACTGTATGTATTTGATCCT***CTAGATTTAAGAAGGAGATATACAT*TGCCCGAAGGTTATGTACAGG | SEQ ID No. 13 |
| TMVMP-F1 | **GGAAAACTGTATGTATTTGATCCT***CTAGATTTAAGAAGGAGATATACAT*TCTCGGATCTTACTACACAGCAGC | SEQ ID No. 14 |
| TMVMP-R1 | **TAGCAGAGGAGGAG**TTCCCTTTGCGGACATCAC | SEQ ID No. 15 |
| TMVMP-WRKY-F1 | **CCGCAAAGGGAA**CTCCTCCTCTGCTAACGTAAGCC | SEQ ID No. 16 |
| TMVMP-WRKY-R1 | **CCGCAAAGGGAA**CTGTGGTTGGAGAAGCTAGAACC | SEQ ID No. 17 |
| TMVMP-F2 | **CTCCAACCACAG**TTCCCTTTGCGGACATCACTCT | SEQ ID No. 18 |
| TMVMP-R2 | **AAGTTAAGGGATGCAGTTTATGCA**TCTCGGATCTTACTACACAGCAGC | SEQ ID No. 19 |
| | Identification/Sequencing primers | |
| pAD-JD-F1 | GCGTGCAAACGCATGAATATC | SEQ ID No. 20 |
| PAD-JD-R1 | AGGGCCTCGTGATACGCCT | SEQ ID No. 21 |
| WRKY-JD-F1 | ATCGTGATCGGAAGTGATAAAG | SEQ ID No. 22 |
| OXB-JD-F1 | GCTTCCGAGCTCTCGAATTC | SEQ ID No. 23 |
| adh-JD-F1 | CGATGAACAGTGCCGCAG | SEQ ID No. 24 |
| adh-JD-F2 | TGAGTGGCCCTGTTTCTCG | SEQ ID No. 25 |

TABLE 2

Primers used in construction of M-JM109-GY1 and M-JM109-GHY2. Underlined bases are 50 bp homologous sequences to the *E.coli* rnc gene. The italicized bases are primers used for amplification of the Kanamycin resistance marker. *Denoting the phosphorothioated primers. SEQ. ID No. 45 through 52, numbered sequentially from top to bottom of middle column.

| Primers | Primer sequence (5'→3')[a] | Specific use |
|---|---|---|
| Ec_RNaseIII50-5 | ATGAACCCCATCGTAATTAATCGG<br>CTTCAACGGAAGCTGGGCTACACT<br>TT*AGCGATTGTGTAGGCTGGAG* | Target primer, underlined sequence is 50 bp homologous sequence |
| Ec_RNaseIII50-3 | CTGATCGTGCGCTTCGCCACGTAC<br>CTGGACTACCAGATAAGTCGGCAG<br>CG*TTAACGGCTGACATGGGAATTAG* | Target primer, underlined sequence is 50 bp homologous sequence |
| Ec_phos_50-5 | A*T*G*A*ACCCCATCGTAATTAAT CGGC | phosphorothioated primers |
| Ec_phos_50-3 | C*T*G*A*TCGTGCGCTTCGC | phosphorothioated primers |
| JD-5 | ACCGGTAAACTGAAACTGCA | Mutant screening |
| JD-3 | TGGAGATTTTCTGCCCCAG | Mutant screening |
| Cat-5 | AGCGATTGTGTAGGCTGGAGCT | mutant screening |
| Cat-3 | TTAACGGCTGACATGGGAATTAGC | mutant screening |

TABLE 3

*E. coli* RNaseIII mutants and associated plasmids encoding hpRNAs, plus *Agrobacterium* utilized in tobacco plant infiltration assays

| Plasmid/RNaseIII mutants | Purposes | Specificity | References |
|---|---|---|---|
| pAD-WRKY-GHY1 | hpRNA to target GFP from TMV-GFP | Pupp (uracil phosphoribosyl transferase) promoter, shuttle vector, low-copy number, containing *Arabidopsis* WRKYtranscription factor 33 intron | This study |
| pAD-ADH-GHY2 | hpRNA to target GFP from TMV-GFP | Pupp ((uracil phosphoribosyl transferase) promoter, shuttle vector, low-copy number, containing maize adh1 intron | This study |
| pOXB-WRKY-GHY3 | hpRNA to target GFP from TMV-GFP | LacUV5 promoter, pUC high copy number vector for *E. coli*, containing *Arabidopsis* WRKY transcription factor 33 intron | This study |
| pOXB-ADH-GHY4 | hpRNA to target GFP from TMV-GFP | LacUV5 promoter, pUC high copy number vector for *E.coli*, containing maize adh1 intron | This study |
| pAD-WRKY-GHY5 | hpRNA to target GFP from TMV-GFP | Pupp (uracil phosphoribosyl transferase) promoter, shuttle vector, low-copy number, containing *Arabidopsis* WRKY transcription factor 33 intron | This study |
| pAD-ADH-GHY6 | hpRNA to target GFP from TMV-GFP | Pupp ((uracil phosphoribosyl transferase) promoter, shuttle vector, low-copy number, containing maize adh1 intron | This study |
| pAD-WRKY-GHY7 | hpRNA to target GFP from TMV-GFP | Pupp ((uracil phosphoribosyl transferase) promoter, shuttle vector, low-copy number, containing *Arabidopsis* WRKY transcription factor 33 intron | This study |
| pJL-TRBO-G | Used to express TMV encoded GFP signal | Kanamycin resistance | (Lindbo 2007) |
| M-JM109-GHY2 | RNaseIII mutant, genotype: endA1, recA1, gyrA96, thi, hsdR17 (rk→, mk+), relA1, supE44, λ→, Δ(lac-proAB), [F', traD36, proAB, lacIqZΔM15], IDE3. | No antibiotic resistance | This study |

TABLE 3-continued

*E. coli* RNaseIII mutants and associated plasmids encoding hpRNAs, plus *Agrobacterium* utilized in tobacco plant infiltration assays

| Plasmid/RNaseIII mutants | Purposes | Specificity | References |
|---|---|---|---|
| HT27 | RNaseIII mutant, as a “helper” hyper-vesiculating phenotype which we predicted would facilitate packaging and transfer of dsRNAto the host (hypervesiculating amino acid auxotrophic mutant), genotype: his-, ilv-, pglA8 | Tetracycline resistance | (Takiff and Chen 1989) |
| CCB422 | RNaseIII mutant | Kanamycin and spectinomycin resistance | (Durand et al. 2012) |
| *Bacillus cereus* 53522 | Endophytic in plant, RNaseIII wide-type | no antibiotic resistance, used to check the colonization of bacteria in plants and express dsRNA | (Lozano et al. 2016; Raffel et al. 1996) |
| *Agrobacterium tumefaciens* GV3101 | was used to infiltration tobacco | Rifampin resistance | (Lindbo 2007) |

TABLE 4

Primers used for identification and verification of *Bacillus* spp. SEQ. ID No. 53 through 62 numbered from top to bottom or middle column.

| Genes | Upper primers | Size (bp) | Purposes |
|---|---|---|---|
| 16S rRNA | 8F: AGAGTTTGATCCTGGCTCAG<br>1492R: CGGTTACCTTGITACGACTT | ~1500 | Non-coding 168 rRNA gene |
| 23S rDNA | BAC11: AGAGTGCGTAATAGCTCAC<br>BAC19: CGGTCTAGAACTTACCGACAAGG | 880 | Non-coding 23S rDNA |
| motB | BCFomp1: ATCGCCTCGTTGGATGACGA<br>BCRomp1: CTGCATATCCTACCGCAGCTA | 575 | encoding flagellar motor protein; a unique conserved sequence from B. |
| endo-b-1,4-glucanase genes | EN1F: CCAGTAGCCAAGAATGGCCAGC<br>EN1R: GGAATAATCGCCGCTTTGTGC | 1311 | Encoding the endoglucanase gene |
| SCAR | PAGA1: ATGAGCCCTGTGATCAGGAAGATCG<br>PAGB1: ACGATGAGCCTTCTCAGCAAATGCG | 270 | Sequence-characterized amplified regions |

TABLE 5

Additional mobilization Genes

| Reduced RNA silencing spread | Enhanced RNA silencing spread | Do not affect PDS and/or SUL silencing spread |
|---|---|---|
| ago1[a] | ago4[b,c,d] | ago4[a,d] |
| clsy1[b] | dcl3[b,d] | dcl2[a] |
| dcl1[a] | | dcl3[a,d] |
| dcl4[b,e] | | drb4[a] |
| fca[f] | | hst1[g] |
| fpa[f] | | hyl1[a] |
| fy[h] | | rdr1[a] |
| jmj14[c] | | rdr6[i] |
| hen1[a] | | sde3[i] |
| hpr1[j] | | sde5[j,k] |
| nrpd1[a,b] | | |
| nrpd2a[b] | | |
| rdr2[a,b] | | |
| tex1[l] | | |

TABLE 6

Primers used for qRT-PCR in FIG. 22 including SEQ ID NOs 63-66)

| Primer names | Sequences (5-3) | Purpose and references |
|---|---|---|
| L25F1 | CCCCTCACCACAGAGTCTGC (SEQ ID NO. 63) | N. tabacum reference gene, (Schmidt & Delaney, 2010) |
| L25R1 | AAGGGTGTTGTTGTCCTCAATCTT (SEQ ID NO. 64) | |
| TMV-GFP-F2 | GATGACGGGAACTACAAGACG (SEQ ID NO. 65) | Amplification TMV-GFP, designed in this study |
| TMV-GFP-R2 | GTTTGTGTCCGAGAATGTTTCC (SEQ ID NO. 66) | |

TABLE 7

| Helper gene strains that enhance dsRNA delivery. | |
|---|---|
| Bacterial Strains | Helper Activity |
| HT115 | *E. coli* RNase III deficient strain suitable for production of dsRNA. Used in many studies for trans-kingdom delivery of dsRNA |
| HT27 | *E. coli* RNase III deficient strain suitable for production of dsRNA. It also has two auxotrophies (histidine and isoleucine). Auxotrophy has been shown to enhance nanotube formation with other bacteria. These nanotubes facilitate transfer of biomaterial (proteins, nucleic acids) |
| JC8031 | *E. coli* with enhanced hyper-vesiculation activity |

TABLE 8

| Helper genes that enhance dsRNA delivery. | |
|---|---|
| Helper Gene | Activity |
| VrrA | Small non-coding RNA that upon binding to OmpA mRNA increases bacterial hyper-vesiculation activity |
| SID1 | dsRNA-specific transporter that facilitates systemic RNAi |
| SID2 | Membrane protein that is required for uptake of ingested dsRNA |
| AGO1, AGO2 and AGO7 | Member of Argonaute family that is specific to provide host defense against RNA viruses |
| YmdB | Bacterial regulatory protein that suppresses RNase III cleavage |
| YmdB | Bacterial regulatory protein that suppresses RNase III cleavage |
| dsRNA-binding proteins: Staufen and RDE-4 | Staufen and RDE-4 proteins can bind dsRNA. Co-expression of these proteins and dsRNA in bacteria can enhance the lifetime of the produced dsRNA and facilitate their transport into cells |
| HlyA | Use of Hemolysin Atransport signal to enhance secretion of dsRNA-binding proteins |
| Sec- and Tat-secretory signal peptides | Use of Sec and Tat signaling peptides to enhance secretion of dsRNA-binding proteins |
| Cell-penetrating peptides (CPPs): Tat and Antennapedia | Use of CPPs such as Tat and Antennapedia or similar peptides to enhance uptake of dsRNA-binding proteins in cells. Can be combined with secretory peptides |
| ACC deaminase | 1-aminocyclopropane-1-carboxylate (ACC) deaminase, enzyme responsible for degradation of plant ethylene precursor and hence reduction of plant ethylene levels |
| Phloem RNA transporters; PP2-A1 and PSRP1 | involved in mobilization to and transport of mRNAand smRNAs in the phloem |
| DRB1 and DRB4 | bind dsRNA miRNA precursors and siRNA precursors, respectively, and are required for recruitment of downstream RNA processing enzymes. |
| HEN1 | Protein involved in smRNA stabilization via methylation of 3'-end of smRNA duplexes |

TABLE 8-continued

| Helper genes that enhance dsRNA delivery. | |
|---|---|
| Helper Gene | Activity |
| STV1 | ribosomal protein involved in miRNA biogenesis, required for localization of pri-miRNA precursors to nuclear dicing bodies |

SEQUENCE LISTINGS

SEQ ID NO. 1
DNA
Primers used for the construction of hpRNAs
Artificial
ggaaaactgtatgtatttgatccttgcccgaaggttatgtacagg
SEQ ID NO. 2
DNA
Primers used for the construction of hpRNAs
Artificial
gcagaggaggagaaagggcagattgtgtcgaca
SEQ ID NO. 3
DNA
Primers used for the construction of hpRNAs
Artificial
caatctgccctttctcctcctctgctaacgtaag
SEQ ID NO. 4
DNA
Primers used for the construction of hpRNAs
Artificial
caatctgccctttctgtggttggagaagctag
SEQ ID NO. 5
DNA
Primers used for the construction of hpRNAs
Artificial
ctccaaccacagaaagggcagattgtgtcgaca
SEQ ID NO. 6
DNA
Primers used for the construction of hpRNAs
Artificial
aagttaagggatgcagtttatgcatgcccgaaggttatgtacagg
SEQ ID NO. 7
DNA
Primers used for the construction of hpRNAs
Artificial
ttgcacttgatcaaagggcagattgtgtcgaca
SEQ ID NO. 8
DNA
Primers used for the construction of hpRNAs
Artificial
gtgcagctgcggaaagggcagattgtgtcgaca
SEQ ID NO. 9
DNA
Primers used for the construction of hpRNAs
Artificial
caatctgccctttgatcaagtgcaaaggtccgccttg
SEQ ID NO. 10
DNA
Primers used for the construction of hpRNAs
Artificial
caatctgccctttccgcagctgcacgggtcc
SEQ ID NO. 11
DNA
Primers used for the construction of hpRNAs Artificial
accgcgatatctacctcgaggttttgcccgaaggttatgtacagg
SEQ ID NO. 12
DNA
Primers used for the construction of hpRNAs
Artificial
agtcagtgcaggaggagacaactttgcccgaaggttatgtacagg
SEQ ID NO. 13
DNA
Primers used for the construction of hpRNAs
Artificial
ggaaaactgtatgtatttgatcctctagatttaagaaggagatatacat-tgcccgaaggttatgtacagg
SEQ ID NO. 14
DNA
Primers used for the construction of hpRNAs
Artificial
ggaaaactgtatgtatttgatcctctagatttaagaaggagatatacattctcggatct-tactacacagcagc
SEQ ID NO. 15
DNA
Primers used for the construction of hpRNAs
Artificial
tagcagaggaggagttccctttgcggacatcac
SEQ ID NO. 16
DNA
Primers used for the construction of hpRNAs
Artificial
ccgcaaagggaactcctcctctgctaacgtaagcc
SEQ ID NO. 17
DNA
Primers used for the construction of hpRNAs
Artificial
ccgcaaagggaactgtggttggagaagctagaacc
SEQ ID NO. 18
DNA
Primers used for the construction of hpRNAs
Artificial
ctccaaccacagttccctttgcggacatcactct
SEQ ID NO. 19
DNA
Primers used for the construction of hpRNAs
Artificial
aagttaagggatgcagtttatgcatctcggatcttactacacagcagc
SEQ ID NO. 20
DNA
Primers used for the construction of hpRNAs
Artificial
gcgtgcaaacgcatgaatatc
SEQ ID NO. 21
DNA
Primers used for the construction of hpRNAs
Artificial
agggcctcgtgatacgcct
SEQ ID NO. 22
DNA
Primers used for the construction of hpRNAs
Artificial
atcgtgatcggaagtgataaag
SEQ ID NO. 23
DNA
Primers used for the construction of hpRNAs
Artificial
gcttccgagctctcgaattc
SEQ ID NO. 24
DNA
Primers used for the construction of hpRNAs
Artificial
cgatgaacagtgccgcag
SEQ ID NO. 25
DNA
Primers used for the construction of hpRNAs
Artificial
tgagtggccctgtttctcg
SEQ ID NO. 45
DNA
50 bp homologous sequences to the *E. coli* me gene and primers used for amplification of the Kanamycin resistance marker
Artificial
atgaaccccatcgtaattaatcggcttcaacggaagctgggctacactttagcgat-tgtgtaggctggag
SEQ ID NO. 46
DNA
50 bp homologous sequences to the *E. coli* me gene and primers used for amplification of the Kanamycin resistance marker
Artificial
ctgatcgtgcgcttcgccacgtacctggactaccagataagtcggcagcgt-taacggctgacatgggaattag
SEQ ID NO. 47
DNA
50 bp homologous sequences to the *E. coli* me gene and primers used for amplification of the Kanamycin resistance marker
Artificial
atgaaccccatcgtaattaatcggc
SEQ ID NO. 48
DNA
50 bp homologous sequences to the *E. coli* me gene and primers used for amplification of the Kanamycin resistance marker
Artificial
ctgatcgtgcgcttcgc
SEQ ID NO. 49
DNA
50 bp homologous sequences to the *E. coli* me gene and primers used for amplification of the Kanamycin resistance marker
Artificial
accggtaaactgaaactgca
SEQ ID NO. 50
DNA
50 bp homologous sequences to the *E. coli* me gene and primers used for amplification of the Kanamycin resistance marker
Artificial
tggagattttctgccccag
SEQ ID NO. 51
DNA
50 bp homologous sequences to the *E. coli* me gene and primers used for amplification of the Kanamycin resistance marker
Artificial
agcgattgtgtaggctggagct
SEQ ID NO. 52
DNA
50 bp homologous sequences to the *E. coli* me gene and primers used for amplification of the Kanamycin resistance marker
Artificial
ttaacggctgacatgggaattagc SEQ ID NO. 53
DNA
Primers used for identification and verification of *Bacillus* spp
Artificial
agagtttgatcctggctcag SEQ ID NO. 54
DNA
Primers used for identification and verification of *Bacillus* spp
Artificial
cggttaccttgttacgactt SEQ ID NO. 55
DNA
Artificial
Primers used for identification and verification of *Bacillus* spp
agagtgcgtaatagctcac SEQ ID NO. 56
DNA
Primers used for identification and verification of *Bacillus* spp
Artificial
cggtctagaacttaccgacaagg SEQ ID NO. 57
DNA
Primers used for identification and verification of *Bacillus* spp
Artificial
atcgcctcgttggatgacga SEQ ID NO. 58
DNA
Primers used for identification and verification of *Bacillus* spp
Artificial
ctgcatatcctaccgcagcta SEQ ID NO. 59
DNA
Primers used for identification and verification of *Bacillus* spp
Artificial
ccagtagccaagaatggccagc SEQ ID NO. 60
DNA
Primers used for identification and verification of *Bacillus* spp
Artificial
ggaataatcgccgctttgtgc SEQ ID NO. 61
DNA
Primers used for identification and verification of *Bacillus* spp
Artificial
atgagccctgtgatcaggaagatcg SEQ ID NO. 62
DNA
Primers used for identification and verification of *Bacillus* spp
Artificial
acgatgagccttctcagcaaatgcg

TABLE 9

| Sequence Listing for Introns Sequences |
|---|
| >WRKY_intron-287 (SEQ ID NO. 26)<br>CTCCTCCTCTGCTAACGTAAGCCTCTCTGTTTTTTTTCTCTGTTTCTTTT<br>GAAATGAATCCAATTAGTGATGATAATCTGTGTTTGATGTATCATTGATT<br>TAACATCTTGACAATGAATCGTGATCGGAAGTGATAAAGTTATGGGTCAA<br>CGGTTTCAAAGAGAGAGAAAGACTTTTAGAGTCAACTCTCGACTCTTTCT<br>TAATTATGTTATTGCTATTTGTCTCTTTTCTTGAAGTCTGAACAATTCTT<br>GGGATTGTTTTGCAGGTTCTAGCTTCTCCAACCACAG |
| >adh1_intron-566: (SEQ ID NO. 27)<br>GATCAAGTGCAAAGGTCCGCCTTGTTTCTCCTCTGTCTCTTGATCTGACT<br>AATCTTGGTTTATGATTCGTTGAGTAATTTTGGGGAAAGCTAGCTTCGTC<br>CACAGTTTTTTTTTCGATGAACAGTGCCGCAGTGGCGCTGATCTTGTATG<br>CTATCCTGCAATCGTGGTGAACTTATGTCTTTTATATCCTTCACTACCAT<br>GAAAAGACTAGCTAGTAATCTTTCTCGATGTAACATCGTCCAGCACTGCT<br>ATTACCGTGTGGTCCATCCGACAGTCTGGCTGAACACATCATACGATATT<br>GAGCAAAGATCGATCTATCTTCCCTGTTCTTTAATGAAAGACGTCATTTT<br>CATCAGTATGATCTAAGAATGTTGCAACTTGCAAGGAGGCGTTTCTTTCT<br>TTGAATTTAACTAACTCGTTGAGTGGCCCTGTTTCTCGGACGTAAGGCCT<br>TTGCTGCTCCACACATGTCCATTCGAATTTTACCGTGTTTAGCAAGGGCG<br>AAAAGTTTGCATCTTGATGATTTAGCTTGACTATGCGATTGCTTTCCTGG<br>ACCCGTGCAGCTGCGG |
| >TMV-GFP-dsRNA-360 (SEQ ID NO. 28)<br>TGCCCGAAGGTTATGTACAGGAACGCACTATATCTTTCAAAGATGACGGG<br>AACTACAAGACGCGTGCTGAAGTCAAGTTTGAAGGTGATACCCTTGTTAA<br>TCGTATCGAGTTAAAAGGTATTGATTTTAAAGAAGATGGAAACATTCTCG<br>GACACAAACTCGAGTACAACTATAACTCACACAATGTATACATCACGGCA<br>GACAAACAAAAGAATGGAATCAAAGCTAACTTCAAAATTCGCCACAACAT<br>TGAAGATGGATCCGTTCAACTAGCAGACCATTATCAACAAAATACTCCAA<br>TTGGCGATGGCCCTGTCCTTTTACCAGACAACCATTACCTGTCGACACAA<br>TCTGCCCTTT |
| >TMV-MP-dsRNA-360 (SEQ ID NO. 29)<br>TCTCGGATCTTACTACACAGCAGCTGCAAAGAAAAGATTTCAGTTCAAGG<br>TCGTTCCCAATTATGCTATAACCACCCAGGACGCGATGAAAAACGTCTGG<br>CAAGTTTTAGTTAATATTAGAAATGTGAAGATGTCAGCGGGTTTCTGTCC<br>GCTTTCTCTGGAGTTTGTGTCGGTGTGTATTGTTTATAGAAATAATATAA<br>AATTAGGTTTGAGAGAGAAGATTACAAACGTGAGAGACGGAGGGCCCATG<br>GAACTTACAGAAGAAGTCGTTGATGAGTTCATGGAAGATGTCCCTATGTC<br>GATCAGGCTTGCAAAGTTTCGATCTCGAACCGGAAAAAAGAGTGATGTCC<br>GCAAAGGGAA |

TABLE 10

| Sequence Listing for Exemplary hpRNAs. |
|---|
| >pAD-WRKY-GHY1 (SEQ ID NO. 30)<br>GAATTCGAGCTCGGTACCCGGGGATCGCGTGAAAGAAATTTTCGGCGCAGAGCACGTAAAT<br>GTTCAACCACACTCTGGTGCACAAGCGAACATGGCAGTATACTTCACGATTTTAGAGCAAGG<br>CGATACAGTACTTGGTATGAATTTATCTCATGGTGGTCACTTAACACACGGAAGCCCTGTTA<br>ACTTCAGTGGAGTACAATATAATTTCGTAGAATATGGCGTGGATGCTGACTCTCACCGTATT<br>AATTACGATGATGTATTAGCAAAAGCGAAAGAACATAAACCAAAATTAATCGTTGCAGGTG<br>CAAGTGCATACCCTCGTGTTATCGATTTCAAGCGATTCCGTGAGATTGCAGATGAAGTGGGC<br>GCTTATTTAATGGTTGATATGGCACATATCGCTGGTTTAGTAGCTGCTGGTTTACATCCAAAT<br>CCAGTACCACATGCACATTTCGTTACAACGACAACACATAAAACGTTACGTGGCCCGCGTGG<br>TGGTATGATTTTATGTGAAGAGCAATTTGCAAAACAAATTGATAAATCAATCTTCCCTGGTA<br>TTCAAGGTGGTCCACTTATGCACGTAATCGCTGCAAAAGCTGTTGCGTTTGGTGAAGCACTT<br>CAAGATGATTTCAAAACATATGCACAAAATATCATTAACAATGCGAACCGCTTAGCTGAAG<br>GTCTTCAAAAAGAAGGACTTACACTTGTTTCTGGCGGAACAGACAATCACTTAATCTTGATT<br>GATGTTCGTAACTTAGAAATCACAGGTAAAGTAGCAGAGCACGTATTAGATGAAGTTGGTAT |

TABLE 10-continued

| Sequence Listing for Exemplary hpRNAs. |
|---|
| TACAGTGAACAAAAATACAATTCCATTTGAAACAGCAAGCCCATTTGTAACAAGTGGTGTAC<br>GTATCGGTACAGCAGCTGTAACATCTCGTGGTTTCGGTTTAGAAGAAATGGATGAAATTGCG<br>TCACTTATTGCTTATACATTAAAAAATCATGAAAATGAAGCTGCATTAGAAGAAGTACGTAA<br>GCGTGTAGAAGCGTTAACTAGCAAATTTCCAATGTATCCAAATCTATAATAGATTGAAGAAG<br>ACTGCCGAGACTTAATTGTTTTGGCGGTCTTTTTTGTGGACATATATTATTTTTAAAGTATGT<br>ATACAAATGATGAATAAATTTTGGCGATATAATGAAGGATACAGCTCCCATAATTGGTAAAG<br>ATACTAGATAGATTCATCGTAAAATCATGATTTTGCCAAATTTGCCCTTGAATATTAGTAGCG<br>TTTTCTTTACAATCGTAAATAGTGTAAAAAAGCGTGCAAACGCATGAATATCATCTAAAGGA<br>GAGATTCACATGGGAAAACTGTATGTATTTGATCCTTGCCCGAAGGTTATGTACAGGAACGC<br>ACTATATCTTTCAAAGATGACGGGAACTACAAGACGCGTGCTGAAGTCAAGTTTGAAGGTG<br>ATACCCTTGTTAATCGTATCGAGTTAAAAGGTATTGATTTTAAAGAAGATGGAAACATTCTC<br>GGACACAAACTCGAGTACAACTATAACTCACACAATGTATACATCACGGCAGACAAACAAA<br>AGAATGGAATCAAAGCTAACTTCAAAATTCGCCACAACATTGAAGATGGATCCGTTCAACTA<br>GCAGACCATTATCAACAAAATACTCCAATTGGCGATGGCCCTGTCCTTTTACCAGACAACCA<br>TTACCTGTCGACACAATCTGCCCTTTCTCCTCCTCTGCTAACGTAAGCCTCTCTGTTTTTTTC<br>TCTGTTTCTTTTGAAATGAATCCAATTAGTGATGATAATCTGTGTTTGATGTATCATTGATTT<br>AACATCTTGACAATGAATCGTGATCGGAAGTGATAAAGTTATGGGTCAACGGTTTCAAAGA<br>GAGAGAAAGACTTTTAGAGTCAACTCTCGACTCTTTCTTAATTATGTTATTGCTATTTGTCTC<br>TTTTCTTGAAGTCTGAACAATTCTTGGGATTGTTTTGCAGGTTCTAGCTTCTCCAACCACAGA<br>AAGGGCAGATTGTGTCGACAGGTAATGGTTGTCTGGTAAAAGGACAGGGCCATCGCCAATT<br>GGAGTATTTTGTTGATAATGGTCTGCTAGTTGAACGGATCCATCTTCAATGTTGTGGCGAATT<br>TTGAAGTTAGCTTTGATTCCATTCTTTTGTTTGTCTGCCGTGATGTATACATTGTGTGAGTTAT<br>AGTTGTACTCGAGTTTGTGTCCGAGAATGTTTCCATCTTCTTTAAAATCAATACCTTTTAACT<br>CGATACGATTAACAAGGGTATCACCTTCAAACTTGACTTCAGCACGCGTCTTGTAGTTCCCG<br>TCATCTTTGAAAGATATAGTGCGTTCCTGTACATAACCTTCGGGCATGCATAAACTGCATCCC<br>TTAACTTGTTTTTCGTGTGCCTATTTTTTGTGAATCGCTAAGAAACCATTATTATCATGACATT<br>AACCTATAAAAATAGGCGTATCACGAGGCCCTTTCGTCTCGCGCGTTTCGGTGATGACGGTG<br>AAAACCTCTGACACATGCAGCTCCCGGAGACGGTCACAGCTTGTCTGTAAGCGGATGCCGG<br>GAGCAGACAAGCCCGTCAGGGCGCGTCAGCGGGTGTTGGCGGGTGTCGGGGCTGGCTTAAC<br>TATGCGGCATCAGAGCAGATTGTACTGAGAGTGCACCATACAAAACATATTTCAACACAATA<br>CAAATGGGTTAGTTAAAAAAGCAGGCCTTCTAAAGGTCTGCTTTTTTTATTTGATTATGTAAT<br>TTTTAATGCCAGGATGCCAATAAGCCATAACCTCAAATGCACCATTTGCAACCTCGTCATCTT<br>CTTCCTCAATCTTGACCAGATCGCCGTCCTCCGCATCACCAAGATTCAGCTCTTTATGTATCT<br>CCTTCAAAATGCCACCGTATCCAATTAACCTTCGAGCTGCCAACGCATCATCCAAGTAAAGC<br>ACCGTGTTCAGATTGTCTTCAGTCACCTTATTACCGCGCACACAATCCGTATCCTTAACCGGA<br>TATTTAGAGATTTCGCGAACAGCTTTTTGCTCCATCATTGCGTTCCGCACATCGTTTTCAATC<br>TGTTCAGCGTCAATCTTAGCTTTACCTTTCACTCGACGAATATCGACAATTGGAGTGTAATCC<br>AATTTCATCGCCTTTTTCCAAAGGCTCGTCCACTCCGCCTGCTTAATATAGTTTTTCCCAAAA<br>TAATTTTTCCTTACTGGTATCAACACATGAAAATGAGGATGATATGTATCTTCTTCATGATTT<br>TTGGTAATCTCTAAAGCTCTGAAAAATCCAAGAACCGAAGTTTTTACTTTTTTGTACTGGAAC<br>AGTTTCCTAAAGCCTTCCATCATCGCAGAAATTTGTGGCTTCAGCCGTTCTCCCTTTACATTT<br>CGAATCGTCAGCGTGAGAAAAATCCATCCGCAGCCGTACTGTCTATTGGCTTCCTCTACGAT<br>CAACTTATTGTGATAAGCAATTTTTAACGACCTGCGCCACGCACACATCGGACATAACCTCA<br>CTTTACAAAAATGGGCTTGATACAGTTTTAACTTGCCCGTCTCCGGGTCTCTCTTAAACGAAA<br>GATACTCTGCACAACTAATTAGTTTTTCAGCCTTTTTGCCATAGTAAGGTGCCCCAATCTTAC<br>TCTCTAACGCTTCGTAATGCTCCGCCATGAGGTTCGTCCGTCTCTTTTTCCCCTTCCAATCCCG<br>CTTTTTACCTGTTGCGGTTTTATCTTCGAGGATGCTATAATCATTTTCAGATGAATAAATCAA<br>CAAAAAAACTCCTTCTGAGCTAGTTCTCTAGCATTCTATTATTTTGATTCGACACCTTAATAA<br>TAGCAGAAGGAGTTTTTACCTGTCAAAGAACCATCAAACCCTTGATACACAAGGCTTTGACC<br>TAATTTTGAAAAATGATGTTGTTTCTATATAGTATCAAGATAAGAAAGAAAAGGATTTTTCG<br>CTACGCTCAAATCCTTTAAAAAAACACAAAAGACCACATTTTTTAATGTGGTCTTTATTCTTC<br>AACTAAAGCACCCATTAGTTCAACAAACGAAAATTGGATAAAGTGGGATATTTTTAAAATAT<br>ATATTTATGTTACAGTAATATTGACTTTTAAAAAAGGATTGATTCTAATGAAGAAAGCAGAC<br>AAGTAAGCCTCCTAAATTCACTTTAGATAAAAAATTTAGGAGGCATATCAAATGAACTTTAAT<br>AAAATTGATTTAGACAATTGGAAGAGAAAAGAGATATTTAATCATTATTTGAACCAACAAA<br>CGACTTTTAGTATAACCACAGAAATTGATATTAGTGTTTTATACCGAAACATAAAACAAGAA<br>GGATATAAATTTTACCCTGCATTTATTTTCTTAGTGACAAGGGTGATAAACTCAAATACAGCT<br>TTTAGAACTGGTTACAATAGCGACGGAGAGTTAGGTTATTGGGATAAGTTAGAGCCACTTTA<br>TACAATTTTTGATGGTGTATCTAAAACATTCTCTGGTATTTGGACTCCTGTAAAGAATGACTT<br>CAAAGAGTTTTATGATTTATACCTTTCTGATGTAGAGAAATATAATGGTTCGGGGAAATTGT<br>TTCCCAAAACACCTATACCTGAAAATGCTTTTTCTCTTTCTATTATTCCATGGACTTCATTTAC<br>TGGGTTTAACTTAAATATCAATAATAATAGTAATTACCTTCTACCCATTATTACAGCAGGAA<br>AATTCATTAATAAAGGTAATTCAATATATTTACCGCTATCTTTACAGGTACATCATTCTGTTT<br>GTGATGGTTATCATGCAGGATTGTTTATGAACTCTATTCAGGAATTGTCAGATAGGCCTAAT<br>GACTGGCTTTTATAATATGAGATAATGCCGACTGTACTTTTTACAGTCGGTTTTCTAATGTCA<br>CTAACCTGCCCCGTTAGTCGCCATTCGCCAGCTGCCTCGCGCGTTTCGGTGATGACGGTGAA<br>AACCTCTGACACATGCAGCTCCCGGAGACGGTCACAGCTTGTCTGTAAGCGGATGCCGGGA<br>GCAGACAAGCCCGTCAGGGCGCGTCAGCGGGTGTTGGCGGGTGTCGGGGCGCAGCCATGAC<br>CCAGTCACGTAGCGATAGCGGAGTGTATACTGGCTTAACTATGCGGCATCAGAGCAGATTGT<br>ACTGAGAGTGCACCATATGCGGTGTGAAATACCGCACAGATGCGTAAGGAGAAAATACCGC<br>ATCAGGCGCTCTTCCGCTTCCTCGCTCACTGACTCGCTGCGCTCGGTCGTTCGGCTGCGGCGA<br>GCGGTATCAGCTCACTCAAAGGCGGTAATACGGTTATCCACAGAATCAGGGGATAACGCAG<br>GAAAGAACATGTGAGCAAAAGGCCAGCAAAAGGCCAGGAACCGTAAAAAGGCCGCGTTGC<br>TGGCGTTTTTCCATAGGCTCCGCCCCCCTGACGAGCATCACAAAAATCGACGCTCAAGTCAG<br>AGGTGGCGAAACCCGACAGGACTATAAAGATACCAGGCGTTTCCCCCTGGAAGCTCCCTCGT<br>GCGCTCTCCTGTTCCGACCCTGCCGCTTACCGGATACCTGTCCGCCTTTCTCCCTTCGGGAAG<br>CGTGGCGCTTTCTCAATGCTCACGCTGTAGGTATCTCAGTTCGGTGTAGGTCGTTCGCTCCAA<br>GCTGGGCTGTGTGCACGAACCCCCCGTTCAGCCCGACCGCTGCGCCTTATCCGGTAACTATC |

TABLE 10-continued

Sequence Listing for Exemplary hpRNAs.

GTCTTGAGTCCAACCCGGTAAGACACGACTTATCGCCACTGGCAGCAGCCACTGGTAACAGG
ATTAGCAGAGCGAGGTATGTAGGCGGTGCTACAGAGTTCTTGAAGTGGTGGCCTAACTACG
GCTACACTAGAAGGACAGTATTTGGTATCTGCGCTCTGCTGAAGCCAGTTACCTTCGGAAAA
AGAGTTGGTAGCTCTTGATCCGGCAAACAAACCACCGCTGGTAGCGGTGGTTTTTTTGTTTG
CAAGCAGCAGATTACGCGCAGAAAAAAAGGATCTCAAGAAGATCCTTTGATCTTTTCTACGG
GGTCTGACGCTCAGTGGAACGAAAACTCACGTTAAGGGATTTTGGTCATGAGATTATCAAAA
AGGATCTTCACCTAGATCCTTTTAAATTAAAAATGAAGTTTTAAATCAATCTAAAGTATATAT
GAGTAAACTTGGTCTGACAGTTACCAATGCTTAATCAGTGAGGCACCTATCTCAGCGATCTG
TCTATTTCGTTCATCCATAGTTGCCTGACTCCCCGTCGTGTAGATAACTACGATACGGGAGGG
CTTACCATCTGGCCCCAGTGCTGCAATGATACCGCGAGACCCACGCTCACCGGCTCCAGATT
TATCAGCAATAAACCAGCCAGCCGGAAGGGCCGAGCGCAGAAGTGGTCCTGCAACTTTATC
CGCCTCCATCCAGTCTATTAATTGTTGCCGGGAAGCTAGAGTAAGTAGTTCGCCAGTTAATA
GTTTGCGCAACGTTGTTGCCATTGCTGCAGGCATCGTGGTGTCACGCTCGTCGTTTGGTATGG
CTTCATTCAGCTCCGGTTCCCAACGATCAAGGCGAGTTACATGATCCCCCATGTTGTGCAAA
AAAGCGGTTAGCTCCTTCGGTCCTCCGATCGTTGTCAGAAGTAAGTTGGCCGCAGTGTTATC
ACTCATGGTTATGGCAGCACTGCATAATTCTCTTACTGTCATGCCATCCGTAAGATGCTTTTC
TGTGACTGGTGAGTACTCAACCAAGTCATTCTGAGAATAGTGTATGCGGCGACCGAGTTGCT
CTTGCCCGGCGTCAACACGGGATAATACCGCGCCACATAGCAGAACTTTAAAAGTGCTCATC
ATTGGAAAACGTTCTTCGGGGCGAAAACTCTCAAGGATCTTACCGCTGTTGAGATCCAGTTC
GATGTAACCCACTCGTGCACCCAACTGATCTTCAGCATCTTTTACTTTCACCAGCGTTTCTGG
GTGAGCAAAAACAGGAAGGCAAAATGCCGCAAAAAAGGGAATAAGGGCGACACGGAAATG
TTGAATACTCATACTCTTCCTTTTTCAATATTATTGAAGCATTTATCAGGGTTATTGTCTCATG
AGCGGATACATATTTGAATGTATTTAGAAAAATAAACAAATAGGGGTTCCGCGCACATTTCC
CCGAAAAGTGCCACCTGACGTCTAAGAAACCATTATTATCATGACATTAACCTATAAAAATA
GGCGTATCACGAGGCCCTTTCGTCTTCAA

>pAD-ADH-GHY2 (SEQ ID NO. 31)
GAATTCGAGCTCGGTACCCGGGGATCGCGTGAAAGAAATTTTCGGCGCAGAGCACGTAAA1'
GTTCAACCACACTCTGGTGCACAAGCGAACATGGCAGTATACTTCACGATTTTAGAGCAAGG
CGATACAGTACTTGGTATGAATTTATCTCATGGTGGTCACTTAACACACGGAAGCCCTGTTA
ACTTCAGTGGAGTACAATATAATTTCGTAGAATATGGCGTGGATGCTGACTCTCACCGTATT
AATTACGATGATGTATTAGCAAAAGCGAAAGAACATAAACCAAAATTAATCGTTGCAGGTG
CAAGTGCATACCCTCGTGTTATCGATTTCAAGCGATTCCGTGAGATTGCAGATGAAGTGGGC
GCTTATTTAATGGTTGATATGGCACATATCGCTGGTTTAGTAGCTGCTGGTTTACATCCAAAT
CCAGTACCACATGCACATTTCGTTACAACGACAACACATAAAACGTTACGTGGCCCGCGTGG
TGGTATGATTTTATGTGAAGAGCAATTTGCAAAACAAATTGATAAATCAATCTTCCCTGGTA
TTCAAGGTGGTCCACTTATGCACGTAATCGCTGCAAAAGCTGTTGCGTTTGGTGAAGCACTT
CAAGATGATTTCAAAACATATGCACAAAATATCATTAACAATGCGAACCGCTTAGCTGAAG
GTCTTCAAAAAGAAGGACTTACACTTGTTTCTGGCGGAACAGACAATCACTTAATCTTGATT
GATGTTCGTAACTTAGAAATCACAGGTAAAGTAGCAGAGCACGTATTAGATGAAGTTGGTAT
TACAGTGAACAAAAATACAATTCCATTTGAAACAGCAAGCCCATTTGTAACAAGTGGTGTAC
GTATCGGTACAGCAGCTGTAACATCTCGTGGTTTCGGTTTAGAAGAAATGGATGAAATTGCG
TCACTTATTGCTTATACATTAAAAAATCATGAAAATGAAGCTGCATTAGAAGAAGTACGTAA
GCGTGTAGAAGCGTTAACTAGCAAATTTCCAATGTATCCAAATCTATAATAGATTGAAGAAG
ACTGCCGAGACTTAATTGTTTTGGCGGTCTTTTTTGTGGACATATATTATTTTTAAAGTATGT
ATACAAATGATGAATAAATTTGGCGATATAATGAAGGATACAGCTCCCATAATTGGTAAAG
ATACTAGATAGATTCATCGTAAAATCATGATTTTGCCAAATTTGCCCTTGAATATTAGTAGCG
TTTTCTTTACAATCGTAAATAGTGTAAAAAAGCGTGCAAACGCATGAATATCATCTAAAGGA
GAGATTCACATGGGAAAACTGTATGTATTTGATCCTTGCCCGAAGGTTATGTACAGGAACGC
ACTATATCTTTCAAAGATGACGGGAACTACAAGACGCGTGCTGAAGTCAAGTTTGAAGGTG
ATACCCTTGTTAATCGTATCGAGTTAAAAGGTATTGATTTTAAAGAAGATGGAAACATTCTC
GGACACAAACTCGAGTACAACTATAACTCACACAATGTATACATCACGGCAGACAAACAAA
AGAATGGAATCAAAGCTAACTTCAAAATTCGCCACAACATTGAAGATGGATCCGTTCAACTA
GCAGACCATTATCAACAAAATACTCCAATTGGCGATGGCCCTGTCCTTTTACCAGACAACCA
TTACCTGTCGACACAATCTGCCCTTTGATCAAGTGCAAAGGTCCGCCTTGTTTCTCCTCTGTC
TCTTGATCTGACTAATCTTGGTTTATGATTCGTTGAGTAATTTTGGGGAAAGCTAGCTTCGTC
CACAGTTTTTTTTTCGATGAACAGTGCCGCAGTGGCGCTGATCTTGTATGCTATCCTGCAATC
GTGGTGAACTTATGTCTTTTATATCCTTCACTACCATGAAAAGACTAGCTAGTAATCTTTCTC
GATGTAACATCGTCCAGCACTGCTATTACCGTGTGGTCCATCCGACAGTCTGGCTGAACACA
TCATACGATATTGAGCAAAGATCGATCTATCTTCCCTGTTCTTTAATGAAAGACGTCATTTTC
ATCAGTATGATCTAAGAATGTTGCAACTTGCAAGGAGGCGTTTCTTTCTTTGAATTTAACTAA
CTCGTTGAGTGGCCCTGTTTCTCGGACGTAAGGCCTTTGCTGCTCCACACATGTCCATTCGAA
TTTTACCGTGTTTAGCAAGGGCGAAAGTTTGCATCTTGATGATTTAGCTTGACTATGCGATT
GCTTTCCTGGACCCGTGCAGCTGCGGAAAGGGCAGATTGTGTCGACAGGTAATGGTTGTCTG
GTAAAAGGACAGGGCCATCGCCAATTGGAGTATTTTGTTGATAATGGTCTGCTAGTTGAACG
GATCCATCTTCAATGTTGTGGCGAATTTTGAAGTTAGCTTTGATTCCATTCTTTTGTTTGTCTG
CCGTGATGTATACATTGTGTGAGTTATAGTTGTACTCGAGTTTGTGTCCGAGAATGTTTCCAT
CTTCTTTAAAATCAATACCTTTTAACTCGATACGATTAACAAGGGTATCACCTTCAAACTTGA
CTTCAGCACGCGTCTTGTAGTTCCCGTCATCTTTGAAAGATATAGTGCGTTCCTGTACATAAC
CTTCGGGCATGCATAAACTGCATCCCTTAACTTGTTTTTCGTGTGCCTATTTTTTTGTGAATCGC
TAAGAAACCATTATTATCATGACATTAACCTATAAAAATAGGCGTATCACGAGGCCCTTTCG
TCTCGCGCGTTTCGGTGATGACGGTGAAAACCTCTGACACATGCAGCTCCCGGAGACGGTCA
CAGCTTGTCTGTAAGCGGATGCCGGGAGCAGACAAGCCCGTCAGGGCGCGTCAGCGGGTGT
TGGCGGGTGTCGGGGCTGGCTTAACTATGCGGCATCAGAGCAGATTGTACTGAGAGTGCACC
ATACAAAACATATTTCAACACAATACAAATGGGTTAGTTAAAAAAGCAGGCCTTCTAAAGG
TCTGCTTTTTTTATTTGATTATGTAATTTTTAATGCCAGGATGCCAATAAGCCATAACCTCAA
ATGCACCATTTGCAACCTCGTCATCTTCTTCCTCAATCTTGACCAGATCGCCGTCCTCCGCAT
CACCAAGATTCAGCTCTTTATGTATCTCCTTCAAAATGCCACCGTATCCAATTAACCTTCGAG

TABLE 10-continued

Sequence Listing for Exemplary hpRNAs.

CTGCCAACGCATCATCCAAGTAAAGCACCGTGTTCAGATTGTCTTCAGTCACCTTATTACCGC
GCACACAATCCGTATCCTTAACCGGATATTTAGAGATTTCGCGAACAGCTTTTTGCTCCATCA
TTGCGTTCCGCACATCGTTTTCAATCTGTTCAGCGTCAATCTTAGCTTTACCTTTCACTCGACG
AATATCGACAATTGGAGTGTAATCCAATTTCATCGCCTTTTTCCAAAGGCTCGTCCACTCCGC
CTGCTTAATATAGTTTTTCCCAAAATAATTTTTCCTTACTGGTATCAACACATGAAAATGAGG
ATGATATGTATCTTCTTCATGATTTTTGGTAATCTCTAAAGCTCTGAAAAATCCAAGAACCGA
AGTTTTTACTTTTTTGTACTGGAACAGTTTCCTAAAGCCTTCCATCATCGCAGAAATTTGTGG
CTTCAGCCGTTCTCCCTTTACATTTCGAATCGTCAGCGTGAGAAAAATCCATCCGCAGCCGTA
CTGTCTATTGGCTTCCTCTACGATCAACTTATTGTGATAAGCAATTTTTAACGACCTGCGCCA
CGCACACATCGGACATAACCTCACTTTACAAAAATGGGCTTGATACAGTTTTAACTTGCCCG
TCTCCGGGTCTCTCTTAAACGAAAGATACTCTGCACAACTAATTAGTTTTTCAGCCTTTTTGC
CATAGTAAGGTGCCCCAATCTTACTCTCTAACGCTTCGTAATGCTCCGCCATGAGGTTCGTCC
GTCTCTTTTTCCCCTTCCAATCCCGCTTTTTACCTGTTGCGGTTTTATCTTCGAGGATGCTATA
ATCATTTTCAGATGAATAAATCAACAAAAAAACTCCTTCTGAGCTAGTTCTCTAGCATTCTAT
TATTTTGATTCGACACCTTAATAATAGCAGAAGGAGTTTTTACCTGTCAAAGAACCATCAAA
CCCTTGATACACAAGGCTTTGACCTAATTTTGAAAAATGATGTTGTTTCTATATAGTATCAAG
ATAAGAAAGAAAAGGATTTTTCGCTACGCTCAAATCCTTTAAAAAAACACAAAAGACCACA
TTTTTTAATGTGGTCTTTATTCTTCAACTAAAGCACCCATTAGTTCAACAAACGAAAATTGGA
TAAAGTGGGATATTTTTAAAATATATATTTATGTTACAGTAATATTGACTTTTAAAAAAGGAT
TGATTCTAATGAAGAAAGCAGACAAGTAAGCCTCCTAAATTCACTTTAGATAAAAAATTTAGG
AGGCATATCAAATGAACTTTAATAAAATTGATTTAGACAATTGGAAGAGAAAAGAGATATT
TAATCATTATTTGAACCAACAAACGACTTTTAGTATAACCACAGAAATTGATATTAGTGTTTT
ATACCGAAACATAAAACAAGAAGGATATAAATTTTACCCTGCATTTATTTTCTTAGTGACAA
GGGTGATAAACTCAAATACAGCTTTTAGAACTGGTTACAATAGCGACGGAGAGTTAGGTTAT
TGGGATAAGTTAGAGCCACTTTATACAATTTTTGATGGTGTATCTAAAACATTCTCTGGTATT
TGGACTCCTGTAAAGAATGACTTCAAAGAGTTTTATGATTTATACCTTTCTGATGTAGAGAA
ATATAATGGTTCGGGGAAATTGTTTCCCAAAACACCTATACCTGAAAATGCTTTTTCTCTTTC
TATTATTCCATGGACTTCATTTACTGGGTTTAACTTAAATATCAATAATAATAGTAATTACCT
TCTACCCATTATTACAGCAGGAAAATTCATTAATAAAGGTAATTCAATATATTTACCGCTATC
TTTACAGGTACATCATTCTGTTTGTGATGGTTATCATGCAGGATTGTTTATGAACTCTATTCA
GGAATTGTCAGATAGGCCTAATGACTGGCTTTTATAATATGAGATAATGCCGACTGTACTTT
TTACAGTCGGTTTTCTAATGTCACTAACCTGCCCCGTTAGTCGCCATTCGCCAGCTGCCTCGC
GCGTTTCGGTGATGACGGTGAAAACCTCTGACACATGCAGCTCCCGGAGACGGTCACAGCTT
GTCTGTAAGCGGATGCCGGGAGCAGACAAGCCCGTCAGGGCGCGTCAGCGGGTGTTGGCGG
GTGTCGGGGCGCAGCCATGACCCAGTCACGTAGCGATAGCGGAGTGTATACTGGCTTAACTA
TGCGGCATCAGAGCAGATTGTACTGAGAGTGCACCATATGCGGTGTGAAATACCGCACAGA
TGCGTAAGGAGAAAATACCGCATCAGGCGCTCTTCCGCTTCCTCGCTCACTGACTCGCTGCG
CTCGGTCGTTCGGCTGCGGCGAGCGGTATCAGCTCACTCAAAGGCGGTAATACGGTTATCCA
CAGAATCAGGGGATAACGCAGGAAAGAACATGTGAGCAAAAGGCCAGCAAAAGGCCAGGA
ACCGTAAAAAGGCCGCGTTGCTGGCGTTTTTCCATAGGCTCCGCCCCCCTGACGAGCATCAC
AAAAATCGACGCTCAAGTCAGAGGTGGCGAAACCCGACAGGACTATAAAGATACCAGGCGT
TTCCCCCTGGAAGCTCCCTCGTGCGCTCTCCTGTTCCGACCCTGCCGCTTACCGGATACCTGT
CCGCCTTTCTCCCTTCGGGAAGCGTGGCGCTTTCTCAATGCTCACGCTGTAGGTATCTCAGTT
CGGTGTAGGTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTATCGCCACT
GGCAGCAGCCACTGGTAACAGGATTAGCAGAGCGAGGTATGTAGGCGGTGCTACAGAGTTC
TTGAAGTGGTGGCCTAACTACGGCTACACTAGAAGGACAGTATTTGGTATCTGCGCTCTGCT
GAAGCCAGTTACCTTCGGAAAAAGAGTTGGTAGCTCTTGATCCGGCAAACAAACCACCGCT
GGTAGCGGTGGTTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTAAGGGA
TTTTGGTCATGAGATTATCAAAAAGGATCTTCACCTAGATCCTTTTAAATTAAAAATGAAGTT
TTAAATCAATCTAAAGTATATATGAGTAAACTTGGTCTGACAGTTACCAATGCTTAATCAGT
GAGGCACCTATCTCAGCGATCTGTCTATTTCGTTCATCCATAGTTGCCTGACTCCCCGTCGTG
TAGATAACTACGATACGGGAGGGCTTACCATCTGGCCCCAGTGCTGCAATGATACCGCGAG
ACCCACGCTCACCGGCTCCAGATTTATCAGCAATAAACCAGCCAGCCGGAAGGGCCGAGCG
CAGAAGTGGTCCTGCAACTTTATCCGCCTCCATCCAGTCTATTAATTGTTGCCGGGAAGCTA
GAGTAAGTAGTTCGCCAGTTAATAGTTTGCGCAACGTTGTTGCCATTGCTGCAGGCATCGTG
GTGTCACGCTCGTCGTTTGGTATGGCTTCATTCAGCTCCGGTTCCCAACGATCAAGGCGAGTT
ACATGATCCCCCATGTTGTGCAAAAAAGCGGTTAGCTCCTTCGGTCCTCCGATCGTTGTCAG
AAGTAAGTTGGCCGCAGTGTTATCACTCATGGTTATGGCAGCACTGCATAATTCTCTTACTGT
CATGCCATCCGTAAGATGCTTTTCTGTGACTGGTGAGTACTCAACCAAGTCATTCTGAGAAT
AGTGTATGCGGCGACCGAGTTGCTCTTGCCCGGCGTCAACACGGGATAATACCGCGCCACAT
AGCAGAACTTTAAAAGTGCTCATCATTGGAAAACGTTCTTCGGGGCGAAAACTCTCAAGGAT
CTTACCGCTGTTGAGATCCAGTTCGATGTAACCCACTCGTGCACCCAACTGATCTTCAGCATC
TTTTACTTTCACCAGCGTTTCTGGGTGAGCAAAAACAGGAAGGCAAAATGCCGCAAAAAAG
GGAATAAGGGCGACACGGAAATGTTGAATACTCATACTCTTCCTTTTTCAATATTATTGAAG
CATTTATCAGGGTTATTGTCTCATGAGCGGATACATATTTGAATGTATTTAGAAAAATAAAC
AAATAGGGGTTCCGCGCACATTTCCCCGAAAAGTGCCACCTGACGTCTAAGAAACCATTATT
ATCATGACATTAACCTATAAAAATAGGCGTATCACGAGGCCCTTTCGTCTTCAA

>pOXB-WRKY-GHY3 (SEQ ID NO. 32)
GCGATCGCGGCTCCCGACATCTTGGACCATTAGCTCCACAGGTATCTTCTTCCCTCTAGTGGT
CATAACAGCAGCTTCAGCTACCTCTCAATTCAAAAAACCCCTCAAGACCCGTTTAGAGGCCC
CAAGGGGTTATGCTATCAATCGTTGCGTTACACACACAAAAAACCAACACACATCCATCTTC
GATGGATAGCGATTTTATTATCTAACTGCTGATCGAGTGTAGCCAGATCTAAGCTGTTGTGA
CCGCTTGCTCTAGCCAGCTATCGAGTTGTGAACCGATCCATCTAGCAATTGGTCTCGATCTAG
CGATAGGCTTCGATCTAGCTATGTATCACTCATTAGGCACCCCAGGCTTTACACTTTATGCTT
CCGGCTCGTATAATGTGTGGTGCTGGTTAGCGCTTGCTATAGATCTTTGTCGATCCTACCATC

TABLE 10-continued

| Sequence Listing for Exemplary hpRNAs. |
|---|
| CACTCGACACACCCGCCAGCGGCCGCTGCCAAGCTTCCGAGCTCTCGAATTCAAAGGAGGTA<br>CCCACCATGGGGTACCGCGATATCTACCTCGAGGTTTTGCCCGAAGGTTATGTACAGGAACG<br>CACTATATCTTTCAAAGATGACGGGAACTACAAGACGCGTGCTGAAGTCAAGTTTGAAGGTG<br>ATACCCTTGTTAATCGTATCGAGTTAAAAGGTATTGATTTTAAAGAAGATGGAAACATTCTC<br>GGACACAAACTCGAGTACAACTATAACTCACACAATGTATACATCACGGCAGACAAACAAA<br>AGAATGGAATCAAAGCTAACTTCAAAATTCGCCACAACATTGAAGATGGATCCGTTCAACTA<br>GCAGACCATTATCAACAAAATACTCCAATTGGCGATGGCCCTGTCCTTTTACCAGACAACCA<br>TTACCTGTCGACACAATCTGCCCTTTCTCCTCCTCTGCTAACGTAAGCCTCTCTGTTTTTTTC<br>TCTGTTTCTTTTGAAATGAATCCAATTAGTGATGATAATCTGTGTTTGATGTATCATTGATTT<br>AACATCTTGACAATGAATCGTGATCGGAAGTGATAAAGTTATGGGTCAACGGTTTCAAAGA<br>GAGAGAAAGACTTTTAGAGTCAACTCTCGACTCTTTCTTAATTATGTTATTGCTATTTGTCTC<br>TTTTCTTGAAGTCTGAACAATTCTTGGGATTGTTTTGCAGGTTCTAGCTTCTCCAACCACAGA<br>AAGGGCAGATTGTGTCGACAGGTAATGGTTGTCTGGTAAAAGGACAGGGCCATCGCCAATT<br>GGAGTATTTTGTTGATAATGGTCTGCTAGTTGAACGGATCCATCTTCAATGTTGTGGCGAATT<br>TTGAAGTTAGCTTTGATTCCATTCTTTTGTTTGTCTGCCGTGATGTATACATTGTGTGAGTTAT<br>AGTTGTACTCGAGTTTGTGTCCGAGAATGTTTCCATCTTCTTTAAAATCAATACCTTTTAACT<br>CGATACGATTAACAAGGGTATCACCTTCAAACTTGACTTCAGCACGCGTCTTGTAGTTCCCG<br>TCATCTTTGAAAGATATAGTGCGTTCCTGTACATAACCTTCGGGCAAAGTTGTCTCCTCCTGC<br>ACTGACTGACTGATACAATCGATTTCTGGATCCGCAGGCCTCTGCTAGCTTGACTGACTGAG<br>ATACAGCGTACCTTCAGCTCACAGACATGATAAGATACATTGATGAGTTTGGACAAACCACA<br>ACTAGAATGCAGTGAAAAAAATGCTTTATTTGTGAAATTTGTGATGCTATTGCTTTATTTGTA<br>ACCATTATAAGCTGCAATAAACAAGTTAACAACAACAATTGCATTCATTTTATGTTTCAGGT<br>TCAGGGGGAGGTGTGGGAGGTTTTTTAAAGCAAGTAAAACCTCTACAAATGTGGTATTGGCC<br>CATCTCTATCGGTATCGTAGCATAACCCCTTGGGGCCTCTAAACGGGTCTTGAGGGGTTTTTT<br>GTGCCCCTCGGGCCGGATTGCTATCTACCGGCATTGGCGCAGAAAAAAATGCCTGATGCGAC<br>GCTGCGCGTCTTATACTCCCACATATGCCAGATTCAGCAACGGATACGGCTTCCCCAACTTG<br>CCCACTTCCATACGTGTCCTCCTTACCAGAAATTTATCCTTAAGGTCGTCAGCTATCCTGCAG<br>GCGATCTCTCGATTTCGATCAAGACATTCCTTTAATGGTCTTTTCTGGACACCACTAGGGGTC<br>AGAAGTAGTTCATCAAACTTTCTTCCCTCCCTAATCTCATTGGTTACCTTGGGCTATCGAAAC<br>TTAATTAACCAGTCAAGTCAGCTACTTGGCGAGATCGACTTGTCTGGGTTTCGACTACGCTC<br>AGAATTGCGTCAGTCAAGTTCGATCTGGTCCTTGCTATTGCACCCGTTCTCCGATTACGAGTT<br>TCATTTAAATCATGTGAGCAAAAGGCCAGCAAAAGGCCAGGAACCGTAAAAAGGCCGCGTT<br>GCTGGCGTTTTTCCATAGGCTCCGCCCCCCTGACGAGCATCACAAAAATCGACGCTCAAGTC<br>AGAGGTGGCGAAACCCGACAGGACTATAAAGATACCAGGCGTTTCCCCCTGGAAGCTCCCT<br>CGTGCGCTCTCCTGTTCCGACCCTGCCGCTTACCGGATACCTGTCCGCCTTTCTCCCTTCGGG<br>AAGCGTGGCGCTTTCTCATAGCTCACGCTGTAGGTATCTCAGTTCGGTGTAGGTCGTTCGCTC<br>CAAGCTGGGCTGTGTGCACGAACCCCCCGTTCAGCCCGACCGCTGCGCCTTATCCGGTAACT<br>ATCGTCTTGAGTCCAACCCGGTAAGACACGACTTATCGCCACTGGCAGCAGCCACTGGTAAC<br>AGGATTAGCAGAGCGAGGTATGTAGGCGGTGCTACAGAGTTCTTGAAGTGGTGGCCTAACT<br>ACGGCTACACTAGAAGAACAGTATTTGGTATCTGCGCTCTGCTGAAGCCAGTTACCTTCGGA<br>AAAAGAGTTGGTAGCTCTTGATCCGGCAAACAAACCACCGCTGGTAGCGGTGGTTTTTTTGT<br>TTGCAAGCAGCAGATTACGCGCAGAAAAAAAGGATCTCAAGAAGATCCTTTGATCTTTTCTA<br>CGGGGTCTGACGCTCAGTGGAACGAAAACTCACGTTAAGGGATTTTGGTCATGAGATTATCA<br>AAAAGGATCTTCACCTAGATCCTTTTAAATTAAAAATGAAGTTTTAAATCAATCTAAAGTAT<br>ATATGAGTAAACTTGGTCTGACAGTTACCAATGCTTAATCAGTGAGGCACCTATCTCAGCGA<br>TCTGTCTATTTCGTTCATCCATAGTTGCATTTAAATTTCCGAACTCTCCAAGGCCCTCGTCGG<br>AAAATCTTCAAACCTTTCGTCCGATCCATCTTGCAGGCTACCTCTCGAACGAACTATCGCAA<br>GTCTCTTGGCCGGCCTTGCGCCTTGGCTATTGCTTGGCAGCGCCTATCGCCAGGTATTACTCC<br>AATCCCGAATATCCGAGATCGGGATCACCCGAGAGAAGTTCAACCTACATCCTCAATCCCGA<br>TCTATCCGAGATCCGAGGAATATCGAAATCGGGGCGCGCCTGGTGTACCGAGAACGATCCTC<br>TCAGTGCGAGTCTCGACGATCCATATCGTTGCTTGGCAGTCAGCCAGTCGGAATCCAGCTTG<br>GGACCCAGGAAGTCCAATCGTCAGATATTGTACTCAAGCCTGGTCACGGCAGCGTACCGATC<br>TGTTTAAACCTAGATATTGATAGTCTGATCGGTCAACGTATAATCGAGTCCTAGCTTTTGCAA<br>ACATCTATCAAGAGACAGGATCAGCAGGAGGCTTTCGCATGATTGAACAAGATGGATTGCA<br>CGCAGGTTCTCCGGCGGCTTGGGTGGAGAGGCTATTCGGCTATGACTGGGCACAACAGACA<br>ATCGGCTGCTCTGATGCCGCCGTGTTCCGGCTGTCAGCGCAGGGGCGTCCGGTTCTTTTTGTC<br>AAGACCGACCTGTCCGGTGCCCTGAATGAACTGCAAGACGAGGCAGCGCGGCTATCGTGGC<br>TGGCGACGACGGGCGTTCCTTGCGCGGCTGTGCTCGACGTTGTCACTGAAGCGGGAAGGGA<br>CTGGCTGCTATTGGGCGAAGTGCCGGGGCAGGATCTCCTGTCATCTCACCTTGCTCCTGCCG<br>AGAAAGTATCCATCATGGCTGATGCAATGCGGCGGCTGCATACGCTTGATCCGGCTACCTGC<br>CCATTCGACCACCAAGCGAAACATCGCATCGAGCGAGCACGTACTCGGATGGAAGCCGGTC<br>TTGTCGATCAGGATGATCTGGACGAAGAGCATCAGGGGCTCGCGCCAGCCGAACTGTTCGCC<br>AGGCTCAAGGCGTCTATGCCCGACGGCGAGGATCTCGTCGTGACCCACGGCGATGCCTGCTT<br>GCCGAATATCATGGTGGAAAATGGCCGCTTTTCTGGATTCATCGACTGTGGCCGTCTGGGTG<br>TGGCGGACCGCTATCAGGACATAGCGTTGGCTACCCGTGATATTGCTGAAGAGCTTGGCGGC<br>GAATGGGCTGACCGCTTCCTTGTGCTTTACGGTATCGCCGCGCCCGATTCGCAGCGCATCGC<br>CTTCTATCGCCTTCTTGACGAGTTCTTCTGACCGATTCTAGGTGCATTGGCGCAGAAAAAAAT<br>GCCTGATGCGACGCTGCGCGTCTTATACTCCCACATATGCCAGATTCAGCAACGGATACGGC<br>TTCCCCAACTTGCCCACTTCCATACGTGTCCTCCTTACCAGAAATTTATCCTTAAGGTCGTTT<br>AAACTCGACTCTGGCTCTATCGAATCTCCGTCGTTTCGAGCTTACGCGAACAGCCGTGGCGC<br>TCATTTGCTCGTCGGGCATCGAATCTCGTCAGCTATCGTCAGCTTACCTTTTTGGCA |
| >pOXB-ADH-GHY4 (SEQ ID NO. 33)<br>GCGATCGCGGCTCCCGACATCTTGGACCATTAGCTCCACAGGTATCTTCTTCCCTCTAGTGGT<br>CATAACAGCAGCTTCAGCTACCTCTCAATTCAAAAAACCCCTCAAGACCCGTTTAGAGGCCC<br>CAAGGGGTTATGCTATCAATCGTTGCGTTACACACACAAAAAACCAACACACATCCATCTTC<br>GATGGATAGCGATTTTATTATCTAACTGCTGATCGAGTGTAGCCAGATCTAAGCTGTTGTGA<br>CCGCTTGCTCTAGCCAGCTATCGAGTTGTGAACCGATCCATCTAGCAATTGGTCTCGATCTAG |

TABLE 10-continued

| Sequence Listing for Exemplary hpRNAs. |
| --- |
| CGATAGGCTTCGATCTAGCTATGTATCACTCATTAGGCACCCCAGGCTTTACACTTTATGCTT<br>CCGGCTCGTATAATGTGTGGTGCTGGTTAGCGCTTGCTATAGATCTTTGTCGATCCTACCATC<br>CACTCGACACACCCGCCAGCGGCCGCTGCCAAGCTTCCGAGCTCTCGAATTCAAAGGAGGTA<br>CCCACCATGGGGTACCGCGATATCTACCTCGAGGTTTTGCCCGAAGGTTATGTACAGGAACG<br>CACTATATCTTTCAAAGATGACGGGAACTACAAGACGCGTGCTGAAGTCAAGTTTGAAGGTG<br>ATACCCTTGTTAATCGTATCGAGTTAAAAGGTATTGATTTTAAAGAAGATGGAAACATTCTC<br>GGACACAAACTCGAGTACAACTATAACTCACACAATGTATACATCACGGCAGACAAACAAA<br>AGAATGGAATCAAAGCTAACTTCAAAATTCGCCACAACATTGAAGATGGATCCGTTCAACTA<br>GCAGACCATTATCAACAAAATACTCCAATTGGCGATGGCCCTGTCCTTTTACCAGACAACCA<br>TTACCTGTCGACACAATCTGCCCTTTGATCAAGTGCAAAGGTCCGCCTTGTTTCTCCTCTGTC<br>TCTTGATCTGACTAATCTTGGTTTATGATTCGTTGAGTAATTTTGGGGAAAGCTAGCTTCGTC<br>CACAGTTTTTTTTTCGATGAACAGTGCCGCAGTGGCGCTGATCTTGTATGCTATCCTGCAATC<br>GTGGTGAACTTATGTCTTTTATATCCTTCACTACCATGAAAAGACTAGCTAGTAATCTTTCTC<br>GATGTAACATCGTCCAGCACTGCTATTACCGTGTGGTCCATCCGACAGTCTGGCTGAACACA<br>TCATACGATATTGAGCAAAGATCGATCTATCTTCCCTGTTCTTTAATGAAAGACGTCATTTTC<br>ATCAGTATGATCTAAGAATGTTGCAACTTGCAAGGAGGCGTTTCTTTCTTTGAATTTAACTAA<br>CTCGTTGAGTGGCCCTGTTTCTCGGACGTAAGGCCTTTGCTGCTCCACACATGTCCATTCGAA<br>TTTTACCGTGTTTAGCAAGGGCGAAAAGTTTGCATCTTGATGATTTAGCTTGACTATGCGATT<br>GCTTTCCTGGACCCGTGCAGCTGCGGAAAGGGCAGATTGTGTCGACAGGTAATGGTTGTCTG<br>GTAAAAGGACAGGGCCATCGCCAATTGGAGTATTTTGTTGATAATGGTCTGCTAGTTGAACG<br>GATCCATCTTCAATGTTGTGGCGAATTTTGAAGTTAGCTTTGATTCCATTCTTTTGTTTGTCTG<br>CCGTGATGTATACATTGTGTGAGTTATAGTTGTACTCGAGTTTGTGTCCGAGAATGTTTCCAT<br>CTTCTTTAAAATCAATACCTTTTAACTCGATACGATTAACAAGGGTATCACCTTCAAACTTGA<br>CTTCAGCACGCGTCTTGTAGTTCCCGTCATCTTTGAAAGATATAGTGCGTTCCTGTACATAAC<br>CTTCGGGCAAAGTTGTCTCCTCCTGCACTGACTGACTGATACAATCGATTTCTGGATCCGCAG<br>GCCTCTGCTAGCTTGACTGACTGAGATACAGCGTACCTTCAGCTCACAGACATGATAAGATA<br>CATTGATGAGTTTGGACAAACCACAACTAGAATGCAGTGAAAAAAATGCTTTATTTGTGAAA<br>TTTGTGATGCTATTGCTTTATTTGTAACCATTATAAGCTGCAATAAACAAGTTAACAACAACA<br>ATTGCATTCATTTTATGTTTCAGGTTCAGGGGGAGGTGTGGGAGGTTTTTTAAAGCAAGTAA<br>AACCTCTACAAATGTGGTATTGGCCCATCTCTATCGGTATCGTAGCATAACCCCTTGGGGCCT<br>CTAAACGGGTCTTGAGGGGTTTTTTGTGCCCCTCGGGCCGGATTGCTATCTACCGGCATTGGC<br>GCAGAAAAAAAATGCCTGATGCGACGCTGCGCGTCTTATACTCCCACATATGCCAGATTCAGC<br>AACGGATACGGCTTCCCCAACTTGCCCACTTCCATACGTGTCCTCCTTACCAGAAATTTATCC<br>TTAAGGTCGTCAGCTATCCTGCAGGCGATCTCTCGATTTCGATCAAGACATTCCTTTAATGGT<br>CTTTTCTGGACACCACTAGGGGTCAGAAGTAGTTCATCAAACTTTCTTCCCTCCCTAATCTCA<br>TTGGTTACCTTGGGCTATCGAAACTTAATTAACCAGTCAAGTCAGCTACTTGGCGAGATCGA<br>CTTGTCTGGGTTTCGACTACGCTCAGAATTGCGTCAGTCAAGTTCGATCTGGTCCTTGCTATT<br>GCACCCGTTCTCCGATTACGAGTTTCATTTAAATCATGTGAGCAAAAGGCCAGCAAAAGGCC<br>AGGAACCGTAAAAAGGCCGCGTTGCTGGCGTTTTTCCATAGGCTCCGCCCCCCTGACGAGCA<br>TCACAAAAATCGACGCTCAAGTCAGAGGTGGCGAAACCCGACAGGACTATAAAGATACCAG<br>GCGTTTCCCCCTGGAAGCTCCCTCGTGCGCTCTCCTGTTCCGACCCTGCCGCTTACCGGATAC<br>CTGTCCGCCTTTCTCCCTTCGGGAAGCGTGGCGCTTTCTCATAGCTCACGCTGTAGGTATCTC<br>AGTTCGGTGTAGGTCGTTCGCTCCAAGCTGGGCTGTGTGCACGAACCCCCCGTTCAGCCCGA<br>CCGCTGCGCCTTATCCGGTAACTATCGTCTTGAGTCCAACCCGGTAAGACACGACTTATCGC<br>CACTGGCAGCAGCCACTGGTAACAGGATTAGCAGAGCGAGGTATGTAGGCGGTGCTACAGA<br>GTTCTTGAAGTGGTGGCCTAACTACGGCTACACTAGAAGAACAGTATTTGGTATCTGCGCTC<br>TGCTGAAGCCAGTTACCTTCGGAAAAAGAGTTGGTAGCTCTTGATCCGGCAAACAAACCACC<br>GCTGGTAGCGGTGGTTTTTTTGTTTGCAAGCAGCAGATTACGCGCAGAAAAAAAGGATCTCA<br>AGAAGATCCTTTGATCTTTTCTACGGGGTCTGACGCTCAGTGGAACGAAAACTCACGTTAAG<br>GGATTTTGGTCATGAGATTATCAAAAAGGATCTTCACCTAGATCCTTTTAAATTAAAAATGA<br>AGTTTTAAATCAATCTAAAGTATATATGAGTAAACTTGGTCTGACAGTTACCAATGCTTAAT<br>CAGTGAGGCACCTATCTCAGCGATCTGTCTATTTCGTTCATCCATAGTTGCATTTAAATTTCC<br>GAACTCTCCAAGGCCCTCGTCGGAAAATCTTCAAACCTTTCGTCCGATCCATCTTGCAGGCT<br>ACCTCTCGAACGAACTATCGCAAGTCTCTTGGCCGGCCTTGCGCCTTGGCTATTGCTTGGCAG<br>CGCCTATCGCCAGGTATTACTCCAATCCCGAATATCCGAGATCGGGATCACCCGAGAGAAGT<br>TCAACCTACATCCTCAATCCCGATCTATCCGAGATCCGAGGAATATCGAAATCGGGGCGCGC<br>CTGGTGTACCGAGAACGATCCTCTCAGTGCGAGTCTCGACGATCCATATCGTTGCTTGGCAG<br>TCAGCCAGTCGGAATCCAGCTTGGGACCCAGGAAGTCCAATCGTCAGATATTGTACTCAAGC<br>CTGGTCACGGCAGCGTACCGATCTGTTTAAACCTAGATATTGATAGTCTGATCGGTCAACGT<br>ATAATCGAGTCCTAGCTTTTGCAAACATCTATCAAGAGACAGGATCAGCAGGAGGCTTTCGC<br>ATGATTGAACAAGATGGATTGCACGCAGGTTCTCCGGCGGCTTGGGTGGAGAGGCTATTCGG<br>CTATGACTGGGCACAACAGACAATCGGCTGCTCTGATGCCGCCGTGTTCCGGCTGTCAGCGC<br>AGGGGCGTCCGGTTCTTTTTGTCAAGACCGACCTGTCCGGTGCCCTGAATGAACTGCAAGAC<br>GAGGCAGCGCGGCTATCGTGGCTGGCGACGACGGGCGTTCCTTGCGCGGCTGTGCTCGACGT<br>TGTCACTGAAGCGGGAAGGGACTGGCTGCTATTGGGCGAAGTGCCGGGGCAGGATCTCCTG<br>TCATCTCACCTTGCTCCTGCCGAGAAAGTATCCATCATGGCTGATGCAATGCGGCGGCTGCA<br>TACGCTTGATCCGGCTACCTGCCCATTCGACCACCAAGCGAAACATCGCATCGAGCGAGCAC<br>GTACTCGGATGGAAGCCGGTCTTGTCGATCAGGATGATCTGGACGAAGAGCATCAGGGGCT<br>CGCGCCAGCCGAACTGTTCGCCAGGCTCAAGGCGTCTATGCCCGACGGCGAGGATCTCGTCG<br>TGACCCACGGCGATGCCTGCTTGCCGAATATCATGGTGGAAAATGGCCGCTTTTCTGGATTC<br>ATCGACTGTGGCCGTCTGGGTGTGGCGGACCGCTATCAGGACATAGCGTTGGCTACCCGTGA<br>TATTGCTGAAGAGCTTGGCGGCGAATGGGCTGACCGCTTCCTTGTGCTTTACGGTATCGCCG<br>CGCCCGATTCGCAGCGCATCGCCTTCTATCGCCTTCTTGACGAGTTCTTCTGACCGATTCTAG<br>GTGCATTGGCGCAGAAAAAAATGCCTGATGCGACGCTGCGCGTCTTATACTCCCACATATGC<br>CAGATTCAGCAACGGATACGGCTTCCCCAACTTGCCCACTTCCATACGTGTCCTCCTTACCAG<br>AAATTTATCCTTAAGGTCGTTTAAACTCGACTCTGGCTCTATCGAATCTCCGTCGTTTCGAGC<br>TTACGCGAACAGCCGTGGCGCTCATTTGCTCGTCGGGCATCGAATCTCGTCAGCTATCGTCA<br>GCTTACCTTTTTGGCA |

TABLE 10-continued

Sequence Listing for Exemplary hpRNAs.

>pAD-WRKY-GHY5 (SEQ ID NO. 34)
GAATTCGAGCTCGGTACCCGGGGATCGCGTGAAAGAAATTTTCGGCGCAGAGCACGTAAAT
GTTCAACCACACTCTGGTGCACAAGCGAACATGGCAGTATACTTCACGATTTTAGAGCAAGG
CGATACAGTACTTGGTATGAATTTATCTCATGGTGGTCACTTAACACACGGAAGCCCTGTTA
ACTTCAGTGGAGTACAATATAATTTCGTAGAATATGGCGTGGATGCTGACTCTCACCGTATT
AATTACGATGATGTATTAGCAAAAGCGAAAGAACATAAACCAAAATTAATCGTTGCAGGTG
CAAGTGCATACCCTCGTGTTATCGATTTCAAGCGATTCCGTGAGATTGCAGATGAAGTGGGC
GCTTATTTAATGGTTGATATGGCACATATCGCTGGTTTAGTAGCTGCTGGTTTACATCCAAAT
CCAGTACCACATGCACATTTCGTTACAACGACAACACATAAAACGTTACGTGGCCCGCGTGG
TGGTATGATTTTATGTGAAGAGCAATTTGCAAAACAAATTGATAAATCAATCTTCCCTGGTA
TTCAAGGTGGTCCACTTATGCACGTAATCGCTGCAAAAGCTGTTGCGTTTGGTGAAGCACTT
CAAGATGATTTCAAAACATATGCACAAAATATCATTAACAATGCGAACCGCTTAGCTGAAG
GTCTTCAAAAAGAAGGACTTACACTTGTTTCTGGCGGAACAGACAATCACTTAATCTTGATT
GATGTTCGTAACTTAGAAATCACAGGTAAAGTAGCAGAGCACGTATTAGATGAAGTTGGTAT
TACAGTGAACAAAAATACAATTCCATTTGAAACAGCAAGCCCATTTGTAACAAGTGGTGTAC
GTATCGGTACAGCAGCTGTAACATCTCGTGGTTTCGGTTTAGAAGAAATGGATGAAATTGCG
TCACTTATTGCTTATACATTAAAAAATCATGAAAATGAAGCTGCATTAGAAGAAGTACGTAA
GCGTGTAGAAGCGTTAACTAGCAAATTTCCAATGTATCCAAATCTATAATAGATTGAAGAAG
ACTGCCGAGACTTAATTGTTTTGGCGGTCTTTTTTGTGGACATATATTATTTTTAAAGTATGT
ATACAAATGATGAATAAATTTTGGCGATATAATGAAGGATACAGCTCCCATAATTGGTAAAG
ATACTAGATAGATTCATCGTAAAATCATGATTTTGCCAAATTTGCCCTTGAATATTAGTAGCG
TTTTCTTTACAATCGTAAATAGTGTAAAAAAGCGTGCAAACGCATGAATATCATCTAAAGGA
GAGATTCACATGGGAAAACTGTATGTATTTGATCCTCTAGATTTAAGAAGGAGATATACATT
GCCCGAAGGTTATGTACAGGAACGCACTATATCTTTCAAAGATGACGGGAACTACAAGACG
CGTGCTGAAGTCAAGTTTGAAGGTGATACCCTTGTTAATCGTATCGAGTTAAAAGGTATTGA
TTTTAAAGAAGATGGAAACATTCTCGGACACAAACTCGAGTACAACTATAACTCACACAATG
TATACATCACGGCAGACAAACAAAAGAATGGAATCAAAGCTAACTTCAAAATTCGCCACAA
CATTGAAGATGGATCCGTTCAACTAGCAGACCATTATCAACAAAATACTCCAATTGGCGATG
GCCCTGTCCTTTTACCAGACAACCATTACCTGTCGACACAATCTGCCCTTTCTCCTCCTCTGC
TAACGTAAGCCTCTCTGTTTTTTTTCTCTGTTTCTTTTGAAATGAATCCAATTAGTGATGATAA
TCTGTGTTTGATGTATCATTGATTTAACATCTTGACAATGAATCGTGATCGGAAGTGATAAA
GTTATGGGTCAACGGTTTCAAAGAGAGAGAAAGACTTTTAGAGTCAACTCTCGACTCTTTCT
TAATTATGTTATTGCTATTTGTCTCTTTTCTTGAAGTCTGAACAATTCTTGGGATTGTTTTGCA
GGTTCTAGCTTCTCCAACCACAGAAAGGGCAGATTGTGTCGACAGGTAATGGTTGTCTGGTA
AAAGGACAGGGCCATCGCCAATTGGAGTATTTTGTTGATAATGGTCTGCTAGTTGAACGGAT
CCATCTTCAATGTTGTGGCGAATTTTGAAGTTAGCTTTGATTCCATTCTTTTGTTTGTCTGCCG
TGATGTATACATTGTGTGAGTTATAGTTGTACTCGAGTTTGTGTCCGAGAATGTTTCCATCTT
CTTTAAAATCAATACCTTTTAACTCGATACGATTAACAAGGGTATCACCTTCAAACTTGACTT
CAGCACGCGTCTTGTAGTTCCCGTCATCTTTGAAAGATATAGTGCGTTCCTGTACATAACCTT
CGGGCATGCATAAACTGCATCCCTTAACTTGTTTTTCGTGTGCCTATTTTTTGTGAATCGCTA
AGAAACCATTATTATCATGACATTAACCTATAAAAATAGGCGTATCACGAGGCCCTTTCGTC
TCGCGCGTTTCGGTGATGACGGTGAAAACCTCTGACACATGCAGCTCCCGGAGACGGTCACA
GCTTGTCTGTAAGCGGATGCCGGGAGCAGACAAGCCCGTCAGGGCGCGTCAGCGGGTGTTG
GCGGGTGTCGGGGCTGGCTTAACTATGCGGCATCAGAGCAGATTGTACTGAGAGTGCACCAT
ACAAAACATATTTCAACACAATACAAATGGGTTAGTTAAAAAAGCAGGCCTTCTAAAGGTCT
GCTTTTTTTATTTGATTATGTAATTTTTAATGCCAGGATGCCAATAAGCCATAACCTCAAATG
CACCATTTGCAACCTCGTCATCTTCTTCCTCAATCTTGACCAGATCGCCGTCCTCCGCATCAC
CAAGATTCAGCTCTTTATGTATCTCCTTCAAAATGCCACCGTATCCAATTAACCTTCGAGCTG
CCAACGCATCATCCAAGTAAAGCACCGTGTTCAGATTGTCTTCAGTCACCTTATTACCGCGC
ACACAATCCGTATCCTTAACCGGATATTTAGAGATTTCGCGAACAGCTTTTTGCTCCATCATT
GCGTTCCGCACATCGTTTTCAATCTGTTCAGCGTCAATCTTAGCTTTACCTTTCACTCGACGA
ATATCGACAATTGGAGTGTAATCCAATTTCATCGCCTTTTTCCAAAGGCTCGTCCACTCCGCC
TGCTTAATATAGTTTTTCCCAAAATAATTTTTCCTTACTGGTATCAACACATGAAAATGAGGA
TGATATGTATCTTCTTCATGATTTTTGGTAATCTCTAAAGCTCTGAAAAATCCAAGAACCGAA
GTTTTTACTTTTTTGTACTGGAACAGTTTCCTAAAGCCTTCCATCATCGCAGAAATTTGTGGC
TTCAGCCGTTCTCCCTTTACATTTCGAATCGTCAGCGTGAGAAAAATCCATCCGCAGCCGTAC
TGTCTATTGGCTTCCTCTACGATCAACTTATTGTGATAAGCAATTTTTAACGACCTGCGCCAC
GCACACATCGGACATAACCTCACTTTACAAAAATGGGCTTGATACAGTTTTAACTTGCCCGT
CTCCGGGTCTCTCTTAAACGAAAGATACTCTGCACAACTAATTAGTTTTTCAGCCTTTTTGCC
ATAGTAAGGTGCCCCAATCTTACTCTCTAACGCTTCGTAATGCTCCGCCATGAGGTTCGTCCG
TCTCTTTTTCCCCTTCCAATCCCGCTTTTTACCTGTTGCGGTTTTATCTTCGAGGATGCTATAA
TCATTTTCAGATGAATAAATCAACAAAAAAACTCCTTCTGAGCTAGTTCTCTAGCATTCTATT
ATTTTGATTCGACACCTTAATAATAGCAGAAGGAGTTTTTACCTGTCAAAGAACCATCAAAC
CCTTGATACACAAGGCTTTGACCTAATTTTGAAAAATGATGTTGTTTCTATATAGTATCAAGA
TAAGAAAGAAAAGGATTTTTCGCTACGCTCAAATCCTTTAAAAAAACACAAAAGACCACAT
TTTTTAATGTGGTCTTTATTCTTCAACTAAAGCACCCATTAGTTCAACAAACGAAAATTGGAT
AAAGTGGGATATTTTTAAAATATATATTTATGTTACAGTAATATTGACTTTTAAAAAAGGATT
GATTCTAATGAAGAAAGCAGACAAGTAAGCCTCCTAAATTCACTTTAGATAAAAATTTAGGA
GGCATATCAAATGAACTTTAATAAAATTGATTTAGACAATTGGAAGAGAAAAGAGATATTT
AATCATTATTTGAACCAACAAACGACTTTTAGTATAACCACAGAAATTGATATTAGTGTTTT
ATACCGAAACATAAAACAAGAAGGATATAAATTTTACCCTGCATTTATTTTCTTAGTGACAA
GGGTGATAAACTCAAATACAGCTTTTAGAACTGGTTACAATAGCGACGGAGAGTTAGGTTAT
TGGGATAAGTTAGAGCCACTTTATACAATTTTTGATGGTGTATCTAAAACATTCTCTGGTATT
TGGACTCCTGTAAAGAATGACTTCAAAGAGTTTTATGATTTATACCTTTCTGATGTAGAGAA
ATATAATGGTTCGGGGAAATTGTTTCCCAAAACACCTATACCTGAAAATGCTTTTTCTCTTTC
TATTATTCCATGGACTTCATTTACTGGGTTTAACTTAAATATCAATAATAATAGTAATTACCT
TCTACCCATTATTACAGCAGGAAAATTCATTAATAAAGGTAATTCAATATATTTACCGCTATC

TABLE 10-continued

| Sequence Listing for Exemplary hpRNAs. |
|---|
| TTTACAGGTACATCATTCTGTTTGTGATGGTTATCATGCAGGATTGTTTATGAACTCTATTCA<br>GGAATTGTCAGATAGGCCTAATGACTGGCTTTTATAATATGAGATAATGCCGACTGTACTTT<br>TTACAGTCGGTTTTCTAATGTCACTAACCTGCCCCGTTAGTCGCCATTCGCCAGCTGCCTCGC<br>GCGTTTCGGTGATGACGGTGAAAACCTCTGACACATGCAGCTCCCGGAGACGGTCACAGCTT<br>GTCTGTAAGCGGATGCCGGGAGCAGACAAGCCCGTCAGGGCGCGTCAGCGGGTGTTGGCGG<br>GTGTCGGGGCGCAGCCATGACCCAGTCACGTAGCGATAGCGGAGTGTATACTGGCTTAACTA<br>TGCGGCATCAGAGCAGATTGTACTGAGAGTGCACCATATGCGGTGTGAAATACCGCACAGA<br>TGCGTAAGGAGAAAATACCGCATCAGGCGCTCTTCCGCTTCCTCGCTCACTGACTCGCTGCG<br>CTCGGTCGTTCGGCTGCGGCGAGCGGTATCAGCTCACTCAAAGGCGGTAATACGGTTATCCA<br>CAGAATCAGGGGATAACGCAGGAAAGAACATGTGAGCAAAAGGCCAGCAAAAGGCCAGGA<br>ACCGTAAAAAGGCCGCGTTGCTGGCGTT1TTCCATAGGCTCCGCCCCCCTGACGAGCATCAC<br>AAAAATCGACGCTCAAGTCAGAGGTGGCGAAACCCGACAGGACTATAAAGATACCAGGCGT<br>TTCCCCCTGGAAGCTCCCTCGTGCGCTCTCCTGTTCCGACCCTGCCGCTTACCGGATACCTGT<br>CCGCCTTTCTCCCTTCGGGAAGCGTGGCGCTTTCTCAATGCTCACGCTGTAGGTATCTCAGTT<br>CGGTGTAGGTCGTTCGCTCCAAGCTGGGCTGTGTGCACGAACCCCCCGTTCAGCCCGACCGC<br>TGCGCCTTATCCGGTAACTATCGTCTTGAGTCCAACCCGGTAAGACACGACTTATCGCCACT<br>GGCAGCAGCCACTGGTAACAGGATTAGCAGAGCGAGGTATGTAGGCGGTGCTACAGAGTTC<br>TTGAAGTGGTGGCCTAACTACGGCTACACTAGAAGGACAGTATTTGGTATCTGCGCTCTGCT<br>GAAGCCAGTTACCTTCGGAAAAAGAGTTGGTAGCTCTTGATCCGGCAAACAAACCACCGCT<br>GGTAGCGGTGGTTTTTTTGTTTGCAAGCAGCAGATTACGCGCAGAAAAAAAGGATCTCAAGA<br>AGATCCTTTGATCTTTTCTACGGGGTCTGACGCTCAGTGGAACGAAAACTCACGTTAAGGGA<br>TTTTGGTCATGAGATTATCAAAAAGGATCTTCACCTAGATCCTTTTAAATTAAAAATGAAGTT<br>TTAAATCAATCTAAAGTATATATGAGTAAACTTGGTCTGACAGTTACCAATGCTTAATCAGT<br>GAGGCACCTATCTCAGCGATCTGTCTATTTCGTTCATCCATAGTTGCCTGACTCCCCGTCGTG<br>TAGATAACTACGATACGGGAGGGCTTACCATCTGGCCCCAGTGCTGCAATGATACCGCGAG<br>ACCCACGCTCACCGGCTCCAGATTTATCAGCAATAAACCAGCCAGCCGGAAGGGCCGAGCG<br>CAGAAGTGGTCCTGCAACTTTATCCGCCTCCATCCAGTCTATTAATTGTTGCCGGGAAGCTA<br>GAGTAAGTAGTTCGCCAGTTAATAGTTTGCGCAACGTTGTTGCCATTGCTGCAGGCATCGTG<br>GTGTCACGCTCGTCGTTTGGTATGGCTTCATTCAGCTCCGGTTCCCAACGATCAAGGCGAGTT<br>ACATGATCCCCCATGTTGTGCAAAAAAGCGGTTAGCTCCTTCGGTCCTCCGATCGTTGTCAG<br>AAGTAAGTTGGCCGCAGTGTTATCACTCATGGTTATGGCAGCACTGCATAATTCTCTTACTGT<br>CATGCCATCCGTAAGATGCTTTTCTGTGACTGGTGAGTACTCAACCAAGTCATTCTGAGAAT<br>AGTGTATGCGGCGACCGAGTTGCTCTTGCCCGGCGTCAACACGGGATAATACCGCGCCACAT<br>AGCAGAACTTTAAAAGTGCTCATCATTGGAAAACGTTCTTCGGGGCGAAAACTCTCAAGGAT<br>CTTACCGCTGTTGAGATCCAGTTCGATGTAACCCACTCGTGCACCCAACTGATCTTCAGCATC<br>TTTTACTTTCACCAGCGTTTCTGGGTGAGCAAAAACAGGAAGGCAAAATGCCGCAAAAAAG<br>GGAATAAGGGCGACACGGAAATGTTGAATACTCATACTCTTCCTTTTTCAATATTATTGAAG<br>CATTTATCAGGGTTATTGTCTCATGAGCGGATACATATTTGAATGTATTTAGAAAAATAAAC<br>AAATAGGGGTTCCGCGCACATTTCCCCGAAAAGTGCCACCTGACGTCTAAGAAACCATTATT<br>ATCATGACATTAACCTATAAAAATAGGCGTATCACGAGGCCCTTTCGTCTTCAA |
| >pAD-ADH-GHY6 (SEQ ID NO. 35)<br>GAATTCGAGCTCGGTACCCGGGGATCGCGTGAAAGAAATTTTCGGCGCAGAGCACGTAAAT<br>GTTCAACCACACTCTGGTGCACAAGCGAACATGGCAGTATACTTCACGATTTTAGAGCAAGG<br>CGATACAGTACTTGGTATGAATTTATCTCATGGTGGTCACTTAACACACGGAAGCCCTGTTA<br>ACTTCAGTGGAGTACAATATAATTTCGTAGAATATGGCGTGGATGCTGACTCTCACCGTATT<br>AATTACGATGATGTATTAGCAAAAGCGAAAGAACATAAACCAAAATTAATCGTTGCAGGTG<br>CAAGTGCATACCCTCGTGTTATCGATTTCAAGCGATTCCGTGAGATTGCAGATGAAGTGGGC<br>GCTTATTTAATGGTTGATATGGCACATATCGCTGGTTTAGTAGCTGCTGGTTTACATCCAAAT<br>CCAGTACCACATGCACATTTCGTTACAACGACAACACATAAAACGTTACGTGGCCCGCGTGG<br>TGGTATGATTTTATGTGAAGAGCAATTTGCAAAACAAATTGATAAATCAATCTTCCCTGGTA<br>TTCAAGGTGGTCCACTTATGCACGTAATCGCTGCAAAAGCTGTTGCGTTTGGTGAAGCACTT<br>CAAGATGATTTCAAAACATATGCACAAAATATCATTAACAATGCGAACCGCTTAGCTGAAG<br>GTCTTCAAAAAGAAGGACTTACACTTGTTTCTGGCGGAACAGACAATCACTTAATCTTGATT<br>GATGTTCGTAACTTAGAAATCACAGGTAAAGTAGCAGAGCACGTATTAGATGAAGTTGGTAT<br>TACAGTGAACAAAAATACAATTCCATTTGAAACAGCAAGCCCATTTGTAACAAGTGGTGTAC<br>GTATCGGTACAGCAGCTGTAACATCTCGTGGTTTCGGTTTAGAAGAAATGGATGAAATTGCG<br>TCACTTATTGCTTATACATTAAAAAATCATGAAAATGAAGCTGCATTAGAAGAAGTACGTAA<br>GCGTGTAGAAGCGTTAACTAGCAAATTTCCAATGTATCCAAATCTATAATAGATTGAAGAAG<br>ACTGCCGAGACTTAATTGTTTTGGCGGTCTTTTTTGTGGACATATATTATTTTTAAAGTATGT<br>ATACAAATGATGAATAAATTTTGGCGATATAATGAAGGATACAGCTCCCATAATTGGTAAAG<br>ATACTAGATAGATTCATCGTAAAATCATGATTTTGCCAAATTTGCCCTTGAATATTAGTAGCG<br>TTTTCTTTACAATCGTAAATAGTGTAAAAAAGCGTGCAAACGCATGAATATCATCTAAAGGA<br>GAGATTCACATGGGAAAACTGTATGTATTTGATCCTCTAGATTTAAGAAGGAGATATACATT<br>GCCCGAAGGTTATGTACAGGAACGCACTATATCTTTCAAAGATGACGGGAACTACAAGACG<br>CGTGCTGAAGTCAAGTTTGAAGGTGATACCCTTGTTAATCGTATCGAGTTAAAAGGTATTGA<br>TTTTAAAGAAGATGGAAACATTCTCGGACACAAACTCGAGTACAACTATAACTCACACAATG<br>TATACATCACGGCAGACAAACAAAAGAATGGAATCAAAGCTAACTTCAAAATTCGCCACAA<br>CATTGAAGATGGATCCGTTCAACTAGCAGACCATTATCAACAAAATACTCCAATTGGCGATG<br>GCCCTGTCCTTTTACCAGACAACCATTACCTGTCGACACAATCTGCCCTTTGATCAAGTGCAA<br>AGGTCCGCCTTGTTTCTCCTCTGTCTCTTGATCTGACTAATCTTGGTTTATGATTCGTTGAGTA<br>ATTTGGGGAAAGCTAGCTTCGTCCACAGTTTTTTTTTCGATGAACAGTGCCGCAGTGGCGCT<br>GATCTTGTATGCTATCCTGCAATCGTGGTGAACTTATGTCTTTTATATCCTTCACTACCATGA<br>AAAGACTAGCTAGTAATCTTTCTCGATGTAACATCGTCCAGCACTGCTATTACCGTGTGGTCC<br>ATCCGACAGTCTGGCTGAACACATCATACGATATTGAGCAAAGATCGATCTATCTTCCCTGT<br>TCTTTAATGAAAGACGTCATTTTCATCAGTATGATCTAAGAATGTTGCAACTTGCAAGGAGG<br>CGTTTCTTTCTTTGAATTTAACTAACTCGTTGAGTGGCCCTGTTTCTCGGACGTAAGGCCTTT<br>GCTGCTCCACACATGTCCATTCGAATTTTACCGTGTTTAGCAAGGGCGAAAAGTTTGCATCTT |

TABLE 10-continued

| Sequence Listing for Exemplary hpRNAs. |
| --- |
| GATGATTTAGCTTGACTATGCGATTGCTTTCCTGGACCCGTGCAGCTGCGGAAAGGGCAGAT<br>TGTGTCGACAGGTAATGGTTGTCTGGTAAAAGGACAGGGCCATCGCCAATTGGAGTATTTTG<br>TTGATAATGGTCTGCTAGTTGAACGGATCCATCTTCAATGTTGTGGCGAATTTTGAAGTTAGC<br>TTTGATTCCATTCTTTTGTTTGTCTGCCGTGATGTATACATTGTGTGAGTTATAGTTGTACTCG<br>AGTTTGTGTCCGAGAATGTTTCCATCTTCTTTAAAATCAATACCTTTTAACTCGATACGATTA<br>ACAAGGGTATCACCTTCAAACTTGACTTCAGCACGCGTCTTGTAGTTCCCGTCATCTTTGAAA<br>GATATAGTGCGTTCCTGTACATAACCTTCGGGCATGCATAAACTGCATCCCTTAACTTGTTTT<br>TCGTGTGCCTATTTTTTGTGAATCGCTAAGAAACCATTATTATCATGACATTAACCTATAAAA<br>ATAGGCGTATCACGAGGCCCTTTCGTCTCGCGCGTTTCGGTGATGACGGTGAAAACCTCTGA<br>CACATGCAGCTCCCGGAGACGGTCACAGCTTGTCTGTAAGCGGATGCCGGGAGCAGACAAG<br>CCCGTCAGGGCGCGTCAGCGGGTGTTGGCGGGTGTCGGGGCTGGCTTAACTATGCGGCATCA<br>GAGCAGATTGTACTGAGAGTGCACCATACAAAACATATTTCAACACAATACAAATGGGTTA<br>GTTAAAAAAGCAGGCCTTCTAAAGGTCTGCTTTTTTTATTTGATTATGTAATTTTTAATGCCA<br>GGATGCCAATAAGCCATAACCTCAAATGCACCATTTGCAACCTCGTCATCTTCTTCCTCAATC<br>TTGACCAGATCGCCGTCCTCCGCATCACCAAGATTCAGCTCTTTATGTATCTCCTTCAAAATG<br>CCACCGTATCCAATTAACCTTCGAGCTGCCAACGCATCATCCAAGTAAAGCACCGTGTTCAG<br>ATTGTCTTCAGTCACCTTATTACCGCGCACACAATCCGTATCCTTAACCGGATATTTAGAGAT<br>TTCGCGAACAGCTTTTTGCTCCATCATTGCGTTCCGCACATCGTTTTCAATCTGTTCAGCGTC<br>AATCTTAGCTTTACCTTTCACTCGACGAATATCGACAATTGGAGTGTAATCCAATTTCATCGC<br>CTTTTTCCAAAGGCTCGTCCACTCCGCCTGCTTAATATAGTTTTTCCCAAAATAATTTTTCCTT<br>ACTGGTATCAACACATGAAAATGAGGATGATATGTATCTTCTTCATGATTTTTGGTAATCTCT<br>AAAGCTCTGAAAAATCCAAGAACCGAAGTTTTTACTTTTTTGTACTGGAACAGTTTCCTAAA<br>GCCTTCCATCATCGCAGAAATTTGTGGCTTCAGCCGTTCTCCCTTTACATTTCGAATCGTCAG<br>CGTGAGAAAAATCCATCCGCAGCCGTACTGTCTATTGGCTTCCTCTACGATCAACTTATTGTG<br>ATAAGCAATTTTTAACGACCTGCGCCACGCACACATCGGACATAACCTCACTTTACAAAAAT<br>GGGCTTGATACAGTTTTAACTTGCCCGTCTCCGGGTCTCTCTTAAACGAAAGATACTCTGCAC<br>AACTAATTAGTTTTTCAGCCTTTTTGCCATAGTAAGGTGCCCCAATCTTACTCTCTAACGCTT<br>CGTAATGCTCCGCCATGAGGTTCGTCCGTCTCTTMCCCCTTCCAATCCCGCTTTTTACCTGT<br>TGCGGTTTTATCTTCGAGGATGCTATAATCATTTTCAGATGAATAAATCAACAAAAAAACTC<br>CTTCTGAGCTAGTTCTCTAGCATTCTATTATTTTGATTCGACACCTTAATAATAGCAGAAGGA<br>GTTTTTACCTGTCAAAGAACCATCAAACCCTTGATACACAAGGCTTTGACCTAATTTTGAAA<br>AATGATGTTGTTTCTATATAGTATCAAGATAAGAAAGAAAAGGATTTTTCGCTACGCTCAAA<br>TCCTTTAAAAAAACACAAAAGACCACATTTTTTAATGTGGTCTTTATTCTTCAACTAAAGCAC<br>CCATTAGTTCAACAAACGAAAATTGGATAAAGTGGGATATTTTTAAAATATATATTTATGTT<br>ACAGTAATATTGACTTTTAAAAAAGGATTGATTCTAATGAAGAAAGCAGACAAGTAAGCCT<br>CCTAAATTCACTTTAGATAAAAATTTAGGAGGCATATCAAATGAACTTTAATAAAATTGATT<br>TAGACAATTGGAAGAGAAAAGAGATATTTAATCATTATTTGAACCAACAAACGACTTTTAGT<br>ATAACCACAGAAATTGATATTAGTGTTTTATACCGAAACATAAAACAAGAAGGATATAAATT<br>TTACCCTGCATTTATTTTCTTAGTGACAAGGGTGATAAACTCAAATACAGCTTTTAGAACTGG<br>TTACAATAGCGACGGAGAGTTAGGTTATTGGGATAAGTTAGAGCCACTTTATACAATTTTTG<br>ATGGTGTATCTAAAACATTCTCTGGTATTTGGACTCCTGTAAAGAATGACTTCAAAGAGTTTT<br>ATGATTTATACCTTTCTGATGTAGAGAAATATAATGGTTCGGGGAAATTGTTTCCCAAAACA<br>CCTATACCTGAAAATGCTTTTTCTCTTTCTATTATTCCATGGACTTCATTTACTGGGTTTAACT<br>TAAATATCAATAATAATAGTAATTACCTTCTACCCATTATTACAGCAGGAAAATTCATTAAT<br>AAAGGTAATTCAATATATTTACCGCTATCTTTACAGGTACATCATTCTGTTTGTGATGGTTAT<br>CATGCAGGATTGTTTATGAACTCTATTCAGGAATTGTCAGATAGGCCTAATGACTGGCTTTTA<br>TAATATGAGATAATGCCGACTGTACTTTTTACAGTCGGTTTTCTAATGTCACTAACCTGCCCC<br>GTTAGTCGCCATTCGCCAGCTGCCTCGCGCGTTTCGGTGATGACGGTGAAAACCTCTGACAC<br>ATGCAGCTCCCGGAGACGGTCACAGCTTGTCTGTAAGCGGATGCCGGGAGCAGACAAGCCC<br>GTCAGGGCGCGTCAGCGGGTGTTGGCGGGTGTCGGGGCGCAGCCATGACCCAGTCACGTAG<br>CGATAGCGGAGTGTATACTGGCTTAACTATGCGGCATCAGAGCAGATTGTACTGAGAGTGCA<br>CCATATGCGGTGTGAAATACCGCACAGATGCGTAAGGAGAAAATACCGCATCAGGCGCTCT<br>TCCGCTTCCTCGCTCACTGACTCGCTGCGCTCGGTCGTTCGGCTGCGGCGAGCGGTATCAGCT<br>CACTCAAAGGCGGTAATACGGTTATCCACAGAATCAGGGGATAACGCAGGAAAGAACATGT<br>GAGCAAAAGGCCAGCAAAAGGCCAGGAACCGTAAAAAGGCCGCGTTGCTGGCGTTTTTCCA<br>TAGGCTCCGCCCCCCTGACGAGCATCACAAAAATCGACGCTCAAGTCAGAGGTGGCGAAAC<br>CCGACAGGACTATAAAGATACCAGGCGTTTCCCCCTGGAAGCTCCCTCGTGCGCTCTCCTGT<br>TCCGACCCTGCCGCTTACCGGATACCTGTCCGCCTTTCTCCCTTCGGGAAGCGTGGCGCTTTC<br>TCAATGCTCACGCTGTAGGTATCTCAGTTCGGTGTAGGTCGTTCGCTCCAAGCTGGGCTGTGT<br>GCACGAACCCCCCGTTCAGCCCGACCGCTGCGCCTTATCCGGTAACTATCGTCTTGAGTCCA<br>ACCCGGTAAGACACGACTTATCGCCACTGGCAGCAGCCACTGGTAACAGGATTAGCAGAGC<br>GAGGTATGTAGGCGGTGCTACAGAGTTCTTGAAGTGGTGGCCTAACTACGGCTACACTAGAA<br>GGACAGTATTTGGTATCTGCGCTCTGCTGAAGCCAGTTACCTTCGGAAAAAGAGTTGGTAGC<br>TCTTGATCCGGCAAACAAACCACCGCTGGTAGCGGTGGTTTTTTTGTTTGCAAGCAGCAGAT<br>TACGCGCAGAAAAAAAGGATCTCAAGAAGATCCTTTGATCTTTTCTACGGGGTCTGACGCTC<br>AGTGGAACGAAAACTCACGTTAAGGGATTTTGGTCATGAGATTATCAAAAAGGATCTTCACC<br>TAGATCCTTTTAAATTAAAAATGAAGTTTTAAATCAATCTAAAGTATATATGAGTAAACTTG<br>GTCTGACAGTTACCAATGCTTAATCAGTGAGGCACCTATCTCAGCGATCTGTCTATTTCGTTC<br>ATCCATAGTTGCCTGACTCCCCGTCGTGTAGATAACTACGATACGGGAGGGCTTACCATCTG<br>GCCCCAGTGCTGCAATGATACCGCGAGACCCACGCTCACCGGCTCCAGATTTATCAGCAATA<br>AACCAGCCAGCCGGAAGGGCCGAGCGCAGAAGTGGTCCTGCAACTTTATCCGCCTCCATCC<br>AGTCTATTAATTGTTGCCGGGAAGCTAGAGTAAGTAGTTCGCCAGTTAATAGTTTGCGCAAC<br>GTTGTTGCCATTGCTGCAGGCATCGTGGTGTCACGCTCGTCGTTTGGTATGGCTTCATTCAGC<br>TCCGGTTCCCAACGATCAAGGCGAGTTACATGATCCCCCATGTTGTGCAAAAAAGCGGTTAG<br>CTCCTTCGGTCCTCCGATCGTTGTCAGAAGTAAGTTGGCCGCAGTGTTATCACTCATGGTTAT<br>GGCAGCACTGCATAATTCTCTTACTGTCATGCCATCCGTAAGATGCTTTTCTGTGACTGGTGA<br>GTACTCAACCAAGTCATTCTGAGAATAGTGTATGCGGCGACCGAGTTGCTCTTGCCCGGCGT<br>CAACACGGGATAATACCGCGCCACATAGCAGAACTTTAAAAGTGCTCATCATTGGAAAACG |

TABLE 10-continued

| Sequence Listing for Exemplary hpRNAs. |
| --- |

TTCTTCGGGGCGAAAACTCTCAAGGATCTTACCGCTGTTGAGATCCAGTTCGATGTAACCCA
CTCGTGCACCCAACTGATCTTCAGCATCTTTTACTTTCACCAGCGTTTCTGGGTGAGCAAAAA
CAGGAAGGCAAAATGCCGCAAAAAAGGGAATAAGGGCGACACGGAAATGTTGAATACTCA
TACTCTTCCTTTTTCAATATTATTGAAGCATTTATCAGGGTTATTGTCTCATGAGCGGATACA
TATTTGAATGTATTTAGAAAAATAAACAAATAGGGGTTCCGCGCACATTTCCCCGAAAAGTG
CCACCTGACGTCTAAGAAACCATTATTATCATGACATTAACCTATAAAAATAGGCGTATCAC
GAGGCCCTTTCGTCTTCAA

>pAD-WRKY-GRY7 (SEQ ID NO. 36)
GAATTCGAGCTCGGTACCCGGGGATCGCGTGAAAGAAATTTTCGGCGCAGAGCACGTAAAT
GTTCAACCACACTCTGGTGCACAAGCGAACATGGCAGTATACTTCACGATTTTAGAGCAAGG
CGATACAGTACTTGGTATGAATTTATCTCATGGTGGTCACTTAACACACGGAAGCCCTGTTA
ACTTCAGTGGAGTACAATATAATTTCGTAGAATATGGCGTGGATGCTGACTCTCACCGTATT
AATTACGATGATGTATTAGCAAAAGCGAAAGAACATAAACCAAAATTAATCGTTGCAGGTG
CAAGTGCATACCCTCGTGTTATCGATTTCAAGCGATTCCGTGAGATTGCAGATGAAGTGGGC
GCTTATTTAATGGTTGATATGGCACATATCGCTGGTTTAGTAGCTGCTGGTTTACATCCAAAT
CCAGTACCACATGCACATTTCGTTACAACGACAACACATAAAACGTTACGTGGCCCGCGTGG
TGGTATGATTTTATGTGAAGAGCAATTTGCAAAACAAATTGATAAATCAATCTTCCCTGGTA
TTCAAGGTGGTCCACTTATGCACGTAATCGCTGCAAAAGCTGTTGCGTTTGGTGAAGCACTT
CAAGATGATTTCAAAACATATGCACAAAATATCATTAACAATGCGAACCGCTTAGCTGAAG
GTCTTCAAAAAGAAGGACTTACACTTGTTTCTGGCGGAACAGACAATCACTTAATCTTGATT
GATGTTCGTAACTTAGAAATCACAGGTAAAGTAGCAGAGCACGTATTAGATGAAGTTGGTAT
TACAGTGAACAAAAATACAATTCCATTTGAAACAGCAAGCCCATTTGTAACAAGTGGTGTAC
GTATCGGTACAGCAGCTGTAACATCTCGTGGTTTCGGTTTAGAAGAAATGGATGAAATTGCG
TCACTTATTGCTTATACATTAAAAAATCATGAAAATGAAGCTGCATTAGAAGAAGTACGTAA
GCGTGTAGAAGCGTTAACTAGCAAATTTCCAATGTATCCAAATCTATAATAGATTGAAGAAG
ACTGCCGAGACTTAATTGTTTTGGCGGTCTTTTTTGTGGACATATATTATTTTTAAAGTATGT
ATACAAATGATGAATAAATTTTGGCGATATAATGAAGGATACAGCTCCCATAATTGGTAAAG
ATACTAGATAGATTCATCGTAAAATCATGATTTTGCCAAATTTGCCCTTGAATATTAGTAGCG
TTTTCTTTACAATCGTAAATAGTGTAAAAAAGCGTGCAAACGCATGAATATCATCTAAAGGA
GAGATTCACATGGGAAAACTGTATGTATTTGATCCTCTAGATTTAAGAAGGAGATATACATT
CTCGGATCTTACTACACAGCAGCTGCAAAGAAAAGATTTCAGTTCAAGGTCGTTCCCAATTA
TGCTATAACCACCCAGGACGCGATGAAAAACGTCTGGCAAGTTTTAGTTAATATTAGAAATG
TGAAGATGTCAGCGGGTTTCTGTCCGCTTTCTCTGGAGTTTGTGTCGGTGTGTATTGTTTATA
GAAATAATATAAAATTAGGTTTGAGAGAGAAGATTACAAACGTGAGAGACGGAGGGCCCAT
GGAACTTACAGAAGAAGTCGTTGATGAGTTCATGGAAGATGTCCCTATGTCGATCAGGCTTG
CAAAGTTTCGATCTCGAACCGGAAAAAAGAGTGATGTCCGCAAAGGGAACTCCTCCTCTGCT
AACGTAAGCCTCTCTGTTTTTTTCTCTGTTTCTTTTGAAATGAATCCAATTAGTGATGATAAT
CTGTGTTTGATGTATCATTGATTTAACATCTTGACAATGAATCGTGATCGGAAGTGATAAAG
TTATGGGTCAACGGTTTCAAAGAGAGAGAAAGACTTTTAGAGTCAACTCTCGACTCTTTCTT
AATTATGTTATTGCTATTTGTCTCTTTTCTTGAAGTCTGAACAATTCTTGGGATTGTTTTGCAG
GTTCTAGCTTCTCCAACCACAGTTCCCTTTGCGGACATCACTCTTTTTTCCGGTTCGAGATCG
AAACTTTGCAAGCCTGATCGACATAGGGACATCTTCCATGAACTCATCAACGACTTCTTCTG
TAAGTTCCATGGGCCCTCCGTCTCTCACGTTTGTAATCTTCTCTCTCAAACCTAATTTTATATT
ATTTCTATAAACAATACACACCGACACAAACTCCAGAGAAAGCGGACAGAAACCCGCTGAC
ATCTTCACATTTCTAATATTAACTAAAACTTGCCAGACGTTTTTCATCGCGTCCTGGGTGGTT
ATAGCATAATTGGGAACGACCTTGAACTGAAATCTTTTCTTTGCAGCTGCTGTGTAGTAAGA
TCCGAGATGCATAAACTGCATCCCTTAACTTGTTTTTCGTGTGCCTATTTTTTGTGAATCGCT
AAGAAACCATTATTATCATGACATTAACCTATAAAAATAGGCGTATCACGAGGCCCTTTCGT
CTCGCGCGTTTCGGTGATGACGGTGAAAACCTCTGACACATGCAGCTCCCGGAGACGGTCAC
AGCTTGTCTGTAAGCGGATGCCGGGAGCAGACAAGCCCGTCAGGGCGCGTCAGCGGGTGTT
GGCGGGTGTCGGGGCTGGCTTAACTATGCGGCATCAGAGCAGATTGTACTGAGAGTGCACC
ATACAAAACATATTTCAACACAATACAAATGGGTTAGTTAAAAAAGCAGGCCTTCTAAAGG
TCTGCTTTTTTTATTTGATTATGTAATTTTTAATGCCAGGATGCCAATAAGCCATAACCTCAA
ATGCACCATTTGCAACCTCGTCATCTTCTTCCTCAATCTTGACCAGATCGCCGTCCTCCGCAT
CACCAAGATTCAGCTCTTTATGTATCTCCTTCAAAATGCCACCGTATCCAATTAACCTTCGAG
CTGCCAACGCATCATCCAAGTAAAGCACCGTGTTCAGATTGTCTTCAGTCACCTTATTACCGC
GCACACAATCCGTATCCTTAACCGGATATTTAGAGATTTCGCGAACAGCTTTTTGCTCCATCA
TTGCGTTCCGCACATCGTTTTCAATCTGTTCAGCGTCAATCTTAGCTTTACCTTTCACTCGACG
AATATCGACAATTGGAGTGTAATCCAATTTCATCGCCTTTTTCCAAAGGCTCGTCCACTCCGC
CTGCTTAATATAGTTTTTCCCAAAATAATTTTTCCTTACTGGTATCAACACATGAAAATGAGG
ATGATATGTATCTTCTTCATGATTTTTGGTAATCTCTAAAGCTCTGAAAAAATCCAAGAACCGA
AGTTTTTACTTTTTGTACTGGAACAGTTTCCTAAAGCCTTCCATCATCGCAGAAATTTGTGG
CTTCAGCCGTTCTCCCTTTACATTTCGAATCGTCAGCGTGAGAAAAATCCATCCGCAGCCGTA
CTGTCTATTGGCTTCCTCTACGATCAACTTATTGTGATAAGCAATTTTTAACGACCTGCGCCA
CGCACACATCGGACATAACCTCACTTTACAAAAATGGGCTTGATACAGTTTAACTTGCCCG
TCTCCGGGTCTCTCTTAAACGAAAGATACTCTGCACAACTAATTAGTTTTTCAGCCTTTTTGC
CATAGTAAGGTGCCCCAATCTTACTCTCTAACGCTTCGTAATGCTCCGCCATGAGGTTCGTCC
GTCTCTTTTTCCCCTTCCAATCCCGCTTTTTACCTGTTGCGGTTTTATCTTCGAGGATGCTATA
ATCATTTTCAGATGAATAAATCAACAAAAAAACTCCTTCTGAGCTAGTTCTCTAGCATTCTAT
TATTTTGATTCGACACCTTAATAATAGCAGAAGGAGTTTTTACCTGTCAAAGAACCATCAAA
CCCTTGATACACAAGGCTTTGACCTAATTTTGAAAAATGATGTTGTTTCTATATAGTATCAAG
ATAAGAAAGAAAAGGATTTTTCGCTACGCTCAAATCCTTTAAAAAAACACAAAAGACCACA
TTTTTTAATGTGGTCTTTATTCTTCAACTAAAGCACCCATTAGTTCAACAAACGAAAATTGGA
TAAAGTGGGATATTTTTAAAATATATATTTATGTTACAGTAATATTGACTTTTAAAAAAGGAT
TGATTCTAATGAAGAAAGCAGACAAGTAAGCCTCCTAAATTCACTTTAGATAAAAAATTTAGG
AGGCATATCAAATGAACTTTAATAAAATTGATTTAGACAATTGGAAGAGAAAAGAGATATT
TAATCATTATTTGAACCAACAAACGACTTTTAGTATAACCACAGAAATTGATATTAGTGTTTT

TABLE 10-continued

| Sequence Listing for Exemplary hpRNAs. |
|---|
| ATACCGAAACATAAAACAAGAAGGATATAAATTTTACCCTGCATTTATTTTCTTAGTGACAA |
| GGGTGATAAACTCAAATACAGCTTTTAGAACTGGTTACAATAGCGACGGAGAGTTAGGTTAT |
| TGGGATAAGTTAGAGCCACTTTATACAATTTTTGATGGTGTATCTAAAACATTCTCTGGTATT |
| TGGACTCCTGTAAAGAATGACTTCAAAGAGTTTTATGATTTATACCTTTCTGATGTAGAGAA |
| ATATAATGGTTCGGGGAAATTGTTTCCCAAAACACCTATACCTGAAAATGCTTTTTCTCTTTC |
| TATTATTCCATGGACTTCATTTACTGGGTTTAACTTAAATATCAATAATAATAGTAATTACCT |
| TCTACCCATTATTACAGCAGGAAAATTCATTAATAAAGGTAATTCAATATATTTACCGCTATC |
| TTTACAGGTACATCATTCTGTTTGTGATGGTTATCATGCAGGATTGTTTATGAACTCTATTCA |
| GGAATTGTCAGATAGGCCTAATGACTGGCTTTTATAATATGAGATAATGCCGACTGTACTTT |
| TTACAGTCGGTTTTCTAATGTCACTAACCTGCCCCGTTAGTCGCCATTCGCCAGCTGCCTCGC |
| GCGTTTCGGTGATGACGGTGAAAACCTCTGACACATGCAGCTCCCGGAGACGGTCACAGCTT |
| GTCTGTAAGCGGATGCCGGGAGCAGACAAGCCCGTCAGGGCGCGTCAGCGGGTGTTGGCGG |
| GTGTCGGGGCGCAGCCATGACCCAGTCACGTAGCGATAGCGGAGTGTATACTGGCTTAACTA |
| TGCGGCATCAGAGCAGATTGTACTGAGAGTGCACCATATGCGGTGTGAAATACCGCACAGA |
| TGCGTAAGGAGAAAATACCGCATCAGGCGCTCTTCCGCTTCCTCGCTCACTGACTCGCTGCG |
| CTCGGTCGTTCGGCTGCGGCGAGCGGTATCAGCTCACTCAAAGGCGGTAATACGGTTATCCA |
| CAGAATCAGGGGATAACGCAGGAAAGAACATGTGAGCAAAAGGCCAGCAAAAGGCCAGGA |
| ACCGTAAAAAGGCCGCGTTGCTGGCGTTTTTCCATAGGCTCCGCCCCCCTGACGAGCATCAC |
| AAAAATCGACGCTCAAGTCAGAGGTGGCGAAACCCGACAGGACTATAAAGATACCAGGCGT |
| TTCCCCCTGGAAGCTCCCTCGTGCGCTCTCCTGTTCCGACCCTGCCGCTTACCGGATACCTGT |
| CCGCCTTTCTCCCTTCGGGAAGCGTGGCGCTTTCTCAATGCTCACGCTGTAGGTATCTCAGTT |
| CGGTGTAGGTCGTTCGCTCCAAGCTGGGCTGTGTGCACGAACCCCCCGTTCAGCCCGACCGC |
| TGCGCCTTATCCGGTAACTATCGTCTTGAGTCCAACCCGGTAAGACACGACTTATCGCCACT |
| GGCAGCAGCCACTGGTAACAGGATTAGCAGAGCGAGGTATGTAGGCGGTGCTACAGAGTTC |
| TTGAAGTGGTGGCCTAACTACGGCTACACTAGAAGGACAGTATTTGGTATCTGCGCTCTGCT |
| GAAGCCAGTTACCTTCGGAAAAAGAGTTGGTAGCTCTTGATCCGGCAAACAAACCACCGCT |
| GGTAGCGGTGGTTTTTTTGTTTGCAAGCAGCAGATTACGCGCAGAAAAAAAGGATCTCAAGA |
| AGATCCTTTGATCTTTTCTACGGGGTCTGACGCTCAGTGGAACGAAAACTCACGTTAAGGGA |
| TTTTGGTCATGAGATTATCAAAAAGGATCTTCACCTAGATCCTTTTAAATTAAAAATGAAGTT |
| TTAAATCAATCTAAAGTATATATGAGTAAACTTGGTCTGACAGTTACCAATGCTTAATCAGT |
| GAGGCACCTATCTCAGCGATCTGTCTATTTCGTTCATCCATAGTTGCCTGACTCCCCGTCGTG |
| TAGATAACTACGATACGGGAGGGCTTACCATCTGGCCCCAGTGCTGCAATGATACCGCGAG |
| ACCCACGCTCACCGGCTCCAGATTTATCAGCAATAAACCAGCCAGCCGGAAGGGCCGAGCG |
| CAGAAGTGGTCCTGCAACTTTATCCGCCTCCATCCAGTCTATTAATTGTTGCCGGGAAGCTA |
| GAGTAAGTAGTTCGCCAGTTAATAGTTTGCGCAACGTTGTTGCCATTGCTGCAGGCATCGTG |
| GTGTCACGCTCGTCGTTTGGTATGGCTTCATTCAGCTCCGGTTCCCAACGATCAAGGCGAGTT |
| ACATGATCCCCCATGTTGTGCAAAAAAGCGGTTAGCTCCTTCGGTCCTCCGATCGTTGTCAG |
| AAGTAAGTTGGCCGCAGTGTTATCACTCATGGTTATGGCAGCACTGCATAATTCTCTTACTGT |
| CATGCCATCCGTAAGATGCTTTTCTGTGACTGGTGAGTACTCAACCAAGTCATTCTGAGAAT |
| AGTGTATGCGGCGACCGAGTTGCTCTTGCCCGGCGTCAACACGGGATAATACCGCGCCACAT |
| AGCAGAACTTTAAAAGTGCTCATCATTGGAAAACGTTCTTCGGGGCGAAAACTCTCAAGGAT |
| CTTACCGCTGTTGAGATCCAGTTCGATGTAACCCACTCGTGCACCCAACTGATCTTCAGCATC |
| TTTTACTTTCACCAGCGTTTCTGGGTGAGCAAAAACAGGAAGGCAAAATGCCGCAAAAAAG |
| GGAATAAGGGCGACACGGAAATGTTGAATACTCATACTCTTCCTTTTTCAATATTATTGAAG |
| CATTTATCAGGGTTATTGTCTCATGAGCGGATACATATTTGAATGTATTTAGAAAAATAAAC |
| AAATAGGGGTTCCGCGCACATTTCCCCGAAAAGTGCCACCTGACGTCTAAGAAACCATTATT |
| ATCATGACATTAACCTATAAAAATAGGCGTATCACGAGGCCCTTTCGTCTTCAA |

TABLE 11

| Sequence Listing for RNaseIII mutants |
|---|
| >*Escherichia_coli*_str._K-12_substr. MG1655_rnc gene (SEQ ID NO. 37) |
| ATGAACCCCATCGTAATTAATCGGCTTCAACGGAAGCTGGGCTACACTTTTAATCATCAGGA |
| ACTGTTGCAGCAGGCATTAACTCATCGTAGTGCCAGCAGTAAACATAACGAGCGTTTAGAAT |
| TTTTAGGCGACTCTATTCTGAGCTACGTTATCGCCAATGCGCTTTATCACCGTTTCCCTCGTG |
| TGGATGAAGGCGATATGAGCCGGATGCGCGCCACGCTGGTCCGTGGCAATACGCTGGCGGA |
| ACTGGCGCGCGAATTTGAGTTAGGCGAGTGCTTACGTTTAGGGCCAGGTGAACTTAAAAGCG |
| GTGGATTTCGTCGTGAGTCAATTCTCGCCGACACCGTCGAAGCATTAATTGGTGGCGTATTC |
| CTCGACAGTGATATTCAAACCGTCGAGAAATTAATCCTCAACTGGTATCAAACTCGTTTGGA |
| CGAAATTAGCCCAGGCGATAAACAAAAAGATCCGAAAACGCGCTTGCAAGAATATTTGCAG |
| GGTCGCCATCTGCCGCTGCCGACTTATCTGGTAGTCCAGGTACGTGGCGAAGCGCACGATCA |
| GGAATTTACTATCCACTGCCAGGTCAGCGGCCTGAGTGAACCGGTGGTTGGCACAGGTTCAA |
| GCCGTCGTAAGGCTGAGCAGGCTGCCGCCGAACAGGCGTTGAAAAAACTGGAGCTGGAATG |
| A |
| |
| >M-JM109-GHY1-Kanymycin-resistant-mutant-1936 bp (SEQ ID NO. 38) |
| ACCGGTAAACTGAAACTGCAGCGAAGCAGTTAGCAGAACCATGTATATCAGGTCTGTTTCGT |
| GTGCTGAATTGTTGACGCATTTATTTATTGGTATCGCATGAACCCCATCGTAATTAATCGGCT |
| TCAACGGAAGCTGGGCTACACTTTAGCGATTGTGTAGGCTGGAGCTGCTTCGAAGTTCCTAT |
| ACTTTCTAGAGAATAGGAACTTCGGAATAGGAACTTCAAGATCCCCTCACGCTGCCGCAAGC |
| ACTCAGGGCGCAAGGGCTGCTAAAGGAAGCGGAACACGTAGAAAGCCAGTCCOCAGAAAC |
| GGTGCTGACCCCGGATGAATGTCAGCTACTGGGCTATCTGGACAAGGGAAAACGCAAGCGC |
| AAAGAGAAAGCAGGTAGCTTGCAGTGGGCTTACATGGCGATAGCTAGACTGGGCGGTTTTA |
| TGGACAGCAAGCGAACCGGAATTGCCAGCTGGGGCGCCCTCTGGTAAGGTTGGGAAGCCCT |

TABLE 11-continued

Sequence Listing for RNaseIII mutants

GCAAAGTAAACTGGATGGCTTTCTTGCCGCCAAGGATCTGATGGCGCAGGGGATCAAGATCT
GATCAAGAGACAGGATGAGGATCGTTTCGCATGATTGAACAAGATGGATTGCACGCAGGTT
CTCCGGCCGCTTGGGTGGAGAGGCTATTCGGCTATGACTGGGCACAACAGACAATCGGCTGC
TCTGATGCCGCCGTGTTCCGGCTGTCAGCGCAGGGGCGCCCGGTTCTTTTTGTCAAGACCGA
CCTGTCCGGTGCCCTGAATGAACTGCAGGACGAGGCAGCGCGGCTATCGTGGCTGGCCACG
ACGGGCGTTCCTTGCGCAGCTGTGCTCGACGTTGTCACTGAAGCGGGAAGGGACTGGCTGCT
ATTGGGCGAAGTGCCGGGGCAGGATCTCCTGTCATCTCACCTTGCTCCTGCCGAGAAAGTAT
CCATCATGGCTGATGCAATGCGGCGGCTGCATACGCTTGATCCGGCTACCTGCCCATTCGAC
CACCAAGCGAAACATCGCATCGAGCGAGCACCTTACTCGGATGGAAGCCGGTCTTGTCGATC
AGGATGATCTGGACGAAGAGCATCAGGGGCTCGCGCCAGCCGAACTGTTCGCCAGGCTCAA
GGCGCGCATGCCCGACGGCGAGGATCTCGTCGTGACCCATGGCGATGCCTGCTTGCCGAATA
TCATGGTGGAAAATGGCCGCTTTTCTGGATTCATCGACTGTGGCCGGCTGGGTGTGGCGGAC
CGCTATCAGGACATAGCGTTGGCTACCCGTGATATTGCTGAAGAGCTTGGCGGCGAATGGGC
TGACCGCTTCCTCGTGCTTTACGGTATCGCCGCTCCCGATTCGCAGCGCATCGCCTTCTATCG
CCTTCTTGACGAGTTCTTCTGAGCGGGACTCTGGGGTTCGAAATGACCGACCAAGCGACGCC
CAACCTGCCATCACGAGATTTCGATTCCACCGCCGCCTTCTATGAAAGGTTGGGCTTCGGAA
TCGTTTTCCGGGACGCCGGCTGGATGATCCTCCAGCGCGGGGATCTCATGCTGGAGTTCTTC
GCCCACCCCAGCTTCAAAAGCGCTCTGAAGTTCCTATACTTTCTAGAGAATAGGAACTTCGG
AATAGGAACTAAGGAGGATATTCATATGGACCATGGCTAATTCCCATGTCAGCCGTTAACGC
TGCCGACTTATCTGGTAGTCCAGGTACGTGGCGAAGCGCACGATCAGGAATTTACTATCCAC
TGCCAGGTGAGCGGCCTGAGTGAACCGGTGGTTGGCACAGGTTCAAGCCGTCGTAAGGCTG
AGCAGGCTGCCGCCGAACAGGCGTTGAAAAAACTGGAGCTGGAATGAGCATCGATAAAAGT
TACTGCGGATTTATTGCCATCGTCGGACGTCCGAACGTTGGCAAATCCACATTGTTGAACAA
ACTGCTGGGGCAGAAAATCTCCA

>M-JM109-GHY1-mutant-543 bp (SEQ ID NO. 39)
ACCGGTAAACTGAAACTGCAGCGAAGCAGTTAGCAGAACCATGTATATCAGGTCTGTTTCGT
GTGCTGAATTGTTGACGCATTTATTTATTGGTATCGCATGAACCCCATCGTAATTAATCGGCT
TCAACGGAAGCTGGGCTACACTTTAGCGATTGTGTAGGCTGGAGCTGCTTCGAAGTTCCTAT
ACTTTCTAGAGAATAGGAACTTCGGAATAGGAACTAAGGAGGATATTCATATGGACCATGG
CTAATTCCCATGTCAGCCGTTAACGCTGCCGACTTATCTGGTAGTCCAGGTACGTGGCGAAG
CGCACGATCAGGAATTTACTATCCACTGCCAGGTCAGCGGCCTGAGTGAACCGGTGGTTGGC
ACAGGTTCAAGCCGTCGTAAGGCTGAGCAGGCTGCCGCCGAACAGGCGTTGAAAAAACTGG
AGCTGGAATGAGCATCGATAAAAGTTACTGCGGATTTATTGCCATCGTCGGACGTCCGAACG
TTGGCAAATCCACATTGTTGAACAAACTGCTGGGGCAGAAAATCTCCA

TABLE 12

Sequence Listing *B. cereus* 53522 (UW85) sequencing

>Bc53522-16SrRNA-complete-1514 (SEQ ID NO. 40)
AGAGTTTGATCCTGGCTCAGGATGAACGCTGGCGGCGTGCCTAATACATGCAAGTCGAGCG
AATGGATTGAGAGCTTGCTCTCAAGAAGTTAGCGGCGGACGGGTGAGTAACACGTGGGTAA
CCTGCCCATAAGACTGGGATAACTCCGGGAAACCGGGGCTAATACCGGATAACATTTTGAA
CTGCATGGTTCGAAATTGAAAGGCGGCTTCGGCTGTCACTTATGGATGGACCCGCGTCGCAT
TAGCTAGTTGGTGAGGTAACGGCTCACCAAGGCAACGATGCGTAGCCGACCTGAGAGGGTG
ATCGGCCACACTGGGACTGAGACACGGCCCAGACTCCTACGGGAGGCAGCAGTAGGGAATC
TTCCGCAATGGACGAAAGTCTGACGGAGCAACGCCGCGTGAGTGATGAAGGCTTTCGGGTC
GTAAAACTCTGTTGTTAGGGAAGAACAAGTGCTAGTTGAATAAGCTGGCACCTTGACGGTAC
CTAACCAGAAAGCCACGGCTAACTACGTGCCAGCAGCCGCGGTAATACGTAGGTGGCAAGC
GTTATCCGGAATTATTGGGCGTAAAGCGCGCGCAGGTGGTTTCTTAAGTCTGATGTGAAAGC
CCACGGCTCAACCGTGGAGGGTCATTGGAAACTGGGAGACTTGAGTGCAGAAGAGGAAAGT
GGAATTCCATGTGTAGCGGTGAAATGCGTAGAGATATGGAGGAACACCAGTGGCGAAGGCG
ACTTTCTGGTCTGTAACTGACACTGAGGCGCGAAAGCGTGGGGAGCAAACAGGATTAGATA
CCCTGGTAGTCCACGCCGTAAACGATGAGTGCTAAGTGTTAGAGGGTTTCCGCCCTTTAGTG
CTGAAGTTAACGCATTAAGCACTCCGCCTGGGGAGTACGGCCGCAAGGCTGAAACTCAAAG
GAATTGACGGGGGCCCGCACAAGCGGTGGAGCATGTGGTTTAATTCGAAGCAACGCGAAGA
ACCTTACCAGGTCTTGACATCCTCTGAAAACCCTAGAGATAGGGCTTCTCCTTCGGGAGCAG
AGTGACAGGTGGTGCATGGTTGTCGTCAGCTCGTGTCGTGAGATGTTGGGTTAAGTCCCGCA
ACGAGCGCAACCCTTGATCTTAGTTGCCATCATTAAGTTGGGCACTCTAAGGTGACTGCCGG
TGACAAACCGGAGGAAGGTGGGGATGACGTCAAATCATCATGCCCCTTATGACCTGGGCTA
CACACGTGCTACAATGGACGGTACAAAGAGCTGCAAGACCGCGAGGTGGAGCTAATCTCAT
AAAACCGTTCTCAGTTCGGATTGTAGGCTGCAACTCGCCTACATGAAGCTGGAATCGCTAGT
AATCGCGGATCAGCATGCCGCGGTGAATACGTTCCCGGGCCTTGTACACACCGCCCGTCACA
CCACGAGAGTTTGTAACACCCGAAGTCGGTGGGGTAACCTTTTTGGAGCCAGCCGCCTAAGG
TGGGACAGATGATTGGGGTGAAGTCGTAACAAGGTAACCG >BC53522-23S-rRNA-complete-855 (SEQ ID NO. 41)
AGAGTGCGTAATAGCTCACTAGTCGAGTGACTCTGCGCCGAAAATGTACCGGGGCTAAATA
CACCACCGAAGCTGCGAATTGATACCAATGGTATCAGTGGTAGGGGAGCGTTCTAAGTGCA
GTGAAGTCAGACCGGAAGGACTGGTGGAGCGCTTAGAAGTGAGAATGCCGGTATGAGTAGC
GAAAGACGGGTGAGAATCCCGTCCACCGAATGCCTAAGGTTTCCTGAGGAAGGCTCGTCCG
CTCAGGGTTAGTCAGGACCTAAGCCGAGGCCGACAGGCGTAGGCGATGGACAACAGGTTGA
TATTCCTGTACCACCTCTTTATCGTTTGAGCAATGGAGGGACGCAGAAGGATAGAAGAAGCG
TGCGATTGGTTGTGCACGTCCAAGCAGTTAGGCTGATAAGTAGGCAAATCCGCTTATCGTGA TABLE 12-continued Sequence Listing *B. cereus* 53522 (UW85) sequencing

```
AGGCTGAGCTGTGATGGGGAAGCTCCTTATGGAGCGAAGTCTTTGATTCCCCGCTGCCAAGA
AAAGCTTCTAGCGAGATAAAAGGTGCCTGTACCGCAAACCGACACAGGTAGGCGAGGAGAG
AATCCTAAGGTGTGCGAGAGAACTCTGGTTAAGGAACTCGGCAAAATGACCCCGTAACTTC
GGGAGAAGGGGTGCTTTCTTAACGGAAAGCCGCAGTGAATAGGCCCAAGCGACTGTTTAGC
AAAAACACAGCTCTCTGCGAAGCCGTAAGGCGAAGTATAGGGGGTGACACCTGCCCGGTGC
TGGAAGGTTAAGGAGAGGGGTTAGCGTAAGCGAAGCTCTGAACTGAAGCCCCAGTAAACGG
CGGCCGTAACTATAACGGTCCTAAGGTAGCGAAATTCCTTGTCGGTAAGTTCTAGACCG

>BC53522-motB-574 (SEQ ID NO. 42)
TCGCCTCGTTGGATGACGACTTTTACAGATTTAACGATGTTATTATTAACTTTCTTCGTATTA
CTAGTTGCTACATCAAAGCAAGATGCAGTAAAATTGTCAAAGATGCTTGAAAATTTTAGTGA
TACGGGGCAAGTAGATGCAAAAGTAATGGAAAATACAATACCAGATATTTCACATGAAAAA
AATGATGAAAAAATGATCTCAAAAAAGAGAATGGATGAATTATATAAGAAGTTGAAAGCGT
ATGTAGATAATAACGGTATTAGTCAAGTGAATGTATATCGAGAGGATACAGGGGTAAGCGT
CGTTATAGTAGATAATTTAATATTTGATACAGGCGATGCGAACGTTAAGCCCGAAGCGAAAG
GGATAATAAGTCAATTAGTTGGATTTTTTCAATCCGTACCTAACCCAATTGTTGTAGAGGGA
CATACAGATAGTAGACCTATTCATAACGAGAAATTCCCTTCTAATTGGGAGTTATCTTCAGC
ACGAGCGGCAAATATGATTCACCATTTAATTGAAGTGTATAATGTGGATGATAAAAGGCTAG
CTGCGGTAGGATATGCAG

>Bc53522-endoglucanase-complete-659 (SEQ ID NO. 43)
CCAGTAGCCAAGAATGGCCAGCAACCAGCAAGTGGATTCCAACCGCCTGATTTCATTAGTTC
TGACATTTCTTTTTGATACTGCTTTTGTTTTTCAAGGTCTTTGCTTACATCACCGTACTTTTTCT
TTAGCTTCTGCAGTTCAGGTTGCATTTTCTTCATTTTCGCTTGACTGCGATATTGCGAAACAG
CTAATGGAATCATTGCTGAACGAATAACGAGCGTCATAATAATGATGGCAATCCCAAAGCT
AGCTCCAGGTATATGATGAGCGACAAATTGAATCATAAACGAGATTGGATATACAAAATAA
TGATCCCAAATCCCAGTACTATGTGCATCAATTGGGGCTGCATTACTGCAACCAGATAAAAC
AAAAACAAATAATAATGATAAACTAACGAGCACAGCTCGGTATGATTTTAACATGTTCATTC
CTCCAATGTTTCGTAATTATTTAGCGAAACATTGGTGTATACGGACCGACCTCGTCATTCTCT
TCACTTGATTCTTGTCTGCGTACAGAACGAATCATTCCATATTTATAAAAAATAGAAAATAG
CGGTACATTTCCCGCACTATCTTCACATGTATCAACTAGCGCAAAAGCTCTTTGTCTACCGCT
TGATGCTTGTTGACGCACAAAGCGGCGATTATTCC

>Bacillus-cereus-53522-correct-rnc-738 (SEQ ID NO. 44)
ATGCCGTACCGAAAATATAGAGAAAAAAAATACGAAACAAAATATCGTGAAGCATTTAAAG
TGTTTCAAGAAAAGATAGGTATTACGTTTACAGATGAAAAATTATTGATTCAAGCATTTACG
CATTCATCGTATGTGAATGAGCATCGAAAAAAACCGCATGAAGATAATGAGCGTCTTGAATT
TCTTGGAGATGCAGTATTGGAACTTACTGTATCGCAGTATCTGTTTCAAAAATATCCGACAA
TGAGCGAAGGAGAGTTAACAAAACTACGTGCAGCTATTGTATGTGAGCCATCTCTTGTTCGT
TTTGCGAACGAATTGTCATTTGGTAGCCTTGTTTTATTAGGAAAAGGTGAAGAAATGACAGG
TGGACGTGAACGACCAGCTTTATTAGCGGATGTCTTTGAAGCGTTTATTGGTGCCCTTTATCT
TGATCAAGGGTTAGAAACAGTTTGGGAATTCTTAAAAGAAATTGTATATCCGAAAATTAATG
AGGGTGCTTTTTCTCATGTGATGGATTATAAGAGTCAGTTACAAGAATTGATTCAGCGTGAT
GGTAGTGGCAATGTTGAGTATCAAATTTTGCAAGAAAAAGGACCAGCTCACAATCGAGAAT
TTGTGTCACGTGTTACGTTAAATAACGTAGCTTTAGGTCTTGGTAGTGGTAAGTCGAAAAAA
GAAGCAGAGCAACAAGCTGCTGCAGAAGCATTGAAAAAATTAAAAGAACAACTATAA
```

SEQ ID NO. 45
DNA
50 bp homologous sequences to the *E. coli* me gene and primers used for amplification of the Kanamycin resistance marker
Artificial
atgaaccccatcgtaattaatcggcttcaacggaagctgggctacactttagcgattgtgtaggctggag SEQ ID NO. 46
DNA
50 bp homologous sequences to the *E. coli* me gene and primers used for amplification of the Kanamycin resistance marker
Artificial
ctgatcgtgcgcttcgccacgtacctggactaccagataagtcggcagcgttaacggctgacatgggaattag SEQ ID NO. 47
DNA
50 bp homologous sequences to the *E. coli* me gene and primers used for amplification of the Kanamycin resistance marker
Artificial
atgaaccccatcgtaattaatcggc SEQ ID NO. 48
DNA
50 bp homologous sequences to the *E. coli* me gene and primers used for amplification of the Kanamycin resistance marker
Artificial
ctgatcgtgcgcttcgc SEQ ID NO. 49
DNA
50 bp homologous sequences to the *E. coli* me gene and primers used for amplification of the Kanamycin resistance marker
Artificial
accggtaaactgaaactgca SEQ ID NO. 50
DNA
50 bp homologous sequences to the *E. coli* me gene and primers used for amplification of the Kanamycin resistance marker
Artificial
tggagattttctgccccag SEQ ID NO. 51
DNA
50 bp homologous sequences to the *E. coli* me gene and primers used for amplification of the Kanamycin resistance marker Artificial
agcgattgtgtaggctggagct
SEQ ID NO. 52
DNA
50 bp homologous sequences to the *E. coli* me gene and primers used for amplification of the Kanamycin resistance marker
Artificial
ttaacggctgacatgggaattagc
SEQ ID NO. 53
DNA
Primers used for identification and verification of *Bacillus* spp
Artificial
agagtttgatcctggctcag
SEQ ID NO. 54
DNA
Primers used for identification and verification of *Bacillus* spp
Artificial
cggttaccttgttacgactt
SEQ ID NO. 55
DNA
Artificial
Primers used for identification and verification of *Bacillus* spp
agagtgcgtaatagctcac
SEQ ID NO. 56
DNA
Primers used for identification and verification of *Bacillus* spp
Artificial
cggtctagaacttaccgacaagg
SEQ ID NO. 57
DNA
Primers used for identification and verification of *Bacillus* spp
Artificial
atcgcctcgttggatgacga
SEQ ID NO. 58
DNA
Primers used for identification and verification of *Bacillus* spp
Artificial
ctgcatatcctaccgcagcta
SEQ ID NO. 59
DNA
Primers used for identification and verification of *Bacillus* spp
Artificial
ccagtagccaagaatggccagc
SEQ ID NO. 60
DNA
Primers used for identification and verification of *Bacillus* spp
Artificial
ggaataatcgccgctttgtgc
SEQ ID NO. 61
DNA
Primers used for identification and verification of *Bacillus* spp
Artificial
atgagccctgtgatcaggaagatcg
SEQ ID NO. 62
DNA
Primers used for identification and verification of *Bacillus* spp
Artificial
acgatgagccttctcagcaaatgcg
SEQ ID NO. 63
DNA
Primer for *N. tabacum* reference gene
Artificial
CCCCTCACCACAGAGTCTGC
SEQ ID NO. 64
DNA
Primer for *N. tabacum* reference gene
Artificial
AAGGGTGTTGTTGTCCTCAATCTT
SEQ ID NO. 65
DNA
Primer for TMV-GFP-F2
Artificial
GATGACGGGAACTACAAGACG
SEQ ID NO. 65
DNA
Primer for TMV-GFP-F2
Artificial
GTTTGTGTCCGAGAATGTTTCC

REFERENCES

The following references are hereby incorporated in their entirety by reference:

1. Ashe S, Maji U, Sen R, Mohanty S, Maiti N. 2014. Specific oligonucleotide primers for detection of endoglucanase positive *Bacillus subtilis* by PCR. 3 Biotech 4(5):461-465.
2. Dunn A K, Handelsman J. 1999. A vector for promoter trapping in *Bacillus cereus*. Gene 226(2):297-305.
3. Durand S, Gilet L, Condon C. 2012. The essential function of *B. subtilis* RNase III is to silence foreign toxin genes. PLoS Genetics 8(12):e1003181.
4. Eamens A, Wang M-B, Smith N A, Waterhouse P M. 2008. RNA silencing in plants: yesterday, today, and tomorrow. Plant Physiology 147(2):456-468.
5. Graumann P. 2012. *Bacillus*: cellular and molecular biology. Horizon Scientific Press.
6. Hong C E, Jo S H, Moon J Y, Lee J-S, Kwon S-Y, Park J M. 2015. Isolation of novel leaf-inhabiting endophytic bacteria in *Arabidopsis thaliana* and their antagonistic effects on phytophathogens. Plant Biotechnology Reports 9(6):451-458.
7. Jensen S I, Lennen R M, Herrgird M J, Nielsen A T. 2015. Seven gene deletions in seven days: Fast generation of *Escherichia coli* strains tolerant to acetate and osmotic stress. Scientific Reports 5:17874.
8. Lindbo J A. 2007. TRBO: a high-efficiency tobacco mosaic virus RNA-based overexpression vector. Plant physiology 145(4):1232-1240.
9. Lozano G L, Holt J, Ravel J, Rasko D A, Thomas M G, Handelsman J. 2016. Draft genome sequence of biocontrol agent *Bacillus cereus* UW85. Genome Announcements 4(5):e00910-16.
10. Nunes C, Bajji M, Stepien V, Manso T, Torres R, Usall J, Jijakli M H. 2008. Development and application of a SCAR marker to monitor and quantify populations of the postharvest biocontrol agent *Pantoea agglomerans* CPA-2. Postharvest Biology and Technology 47(3):422-428.
11. Oehrle N W, Karr D B, Kremer R J, Emerich D W. 2000. Enhanced attachment of *Bradyrhizobium japonicum* to soybean through reduced root colonization of internally seedborne microorganisms. Canadian Journal of Microbiology 46(7):600-606.

12. Oliwa-Stasiak K, Molnar C, Arshak K, Bartoszcze M, Adley C. 2010. Development of a PCR assay for identification of the *Bacillus cereus* group species. Journal of Applied Microbiology 108(1):266-273.
13. Petersen D J, Shishido M, Holl F B, Chanway C P. 1995. Use of species- and strain-specific PCR primers for identification of conifer root-associated *Bacillus* spp. FEMS Microbiology Letters 133(1-2):71-76.
14. Raffel S J, Stabb E V, Milner J L, Handelsman J. 1996. Genotypic and phenotypic analysis of zwittermicin A-producing strains of *Bacillus cereus*. Microbiology 142(12):3425-3436.
15. Rajendran G, Sing F, Desai A J, Archana G. 2008. Enhanced growth and nodulation of pigeon pea by co-inoculation of *Bacillus* strains with *Rhizobium* spp. Bioresource Technology 99(11):4544-4550.
16. Selvakumar G, Kundu S, Gupta A D, Shouche Y S, Gupta H S. 2008. Isolation and characterization of non-rhizobial plant growth promoting bacteria from nodules of Kudzu (*Pueraria thunbergiana*) and their effect on wheat seedling growth. Current Microbiology 56(2):134-139.
17. Smith N A, Singh S P, Wang M-B, Stoutjesdijk P A, Green A G, Waterhouse P M. 2000. Gene expression: total silencing by intron-spliced hairpin RNAs. Nature 407 (6802):319-320.
18. Takiff H E, Chen S-M. 1989. Genetic analysis of the me operon of *Escherichia coli*. Journal of Bacteriology 171 (5):2581-2590.
19. Weisburg W G, Barns S M, Pelletier D A, Lane D J. 1991. 16S ribosomal DNA amplification for phylogenetic study. Journal of Bacteriology 173(2):697-703.
20. Yin G, Sun Z, Liu N, Zhang L, Song Y, Zhu C, Wen F. 2009. Production of double-stranded RNA for interference with TMV infection utilizing a bacterial prokaryotic expression system. Applied Microbiology and Biotechnology 84(2):323-333.
21. Baumberger N, Baulcombe D C, (2005) *Arabidopsis* ARGONAUTE1 is an RNA Slicer that selectively recruits microRNAs and short interfering RNAs, PNAS 102(33): 11928-33
22. Durand S, Gilet L, Condon C, (2012) The Essential Function of *B. subtilis* RNase III Is to Silence Foreign Toxin Genes, Plos Genet 8(12): e1003181
23. Schmidt, G. W. and Delaney, S. K. 2010. Stable internal reference genes for normalization of real-time R T-PCR in tobacco (*Nicotiana tabacum*) during development and abiotic stress. *Molecular Genetics and Genomics.* 283: 233-241.
24. Bindschedler, L. V., Panstruga, R. and Spanu, P. D. 2016. Mildew-omics: how global analyses aid the understanding of life and evolution of powdery mildews. *Frontiers in Plant Science.* 7:
25. Brading, P. A., Verstappen, E. C., Kema, G. H. and Brown, J. K. 2002. A gene-for-gene relationship between wheat and *Mycosphaerella graminicola*, the *Septoria tritici* blotch pathogen. *Phytopathology.* 92: 439-445.
26. Cannon, P., Damm, U., Johnston, P. and Weir, B. 2012. *Colletotrichum*-current status and future directions. *Studies in Mycology.* 73: 181-213.
27. Cantu, D., Segovia, V., Maclean, D., Bayles, R., Chen, X., Kamoun, S., Dubcovsky, J., Saunders, D. G. and Uauy, C. 2013. Genome analyses of the wheat yellow (stripe) rust pathogen *Puccinia striiformis* f. sp. *tritici* reveal polymorphic and haustorial expressed secreted proteins as candidate effectors. *BMC Genomics.* 14: 270.
28. Chen, X. 2005. Epidemiology and control of stripe rust [*Puccinia striiformis* f. sp. *tritici*] on wheat. *Canadian Journal of Plant Pathology.* 27: 314-337.
29. Di Pietro, A., Garcia-Maceira, F. I., Meglecz, E. and Roncero, M. I. G. 2001. A MAP kinase of the vascular wilt fungus *Fusarium oxysporum* is essential for root penetration and pathogenesis. *Molecular Microbiology.* 39: 1140-1152.
30. Di Pietro, A. and Roncero, M. I. G. 1998. Cloning, expression, and role in pathogenicity of pg1 encoding the major extracellular endopolygalacturonase of the vascular wilt pathogen *Fusarium oxysporum. Molecular Plant-Microbe Interactions.* 11: 91-98.
31. Dong, Y., Li, Y., Zhao, M., Jing, M., Liu, X., Liu, M., Guo, X., Zhang, X., Chen, Y. and Liu, Y. 2015. Global genome and transcriptome analyses of *Magnaporthe oryzae* epidemic isolate 98-06 uncover novel effectors and pathogenicity-related genes, revealing gene gain and lose dynamics in genome evolution. *PLoS Pathogens.* 11: e1004801.
32. Dufresne, M., Bailey, J. A., Dron, M. and Langin, T. 1998. clk1, a serine/threonine protein kinase-encoding gene, is involved in pathogenicity of *Colletotrichum lindemuthianum* on common bean. *Molecular Plant-Microbe Interactions.* 11: 99-108.
33. Durrenberger, F. and Kronstad, J. 1999. The ukc1 gene encodes a protein kinase involved in morphogenesis, pathogenicity and pigment formation in *Ustilago maydis. Molecular and General Genetics MGG.* 261: 281-289.
34. Flor, H. 1956. The complementary genic systems in flax and flax rust. *Advances in Genetics.* 8: 29-54.
35. Goodwin, S. B., M'barek, S. B., Dhillon, B., Wittenberg, A. H., Crane, C. F., Hane, J. K., Foster, A. J., Van Der Lee, T. A., Grimwood, J. and Aerts, A. 2011. Finished genome of the fungal wheat pathogen *Mycosphaerella graminicola* reveals dispensome structure, chromosome plasticity, and stealth pathogenesis. *PLoS Genetics.* 7: e1002070.
36. Goswami, R. S. and Kistler, H. C. 2004. Heading for disaster: *Fusarium graminearum* on cereal crops. *Molecular Plant Pathology.* 5: 515-525.
37. Have, A. T., Mulder, W., Visser, J. and Van Kan, J. A. 1998. The endopolygalacturonase gene Bcpg1 is required for full virulence of *Botrytis cinerea. Molecular Plant-Microbe Interactions.* 11: 1009-1016.
38. Jenczmionka, N. J., Maier, F. J., Lösch, A. P. and Schafer, W. 2003. Mating, conidiation and pathogenicity of *Fusarium graminearum*, the main causal agent of the head-blight disease of wheat, are regulated by the MAP kinase gpmk1. *Current Genetics.* 43: 87-95.
39. Kamper, J., Kahmann, R., Bolker, M., Ma, L.-J., Brefort, T., Saville, B. J., Banuett, F., Kronstad, J. W., Gold, S. E. and Muller, O. 2006. Insights from the genome of the biotrophic fungal plant pathogen *Ustilago maydis. Nature.* 444: 97-101.
40. Lawrence, G., Mayo, G. and Shepherd, K. 1981. Interactions between genes controlling pathogenicity in the flax rust fungus [*Melampsora lini*]. *Phytopathology (USA).*
41. Lo, S.-C. C., Hipskind, J. D. and Nicholson, R. L. 1999. cDNA cloning of a sorghum pathogenesis-related protein (PR-10) and differential expression of defense-related genes following inoculation with *Cochliobolus heterostrophus* or *Colletotrichum sublineolum. Molecular Plant-Microbe Interactions.* 12: 479-489.
42. Mehrabi, R., Van Der Lee, T., Waalwijk, C. and Kema, G. H. 2006. MgSlt2, a cellular integrity MAP kinase gene of the fungal wheat pathogen *Mycosphaerella gramini-*

*cola*, is dispensable for penetration but essential for invasive growth. *Molecular Plant-Microbe Interactions.* 19: 389-398.

43. Michielse, C. B. and Rep, M. 2009. Pathogen profile update: *Fusarium oxysporum. Molecular Plant Pathology.* 10: 311-324.
44. Muller, P., Aichinger, C., Feldbrugge, M. and Kahmann, R. 1999. The MAP kinase kpp2 regulates mating and pathogenic development in *Ustilago maydis. Molecular Microbiology.* 34: 1007-1017.
45. Nemri, A., Saunders, D. G., Anderson, C., Upadhyaya, N. M., Win, J., Lawrence, G. J., Jones, D. A., Kamoun, S., Ellis, J. G. and Dodds, P. N. 2014. The genome sequence and effector complement of the flax rust pathogen *Melampsora lini. Frontiers in Plant Science.* 5:
46. Nowara, D., Gay, A., Lacomme, C., Shaw, J., Ridout, C., Douchkov, D., Hensel, G., Kumlehn, J. and Schweizer, P. 2010. HIGS: host-induced gene silencing in the obligate biotrophic fungal pathogen *Blumeria graminis. The Plant Cell.* 22: 3130-3141.
47. Panwar, V., Mccallum, B. and Bakkeren, G. 2013. Host-induced gene silencing of wheat leaf rust fungus *Puccinia triticina* pathogenicity genes mediated by the *Barley stripe mosaic virus. Plant Molecular Biology.* 81: 595-608.
48. Rampitsch, C., Bykova, N. V., Mccallum, B., Beimcik, E. and Ens, W. 2006. Analysis of the wheat and *Puccinia triticina* (leaf rust) proteomes during a susceptible host-pathogen interaction. *Proteomics.* 6: 1897-1907.
49. Stakman, E. C. and Levine, M. N. 1944. *Identification of physiologic races of Puccinia graminis tritici*, United State Department Of Agriculture.
50. Takano, Y., Kikuchi, T., Kubo, Y., Hamer, J. E., Mise, K. and Furusawa, I. 2000. The *Colletotrichum lagenarium* MAP kinase gene CMK1 regulates diverse aspects of fungal pathogenesis. *Molecular Plant-Microbe Interactions.* 13: 374-383.
51. Urban, M., Mott, E., Farley, T. and Hammond-Kosack, K. 2003. The *Fusarium graminearum* MAP1 gene is essential for pathogenicity and development of perithecia. *Molecular Plant Pathology.* 4: 347-359.
52. Williamson, B., Tudzynski, B., Tudzynski, P. and Van Kan, J. A. 2007. *Botrytis cinerea*: the cause of grey mould disease. *Molecular Plant Pathology.* 8: 561-580.
53. Zheng, L., Campbell, M., Murphy, J., Lam, S. and Xu, J.-R. 2000. The BMP1 gene is essential for pathogenicity in the gray mold fungus *Botrytis cinerea. Molecular Plant-Microbe Interactions.* 13: 724-732.
54. Zhu, L., Zhu, J., Liu, Z., Wang, Z., Zhou, C. and Wang, H. 2017. Host-induced gene silencing of rice blast fungus *Magnaporthe oryzae* pathogenicity genes mediated by the *Brome Mosaic Virus. Genes.* 8: 241.
55. Zwiers, L.-H. and De Waard, M. A. 2000. Characterization of the ABC transporter genes MgAtr1 and MgAtr2 from the wheat pathogen *Mycosphaerella graminicola. Fungal Genetics and Biology.* 30: 115-125.
56. Timmons L, Court D L, Fire A (2001). Ingestion of bacterially expressed dsRNAs can produce specific and potent genetic interference in *Caenorhabditis elegans*. Gene 263(1-2):103-112
57. Glick B (2013). Bacteria with ACC deaminase csan promote plant growth and help to feed the world. Microbiological Research 169(2014): 30-39
58. Pande S, Shitut S, Freund L, Westerman M, Bertels F, Colesie C, Bischofs I B, Kost C (2015). Metabolic cross-feeding via intercellular nanotubes among bacteria. Nature Comm 6: DOI: 10.1038/ncomms7238
59. Takiff H E, Chen, S M, Court D L (1989). Genetic analysis of the me operon of *Escherichia coli*. Journal of Bacteriology 171(5): 2581-2590
60. Derouiche R, Benedetti H, Lazzaroni J C, Lazdunski C, Lloubes R (1995). Protein complex within *Escherichia coli* inner membrane. tolA N-terminal domain interacts with TolQ and TolR proteins. J. Biological Chemistry 270: 11078-11084
61. Shih J D, Fitzgerald M C, Sutherlin M, Hunter C P (2009). The SID-1 double stranded RNA transporter is not selective for dsRNA length. RNA 15:384-390
62. McEwan D L, Weisman A S, Hunter C P (2012). Uptake of extracellular double-stranded RNA by SID-2
63. Pallas V, Gómez G (2013). Phloem RNA-binding proteins as potential components of the long-distance RNA transport system. Front Plant Sci 4: 130
64. Garcia-Ruiz H, Carbonell, Steen Hoyer J et al. (2015) Roles and programming of *Arabidopsis* ARGONAUTE proteins during Turnip Mosaic Virus infection. PLOS pathogens. https://doi.org/10.1371/journal.ppat.1004755
65. Kim K, Manasherob R, Cohen S N (2008). YmdB: a stress-responsive ribonuclease-binding regulator of *E. coli* RNaseIII activity. Genes & Development 22: 3497-3508.
66. Ren Z, Veksler-Lublinsky I, Morrissey D, Ambros V (2016) Staufen negatively modulates microRNA activity in *Caenorhabditis elegans*. G3 6(5): 1227-1237
67. Raman P, Zaghab S M, Traver E C, Jose A M (2017). The double-stranded RNA binding protein RDE-4 can act cell autonomously during feeding RNAi in *C. elegans*. Nucleic Acids Res 45(14): 8463-8473
68. Han M, Goud S, Song L, Fedoroff N (2003). The *Arabidopsis* double-stranded RNA-binding protein HYL1 plays a role in microRNA-mediated gene regulation. PNAS 101(4): 1093:1098
69. Adenot X, Elmayan T, Lauressergues D, Boutet S, Bouche N, Gasciolli v, Vacheret H (2006). DRB4-depedent TAS3 tras-acting siRNAs control leaf morphology through AGO7. Curr Biol 16(9): 927-932
70. Ji L, Chen X (2012). Regulation of small RNA stability: methylation and beyond. Cell Res. 22: 624-636
71. Li S, Liu K, Zhang S, Wang X, Rogers K, Ren G, Zhang C, Yu B (2017). STV1, a ribosomal protein, binds primary microRNA transcripts to promote their interaction with the processing complex in *Arabidopsis*. PNAS 114(6): 1424-1429
72. Zhang F, Greig D I, Ling V (1993). Functional replacement of the hemolysin A transport signal by a different primary sequence. PNAS 90: 4211-4215
73. Natale P, Bruser T, Driessen A J M (2008). Sec- and Tat-mediated prtein secretion across the bacterial cytoplasmic membrane—Distinct translocases and mechanisms. Biochimica Biophy. Acta 9: 1735-1756
74. Jones S W, Christison R, Bundell K, Voyce C J, Brockbank S M V, Newham P, Lindsay (2005). Characterisation of ce;ll-penetrating peptide-mediated peptide delivery. British Journal of Pharmacology. DOI: 10.1038/sj.bjp.0706279

What is claimed is:

1. A method for the bio-control of a plant pathogen comprising the steps of:

providing a genetically modified endophyte bacteria that is an RNaseIII mutant having suppressed RNaseIII activity relative to a wild type endophyte bacteria, wherein said genetically modified endophyte bacteria is also transformed with a nucleic acid construct comprising a polynucleotide sequence operably linked to a promoter encoding at least one small inhibitory ribonucleic acid (siRNA) that forms a double-stranded RNA (dsRNA) or a hairpin (hpRNA) directed to at least one target sequence in a plant pathogen, wherein said genetically modified endophyte bacteria is *Bacillus subtilis* or *Bacillus cereus*; and introducing said genetically modified endophyte bacteria to a plant, wherein said genetically modified endophyte bacteria colonizes or lives in the leaves, stem, or roots of said plant and stably expresses said dsRNA or hpRNA in said plant for a time sufficient to induce an RNA interference (RNAi) mechanism in said plant that downregulates said at least one target sequence in a plant pathogen.

2. The method of claim 1, wherein said step of introducing said genetically modified endophyte bacteria to a plant comprises a method selected from the group consisting of: soaking, spraying, injecting, feeding, introducing to through an aerosolized disbursement, introducing to through an environmental aerosolized disbursement, introducing to through an environmental aerosolized disbursement in water sources, brushing, dressing, dripping, and coating the mosquito and wherein during the introduction the bacteria is lyophilized, freeze-dried, microencapsulated, desiccated, in an aqueous carrier or in a solution.

3. The method of claim 2, wherein said plant is a monocot or a dicot.

4. The method of claim 3, wherein said plant is selected from the group consisting of: grains, corn, wheat, rice, barley, oats, sorghum, millet, sunflower, safflower, cotton, soy, canola, alfalfa, *Arabidopsis, cannabis*, potato, *Brassica*, peanut, tobacco, tropical fruits and flowers, banana, duckweed, *gladiolus*, sugar cane, pineapples, dates, onions, pineapple, cashews, pistachios, flowers, ornamentals, conifers, deciduous, grapes, citrus, roses, apples, peaches, strawberries, almonds, coffee, oaks, beans, legumes, watermelon, squashes, cabbage, turnip, mustard, cacti, pecans, flax, sweet potato, soybean, coconut, avocado, beets, cantaloupe and vegetables.

5. The method of claim 4, wherein said plant pathogen comprises a plant pathogen selected from the group consisting of: a plant virus; a plant viroid; a fungus; a pest, a herbivore, and a mold.

6. The method of claim 5, wherein said plant virus is selected from the group consisting of: Tobacco mosaic virus (TMV); Tomato spotted wilt virus (TSWV); Tomato yellow leaf curl virus (TYLCV); Cucumber mosaic virus (CMV); Potato virus Y (PVY); Cauliflower mosaic virus (CaMV); African cassava mosaic virus (ACMV); Plum pox virus (PPV); Brome mosaic virus (BMV); Potato virus X (PVX); *Citrus tristeza* virus, Barley yellow dwarf virus, Potato leafroll virus and Tomato and bushy stunt virus.

7. The method of claim 6, wherein said target sequence is selected from the group consisting of a sequence of a critical region of a virus, a conserved sequence of a family of viruses, and a conserved sequence among members of different viral families.

8. The method of claim 6, wherein said target sequence which is suppressed is selected from the group consisting of: replicase gene, movement protein, coat protein in said Tobacco mosaic virus; glycoproteins (GPs), NSm protein, NSs protein, virus RNA genomic segment L, M, S in said Tomato spotted wilt virus; V1, V2, C1, C2, C3, C4, V1 protein in said Tomato yellow leaf curl virus; 1a, 2a2b protein, 3a, coat protein in said Cucumber mosaic virus; P1, HC-Pro, P3, 6k1, CI, 6k2, NIa, Nib, CP in said Potato virus Y; Movement protein, two aphid transmission factors (P2 and/or P3), the precursor of the capsid proteins (P4), polyprotein precursor of proteinase, P5, P6 protein in said Cauliflower mosaic virus; AV1, AV2, AC1, AC2, AC3, AC4, BC1, BV1 in said African cassava mosaic virus; P1, HC-Pro, P3, 6k1, CI, 6k2, NIa, Nib, CP in said Plum pox virus; 1a, 2a, movement protein, coat protein in said Brome mosaic virus; replicase, TGB1, TGB2, TGB3, coat protein in said Potato virus X.

9. The method of claim 8, wherein said target sequence is selected from the group consisting of a sequence of a critical region of a fungus essential gene, a conserved sequence of a family of essential genes, and a conserved essential genes among members of different viral families.

10. The method of claim 9, wherein said target sequence is selected from the group consisting of: a non-coding region of RNA, a coding region of RNA; the target sequence containing a splice site of RNA.

11. The method of claim 1, wherein the nucleic acid construct is a plasmid.

12. The method of claim 11, wherein said plasmid is modified to include the target sequence from the group of plasmids consisting of: pAD-WRKY-GHY1; pAD-ADH-GHY2; pOXB-WRKY-GHY3; pOXB-ADH-GHY4; pAD-WRKY-GHY5; hpRNA pAD-ADH-GHY6; and hpRNA pAD-WRKY-GHY7.

13. The method of claim 1, wherein said promoter comprises a promoter selected from the group consisting of: a non-constitutive promotor; an inducible promotor, a pathogen-inducible promoter; a tissue-preferred; a tissue-specific promotor, a plant-specific promotor, or a constitutive promotor.

14. The method of claim 1, wherein said siRNA migrates throughout the plant.

15. The method of claim 1, wherein said genetically modified endophyte bacteria continually expresses said nucleic acid construct thereby initiating a sustained RNAi mechanism in said plant, wherein said plant has a greater than wildtype resistance to said plant pathogen infection.

16. The method of claim 1, wherein said genetically modified endophyte bacteria further co-expresses in said plant a nucleotide sequence operably linked to a promoter encoding at least one helper gene.

17. The method of claim 1, wherein said genetically modified endophyte bacteria further co-expresses at least one additional siRNA molecule in said plant directed to at least one different target sequence in a plant pathogen.

18. The method of claim 16, wherein said helper gene is selected from the group consisting of: VrrA; SID1; SID2; AGO1; AGO2; AGO7; YmdB; YmdB; Staufen; RDE-4; HlyA; Sec- and Tat-secretory signal peptides; one or more cell-penetrating peptides (CPPs); Tat; Antennapedia; ACC deaminase; one or more phloem RNA transporters; PP2-A1; PSRP1; DRB1; DRB4; HEN1 and STV1.

19. The method of claim 1, wherein said siRNA is configured to have one or more specific RNA motifs incorporated into said dsRNA to facilitate its transmission through phloem of the plant.

20. The method of claim 1, wherein said polynucleotide sequence encoding said at least one small inhibitory ribonucleic acid (siRNA) is selected from the group consisting of SEQ ID NOs. 30, 31, 32, 33, 34, 35 and 36.

* * * * *

SEQUENCE LISTING

<160> NUMBER OF SEQ ID NOS: 66

<210> SEQ ID NO 1
<211> LENGTH: 45
<212> TYPE: DNA
<213> ORGANISM: Artificial Sequence
<220> FEATURE:
<223> OTHER INFORMATION: Primers used for the construction of hpRNAs.

<400> SEQUENCE: 1
ggaaaactgt atgtatttga tccttgcccg aaggttatgt acagg 45

<210> SEQ ID NO 2
<211> LENGTH: 33
<212> TYPE: DNA
<213> ORGANISM: Artificial Sequence
<220> FEATURE:
<223> OTHER INFORMATION: Primers used for the construction of hpRNAs.

<400> SEQUENCE: 2
gcagaggagg agaaagggca gattgtgtcg aca 33

<210> SEQ ID NO 3
<211> LENGTH: 34
<212> TYPE: DNA
<213> ORGANISM: Artificial Sequence
<220> FEATURE:
<223> OTHER INFORMATION: Primers used for the construction of hpRNAs.

<400> SEQUENCE: 3
caatctgccc tttctcctcc tctgctaacg taag 34

<210> SEQ ID NO 4
<211> LENGTH: 32
<212> TYPE: DNA
<213> ORGANISM: Artificial Sequence
<220> FEATURE:
<223> OTHER INFORMATION: Primers used for the construction of hpRNAs.

<400> SEQUENCE: 4
caatctgccc tttctgtggt tggagaagct ag 32

<210> SEQ ID NO 5
<211> LENGTH: 33
<212> TYPE: DNA
<213> ORGANISM: Artificial Sequence
<220> FEATURE:
<223> OTHER INFORMATION: Primers used for the construction of hpRNAs.

<400> SEQUENCE: 5
ctccaaccac agaaagggca gattgtgtcg aca 33

<210> SEQ ID NO 6
<211> LENGTH: 45
<212> TYPE: DNA
<213> ORGANISM: Artificial Sequence
<220> FEATURE:
<223> OTHER INFORMATION: Primers used for the construction of hpRNAs.

<400> SEQUENCE: 6
aagttaaggg atgcagttta tgcatgcccg aaggttatgt acagg 45

<210> SEQ ID NO 7
<211> LENGTH: 33
<212> TYPE: DNA
<213> ORGANISM: Artificial Sequence
<220> FEATURE:
<223> OTHER INFORMATION: Primers used for the construction of hpRNAs.

<400> SEQUENCE: 7
ttgcacttga tcaaagggca gattgtgtcg aca 33

<210> SEQ ID NO 8
<211> LENGTH: 33
<212> TYPE: DNA
<213> ORGANISM: Artificial Sequence
<220> FEATURE:
<223> OTHER INFORMATION: Primers used for the construction of hpRNAs.

<400> SEQUENCE: 8
gtgcagctgc ggaaagggca gattgtgtcg aca 33

<210> SEQ ID NO 9
<211> LENGTH: 37
<212> TYPE: DNA
<213> ORGANISM: Artificial Sequence
<220> FEATURE:
<223> OTHER INFORMATION: Primers used for the construction of hpRNAs.

<400> SEQUENCE: 9
caatctgccc tttgatcaag tgcaaaggtc cgccttg 37

<210> SEQ ID NO 10
<211> LENGTH: 31
<212> TYPE: DNA
<213> ORGANISM: Artificial Sequence
<220> FEATURE:
<223> OTHER INFORMATION: Primers used for the construction of hpRNAs.

<400> SEQUENCE: 10
caatctgccc tttccgcagc tgcacgggtc c 31

<210> SEQ ID NO 11
<211> LENGTH: 45
<212> TYPE: DNA
<213> ORGANISM: Artificial Sequence
<220> FEATURE:
<223> OTHER INFORMATION: Primers used for the construction of hpRNAs.

<400> SEQUENCE: 11
accgcgatat ctacctcgag gttttgcccg aaggttatgt acagg 45

<210> SEQ ID NO 12
<211> LENGTH: 45
<212> TYPE: DNA
<213> ORGANISM: Artificial Sequence
<220> FEATURE:
<223> OTHER INFORMATION: Primers used for the construction of hpRNAs.

<400> SEQUENCE: 12
agtcagtgca ggaggagaca actttgcccg aaggttatgt acagg 45

<210> SEQ ID NO 13
<211> LENGTH: 70
<212> TYPE: DNA
<213> ORGANISM: Artificial Sequence
<220> FEATURE:
<223> OTHER INFORMATION: Primers used for the construction of hpRNAs.

<400> SEQUENCE: 13
ggaaaactgt atgtatttga tcctctagat ttaagaagga gatatacatt gcccgaaggt 60
tatgtacagg 70

<210> SEQ ID NO 14
<211> LENGTH: 73
<212> TYPE: DNA
<213> ORGANISM: Artificial Sequence
<220> FEATURE:
<223> OTHER INFORMATION: Primers used for the construction of hpRNAs.

<400> SEQUENCE: 14
ggaaaactgt atgtatttga tcctctagat ttaagaagga gatatacatt ctcggatctt 60
actacacagc agc 73

<210> SEQ ID NO 15
<211> LENGTH: 33
<212> TYPE: DNA
<213> ORGANISM: Artificial Sequence
<220> FEATURE:
<223> OTHER INFORMATION: Primers used for the construction of hpRNAs.

<400> SEQUENCE: 15
tagcagagga ggagttccct ttgcggacat cac 33

<210> SEQ ID NO 16
<211> LENGTH: 35
<212> TYPE: DNA
<213> ORGANISM: Artificial Sequence
<220> FEATURE:
<223> OTHER INFORMATION: Primers used for the construction of hpRNAs.

<400> SEQUENCE: 16
ccgcaaaggg aactcctcct ctgctaacgt aagcc 35

<210> SEQ ID NO 17
<211> LENGTH: 35
<212> TYPE: DNA
<213> ORGANISM: Artificial Sequence
<220> FEATURE:
<223> OTHER INFORMATION: Primers used for the construction of hpRNAs.

<400> SEQUENCE: 17
ccgcaaaggg aactgtggtt ggagaagcta gaacc 35

<210> SEQ ID NO 18
<211> LENGTH: 34
<212> TYPE: DNA
<213> ORGANISM: Artificial Sequence
<220> FEATURE:
<223> OTHER INFORMATION: Primers used for the construction of hpRNAs.

<400> SEQUENCE: 18
ctccaaccac agttcccttt gcggacatca ctct 34

<210> SEQ ID NO 19
<211> LENGTH: 48
<212> TYPE: DNA
<213> ORGANISM: Artificial Sequence
<220> FEATURE:
<223> OTHER INFORMATION: Primers used for the construction of hpRNAs.

<400> SEQUENCE: 19
aagttaaggg atgcagttta tgcatctcgg atcttactac acagcagc 48

<210> SEQ ID NO 20
<211> LENGTH: 21

<212> TYPE: DNA
<213> ORGANISM: Artificial Sequence
<220> FEATURE:
<223> OTHER INFORMATION: Primers used for the construction of hpRNAs.

<400> SEQUENCE: 20
gcgtgcaaac gcatgaatat c 21

<210> SEQ ID NO 21
<211> LENGTH: 19
<212> TYPE: DNA
<213> ORGANISM: Artificial Sequence
<220> FEATURE:
<223> OTHER INFORMATION: Primers used for the construction of hpRNAs.

<400> SEQUENCE: 21
agggcctcgt gatacgcct 19

<210> SEQ ID NO 22
<211> LENGTH: 22
<212> TYPE: DNA
<213> ORGANISM: Artificial Sequence
<220> FEATURE:
<223> OTHER INFORMATION: Primers used for the construction of hpRNAs.

<400> SEQUENCE: 22
atcgtgatcg gaagtgataa ag 22

<210> SEQ ID NO 23
<211> LENGTH: 20
<212> TYPE: DNA
<213> ORGANISM: Artificial Sequence
<220> FEATURE:
<223> OTHER INFORMATION: Primers used for the construction of hpRNAs.

<400> SEQUENCE: 23
gcttccgagc tctcgaattc 20

<210> SEQ ID NO 24
<211> LENGTH: 18
<212> TYPE: DNA
<213> ORGANISM: Artificial Sequence
<220> FEATURE:
<223> OTHER INFORMATION: Primers used for the construction of hpRNAs.

<400> SEQUENCE: 24
cgatgaacag tgccgcag 18

<210> SEQ ID NO 25
<211> LENGTH: 19
<212> TYPE: DNA
<213> ORGANISM: Artificial Sequence
<220> FEATURE:
<223> OTHER INFORMATION: Primers used for the construction of hpRNAs.

<400> SEQUENCE: 25
tgagtggccc tgtttctcg 19

<210> SEQ ID NO 26
<211> LENGTH: 287
<212> TYPE: DNA
<213> ORGANISM: Arabidopsis thaliana

<400> SEQUENCE: 26
ctcctcctct gctaacgtaa gcctctctgt ttttttctc tgtttctttt gaaatgaatc 60

-continued

```
caattagtga tgataatctg tgtttgatgt atcattgatt taacatcttg acaatgaatc    120

gtgatcggaa gtgataaagt tatgggtcaa cggtttcaaa gagagagaaa gacttttaga    180

gtcaactctc gactctttct taattatgtt attgctattt gtctcttttc ttgaagtctg    240

aacaattctt gggattgttt tgcaggttct agcttctcca accacag                  287
```

<210> SEQ ID NO 27
<211> LENGTH: 566
<212> TYPE: DNA
<213> ORGANISM: Zea mays

<400> SEQUENCE: 27

```
gatcaagtgc aaaggtccgc cttgtttctc ctctgtctct tgatctgact aatcttggtt     60

tatgattcgt tgagtaattt tggggaaagc tagcttcgtc cacagttttt ttttcgatga    120

acagtgccgc agtggcgctg atcttgtatg ctatcctgca atcgtggtga acttatgtct    180

tttatatcct tcactaccat gaaaagacta gctagtaatc tttctcgatg taacatcgtc    240

cagcactgct attaccgtgt ggtccatccg acagtctggc tgaacacatc atacgatatt    300

gagcaaagat cgatctatct tccctgttct ttaatgaaag acgtcatttt catcagtatg    360

atctaagaat gttgcaactt gcaaggaggc gtttctttct ttgaatttaa ctaactcgtt    420

gagtggccct gtttctcgga cgtaaggcct ttgctgctcc acacatgtcc attcgaattt    480

taccgtgttt agcaagggcg aaaagtttgc atcttgatga tttagcttga ctatgcgatt    540

gctttcctgg acccgtgcag ctgcgg                                         566
```

<210> SEQ ID NO 28
<211> LENGTH: 360
<212> TYPE: DNA
<213> ORGANISM: Zea mays

<400> SEQUENCE: 28

```
tgcccgaagg ttatgtacag gaacgcacta tatctttcaa agatgacggg aactacaaga     60

cgcgtgctga agtcaagttt gaaggtgata cccttgttaa tcgtatcgag ttaaaaggta    120

ttgattttaa agaagatgga aacattctcg gacacaaact cgagtacaac tataactcac    180

acaatgtata catcacggca gacaaacaaa agaatggaat caaagctaac ttcaaaattc    240

gccacaacat tgaagatgga tccgttcaac tagcagacca ttatcaacaa aatactccaa    300

ttggcgatgg ccctgtcctt ttaccagaca accattacct gtcgacacaa tctgcccttt    360
```

<210> SEQ ID NO 29
<211> LENGTH: 360
<212> TYPE: DNA
<213> ORGANISM: Zea mays

<400> SEQUENCE: 29

```
tctcggatct tactacacag cagctgcaaa gaaaagattt cagttcaagg tcgttcccaa     60

ttatgctata accacccagg acgcgatgaa aaacgtctgg caagttttag ttaatattag    120

aaatgtgaag atgtcagcgg gtttctgtcc gctttctctg gagtttgtgt cggtgtgtat    180

tgtttataga aataatataa aattaggttt gagagagaag attacaaacg tgagagacgg    240

agggcccatg gaacttacag aagaagtcgt tgatgagttc atggaagatg tccctatgtc    300

gatcaggctt gcaaagtttc gatctcgaac cggaaaaaag agtgatgtcc gcaaagggaa    360
```

<210> SEQ ID NO 30
<211> LENGTH: 7187

<212> TYPE: DNA
<213> ORGANISM: Artificial Sequence
<220> FEATURE:
<223> OTHER INFORMATION: Pupp (uracil phosphoribosyl transferase) promoter, shuttle vector, low-copy number, containing Arabidopsis WRKY transcription factor 33 intron

<400> SEQUENCE: 30

```
gaattcgagc tcggtacccg gggatcgcgt gaaagaaatt ttcggcgcag agcacgtaaa     60
tgttcaacca cactctggtg cacaagcgaa catggcagta tacttcacga ttttagagca    120
aggcgataca gtacttggta tgaatttatc tcatggtggt cacttaacac acggaagccc    180
tgttaacttc agtggagtac aatataattt cgtagaatat ggcgtggatg ctgactctca    240
ccgtattaat tacgatgatg tattagcaaa agcgaaagaa cataaaccaa aattaatcgt    300
tgcaggtgca agtgcatacc ctcgtgttat cgatttcaag cgattccgtg agattgcaga    360
tgaagtgggc gcttatttaa tggttgatat ggcacatatc gctggtttag tagctgctgg    420
tttacatcca aatccagtac cacatgcaca tttcgttaca acgacaacac ataaaacgtt    480
acgtggcccg cgtggtggta tgattttatg tgaagagcaa tttgcaaaac aaattgataa    540
atcaatcttc cctggtattc aaggtggtcc acttatgcac gtaatcgctg caaaagctgt    600
tgcgtttggt gaagcacttc aagatgattt caaaacatat gcacaaaata tcattaacaa    660
tgcgaaccgc ttagctgaag gtcttcaaaa agaaggactt acacttgttt ctggcggaac    720
agacaatcac ttaatcttga ttgatgttcg taacttagaa atcacaggta aagtagcaga    780
gcacgtatta gatgaagttg gtattacagt gaacaaaaat acaattccat ttgaaacagc    840
aagcccattt gtaacaagtg gtgtacgtat cggtacagca gctgtaacat ctcgtggttt    900
cggtttagaa gaaatggatg aaattgcgtc acttattgct tatacattaa aaaatcatga    960
aaatgaagct gcattagaag aagtacgtaa gcgtgtagaa gcgttaacta gcaaatttcc   1020
aatgtatcca aatctataat agattgaaga agactgccga gacttaattg ttttggcggt   1080
ctttttgtg gacatatatt atttttaaag tatgtataca aatgatgaat aaattttggc   1140
gatataatga aggatacagc tcccataatt ggtaaagata ctagatagat tcatcgtaaa   1200
atcatgattt tgccaaattt gcccttgaat attagtagcg ttttctttac aatcgtaaat   1260
agtgtaaaaa agcgtgcaaa cgcatgaata tcatctaaag gagagattca catgggaaaa   1320
ctgtatgtat ttgatccttg cccgaaggtt atgtacagga acgcactata tctttcaaag   1380
atgacgggaa ctacaagacg cgtgctgaag tcaagtttga aggtgatacc cttgttaatc   1440
gtatcgagtt aaaaggtatt gattttaaag aagatggaaa cattctcgga cacaaactcg   1500
agtacaacta taactcacac aatgtataca tcacggcaga caaacaaaag aatggaatca   1560
aagctaactt caaaattcgc cacaacattg aagatggatc cgttcaacta gcagaccatt   1620
atcaacaaaa tactccaatt ggcgatggcc ctgtcctttt accagacaac cattacctgt   1680
cgacacaatc tgccctttct cctcctctgc taacgtaagc ctctctgttt tttttctctg   1740
tttcttttga aatgaatcca attagtgatg ataatctgtg tttgatgtat cattgattta   1800
acatcttgac aatgaatcgt gatcggaagt gataaagtta tgggtcaacg gtttcaaaga   1860
gagagaaaga cttttagagt caactctcga ctctttctta attatgttat tgctatttgt   1920
ctcttttctt gaagtctgaa caattcttgg gattgttttg caggttctag cttctccaac   1980
cacagaaagg gcagattgtg tcgacaggta atggttgtct ggtaaaagga cagggccatc   2040
gccaattgga gtattttgtt gataatggtc tgctagttga acggatccat cttcaatgtt   2100
```

-continued gtggcgaatt ttgaagttag ctttgattcc attcttttgt ttgtctgccg tgatgtatac 2160
attgtgtgag ttatagttgt actcgagttt gtgtccgaga atgtttccat cttctttaaa 2220
atcaatacct tttaactcga tacgattaac aagggtatca ccttcaaact tgacttcagc 2280
acgcgtcttg tagttcccgt catctttgaa agatatagtg cgttcctgta cataaccttc 2340
gggcatgcat aaactgcatc ccttaacttg tttttcgtgt gcctattttt tgtgaatcgc 2400
taagaaacca ttattatcat gacattaacc tataaaaata ggcgtatcac gaggcccttt 2460
cgtctcgcgc gtttcggtga tgacggtgaa aacctctgac acatgcagct cccggagacg 2520
gtcacagctt gtctgtaagc ggatgccggg agcagacaag cccgtcaggg cgcgtcagcg 2580
ggtgttggcg ggtgtcgggg ctggcttaac tatgcggcat cagagcagat tgtactgaga 2640
gtgcaccata caaaacatat ttcaacacaa tacaaatggg ttagttaaaa aagcaggcct 2700
tctaaaggtc tgcttttttt atttgattat gtaattttta atgccaggat gccaataagc 2760
cataacctca aatgcaccat ttgcaacctc gtcatcttct tcctcaatct tgaccagatc 2820
gccgtcctcc gcatcaccaa gattcagctc tttatgtatc tccttcaaaa tgccaccgta 2880
tccaattaac cttcgagctg ccaacgcatc atccaagtaa agcaccgtgt tcagattgtc 2940
ttcagtcacc ttattaccgc gcacacaatc cgtatcctta accggatatt tagagatttc 3000
gcgaacagct ttttgctcca tcattgcgtt ccgcacatcg ttttcaatct gttcagcgtc 3060
aatcttagct ttacctttca ctcgacgaat atcgacaatt ggagtgtaat ccaatttcat 3120
cgcctttttc caaaggctcg tccactccgc ctgcttaata tagtttttcc caaaataatt 3180
tttccttact ggtatcaaca catgaaaatg aggatgatat gtatcttctt catgattttt 3240
ggtaatctct aaagctctga aaaatccaag aaccgaagtt tttacttttt tgtactggaa 3300
cagtttccta aagccttcca tcatcgcaga aatttgtggc ttcagccgtt ctccctttac 3360
atttcgaatc gtcagcgtga gaaaaatcca tccgcagccg tactgtctat tggcttcctc 3420
tacgatcaac ttattgtgat aagcaatttt taacgacctg cgccacgcac acatcggaca 3480
taacctcact ttacaaaaat gggcttgata cagttttaac ttgcccgtct ccgggtctct 3540
cttaaacgaa agatactctg cacaactaat tagtttttca gccttttttgc catagtaagg 3600 tgccccaatc ttactctcta acgcttcgta atgctccgcc atgaggttcg tccgtctctt 3660
tttccccttc caatcccgct ttttacctgt tgcggtttta tcttcgagga tgctataatc 3720
attttcagat gaataaatca acaaaaaaac tccttctgag ctagttctct agcattctat 3780
tattttgatt cgacacctta ataatagcag aaggagtttt tacctgtcaa agaaccatca 3840 aaccccttgat acacaaggct ttgacctaat tttgaaaaat gatgttgttt ctatatagta 3900
tcaagataag aaagaaaagg atttttcgct acgctcaaat cctttaaaaa aacacaaaag 3960
accacatttt ttaatgtggt ctttattctt caactaaagc acccattagt tcaacaaacg 4020
aaaattggat aaagtgggat atttttaaaa tatatattta tgttacagta atattgactt 4080
ttaaaaaagg attgattcta atgaagaaag cagacaagta agcctcctaa attcacttta 4140
gataaaaatt taggaggcat atcaaatgaa ctttaataaa attgatttag acaattggaa 4200
gagaaaagag atatttaatc attatttgaa ccaacaaacg acttttagta taaccacaga 4260
aattgatatt agtgttttat accgaaacat aaaacaagaa ggatataaat tttaccctgc 4320
atttattttc ttagtgacaa gggtgataaa ctcaaataca gcttttagaa ctggttacaa 4380
tagcgacgga gagttaggtt attgggataa gttagagcca ctttatacaa tttttgatgg 4440
tgtatctaaa acattctctg gtatttggac tcctgtaaag aatgacttca aagagtttta 4500

-continued

```
tgatttatac ctttctgatg tagagaaata taatggttcg gggaaattgt ttcccaaaac   4560
acctatacct gaaaatgctt tttctctttc tattattcca tggacttcat ttactgggtt   4620
taacttaaat atcaataata atagtaatta ccttctaccc attattacag caggaaaatt   4680
cattaataaa ggtaattcaa tatatttacc gctatcttta caggtacatc attctgtttg   4740
tgatggttat catgcaggat tgtttatgaa ctctattcag gaattgtcag ataggcctaa   4800
tgactggctt ttataatatg agataatgcc gactgtactt tttacagtcg gttttctaat   4860
gtcactaacc tgccccgtta gtcgccattc gccagctgcc tcgcgcgttt cggtgatgac   4920
ggtgaaaacc tctgacacat gcagctcccg gagacggtca cagcttgtct gtaagcggat   4980
gccgggagca gacaagcccg tcagggcgcg tcagcgggtg ttggcgggtg tcggggcgca   5040
gccatgaccc agtcacgtag cgatagcgga gtgtatactg gcttaactat gcggcatcag   5100
agcagattgt actgagagtg caccatatgc ggtgtgaaat accgcacaga tgcgtaagga   5160
gaaaataccg catcaggcgc tcttccgctt cctcgctcac tgactcgctg cgctcggtcg   5220
ttcggctgcg gcgagcggta tcagctcact caaaggcggt aatacggtta tccacagaat   5280
caggggataa cgcaggaaag aacatgtgag caaaaggcca gcaaaaggcc aggaaccgta   5340
aaaaggccgc gttgctggcg tttttccata ggctccgccc ccctgacgag catcacaaaa   5400
atcgacgctc aagtcagagg tggcgaaacc cgacaggact ataaagatac caggcgtttc   5460
cccctggaag ctccctcgtg cgctctcctg ttccgaccct gccgcttacc ggatacctgt   5520
ccgcctttct cccttcggga agcgtggcgc tttctcaatg ctcacgctgt aggtatctca   5580
gttcggtgta ggtcgttcgc tccaagctgg gctgtgtgca cgaacccccc gttcagcccg   5640
accgctgcgc cttatccggt aactatcgtc ttgagtccaa cccggtaaga cacgacttat   5700
cgccactggc agcagccact ggtaacagga ttagcagagc gaggtatgta ggcggtgcta   5760
cagagttctt gaagtggtgg cctaactacg gctacactag aaggacagta tttggtatct   5820
gcgctctgct gaagccagtt accttcggaa aaagagttgg tagctcttga tccggcaaac   5880
aaaccaccgc tggtagcggt ggtttttttg tttgcaagca gcagattacg cgcagaaaaa   5940
aaggatctca agaagatcct ttgatctttt ctacggggtc tgacgctcag tggaacgaaa   6000
actcacgtta agggattttg gtcatgagat tatcaaaaag gatcttcacc tagatccttt   6060
taaattaaaa atgaagtttt aaatcaatct aaagtatata tgagtaaact tggtctgaca   6120
gttaccaatg cttaatcagt gaggcaccta tctcagcgat ctgtctattt cgttcatcca   6180
tagttgcctg actccccgtc gtgtagataa ctacgatacg ggagggctta ccatctggcc   6240
ccagtgctgc aatgataccg cgagacccac gctcaccggc tccagattta tcagcaataa   6300
accagccagc cggaagggcc gagcgcagaa gtggtcctgc aactttatcc gcctccatcc   6360
agtctattaa ttgttgccgg gaagctagag taagtagttc gccagttaat agtttgcgca   6420
acgttgttgc cattgctgca ggcatcgtgg tgtcacgctc gtcgtttggt atggcttcat   6480
tcagctccgg ttcccaacga tcaaggcgag ttacatgatc ccccatgttg tgcaaaaaag   6540
cggttagctc cttcggtcct ccgatcgttg tcagaagtaa gttggccgca gtgttatcac   6600
tcatggttat ggcagcactg cataattctc ttactgtcat gccatccgta agatgctttt   6660
ctgtgactgg tgagtactca accaagtcat tctgagaata gtgtatgcgg cgaccgagtt   6720
gctcttgccc ggcgtcaaca cgggataata ccgcgccaca tagcagaact ttaaaagtgc   6780
tcatcattgg aaaacgttct tcggggcgaa aactctcaag gatcttaccg ctgttgagat   6840
```

-continued

```
ccagttcgat gtaacccact cgtgcaccca actgatcttc agcatctttt actttcacca   6900

gcgtttctgg gtgagcaaaa acaggaaggc aaaatgccgc aaaaaaggga ataagggcga   6960

cacggaaatg ttgaatactc atactcttcc tttttcaata ttattgaagc atttatcagg   7020

gttattgtct catgagcgga tacatatttg aatgtattta gaaaaataaa caaatagggg   7080

ttccgcgcac atttccccga aaagtgccac ctgacgtcta agaaaccatt attatcatga   7140

cattaaccta taaaaatagg cgtatcacga ggccctttcg tcttcaa                7187


<210> SEQ ID NO 31
<211> LENGTH: 7466
<212> TYPE: DNA
<213> ORGANISM: Artificial Sequence
<220> FEATURE:
<223> OTHER INFORMATION: Pupp (uracil phosphoribosyl transferase)
      promoter, shuttle vector, low-copy number, containing maize adh1
      intron

<400> SEQUENCE: 31

gaattcgagc tcggtacccg gggatcgcgt gaaagaaatt ttcggcgcag agcacgtaaa     60

tgttcaacca cactctggtg cacaagcgaa catggcagta tacttcacga ttttagagca    120

aggcgataca gtacttggta tgaatttatc tcatggtggt cacttaacac acggaagccc    180

tgttaacttc agtggagtac aatataattt cgtagaatat ggcgtggatg ctgactctca    240

ccgtattaat tacgatgatg tattagcaaa agcgaaagaa cataaaccaa aattaatcgt    300

tgcaggtgca agtgcatacc ctcgtgttat cgatttcaag cgattccgtg agattgcaga    360

tgaagtgggc gcttatttaa tggttgatat ggcacatatc gctggtttag tagctgctgg    420

tttacatcca aatccagtac cacatgcaca tttcgttaca acgacaacac ataaaacgtt    480

acgtggcccg cgtggtggta tgattttatg tgaagagcaa tttgcaaaac aaattgataa    540

atcaatcttc cctggtattc aaggtggtcc acttatgcac gtaatcgctg caaaagctgt    600

tgcgtttggt gaagcacttc aagatgattt caaaacatat gcacaaaata tcattaacaa    660

tgcgaaccgc ttagctgaag gtcttcaaaa agaaggactt acacttgttt ctggcggaac    720

agacaatcac ttaatcttga ttgatgttcg taacttagaa atcacaggta aagtagcaga    780

gcacgtatta gatgaagttg gtattacagt gaacaaaaat acaattccat ttgaaacagc    840

aagcccattt gtaacaagtg gtgtacgtat cggtacagca gctgtaacat ctcgtggttt    900

cggtttagaa gaaatggatg aaattgcgtc acttattgct tatacattaa aaaatcatga    960

aaatgaagct gcattagaag aagtacgtaa gcgtgtagaa gcgttaacta gcaaatttcc   1020

aatgtatcca aatctataat agattgaaga agactgccga gacttaattg ttttggcggt   1080

ctttttgtg gacatatatt atttttaaag tatgtataca aatgatgaat aaattttggc   1140

gatataatga aggatacagc tcccataatt ggtaaagata ctagatagat tcatcgtaaa   1200

atcatgattt tgccaaattt gcccttgaat attagtagcg ttttctttac aatcgtaaat   1260

agtgtaaaaa agcgtgcaaa cgcatgaata tcatctaaag gagagattca catgggaaaa   1320

ctgtatgtat ttgatccttg cccgaaggtt atgtacagga acgcactata tctttcaaag   1380

atgacgggaa ctacaagacg cgtgctgaag tcaagtttga aggtgatacc cttgttaatc   1440

gtatcgagtt aaaaggtatt gattttaaag aagatggaaa cattctcgga cacaaactcg   1500

agtacaacta taactcacac aatgtataca tcacggcaga caaacaaaag aatggaatca   1560

aagctaactt caaaattcgc cacaacattg aagatggatc cgttcaacta gcagaccatt   1620

atcaacaaaa tactccaatt ggcgatggcc ctgtcctttt accagacaac cattacctgt   1680
```

cgacacaatc tgccctttga tcaagtgcaa aggtccgcct tgtttctcct ctgtctcttg 1740
atctgactaa tcttggttta tgattcgttg agtaattttg gggaaagcta gcttcgtcca 1800
cagttttttt ttcgatgaac agtgccgcag tggcgctgat cttgtatgct atcctgcaat 1860
cgtggtgaac ttatgtcttt tatatccttc actaccatga aaagactagc tagtaatctt 1920
tctcgatgta acatcgtcca gcactgctat taccgtgtgg tccatccgac agtctggctg 1980
aacacatcat acgatattga gcaaagatcg atctatcttc cctgttcttt aatgaaagac 2040
gtcattttca tcagtatgat ctaagaatgt tgcaacttgc aaggaggcgt ttctttcttt 2100
gaatttaact aactcgttga gtggccctgt ttctcggacg taaggccttt gctgctccac 2160
acatgtccat tcgaatttta ccgtgtttag caagggcgaa aagtttgcat cttgatgatt 2220
tagcttgact atgcgattgc tttcctggac ccgtgcagct gcggaaaggg cagattgtgt 2280
cgacaggtaa tggttgtctg gtaaaaggac agggccatcg ccaattggag tattttgttg 2340
ataatggtct gctagttgaa cggatccatc ttcaatgttg tggcgaattt tgaagttagc 2400
tttgattcca ttcttttgtt tgtctgccgt gatgtataca ttgtgtgagt tatagttgta 2460
ctcgagtttg tgtccgagaa tgtttccatc ttctttaaaa tcaatacctt ttaactcgat 2520
acgattaaca agggtatcac cttcaaactt gacttcagca cgcgtcttgt agttcccgtc 2580
atctttgaaa gatatagtgc gttcctgtac ataaccttcg ggcatgcata aactgcatcc 2640
cttaacttgt ttttcgtgtg cctatttttt gtgaatcgct aagaaaccat tattatcatg 2700
acattaacct ataaaaatag gcgtatcacg aggccctttc gtctcgcgcg tttcggtgat 2760
gacggtgaaa acctctgaca catgcagctc ccggagacgg tcacagcttg tctgtaagcg 2820
gatgccggga gcagacaagc ccgtcagggc gcgtcagcgg gtgttggcgg gtgtcggggc 2880
tggcttaact atgcggcatc agagcagatt gtactgagag tgcaccatac aaaacatatt 2940
tcaacacaat acaaatgggt tagttaaaaa agcaggcctt ctaaaggtct gcttttttta 3000
tttgattatg taatttttaa tgccaggatg ccaataagcc ataacctcaa atgcaccatt 3060
tgcaacctcg tcatcttctt cctcaatctt gaccagatcg ccgtcctccg catcaccaag 3120
attcagctct ttatgtatct ccttcaaaat gccaccgtat ccaattaacc ttcgagctgc 3180
caacgcatca tccaagtaaa gcaccgtgtt cagattgtct tcagtcacct tattaccgcg 3240
cacacaatcc gtatccttaa ccggatattt agagatttcg cgaacagctt tttgctccat 3300
cattgcgttc cgcacatcgt tttcaatctg ttcagcgtca atcttagctt tacctttcac 3360
tcgacgaata tcgacaattg gagtgtaatc caatttcatc gccttttttcc aaaggctcgt 3420
ccactccgcc tgcttaatat agtttttccc aaaataattt ttccttactg gtatcaacac 3480
atgaaaatga ggatgatatg tatcttcttc atgatttttg gtaatctcta aagctctgaa 3540
aaatccaaga accgaagttt ttactttttt gtactggaac agtttcctaa agccttccat 3600
catcgcagaa atttgtggct tcagccgttc tccctttaca tttcgaatcg tcagcgtgag 3660
aaaaatccat ccgcagccgt actgtctatt ggcttcctct acgatcaact tattgtgata 3720
agcaattttt aacgacctgc gccacgcaca catcggacat aacctcactt tacaaaaatg 3780
ggcttgatac agttttaact tgcccgtctc cgggtctctc ttaaacgaaa gatactctgc 3840
acaactaatt agtttttcag ccttttttgcc atagtaaggt gccccaatct tactctctaa 3900
cgcttcgtaa tgctccgcca tgaggttcgt ccgtctcttt ttccccttcc aatcccgctt 3960
tttacctgtt gcggttttat cttcgaggat gctataatca ttttcagatg aataaatcaa 4020

-continued

```
caaaaaaact ccttctgagc tagttctcta gcattctatt attttgattc gacaccttaa   4080
taatagcaga aggagttttt acctgtcaaa gaaccatcaa acccttgata cacaaggctt   4140
tgacctaatt ttgaaaaatg atgttgtttc tatatagtat caagataaga aagaaaagga   4200
tttttcgcta cgctcaaatc ctttaaaaaa acacaaaaga ccacattttt taatgtggtc   4260
tttattcttc aactaaagca cccattagtt caacaaacga aaattggata aagtgggata   4320
tttttaaaat atatatttat gttacagtaa tattgacttt taaaaaagga ttgattctaa   4380
tgaagaaagc agacaagtaa gcctcctaaa ttcactttag ataaaaattt aggaggcata   4440
tcaaatgaac tttaataaaa ttgatttaga caattggaag agaaaagaga tatttaatca   4500
ttatttgaac caacaaacga cttttagtat aaccacagaa attgatatta gtgttttata   4560
ccgaaacata aaacaagaag gatataaatt ttaccctgca tttattttct tagtgacaag   4620
ggtgataaac tcaaatacag cttttagaac tggttacaat agcgacggag agttaggtta   4680
ttgggataag ttagagccac tttatacaat tttgatggt gtatctaaaa cattctctgg   4740
tatttggact cctgtaaaga atgacttcaa agagttttat gatttatacc tttctgatgt   4800
agagaaatat aatggttcgg ggaaattgtt tcccaaaaca cctataccctg aaaatgcttt   4860
ttctctttct attattccat ggacttcatt tactgggttt aacttaaata tcaataataa   4920
tagtaattac cttctaccca ttattacagc aggaaaattc attaataaag gtaattcaat   4980
atatttaccg ctatctttac aggtacatca ttctgtttgt gatggttatc atgcaggatt   5040
gtttatgaac tctattcagg aattgtcaga taggcctaat gactggcttt tataatatga   5100
gataatgccg actgtacttt ttacagtcgg ttttctaatg tcactaacct gccccgttag   5160
tcgccattcg ccagctgcct cgcgcgtttc ggtgatgacg gtgaaaacct ctgacacatg   5220
cagctcccgg agacggtcac agcttgtctg taagcggatg ccgggagcag acaagcccgt   5280
cagggcgcgt cagcgggtgt tggcgggtgt cggggcgcag ccatgaccca gtcacgtagc   5340
gatagcggag tgtatactgg cttaactatg cggcatcaga gcagattgta ctgagagtgc   5400
accatatgcg gtgtgaaata ccgcacagat gcgtaaggag aaaataccgc atcaggcgct   5460
cttccgcttc ctcgctcact gactcgctgc gctcggtcgt tcggctgcgg cgagcggtat   5520
cagctcactc aaaggcggta atacggttat ccacagaatc aggggataac gcaggaaaga   5580
acatgtgagc aaaaggccag caaaaggcca ggaaccgtaa aaaggccgcg ttgctggcgt   5640
ttttccatag gctccgcccc cctgacgagc atcacaaaaa tcgacgctca agtcagaggt   5700
ggcgaaaccc gacaggacta taaagatacc aggcgtttcc ccctggaagc tccctcgtgc   5760
gctctcctgt tccgaccctg ccgcttaccg gatacctgtc cgcctttctc ccttcgggaa   5820
gcgtggcgct ttctcaatgc tcacgctgta ggtatctcag ttcggtgtag gtcgttcgct   5880
ccaagctggg ctgtgtgcac gaaccccccg ttcagcccga ccgctgcgcc ttatccggta   5940
actatcgtct tgagtccaac ccggtaagac acgacttatc gccactggca gcagccactg   6000
gtaacaggat tagcagagcg aggtatgtag gcggtgctac agagttcttg aagtggtggc   6060
ctaactacgg ctacactaga aggacagtat ttggtatctg cgctctgctg aagccagtta   6120
ccttcggaaa aagagttggt agctcttgat ccggcaaaca aaccaccgct ggtagcggtg   6180
gtttttttgt ttgcaagcag cagattacgc gcagaaaaaa aggatctcaa gaagatcctt   6240
tgatcttttc tacggggtct gacgctcagt ggaacgaaaa ctcacgttaa gggattttgg   6300
tcatgagatt atcaaaaagg atcttcacct agatcctttt aaattaaaaa tgaagtttta   6360
aatcaatcta aagtatatat gagtaaactt ggtctgacag ttaccaatgc ttaatcagtg   6420
```

```
aggcacctat ctcagcgatc tgtctatttc gttcatccat agttgcctga ctccccgtcg   6480
tgtagataac tacgatacgg gagggcttac catctggccc cagtgctgca atgataccgc   6540
gagacccacg ctcaccggct ccagatttat cagcaataaa ccagccagcc ggaagggccg   6600
agcgcagaag tggtcctgca actttatccg cctccatcca gtctattaat tgttgccggg   6660
aagctagagt aagtagttcg ccagttaata gtttgcgcaa cgttgttgcc attgctgcag   6720
gcatcgtggt gtcacgctcg tcgtttggta tggcttcatt cagctccggt tcccaacgat   6780
caaggcgagt tacatgatcc cccatgttgt gcaaaaaagc ggttagctcc ttcggtcctc   6840
cgatcgttgt cagaagtaag ttggccgcag tgttatcact catggttatg gcagcactgc   6900
ataattctct tactgtcatg ccatccgtaa gatgcttttc tgtgactggt gagtactcaa   6960
ccaagtcatt ctgagaatag tgtatgcggc gaccgagttg ctcttgcccg gcgtcaacac   7020
gggataatac cgcgccacat agcagaactt taaaagtgct catcattgga aaacgttctt   7080
cggggcgaaa actctcaagg atcttaccgc tgttgagatc cagttcgatg taacccactc   7140
gtgcacccaa ctgatcttca gcatctttta ctttcaccag cgtttctggg tgagcaaaaa   7200
caggaaggca aaatgccgca aaaaagggaa taagggcgac acggaaatgt tgaatactca   7260
tactcttcct ttttcaatat tattgaagca tttatcaggg ttattgtctc atgagcggat   7320
acatatttga atgtatttag aaaaataaac aaataggggt tccgcgcaca tttccccgaa   7380
aagtgccacc tgacgtctaa gaaaccatta ttatcatgac attaacctat aaaaataggc   7440
gtatcacgag gccctttcgt cttcaa                                         7466
```

<210> SEQ ID NO 32
<211> LENGTH: 4848
<212> TYPE: DNA
<213> ORGANISM: Artificial Sequence
<220> FEATURE:
<223> OTHER INFORMATION: LacUV5 promoter, pUC high copy number vector for E. coli, containing Arabidopsis WRKY transcription factor 33 intron

<400> SEQUENCE: 32

```
gcgatcgcgg ctcccgacat cttggaccat tagctccaca ggtatcttct tccctctagt     60
ggtcataaca gcagcttcag ctacctctca attcaaaaaa cccctcaaga cccgtttaga    120
ggccccaagg ggttatgcta tcaatcgttg cgttacacac acaaaaaacc aacacacatc    180
catcttcgat ggatagcgat tttattatct aactgctgat cgagtgtagc cagatctaag    240
ctgttgtgac cgcttgctct agccagctat cgagttgtga accgatccat ctagcaattg    300
gtctcgatct agcgataggc ttcgatctag ctatgtatca ctcattaggc accccaggct    360
ttacacttta tgcttccggc tcgtataatg tgtggtgctg gttagcgctt gctatagatc    420
tttgtcgatc ctaccatcca ctcgacacac ccgccagcgg ccgctgccaa gcttccgagc    480
tctcgaattc aaaggaggta cccaccatgg ggtaccgcga tatctacctc gaggttttgc    540
ccgaaggtta tgtacaggaa cgcactatat ctttcaaaga tgacgggaac tacaagacgc    600
gtgctgaagt caagtttgaa ggtgataccc ttgttaatcg tatcgagtta aaaggtattg    660
attttaaaga agatggaaac attctcggac acaaactcga gtacaactat aactcacaca    720
atgtatacat cacggcagac aaacaaaaga atggaatcaa agctaacttc aaaattcgcc    780
acaacattga agatggatcc gttcaactag cagaccatta tcaacaaaat actccaattg    840
gcgatggccc tgtcctttta ccagacaacc attacctgtc gacacaatct gccctttctc    900
```

-continued

```
ctcctctgct aacgtaagcc tctctgtttt ttttctctgt ttcttttgaa atgaatccaa    960
ttagtgatga taatctgtgt ttgatgtatc attgatttaa catcttgaca atgaatcgtg   1020
atcggaagtg ataaagttat gggtcaacgg tttcaaagag agagaaagac ttttagagtc   1080
aactctcgac tctttcttaa ttatgttatt gctatttgtc tcttttcttg aagtctgaac   1140
aattcttggg attgttttgc aggttctagc ttctccaacc acagaaaggg cagattgtgt   1200
cgacaggtaa tggttgtctg gtaaaaggac agggccatcg ccaattggag tatttgttg   1260
ataatggtct gctagttgaa cggatccatc ttcaatgttg tggcgaattt tgaagttagc   1320
tttgattcca ttcttttgtt tgtctgccgt gatgtataca ttgtgtgagt tatagttgta   1380
ctcgagtttg tgtccgagaa tgtttccatc ttctttaaaa tcaatacctt ttaactcgat   1440
acgattaaca agggtatcac cttcaaactt gacttcagca cgcgtcttgt agttcccgtc   1500
atctttgaaa gatatagtgc gttcctgtac ataaccttcg ggcaaagttg tctcctcctg   1560
cactgactga ctgatacaat cgatttctgg atccgcaggc ctctgctagc ttgactgact   1620
gagatacagc gtaccttcag ctcacagaca tgataagata cattgatgag tttggacaaa   1680
ccacaactag aatgcagtga aaaaaatgct ttatttgtga aatttgtgat gctattgctt   1740
tatttgtaac cattataagc tgcaataaac aagttaacaa caacaattgc attcatttta   1800
tgtttcaggt tcagggggag gtgtgggagg ttttttaaag caagtaaaac ctctacaaat   1860
gtggtattgg cccatctcta tcggtatcgt agcataaccc cttggggcct ctaaacgggt   1920
cttgaggggt tttttgtgcc cctcgggccg gattgctatc taccggcatt ggcgcagaaa   1980
aaaatgcctg atgcgacgct gcgcgtctta tactcccaca tatgccagat tcagcaacgg   2040
atacggcttc cccaacttgc ccacttccat acgtgtcctc cttaccagaa atttatcctt   2100
aaggtcgtca gctatcctgc aggcgatctc tcgatttcga tcaagacatt cctttaatgg   2160
tcttttctgg acaccactag ggtcagaagg tagttcatca aactttcttc cctccctaat   2220
ctcattggtt accttgggct atcgaaactt aattaaccag tcaagtcagc tacttggcga   2280
gatcgacttg tctgggtttc gactacgctc agaattgcgt cagtcaagtt cgatctggtc   2340
cttgctattg cacccgttct ccgattacga gtttcattta aatcatgtga gcaaaaggcc   2400
agcaaaaggc caggaaccgt aaaaaggccg cgttgctggc gtttttccat aggctccgcc   2460
cccctgacga gcatcacaaa aatcgacgct caagtcagag gtggcgaaac ccgacaggac   2520
tataaagata ccaggcgttt ccccctggaa gctccctcgt gcgctctcct gttccgaccc   2580
tgccgcttac cggatacctg tccgcctttc tcccttcggg aagcgtggcg ctttctcata   2640
gctcacgctg taggtatctc agttcggtgt aggtcgttcg ctccaagctg ggctgtgtgc   2700
acgaaccccc cgttcagccc gaccgctgcg ccttatccgg taactatcgt cttgagtcca   2760
acccggtaag acacgactta tcgccactgg cagcagccac tggtaacagg attagcagag   2820
cgaggtatgt aggcggtgct acagagttct tgaagtggtg gcctaactac ggctacacta   2880
gaagaacagt atttggtatc tgcgctctgc tgaagccagt taccttcgga aaaagagttg   2940
gtagctcttg atccggcaaa caaaccaccg ctggtagcgg tggttttttt gtttgcaagc   3000
agcagattac gcgcagaaaa aaaggatctc aagaagatcc tttgatcttt tctacggggt   3060
ctgacgctca gtggaacgaa aactcacgtt aagggatttt ggtcatgaga ttatcaaaaa   3120
ggatcttcac ctagatcctt ttaaattaaa aatgaagttt taaatcaatc taaagtatat   3180
atgagtaaac ttggtctgac agttaccaat gcttaatcag tgaggcacct atctcagcga   3240
tctgtctatt tcgttcatcc atagttgcat ttaaatttcc gaactctcca aggccctcgt   3300
```

cggaaaatct tcaaaccttt cgtccgatcc atcttgcagg ctacctctcg aacgaactat 3360
cgcaagtctc ttggccggcc ttgcgccttg gctattgctt ggcagcgcct atcgccaggt 3420
attactccaa tcccgaatat ccgagatcgg gatcacccga gagaagttca acctacatcc 3480
tcaatcccga tctatccgag atccgaggaa tatcgaaatc ggggcgcgcc tggtgtaccg 3540
agaacgatcc tctcagtgcg agtctcgacg atccatatcg ttgcttggca gtcagccagt 3600
cggaatccag cttgggaccc aggaagtcca atcgtcagat attgtactca agcctggtca 3660
cggcagcgta ccgatctgtt taaacctaga tattgatagt ctgatcggtc aacgtataat 3720
cgagtcctag cttttgcaaa catctatcaa gagacaggat cagcaggagg ctttcgcatg 3780
attgaacaag atggattgca cgcaggttct ccggcggctt gggtggagag gctattcggc 3840
tatgactggg cacaacagac aatcggctgc tctgatgccg ccgtgttccg gctgtcagcg 3900
caggggcgtc cggttctttt tgtcaagacc gacctgtccg gtgccctgaa tgaactgcaa 3960
gacgaggcag cgcggctatc gtggctggcg acgacgggcg ttccttgcgc ggctgtgctc 4020
gacgttgtca ctgaagcggg aagggactgg ctgctattgg gcgaagtgcc ggggcaggat 4080
ctcctgtcat ctcaccttgc tcctgccgag aaagtatcca tcatggctga tgcaatgcgg 4140
cggctgcata cgcttgatcc ggctacctgc ccattcgacc accaagcgaa acatcgcatc 4200
gagcgagcac gtactcggat ggaagccggt cttgtcgatc aggatgatct ggacgaagag 4260
catcaggggc tcgcgccagc cgaactgttc gccaggctca aggcgtctat gcccgacggc 4320
gaggatctcg tcgtgaccca cggcgatgcc tgcttgccga atatcatggt ggaaaatggc 4380
cgcttttctg gattcatcga ctgtggccgt ctgggtgtgg cggaccgcta tcaggacata 4440
gcgttggcta cccgtgatat tgctgaagag cttggcggcg aatgggctga ccgcttcctt 4500
gtgctttacg gtatcgccgc gcccgattcg cagcgcatcg ccttctatcg ccttcttgac 4560
gagttcttct gaccgattct aggtgcattg gcgcagaaaa aaatgcctga tgcgacgctg 4620
cgcgtcttat actcccacat atgccagatt cagcaacgga tacggcttcc ccaacttgcc 4680
cacttccata cgtgtcctcc ttaccagaaa tttatcctta aggtcgttta aactcgactc 4740
tggctctatc gaatctccgt cgtttcgagc ttacgcgaac agccgtggcg ctcatttgct 4800
cgtcgggcat cgaatctcgt cagctatcgt cagcttacct ttttggca 4848

<210> SEQ ID NO 33
<211> LENGTH: 5127
<212> TYPE: DNA
<213> ORGANISM: Artificial Sequence
<220> FEATURE:
<223> OTHER INFORMATION: LacUV5 promoter, pUC high copy number vector for E. coli, containing maize adh1 intron

<400> SEQUENCE: 33
gcgatcgcgg ctcccgacat cttggaccat tagctccaca ggtatcttct tccctctagt 60
ggtcataaca gcagcttcag ctacctctca attcaaaaaa cccctcaaga cccgtttaga 120
ggccccaagg ggttatgcta tcaatcgttg cgttacacac acaaaaaacc aacacacatc 180
catcttcgat ggatagcgat tttattatct aactgctgat cgagtgtagc cagatctaag 240
ctgttgtgac cgcttgctct agccagctat cgagttgtga accgatccat ctagcaattg 300
gtctcgatct agcgataggc ttcgatctag ctatgtatca ctcattaggc accccaggct 360
ttacacttta tgcttccggc tcgtataatg tgtggtgctg gttagcgctt gctatagatc 420
tttgtcgatc ctaccatcca ctcgacacac ccgccagcgg ccgctgccaa gcttccgagc 480

-continued

```
tctcgaattc aaaggaggta cccaccatgg ggtaccgcga tatctacctc gaggttttgc    540
ccgaaggtta tgtacaggaa cgcactatat ctttcaaaga tgacgggaac tacaagacgc    600
gtgctgaagt caagtttgaa ggtgataccc ttgttaatcg tatcgagtta aaaggtattg    660
attttaaaga agatggaaac attctcggac acaaactcga gtacaactat aactcacaca    720
atgtatacat cacggcagac aaacaaaaga atggaatcaa agctaacttc aaaattcgcc    780
acaacattga agatggatcc gttcaactag cagaccatta tcaacaaaat actccaattg    840
gcgatggccc tgtcctttta ccagacaacc attacctgtc gacacaatct gccctttgat    900
caagtgcaaa ggtccgcctt gtttctcctc tgtctcttga tctgactaat cttggtttat    960
gattcgttga gtaattttgg ggaaagctag cttcgtccac agtttttttt tcgatgaaca   1020
gtgccgcagt ggcgctgatc ttgtatgcta tcctgcaatc gtggtgaact tatgtctttt   1080
atatccttca ctaccatgaa aagactagct agtaatcttt ctcgatgtaa catcgtccag   1140
cactgctatt accgtgtggt ccatccgaca gtctggctga acacatcata cgatattgag   1200
caaagatcga tctatcttcc ctgttcttta atgaaagacg tcattttcat cagtatgatc   1260
taagaatgtt gcaacttgca aggaggcgtt tctttctttg aatttaacta actcgttgag   1320
tggccctgtt tctcggacgt aaggcctttg ctgctccaca catgtccatt cgaattttac   1380
cgtgtttagc aagggcgaaa agtttgcatc ttgatgattt agcttgacta tgcgattgct   1440
ttcctggacc cgtgcagctg cggaaagggc agattgtgtc gacaggtaat ggttgtctgg   1500
taaaaggaca gggccatcgc caattggagt attttgttga taatggtctg ctagttgaac   1560
ggatccatct tcaatgttgt ggcgaatttt gaagttagct ttgattccat tcttttgttt   1620
gtctgccgtg atgtatacat tgtgtgagtt atagttgtac tcgagtttgt gtccgagaat   1680
gtttccatct tctttaaaat caataccttt taactcgata cgattaacaa gggtatcacc   1740
ttcaaacttg acttcagcac gcgtcttgta gttcccgtca tctttgaaag atatagtgcg   1800
ttcctgtaca taaccttcgg gcaaagttgt ctcctcctgc actgactgac tgatacaatc   1860
gatttctgga tccgcaggcc tctgctagct tgactgactg agatacagcg taccttcagc   1920
tcacagacat gataagatac attgatgagt ttggacaaac cacaactaga atgcagtgaa   1980
aaaaatgctt tatttgtgaa atttgtgatg ctattgcttt atttgtaacc attataagct   2040
gcaataaaca agttaacaac aacaattgca ttcattttat gtttcaggtt cagggggagg   2100
tgtgggaggt tttttaaagc aagtaaaacc tctacaaatg tggtattggc ccatctctat   2160
cggtatcgta gcataacccc ttggggcctc taaacgggtc ttgaggggtt ttttgtgccc   2220
ctcgggccgg attgctatct accggcattg gcgcagaaaa aaatgcctga tgcgacgctg   2280
cgcgtcttat actcccacat atgccagatt cagcaacgga tacggcttcc ccaacttgcc   2340
cacttccata cgtgtcctcc ttaccagaaa tttatcctta aggtcgtcag ctatcctgca   2400
ggcgatctct cgatttcgat caagacattc ctttaatggt cttttctgga caccactagg   2460
ggtcagaagt agttcatcaa actttcttcc ctccctaatc tcattggtta ccttgggcta   2520
tcgaaactta attaaccagt caagtcagct acttggcgag atcgacttgt ctgggtttcg   2580
actacgctca gaattgcgtc agtcaagttc gatctggtcc ttgctattgc acccgttctc   2640
cgattacgag tttcatttaa atcatgtgag caaaaggcca gcaaaaggcc aggaaccgta   2700
aaaaggccgc gttgctggcg tttttccata ggctccgccc ccctgacgag catcacaaaa   2760
atcgacgctc aagtcagagg tggcgaaacc cgacaggact ataaagatac caggcgtttc   2820
```

-continued

```
ccccctggaag ctccctcgtg cgctctcctg ttccgaccct gccgcttacc ggatacctgt   2880
ccgcctttct cccttcggga agcgtggcgc tttctcatag ctcacgctgt aggtatctca   2940
gttcggtgta ggtcgttcgc tccaagctgg gctgtgtgca cgaacccccc gttcagcccg   3000
accgctgcgc cttatccggt aactatcgtc ttgagtccaa cccggtaaga cacgacttat   3060
cgccactggc agcagccact ggtaacagga ttagcagagc gaggtatgta ggcggtgcta   3120
cagagttctt gaagtggtgg cctaactacg gctacactag aagaacagta tttggtatct   3180
gcgctctgct gaagccagtt accttcggaa aaagagttgg tagctcttga tccggcaaac   3240
aaaccaccgc tggtagcggt ggtttttttg tttgcaagca gcagattacg cgcagaaaaa   3300
aaggatctca agaagatcct ttgatctttt ctacggggtc tgacgctcag tggaacgaaa   3360
actcacgtta agggattttg gtcatgagat tatcaaaaag gatcttcacc tagatccttt   3420
taaattaaaa atgaagtttt aaatcaatct aaagtatata tgagtaaact tggtctgaca   3480
gttaccaatg cttaatcagt gaggcaccta tctcagcgat ctgtctattt cgttcatcca   3540
tagttgcatt taaatttccg aactctccaa ggccctcgtc ggaaaatctt caaacctttc   3600
gtccgatcca tcttgcaggc tacctctcga acgaactatc gcaagtctct tggccggcct   3660
tgcgccttgg ctattgcttg gcagcgccta tcgccaggta ttactccaat cccgaatatc   3720
cgagatcggg atcacccgag agaagttcaa cctacatcct caatcccgat ctatccgaga   3780
tccgaggaat atcgaaatcg gggcgcgcct ggtgtaccga gaacgatcct ctcagtgcga   3840
gtctcgacga tccatatcgt tgcttggcag tcagccagtc ggaatccagc ttgggaccca   3900
ggaagtccaa tcgtcagata ttgtactcaa gcctggtcac ggcagcgtac cgatctgttt   3960
aaacctagat attgatagtc tgatcggtca acgtataatc gagtcctagc ttttgcaaac   4020
atctatcaag agacaggatc agcaggaggc tttcgcatga ttgaacaaga tggattgcac   4080
gcaggttctc cggcggcttg ggtggagagg ctattcggct atgactgggc acaacagaca   4140
atcggctgct ctgatgccgc cgtgttccgg ctgtcagcgc aggggcgtcc ggttcttttt   4200
gtcaagaccg acctgtccgg tgccctgaat gaactgcaag acgaggcagc gcggctatcg   4260
tggctggcga cgacgggcgt tccttgcgcg gctgtgctcg acgttgtcac tgaagcggga   4320
agggactggc tgctattggg cgaagtgccg gggcaggatc tcctgtcatc tcaccttgct   4380
cctgccgaga aagtatccat catggctgat gcaatgcggc ggctgcatac gcttgatccg   4440
gctacctgcc cattcgacca ccaagcgaaa catcgcatcg agcgagcacg tactcggatg   4500
gaagccggtc ttgtcgatca ggatgatctg gacgaagagc atcaggggct cgcgccagcc   4560
gaactgttcg ccaggctcaa ggcgtctatg cccgacggcg aggatctcgt cgtgacccac   4620
ggcgatgcct gcttgccgaa tatcatggtg gaaaatggcc gcttttctgg attcatcgac   4680
tgtggccgtc tgggtgtggc ggaccgctat caggacatag cgttggctac ccgtgatatt   4740
gctgaagagc ttggcggcga atgggctgac cgcttcctcg tgctttacgg tatcgccgcg   4800
cccgattcgc agcgcatcgc cttctatcgc cttcttgacg agttcttctg accgattcta   4860
ggtgcattgg cgcagaaaaa aatgcctgat gcgacgctgc gcgtcttata ctcccacata   4920
tgccagattc agcaacggat acggcttccc caacttgccc acttccatac gtgtcctcct   4980
taccagaaat ttatccttaa ggtcgtttaa actcgactct ggctctatcg aatctccgtc   5040
gtttcgagct tacgcgaaca gccgtggcgc tcatttgctc gtcgggcatc gaatctcgtc   5100
agctatcgtc agcttacctt tttggca                                        5127
```

<210> SEQ ID NO 34
<211> LENGTH: 7212
<212> TYPE: DNA
<213> ORGANISM: Artificial Sequence
<220> FEATURE:
<223> OTHER INFORMATION: Pupp (uracil phosphoribosyl transferase) promoter, shuttle vector, low-copy number, containing Arabidopsis WRKY transcription factor 33 intron

<400> SEQUENCE: 34

```
gaattcgagc tcggtacccg gggatcgcgt gaaagaaatt ttcggcgcag agcacgtaaa     60
tgttcaacca cactctggtg cacaagcgaa catggcagta tacttcacga ttttagagca    120
aggcgataca gtacttggta tgaatttatc tcatggtggt cacttaacac acggaagccc    180
tgttaacttc agtggagtac aatataattt cgtagaatat ggcgtggatg ctgactctca    240
ccgtattaat tacgatgatg tattagcaaa agcgaaagaa cataaaccaa aattaatcgt    300
tgcaggtgca agtgcatacc ctcgtgttat cgatttcaag cgattccgtg agattgcaga    360
tgaagtgggc gcttatttaa tggttgatat ggcacatatc gctggtttag tagctgctgg    420
tttacatcca aatccagtac cacatgcaca tttcgttaca acgacaacac ataaaacgtt    480
acgtggcccg cgtggtggta tgattttatg tgaagagcaa tttgcaaaac aaattgataa    540
atcaatcttc cctggtattc aaggtggtcc acttatgcac gtaatcgctg caaaagctgt    600
tgcgtttggt gaagcacttc aagatgattt caaaacatat gcacaaaata tcattaacaa    660
tgcgaaccgc ttagctgaag gtcttcaaaa agaaggactt acacttgttt ctggcggaac    720
agacaatcac ttaatcttga ttgatgttcg taacttagaa atcacaggta aagtagcaga    780
gcacgtatta gatgaagttg gtattacagt gaacaaaaat acaattccat ttgaaacagc    840
aagcccattt gtaacaagtg gtgtacgtat cggtacagca gctgtaacat ctcgtggttt    900
cggtttagaa gaaatggatg aaattgcgtc acttattgct tatacattaa aaaatcatga    960
aaatgaagct gcattagaag aagtacgtaa gcgtgtagaa gcgttaacta gcaaatttcc   1020
aatgtatcca aatctataat agattgaaga agactgccga gacttaattg ttttggcggt   1080
ctttttgtg gacatatatt atttttaaag tatgtataca aatgatgaat aaattttggc    1140
gatataatga aggatacagc tcccataatt ggtaaagata ctagatagat tcatcgtaaa   1200
atcatgattt tgccaaattt gcccttgaat attagtagcg ttttctttac aatcgtaaat   1260
agtgtaaaaa agcgtgcaaa cgcatgaata tcatctaaag gagagattca catgggaaaa   1320
ctgtatgtat ttgatcctct agatttaaga aggagatata cattgcccga aggttatgta   1380
caggaacgca ctatatcttt caaagatgac gggaactaca agacgcgtgc tgaagtcaag   1440
tttgaaggtg ataccttgt taatcgtatc gagttaaaag gtattgattt taaagaagat    1500
ggaaacattc tcggacacaa actcgagtac aactataact cacacaatgt atacatcacg   1560
gcagacaaac aaaagaatgg aatcaaagct aacttcaaaa ttcgccacaa cattgaagat   1620
ggatccgttc aactagcaga ccattatcaa caaaatactc caattggcga tggccctgtc   1680
cttttaccag acaaccatta cctgtcgaca caatctgccc tttctcctcc tctgctaacg   1740
taagcctctc tgttttttt ctctgtttct tttgaaatga atccaattag tgatgataat    1800
ctgtgtttga tgtatcattg atttaacatc ttgacaatga atcgtgatcg gaagtgataa   1860
agttatgggt caacggtttc aaagagagag aaagactttt agagtcaact ctcgactctt   1920
tcttaattat gttattgcta tttgtctctt ttcttgaagt ctgaacaatt cttgggattg   1980
ttttgcaggt tctagcttct ccaaccacag aaagggcaga ttgtgtcgac aggtaatggt   2040
```

-continued

```
tgtctggtaa aaggacaggg ccatcgccaa ttggagtatt ttgttgataa tggtctgcta   2100
gttgaacgga tccatcttca atgttgtggc gaattttgaa gttagctttg attccattct   2160
tttgtttgtc tgccgtgatg tatacattgt gtgagttata gttgtactcg agtttgtgtc   2220
cgagaatgtt tccatcttct ttaaaatcaa taccttttaa ctcgatacga ttaacaaggg   2280
tatcaccttc aaacttgact tcagcacgcg tcttgtagtt cccgtcatct ttgaaagata   2340
tagtgcgttc ctgtacataa ccttcgggca tgcataaact gcatccctta acttgttttt   2400
cgtgtgccta ttttttgtga atcgctaaga aaccattatt atcatgacat taacctataa   2460
aaataggcgt atcacgaggc cctttcgtct cgcgcgtttc ggtgatgacg gtgaaaacct   2520
ctgacacatg cagctcccgg agacggtcac agcttgtctg taagcggatg ccgggagcag   2580
acaagcccgt cagggcgcgt cagcgggtgt tggcgggtgt cggggctggc ttaactatgc   2640
ggcatcagag cagattgtac tgagagtgca ccatacaaaa catatttcaa cacaatacaa   2700
atgggttagt taaaaaagca ggccttctaa aggtctgctt tttttatttg attatgtaat   2760
ttttaatgcc aggatgccaa taagccataa cctcaaatgc accatttgca acctcgtcat   2820
cttcttcctc aatcttgacc agatcgccgt cctccgcatc accaagattc agctctttat   2880
gtatctcctt caaaatgcca ccgtatccaa ttaaccttcg agctgccaac gcatcatcca   2940
agtaaagcac cgtgttcaga ttgtcttcag tcaccttatt accgcgcaca caatccgtat   3000
ccttaaccgg atatttagag atttcgcgaa cagctttttg ctccatcatt gcgttccgca   3060
catcgttttc aatctgttca gcgtcaatct tagctttacc tttcactcga cgaatatcga   3120
caattggagt gtaatccaat ttcatcgcct ttttccaaag gctcgtccac tccgcctgct   3180
taatatagtt tttcccaaaa taatttttcc ttactggtat caacacatga aaatgaggat   3240
gatatgtatc ttcttcatga tttttggtaa tctctaaagc tctgaaaaat ccaagaaccg   3300
aagtttttac ttttttgtac tggaacagtt tcctaaagcc ttccatcatc gcagaaattt   3360
gtggcttcag ccgttctccc tttacatttc gaatcgtcag cgtgagaaaa atccatccgc   3420
agccgtactg tctattggct tcctctacga tcaacttatt gtgataagca atttttaacg   3480
acctgcgcca cgcacacatc ggacataacc tcactttaca aaaatgggct tgatacagtt   3540
ttaacttgcc cgtctccggg tctctcttaa acgaaagata ctctgcacaa ctaattagtt   3600
tttcagcctt tttgccatag taaggtgccc caatcttact ctctaacgct tcgtaatgct   3660
ccgccatgag gttcgtccgt ctcttttttcc ccttccaatc ccgcttttta cctgttgcgg   3720
ttttatcttc gaggatgcta taatcatttt cagatgaata aatcaacaaa aaaactcctt   3780
ctgagctagt tctctagcat tctattattt tgattcgaca ccttaataat agcagaagga   3840
gtttttacct gtcaaagaac catcaaaccc ttgatacaca aggctttgac ctaattttga   3900
aaaatgatgt tgtttctata tagtatcaag ataagaaaga aaaggatttt tcgctacgct   3960
caaatccttt aaaaaaacac aaaagaccac attttttaat gtggtcttta ttcttcaact   4020
aaagcaccca ttagttcaac aaacgaaaat tggataaagt gggatatttt taaaatatat   4080
atttatgtta cagtaatatt gacttttaaa aaaggattga ttctaatgaa gaaagcagac   4140
aagtaagcct cctaaattca ctttagataa aaatttagga ggcatatcaa atgaacttta   4200
ataaaattga tttagacaat tggaagagaa aagagatatt taatcattat ttgaaccaac   4260
aaacgacttt tagtataacc acagaaattg atattagtgt tttataccga aacataaaac   4320
aagaaggata taaattttac cctgcattta ttttcttagt gacaagggtg ataaactcaa   4380
atacagcttt tagaactggt tacaatagcg acggagagtt aggttattgg gataagttag   4440
```

agccacttta tacaattttt gatggtgtat ctaaaacatt ctctggtatt tggactcctg 4500
taaagaatga cttcaaagag ttttatgatt tatacctttc tgatgtagag aaatataatg 4560
gttcggggaa attgtttccc aaaacaccta tacctgaaaa tgctttttct ctttctatta 4620
ttccatggac ttcatttact gggtttaact taaatatcaa taataatagt aattaccttc 4680
tacccattat tacagcagga aaattcatta ataaaggtaa ttcaatatat ttaccgctat 4740
ctttacaggt acatcattct gtttgtgatg gttatcatgc aggattgttt atgaactcta 4800
ttcaggaatt gtcagatagg cctaatgact ggcttttata atatgagata atgccgactg 4860
tactttttac agtcggtttt ctaatgtcac taacctgccc cgttagtcgc cattcgccag 4920
ctgcctcgcg cgtttcggtg atgacggtga aaacctctga cacatgcagc tcccggagac 4980
ggtcacagct tgtctgtaag cggatgccgg gagcagacaa gcccgtcagg gcgcgtcagc 5040
gggtgttggc gggtgtcggg gcgcagccat gacccagtca cgtagcgata gcggagtgta 5100
tactggctta actatgcggc atcagagcag attgtactga gagtgcacca tatgcggtgt 5160
gaaataccgc acagatgcgt aaggagaaaa taccgcatca ggcgctcttc cgcttcctcg 5220
ctcactgact cgctgcgctc ggtcgttcgg ctgcggcgag cggtatcagc tcactcaaag 5280
gcggtaatac ggttatccac agaatcaggg gataacgcag gaaagaacat gtgagcaaaa 5340
ggccagcaaa aggccaggaa ccgtaaaaag gccgcgttgc tggcgttttt ccataggctc 5400
cgcccccctg acgagcatca caaaaatcga cgctcaagtc agaggtggcg aaacccgaca 5460
ggactataaa gataccaggc gtttccccct ggaagctccc tcgtgcgctc tcctgttccg 5520
accctgccgc ttaccggata cctgtccgcc tttctccctt cgggaagcgt ggcgctttct 5580
caatgctcac gctgtaggta tctcagttcg gtgtaggtcg ttcgctccaa gctgggctgt 5640
gtgcacgaac cccccgttca gcccgaccgc tgcgccttat ccggtaacta tcgtcttgag 5700
tccaacccgg taagacacga cttatcgcca ctggcagcag ccactggtaa caggattagc 5760
agagcgaggt atgtaggcgg tgctacagag ttcttgaagt ggtggcctaa ctacggctac 5820
actagaagga cagtatttgg tatctgcgct ctgctgaagc cagttacctt cggaaaaaga 5880
gttggtagct cttgatccgg caaacaaacc accgctggta gcggtggttt ttttgtttgc 5940
aagcagcaga ttacgcgcag aaaaaaagga tctcaagaag atcctttgat cttttctacg 6000
gggtctgacg ctcagtggaa cgaaaactca cgttaaggga ttttggtcat gagattatca 6060
aaaaggatct tcacctagat ccttttaaat taaaaatgaa gttttaaatc aatctaaagt 6120
atatatgagt aaacttggtc tgacagttac caatgcttaa tcagtgaggc acctatctca 6180
gcgatctgtc tatttcgttc atccatagtt gcctgactcc ccgtcgtgta gataactacg 6240
atacgggagg gcttaccatc tggccccagt gctgcaatga taccgcgaga cccacgctca 6300
ccggctccag atttatcagc aataaaccag ccagccggaa gggccgagcg cagaagtggt 6360
cctgcaactt tatccgcctc catccagtct attaattgtt gccgggaagc tagagtaagt 6420
agttcgccag ttaatagttt gcgcaacgtt gttgccattg ctgcaggcat cgtggtgtca 6480
cgctcgtcgt ttggtatggc ttcattcagc tccggttccc aacgatcaag gcgagttaca 6540
tgatccccca tgttgtgcaa aaaagcggtt agctccttcg gtcctccgat cgttgtcaga 6600
agtaagttgg ccgcagtgtt atcactcatg gttatggcag cactgcataa ttctcttact 6660
gtcatgccat ccgtaagatg cttttctgtg actggtgagt actcaaccaa gtcattctga 6720
gaatagtgta tgcggcgacc gagttgctct tgcccggcgt caacacggga taataccgcg 6780

-continued

```
ccacatagca gaactttaaa agtgctcatc attggaaaac gttcttcggg gcgaaaactc   6840

tcaaggatct taccgctgtt gagatccagt tcgatgtaac ccactcgtgc acccaactga   6900

tcttcagcat cttttacttt caccagcgtt tctgggtgag caaaaacagg aaggcaaaat   6960

gccgcaaaaa agggaataag ggcgacacgg aaatgttgaa tactcatact cttccttttt   7020

caatattatt gaagcattta tcagggttat tgtctcatga gcggatacat atttgaatgt   7080

atttagaaaa ataaacaaat aggggttccg cgcacatttc cccgaaaagt gccacctgac   7140

gtctaagaaa ccattattat catgacatta acctataaaa ataggcgtat cacgaggccc   7200

tttcgtcttc aa                                                        7212
```

<210> SEQ ID NO 35
<211> LENGTH: 7491
<212> TYPE: DNA
<213> ORGANISM: Artificial Sequence
<220> FEATURE:
<223> OTHER INFORMATION: Pupp (uracil phosphoribosyl transferase) promoter, shuttle vector, low-copy number, containing maize adh1 intron

<400> SEQUENCE: 35

```
gaattcgagc tcggtacccg gggatcgcgt gaaagaaatt ttcggcgcag agcacgtaaa     60

tgttcaacca cactctggtg cacaagcgaa catggcagta tacttcacga ttttagagca    120

aggcgataca gtacttggta tgaatttatc tcatggtggt cacttaacac acggaagccc    180

tgttaacttc agtggagtac aatataattt cgtagaatat ggcgtggatg ctgactctca    240

ccgtattaat tacgatgatg tattagcaaa agcgaaagaa cataaaccaa aattaatcgt    300

tgcaggtgca agtgcatacc ctcgtgttat cgatttcaag cgattccgtg agattgcaga    360

tgaagtgggc gcttatttaa tggttgatat ggcacatatc gctggtttag tagctgctgg    420

tttacatcca aatccagtac cacatgcaca tttcgttaca acgacaacac ataaaacgtt    480

acgtggcccg cgtggtggta tgattttatg tgaagagcaa tttgcaaaac aaattgataa    540

atcaatcttc cctggtattc aaggtggtcc acttatgcac gtaatcgctg caaaagctgt    600

tgcgtttggt gaagcacttc aagatgattt caaaacatat gcacaaaata tcattaacaa    660

tgcgaaccgc ttagctgaag gtcttcaaaa agaaggactt acacttgttt ctggcggaac    720

agacaatcac ttaatcttga ttgatgttcg taacttagaa atcacaggta aagtagcaga    780

gcacgtatta gatgaagttg gtattacagt gaacaaaaat acaattccat ttgaaacagc    840

aagcccattt gtaacaagtg gtgtacgtat cggtacagca gctgtaacat ctcgtggttt    900

cggtttagaa gaaatggatg aaattgcgtc acttattgct tatacattaa aaaatcatga    960

aaatgaagct gcattagaag aagtacgtaa gcgtgtagaa gcgttaacta gcaaatttcc   1020

aatgtatcca aatctataat agattgaaga agactgccga gacttaattg ttttggcggt   1080

ctttttttgtg gacatatatt atttttaaag tatgtataca aatgatgaat aaattttggc   1140

gatataatga aggatacagc tcccataatt ggtaaagata ctagatagat tcatcgtaaa   1200

atcatgattt tgccaaattt gcccttgaat attagtagcg ttttctttac aatcgtaaat   1260

agtgtaaaaa agcgtgcaaa cgcatgaata tcatctaaag gagagattca catgggaaaa   1320

ctgtatgtat ttgatcctct agatttaaga aggagatata cattgcccga aggttatgta   1380

caggaacgca ctatatcttt caaagatgac gggaactaca agacgcgtgc tgaagtcaag   1440

tttgaaggtg ataccettgt taatcgtatc gagttaaaag gtattgattt taaagaagat   1500

ggaaacattc tcggacacaa actcgagtac aactataact cacacaatgt atacatcacg   1560
```

gcagacaaac aaaagaatgg aatcaaagct aacttcaaaa ttcgccacaa cattgaagat 1620
ggatccgttc aactagcaga ccattatcaa caaaatactc caattggcga tggccctgtc 1680
cttttaccag acaaccatta cctgtcgaca caatctgccc tttgatcaag tgcaaaggtc 1740
cgccttgttt ctcctctgtc tcttgatctg actaatcttg gtttatgatt cgttgagtaa 1800
ttttggggaa agctagcttc gtccacagtt ttttttcga tgaacagtgc cgcagtggcg 1860
ctgatcttgt atgctatcct gcaatcgtgg tgaacttatg tcttttatat ccttcactac 1920
catgaaaaga ctagctagta atctttctcg atgtaacatc gtccagcact gctattaccg 1980
tgtggtccat ccgacagtct ggctgaacac atcatacgat attgagcaaa gatcgatcta 2040
tcttccctgt tctttaatga aagacgtcat tttcatcagt atgatctaag aatgttgcaa 2100
cttgcaagga ggcgtttctt tctttgaatt taactaactc gttgagtggc cctgtttctc 2160
ggacgtaagg cctttgctgc tccacacatg tccattcgaa ttttaccgtg tttagcaagg 2220
gcgaaaagtt tgcatcttga tgatttagct tgactatgcg attgctttcc tggacccgtg 2280
cagctgcgga aagggcagat tgtgtcgaca ggtaatggtt gtctggtaaa aggacagggc 2340
catcgccaat tggagtattt tgttgataat ggtctgctag ttgaacggat ccatcttcaa 2400
tgttgtggcg aattttgaag ttagctttga ttccattctt ttgtttgtct gccgtgatgt 2460
atacattgtg tgagttatag ttgtactcga gtttgtgtcc gagaatgttt ccatcttctt 2520
taaaatcaat accttttaac tcgatacgat taacaagggt atcaccttca aacttgactt 2580
cagcacgcgt cttgtagttc ccgtcatctt tgaaagatat agtgcgttcc tgtacataac 2640
cttcgggcat gcataaactg catcccttaa cttgttttc gtgtgcctat tttttgtgaa 2700
tcgctaagaa accattatta tcatgacatt aacctataaa aataggcgta tcacgaggcc 2760
ctttcgtctc gcgcgtttcg gtgatgacgg tgaaaacctc tgacacatgc agctcccgga 2820
gacggtcaca gcttgtctgt aagcggatgc cgggagcaga caagcccgtc agggcgcgtc 2880
agcgggtgtt ggcgggtgtc ggggctggct taactatgcg gcatcagagc agattgtact 2940
gagagtgcac catacaaaac atatttcaac acaatacaaa tgggttagtt aaaaaagcag 3000
gccttctaaa ggtctgcttt ttttatttga ttatgtaatt tttaatgcca ggatgccaat 3060
aagccataac ctcaaatgca ccatttgcaa cctcgtcatc ttcttcctca atcttgacca 3120
gatcgccgtc ctccgcatca ccaagattca gctctttatg tatctccttc aaaatgccac 3180
cgtatccaat taaccttcga gctgccaacg catcatccaa gtaaagcacc gtgttcagat 3240
tgtcttcagt caccttatta ccgcgcacac aatccgtatc cttaaccgga tatttagaga 3300
tttcgcgaac agctttttgc tccatcattg cgttccgcac atcgttttca atctgttcag 3360
cgtcaatctt agctttacct ttcactcgac gaatatcgac aattggagtg taatccaatt 3420
tcatcgcctt tttccaaagg ctcgtccact ccgcctgctt aatatagttt ttcccaaaat 3480
aatttttcct tactggtatc aacacatgaa aatgaggatg atatgtatct tcttcatgat 3540
ttttggtaat ctctaaagct ctgaaaaatc caagaaccga agtttttact tttttgtact 3600
ggaacagttt cctaaagcct tccatcatcg cagaaatttg tggcttcagc cgttctccct 3660
ttacatttcg aatcgtcagc gtgagaaaaa tccatccgca gccgtactgt ctattggctt 3720
cctctacgat caacttattg tgataagcaa tttttaacga cctgcgccac gcacacatcg 3780
gacataacct cactttacaa aaatgggctt gatacagttt taacttgccc gtctccgggt 3840
ctctcttaaa cgaaagatac tctgcacaac taattagttt ttcagccttt ttgccatagt 3900

-continued

```
aaggtgcccc aatcttactc tctaacgctt cgtaatgctc cgccatgagg ttcgtccgtc   3960
tctttttccc cttccaatcc cgctttttac ctgttgcggt tttatcttcg aggatgctat   4020
aatcattttc agatgaataa atcaacaaaa aaactccttc tgagctagtt ctctagcatt   4080
ctattatttt gattcgacac cttaataata gcagaaggag tttttacctg tcaaagaacc   4140
atcaaaccct tgatacacaa ggctttgacc taattttgaa aatgatgtt gtttctatat    4200
agtatcaaga taagaaagaa aaggattttt cgctacgctc aaatccttta aaaaaacaca   4260
aaagaccaca ttttttaatg tggtctttat tcttcaacta aagcacccat tagttcaaca   4320
aacgaaaatt ggataaagtg ggatattttt aaaatatata tttatgttac agtaatattg   4380
acttttaaaa aaggattgat tctaatgaag aaagcagaca agtaagcctc ctaaattcac   4440
tttagataaa aatttaggag gcatatcaaa tgaactttaa taaaattgat ttagacaatt   4500
ggaagagaaa agagatattt aatcattatt tgaaccaaca aacgactttt agtataacca   4560
cagaaattga tattagtgtt ttataccgaa acataaaaca agaaggatat aaattttacc   4620
ctgcatttat tttcttagtg acaagggtga taaactcaaa tacagctttt agaactggtt   4680
acaatagcga cggagagtta ggttattggg ataagttaga gccactttat acaatttttg   4740
atggtgtatc taaaacattc tctggtattt ggactcctgt aaagaatgac ttcaaagagt   4800
tttatgattt atacctttct gatgtagaga aatataatgg ttcggggaaa ttgtttccca   4860
aaacacctat acctgaaaat gctttttctc tttctattat tccatggact tcatttactg   4920
ggtttaactt aaatatcaat aataatagta attaccttct acccattatt acagcaggaa   4980
aattcattaa taaaggtaat tcaatatatt taccgctatc tttacaggta catcattctg   5040
tttgtgatgg ttatcatgca ggattgttta tgaactctat tcaggaattg tcagataggc   5100
ctaatgactg gcttttataa tatgagataa tgccgactgt actttttaca gtcggttttc   5160
taatgtcact aacctgcccc gttagtcgcc attcgccagc tgcctcgcgc gtttcggtga   5220
tgacggtgaa aacctctgac acatgcagct cccggagacg gtcacagctt gtctgtaagc   5280
ggatgccggg agcagacaag cccgtcaggg cgcgtcagcg ggtgttggcg ggtgtcgggg   5340
cgcagccatg acccagtcac gtagcgatag cggagtgtat actggcttaa ctatgcggca   5400
tcagagcaga ttgtactgag agtgcaccat atgcggtgtg aaataccgca cagatgcgta   5460
aggagaaaat accgcatcag gcgctcttcc gcttcctcgc tcactgactc gctgcgctcg   5520
gtcgttcggc tgcggcgagc ggtatcagct cactcaaagg cggtaatacg gttatccaca   5580
gaatcagggg ataacgcagg aaagaacatg tgagcaaaag gccagcaaaa ggccaggaac   5640
cgtaaaaagg ccgcgttgct ggcgtttttc cataggctcc gcccccctga cgagcatcac   5700
aaaaatcgac gctcaagtca gaggtggcga aacccgacag gactataaag ataccaggcg   5760
tttccccctg gaagctccct cgtgcgctct cctgttccga ccctgccgct taccggatac   5820
ctgtccgcct ttctcccttc gggaagcgtg gcgctttctc aatgctcacg ctgtaggtat   5880
ctcagttcgg tgtaggtcgt tcgctccaag ctgggctgtg tgcacgaacc ccccgttcag   5940
cccgaccgct gcgccttatc cggtaactat cgtcttgagt ccaacccggt aagacacgac   6000
ttatcgccac tggcagcagc cactggtaac aggattagca gagcgaggta tgtaggcggt   6060
gctacagagt tcttgaagtg gtggcctaac tacggctaca ctagaaggac agtatttggt   6120
atctgcgctc tgctgaagcc agttaccttc ggaaaaagag ttggtagctc ttgatccggc   6180
aaacaaacca ccgctggtag cggtggtttt tttgtttgca agcagcagat tacgcgcaga   6240
aaaaaaggat ctcaagaaga tcctttgatc ttttctacgg ggtctgacgc tcagtggaac   6300
```

```
gaaaactcac gttaagggat tttggtcatg agattatcaa aaaggatctt cacctagatc   6360

cttttaaatt aaaaatgaag ttttaaatca atctaaagta tatatgagta aacttggtct   6420

gacagttacc aatgcttaat cagtgaggca cctatctcag cgatctgtct atttcgttca   6480

tccatagttg cctgactccc cgtcgtgtag ataactacga tacgggaggg cttaccatct   6540

ggccccagtg ctgcaatgat accgcgagac ccacgctcac cggctccaga tttatcagca   6600

ataaaccagc cagccggaag ggccgagcgc agaagtggtc ctgcaacttt atccgcctcc   6660

atccagtcta ttaattgttg ccgggaagct agagtaagta gttcgccagt taatagtttg   6720

cgcaacgttg ttgccattgc tgcaggcatc gtggtgtcac gctcgtcgtt tggtatggct   6780

tcattcagct ccggttccca acgatcaagg cgagttacat gatcccccat gttgtgcaaa   6840

aaagcggtta gctccttcgg tcctccgatc gttgtcagaa gtaagttggc cgcagtgtta   6900

tcactcatgg ttatggcagc actgcataat tctcttactg tcatgccatc cgtaagatgc   6960

ttttctgtga ctggtgagta ctcaaccaag tcattctgag aatagtgtat gcggcgaccg   7020

agttgctctt gcccggcgtc aacacgggat aataccgcgc cacatagcag aactttaaaa   7080

gtgctcatca ttggaaaacg ttcttcgggg cgaaaactct caaggatctt accgctgttg   7140

agatccagtt cgatgtaacc cactcgtgca cccaactgat cttcagcatc ttttactttc   7200

accagcgttt ctgggtgagc aaaaacagga aggcaaaatg ccgcaaaaaa gggaataagg   7260

gcgacacgga aatgttgaat actcatactc ttcctttttc aatattattg aagcatttat   7320

cagggttatt gtctcatgag cggatacata tttgaatgta tttagaaaaa taaacaaata   7380

ggggttccgc gcacatttcc ccgaaaagtg ccacctgacg tctaagaaac cattattatc   7440

atgacattaa cctataaaaa taggcgtatc acgaggccct ttcgtcttca a            7491


<210> SEQ ID NO 36
<211> LENGTH: 7212
<212> TYPE: DNA
<213> ORGANISM: Artificial Sequence
<220> FEATURE:
<223> OTHER INFORMATION: Pupp (uracil phosphoribosyl transferase)
      promoter, shuttle vector, low-copy number, containing Arabidopsis
      WRKY transcription factor 33 intron

<400> SEQUENCE: 36

gaattcgagc tcggtacccg gggatcgcgt gaaagaaatt ttcggcgcag agcacgtaaa     60

tgttcaacca cactctggtg cacaagcgaa catggcagta tacttcacga ttttagagca    120

aggcgataca gtacttggta tgaatttatc tcatggtggt cacttaacac acggaagccc    180

tgttaacttc agtggagtac aatataattt cgtagaatat ggcgtggatg ctgactctca    240

ccgtattaat tacgatgatg tattagcaaa agcgaaagaa cataaaccaa aattaatcgt    300

tgcaggtgca agtgcatacc ctcgtgttat cgatttcaag cgattccgtg agattgcaga    360

tgaagtgggc gcttatttaa tggttgatat ggcacatatc gctggtttag tagctgctgg    420

tttacatcca aatccagtac cacatgcaca tttcgttaca acgacaacac ataaaacgtt    480

acgtggcccg cgtggtggta tgattttatg tgaagagcaa tttgcaaaac aaattgataa    540

atcaatcttc cctggtattc aaggtggtcc acttatgcac gtaatcgctg caaaagctgt    600

tgcgtttggt gaagcacttc aagatgattt caaaacatat gcacaaaata tcattaacaa    660

tgcgaaccgc ttagctgaag gtcttcaaaa agaaggactt acacttgttt ctggcggaac    720

agacaatcac ttaatcttga ttgatgttcg taacttagaa atcacaggta aagtagcaga    780
```

-continued

```
gcacgtatta gatgaagttg gtattacagt gaacaaaaat acaattccat ttgaaacagc    840
aagcccattt gtaacaagtg gtgtacgtat cggtacagca gctgtaacat ctcgtggttt    900
cggtttagaa gaaatggatg aaattgcgtc acttattgct tatacattaa aaaatcatga    960
aaatgaagct gcattagaag aagtacgtaa gcgtgtagaa gcgttaacta gcaaatttcc   1020
aatgtatcca aatctataat agattgaaga agactgccga gacttaattg ttttggcggt   1080
ctttttgtg gacatatatt atttttaaag tatgtataca aatgatgaat aaattttggc   1140
gatataatga aggatacagc tcccataatt ggtaaagata ctagatagat tcatcgtaaa   1200
atcatgattt tgccaaattt gcccttgaat attagtagcg ttttctttac aatcgtaaat   1260
agtgtaaaaa agcgtgcaaa cgcatgaata tcatctaaag gagagattca catgggaaaa   1320
ctgtatgtat ttgatcctct agatttaaga aggagatata cattctcgga tcttactaca   1380
cagcagctgc aaagaaaaga tttcagttca aggtcgttcc caattatgct ataaccaccc   1440
aggacgcgat gaaaaacgtc tggcaagttt tagttaatat tagaaatgtg aagatgtcag   1500
cgggtttctg tccgctttct ctggagtttg tgtcggtgtg tattgtttat agaaataata   1560
taaaattagg tttgagagag aagattacaa acgtgagaga cggagggccc atggaactta   1620
cagaagaagt cgttgatgag ttcatggaag atgtccctat gtcgatcagg cttgcaaagt   1680
ttcgatctcg aaccggaaaa aagagtgatg tccgcaaagg gaactcctcc tctgctaacg   1740
taagcctctc tgttttttt ctctgtttct tttgaaatga atccaattag tgatgataat   1800
ctgtgtttga tgtatcattg atttaacatc ttgacaatga atcgtgatcg gaagtgataa   1860
agttatgggt caacggtttc aaagagagag aaagactttt agagtcaact ctcgactctt   1920
tcttaattat gttattgcta tttgtctctt ttcttgaagt ctgaacaatt cttgggattg   1980
ttttgcaggt tctagcttct ccaaccacag ttccctttgc ggacatcact cttttttccg   2040
gttcgagatc gaaactttgc aagcctgatc gacataggga catcttccat gaactcatca   2100
acgacttctt ctgtaagttc catgggccct ccgtctctca cgtttgtaat cttctctctc   2160
aaacctaatt ttatattatt tctataaaca atacacaccg acacaaactc cagagaaagc   2220
ggacagaaac ccgctgacat cttcacattt ctaatattaa ctaaaacttg ccagacgttt   2280
ttcatcgcgt cctgggtggt tatagcataa ttgggaacga ccttgaactg aaatcttttc   2340
tttgcagctg ctgtgtagta agatccgaga tgcataaact gcatccctta acttgttttt   2400
cgtgtgccta ttttttgtga atcgctaaga aaccattatt atcatgacat taacctataa   2460
aaataggcgt atcacgaggc cctttcgtct cgcgcgtttc ggtgatgacg gtgaaaacct   2520
ctgacacatg cagctcccgg agacggtcac agcttgtctg taagcggatg ccgggagcag   2580
acaagcccgt cagggcgcgt cagcgggtgt tggcgggtgt cggggctggc ttaactatgc   2640
ggcatcagag cagattgtac tgagagtgca ccatacaaaa catatttcaa cacaatacaa   2700
atgggttagt taaaaaagca ggccttctaa aggtctgctt tttttatttg attatgtaat   2760
ttttaatgcc aggatgccaa taagccataa cctcaaatgc accatttgca acctcgtcat   2820
cttcttcctc aatcttgacc agatcgccgt cctccgcatc accaagattc agctctttat   2880
gtatctcctt caaaatgcca ccgtatccaa ttaaccttcg agctgccaac gcatcatcca   2940
agtaaagcac cgtgttcaga ttgtcttcag tcaccttatt accgcgcaca caatccgtat   3000
ccttaaccgg atatttagag atttcgcgaa cagctttttg ctccatcatt gcgttccgca   3060
catcgttttc aatctgttca gcgtcaatct tagctttacc tttcactcga cgaatatcga   3120
caattggagt gtaatccaat ttcatcgcct ttttccaaag gctcgtccac tccgcctgct   3180
```

-continued

```
taatatagtt tttcccaaaa taatttttcc ttactggtat caacacatga aaatgaggat   3240
gatatgtatc ttcttcatga tttttggtaa tctctaaagc tctgaaaaat ccaagaaccg   3300
aagtttttac ttttttgtac tggaacagtt tcctaaagcc ttccatcatc gcagaaattt   3360
gtggcttcag ccgttctccc tttacatttc gaatcgtcag cgtgagaaaa atccatccgc   3420
agccgtactg tctattggct tcctctacga tcaacttatt gtgataagca atttttaacg   3480
acctgcgcca cgcacacatc ggacataacc tcactttaca aaaatgggct tgatacagtt   3540
ttaacttgcc cgtctccggg tctctcttaa acgaaagata ctctgcacaa ctaattagtt   3600
tttcagcctt tttgccatag taaggtgccc caatcttact ctctaacgct tcgtaatgct   3660
ccgccatgag gttcgtccgt ctctttttcc ccttccaatc ccgcttttta cctgttgcgg   3720
ttttatcttc gaggatgcta taatcatttt cagatgaata aatcaacaaa aaaactcctt   3780
ctgagctagt tctctagcat tctattattt tgattcgaca ccttaataat agcagaagga   3840
gtttttacct gtcaaagaac catcaaaccc ttgatacaca aggctttgac ctaattttga   3900
aaaatgatgt tgtttctata tagtatcaag ataagaaaga aaaggatttt tcgctacgct   3960
caaatccttt aaaaaaacac aaaagaccac attttttaat gtggtcttta ttcttcaact   4020
aaagcaccca ttagttcaac aaacgaaaat tggataaagt gggatatttt taaaatatat   4080
atttatgtta cagtaatatt gacttttaaa aaaggattga ttctaatgaa gaaagcagac   4140
aagtaagcct cctaaattca ctttagataa aaatttagga ggcatatcaa atgaacttta   4200
ataaaattga tttagacaat tggaagagaa aagagatatt taatcattat ttgaaccaac   4260
aaacgacttt tagtataacc acagaaattg atattagtgt tttataccga aacataaaac   4320
aagaaggata taaattttac cctgcattta ttttcttagt gacaagggtg ataaactcaa   4380
atacagcttt tagaactggt tacaatagcg acggagagtt aggttattgg gataagttag   4440
agccacttta tacaattttt gatggtgtat ctaaaacatt ctctggtatt tggactcctg   4500
taaagaatga cttcaaagag ttttatgatt tatacctttc tgatgtagag aaatataatg   4560
gttcggggaa attgtttccc aaaacaccta tacctgaaaa tgctttttct ctttctatta   4620
ttccatggac ttcatttact gggtttaact taaatatcaa taataatagt aattaccttc   4680
tacccattat tacagcagga aaattcatta ataaaggtaa ttcaatatat ttaccgctat   4740
ctttacaggt acatcattct gtttgtgatg gttatcatgc aggattgttt atgaactcta   4800
ttcaggaatt gtcagatagg cctaatgact ggcttttata atatgagata atgccgactg   4860
tactttttac agtcggtttt ctaatgtcac taacctgccc cgttagtcgc cattcgccag   4920
ctgcctcgcg cgtttcggtg atgacggtga aaacctctga cacatgcagc tcccggagac   4980
ggtcacagct tgtctgtaag cggatgccgg gagcagacaa gcccgtcagg gcgcgtcagc   5040
gggtgttggc gggtgtcggg gcgcagccat gacccagtca cgtagcgata gcggagtgta   5100
tactggctta actatgcggc atcagagcag attgtactga gagtgcacca tatgcggtgt   5160
gaaataccgc acagatgcgt aaggagaaaa taccgcatca ggcgctcttc cgcttcctcg   5220
ctcactgact cgctgcgctc ggtcgttcgg ctgcggcgag cggtatcagc tcactcaaag   5280
gcggtaatac ggttatccac agaatcaggg gataacgcag gaaagaacat gtgagcaaaa   5340
ggccagcaaa aggccaggaa ccgtaaaaag gccgcgttgc tggcgttttt ccataggctc   5400
cgcccccctg acgagcatca caaaaatcga cgctcaagtc agaggtggcg aaacccgaca   5460
ggactataaa gataccaggc gtttccccct ggaagctccc tcgtgcgctc tcctgttccg   5520
```

-continued

```
accctgccgc ttaccggata cctgtccgcc tttctccctt cgggaagcgt ggcgctttct   5580

caatgctcac gctgtaggta tctcagttcg gtgtaggtcg ttcgctccaa gctgggctgt   5640

gtgcacgaac cccccgttca gcccgaccgc tgcgccttat ccggtaacta tcgtcttgag   5700

tccaacccgg taagacacga cttatcgcca ctggcagcag ccactggtaa caggattagc   5760

agagcgaggt atgtaggcgg tgctacagag ttcttgaagt ggtggcctaa ctacggctac   5820

actagaagga cagtatttgg tatctgcgct ctgctgaagc cagttacctt cggaaaaaga   5880

gttggtagct cttgatccgg caaacaaacc accgctggta gcggtggttt ttttgtttgc   5940

aagcagcaga ttacgcgcag aaaaaaagga tctcaagaag atcctttgat cttttctacg   6000

gggtctgacg ctcagtggaa cgaaaactca cgttaaggga ttttggtcat gagattatca   6060

aaaaggatct tcacctagat ccttttaaat taaaaatgaa gttttaaatc aatctaaagt   6120

atatatgagt aaacttggtc tgacagttac caatgcttaa tcagtgaggc acctatctca   6180

gcgatctgtc tatttcgttc atccatagtt gcctgactcc ccgtcgtgta gataactacg   6240

atacgggagg gcttaccatc tggccccagt gctgcaatga taccgcgaga cccacgctca   6300

ccggctccag atttatcagc aataaaccag ccagccggaa gggccgagcg cagaagtggt   6360

cctgcaactt tatccgcctc catccagtct attaattgtt gccgggaagc tagagtaagt   6420

agttcgccag ttaatagttt gcgcaacgtt gttgccattg ctgcaggcat cgtggtgtca   6480

cgctcgtcgt ttggtatggc ttcattcagc tccggttccc aacgatcaag gcgagttaca   6540

tgatccccca tgttgtgcaa aaaagcggtt agctccttcg gtcctccgat cgttgtcaga   6600

agtaagttgg ccgcagtgtt atcactcatg gttatggcag cactgcataa ttctcttact   6660

gtcatgccat ccgtaagatg cttttctgtg actggtgagt actcaaccaa gtcattctga   6720

gaatagtgta tgcggcgacc gagttgctct tgcccggcgt caacacggga taataccgcg   6780

ccacatagca gaactttaaa agtgctcatc attggaaaac gttcttcggg gcgaaaactc   6840

tcaaggatct taccgctgtt gagatccagt tcgatgtaac ccactcgtgc acccaactga   6900

tcttcagcat cttttacttt caccagcgtt tctgggtgag caaaaacagg aaggcaaaat   6960

gccgcaaaaa agggaataag ggcgacacgg aaatgttgaa tactcatact cttccttttt   7020

caatattatt gaagcattta tcagggttat tgtctcatga gcggatacat atttgaatgt   7080

atttagaaaa ataaacaaat aggggttccg cgcacatttc cccgaaaagt gccacctgac   7140

gtctaagaaa ccattattat catgacatta acctataaaa ataggcgtat cacgaggccc   7200

tttcgtcttc aa                                                        7212
```

<210> SEQ ID NO 37
<211> LENGTH: 681
<212> TYPE: DNA
<213> ORGANISM: Escherichia

<400> SEQUENCE: 37

```
atgaacccca tcgtaattaa tcggcttcaa cggaagctgg gctacacttt taatcatcag     60

gaactgttgc agcaggcatt aactcatcgt agtgccagca gtaaacataa cgagcgttta    120

gaatttttag gcgactctat tctgagctac gttatcgcca atgcgcttta tcaccgtttc    180

cctcgtgtgg atgaaggcga tatgagccgg atgcgcgcca cgctggtccg tggcaatacg    240

ctggcggaac tggcgcgcga atttgagtta ggcgagtgct tacgtttagg gccaggtgaa    300

cttaaaagcg gtggatttcg tcgtgagtca attctcgccg acaccgtcga agcattaatt    360

ggtggcgtat tcctcgacag tgatattcaa accgtcgaga aattaatcct caactggtat    420
```

-continued caaactcgtt tggacgaaat tagcccaggc gataaacaaa aagatccgaa aacgcgcttg 480
caagaatatt tgcagggtcg ccatctgccg ctgccgactt atctggtagt ccaggtacgt 540
ggcgaagcgc acgatcagga atttactatc cactgccagg tcagcggcct gagtgaaccg 600
gtggttggca caggttcaag ccgtcgtaag gctgagcagg ctgccgccga acaggcgttg 660
aaaaaactgg agctggaatg a 681

<210> SEQ ID NO 38
<211> LENGTH: 1936
<212> TYPE: DNA
<213> ORGANISM: Artificial Sequence
<220> FEATURE:
<223> OTHER INFORMATION: The design of RNaseIII mutant was performed using the DNA sequence for the rnc gene of Escherichia coli str. K-12 substr. MG1655

<400> SEQUENCE: 38
accggtaaac tgaaactgca gcgaagcagt tagcagaacc atgtatatca ggtctgtttc 60
gtgtgctgaa ttgttgacgc atttatttat tggtatcgca tgaaccccat cgtaattaat 120
cggcttcaac ggaagctggg ctacacttta gcgattgtgt aggctggagc tgcttcgaag 180
ttcctatact ttctagagaa taggaacttc ggaataggaa cttcaagatc ccctcacgct 240
gccgcaagca ctcagggcgc aagggctgct aaaggaagcg gaacacgtag aaagccagtc 300
cgcagaaacg gtgctgaccc cggatgaatg tcagctactg ggctatctgg acaagggaaa 360
acgcaagcgc aaagagaaag caggtagctt gcagtgggct tacatggcga tagctagact 420
gggcggtttt atggacagca agcgaaccgg aattgccagc tggggcgccc tctggtaagg 480
ttgggaagcc ctgcaaagta aactggatgg ctttcttgcc gccaaggatc tgatggcgca 540
ggggatcaag atctgatcaa gagacaggat gaggatcgtt tcgcatgatt gaacaagatg 600
gattgcacgc aggttctccg gccgcttggg tggagaggct attcggctat gactgggcac 660
aacagacaat cggctgctct gatgccgccg tgttccggct gtcagcgcag gggcgcccgg 720
ttctttttgt caagaccgac ctgtccggtg ccctgaatga actgcaggac gaggcagcgc 780
ggctatcgtg gctggccacg acgggcgttc cttgcgcagc tgtgctcgac gttgtcactg 840
aagcgggaag ggactggctg ctattgggcg aagtgccggg gcaggatctc ctgtcatctc 900
accttgctcc tgccgagaaa gtatccatca tggctgatgc aatgcggcgg ctgcatacgc 960
ttgatccggc tacctgccca ttcgaccacc aagcgaaaca tcgcatcgag cgagcacgta 1020
ctcggatgga agccggtctt gtcgatcagg atgatctgga cgaagagcat caggggctcg 1080
cgccagccga actgttcgcc aggctcaagg cgcgcatgcc cgacggcgag gatctcgtcg 1140
tgacccatgg cgatgcctgc ttgccgaata tcatggtgga aaatggccgc ttttctggat 1200
tcatcgactg tggccggctg ggtgtggcgg accgctatca ggacatagcg ttggctaccc 1260
gtgatattgc tgaagagctt ggcggcgaat gggctgaccg cttcctcgtg ctttacggta 1320
tcgccgctcc cgattcgcag cgcatcgcct tctatcgcct tcttgacgag ttcttctgag 1380
cgggactctg gggttcgaaa tgaccgacca agcgacgccc aacctgccat cacgagattt 1440
cgattccacc gccgccttct atgaaaggtt gggcttcgga atcgttttcc gggacgccgg 1500
ctggatgatc ctccagcgcg gggatctcat gctggagttc ttcgcccacc ccagcttcaa 1560
aagcgctctg aagttcctat actttctaga gaataggaac ttcggaatag gaactaagga 1620
ggatattcat atggaccatg gctaattccc atgtcagccg ttaacgctgc cgacttatct 1680

-continued ggtagtccag gtacgtggcg aagcgcacga tcaggaattt actatccact gccaggtcag 1740
cggcctgagt gaaccggtgg ttggcacagg ttcaagccgt cgtaaggctg agcaggctgc 1800
cgccgaacag gcgttgaaaa aactggagct ggaatgagca tcgataaaag ttactgcgga 1860
tttattgcca tcgtcggacg tccgaacgtt ggcaaatcca cattgttgaa caaactgctg 1920
gggcagaaaa tctcca 1936

<210> SEQ ID NO 39
<211> LENGTH: 543
<212> TYPE: DNA
<213> ORGANISM: Artificial Sequence
<220> FEATURE:
<223> OTHER INFORMATION: The design of RNaseIII mutant was performed using the DNA sequence for the rnc gene of Escherichia coli str. K-12 substr. MG1655

<400> SEQUENCE: 39
accggtaaac tgaaactgca gcgaagcagt tagcagaacc atgtatatca ggtctgtttc 60
gtgtgctgaa ttgttgacgc atttatttat tggtatcgca tgaaccccat cgtaattaat 120
cggcttcaac ggaagctggg ctacacttta gcgattgtgt aggctggagc tgcttcgaag 180
ttcctatact ttctagagaa taggaacttc ggaataggaa ctaaggagga tattcatatg 240
gaccatggct aattcccatg tcagccgtta acgctgccga cttatctggt agtccaggta 300
cgtggcgaag cgcacgatca ggaatttact atccactgcc aggtcagcgg cctgagtgaa 360
ccggtggttg gcacaggttc aagccgtcgt aaggctgagc aggctgccgc cgaacaggcg 420
ttgaaaaaac tggagctgga atgagcatcg ataaaagtta ctgcggattt attgccatcg 480
tcggacgtcc gaacgttggc aaatccacat tgttgaacaa actgctgggg cagaaaatct 540
cca 543

<210> SEQ ID NO 40
<211> LENGTH: 1514
<212> TYPE: DNA
<213> ORGANISM: Bacillus cereus

<400> SEQUENCE: 40
agagtttgat cctggctcag gatgaacgct ggcggcgtgc ctaatacatg caagtcgagc 60
gaatggattg agagcttgct ctcaagaagt tagcggcgga cgggtgagta acacgtgggt 120
aacctgccca taagactggg ataactccgg gaaaccgggg ctaataccgg ataacatttt 180
gaactgcatg gttcgaaatt gaaaggcggc ttcggctgtc acttatggat ggacccgcgt 240
cgcattagct agttggtgag gtaacggctc accaaggcaa cgatgcgtag ccgacctgag 300
agggtgatcg gccacactgg gactgagaca cggcccagac tcctacggga ggcagcagta 360
gggaatcttc cgcaatggac gaaagtctga cggagcaacg ccgcgtgagt gatgaaggct 420
ttcgggtcgt aaaactctgt tgttagggaa gaacaagtgc tagttgaata agctggcacc 480
ttgacggtac ctaaccagaa agccacggct aactacgtgc cagcagccgc ggtaatacgt 540
aggtggcaag cgttatccgg aattattggg cgtaaagcgc gcgcaggtgg tttcttaagt 600
ctgatgtgaa agcccacggc tcaaccgtgg agggtcattg gaaactggga gacttgagtg 660
cagaagagga aagtggaatt ccatgtgtag cggtgaaatg cgtagagata tggaggaaca 720
ccagtggcga aggcgacttt ctggtctgta actgacactg aggcgcgaaa gcgtggggag 780
caaacaggat tagataccct ggtagtccac gccgtaaacg atgagtgcta agtgttagag 840
ggtttccgcc ctttagtgct gaagttaacg cattaagcac tccgcctggg gagtacggcc 900

```
gcaaggctga aactcaaagg aattgacggg ggcccgcaca agcggtggag catgtggttt    960
aattcgaagc aacgcgaaga accttaccag gtcttgacat cctctgaaaa ccctagagat   1020
agggcttctc cttcgggagc agagtgacag gtggtgcatg gttgtcgtca gctcgtgtcg   1080
tgagatgttg ggttaagtcc cgcaacgagc gcaacccttg atcttagttg ccatcattaa   1140
gttgggcact ctaaggtgac tgccggtgac aaaccggagg aaggtgggga tgacgtcaaa   1200
tcatcatgcc ccttatgacc tgggctacac acgtgctaca atggacggta caaagagctg   1260
caagaccgcg aggtggagct aatctcataa aaccgttctc agttcggatt gtaggctgca   1320
actcgcctac atgaagctgg aatcgctagt aatcgcggat cagcatgccg cggtgaatac   1380
gttcccgggc cttgtacaca ccgcccgtca caccacgaga gtttgtaaca cccgaagtcg   1440
gtggggtaac ctttttggag ccagccgcct aaggtgggac agatgattgg ggtgaagtcg   1500
taacaaggta accg                                                     1514
```

<210> SEQ ID NO 41
<211> LENGTH: 855
<212> TYPE: DNA
<213> ORGANISM: Bacillus cereus

<400> SEQUENCE: 41

```
agagtgcgta atagctcact agtcgagtga ctctgcgccg aaaatgtacc ggggctaaat     60
acaccaccga agctgcgaat tgataccaat ggtatcagtg gtaggggagc gttctaagtg    120
cagtgaagtc agaccggaag gactggtgga gcgcttagaa gtgagaatgc cggtatgagt    180
agcgaaagac gggtgagaat cccgtccacc gaatgcctaa ggtttcctga ggaaggctcg    240
tccgctcagg gttagtcagg acctaagccg aggccgacag gcgtaggcga tggacaacag    300
gttgatattc ctgtaccacc tctttatcgt ttgagcaatg gagggacgca gaaggataga    360
agaagcgtgc gattggttgt gcacgtccaa gcagttaggc tgataagtag gcaaatccgc    420
ttatcgtgaa ggctgagctg tgatggggaa gctccttatg gagcgaagtc tttgattccc    480
cgctgccaag aaaagcttct agcgagataa aaggtgcctg taccgcaaac cgacacaggt    540
aggcgaggag agaatcctaa ggtgtgcgag agaactctgg ttaaggaact cggcaaaatg    600
accccgtaac ttcgggagaa ggggtgcttt cttaacggaa agccgcagtg aataggccca    660
agcgactgtt tagcaaaaac acagctctct gcgaagccgt aaggcgaagt atagggggtg    720
acacctgccc ggtgctggaa ggttaaggag aggggttagc gtaagcgaag ctctgaactg    780
aagccccagt aaacggcggc cgtaactata acggtcctaa ggtagcgaaa ttccttgtcg    840
gtaagttcta gaccg                                                     855
```

<210> SEQ ID NO 42
<211> LENGTH: 574
<212> TYPE: DNA
<213> ORGANISM: Bacillus cereus

<400> SEQUENCE: 42

```
tcgcctcgtt ggatgacgac ttttacagat ttaacgatgt tattattaac tttcttcgta     60
ttactagttg ctacatcaaa gcaagatgca gtaaaattgt caaagatgct tgaaaatttt    120
agtgatacgg ggcaagtaga tgcaaaagta atggaaaata caataccaga tatttcacat    180
gaaaaaaatg atgaaaaaat gatctcaaaa aagagaatgg atgaattata taagaagttg    240
aaagcgtatg tagataataa cggtattagt caagtgaatg tatatcgaga ggatacaggg    300
```

```
gtaagcgtcg ttatagtaga taatttaata tttgatacag gcgatgcgaa cgttaagccc    360

gaagcgaaag ggataataag tcaattagtt ggatttttc aatccgtacc taacccaatt     420

gttgtagagg gacatacaga tagtagacct attcataacg agaaattccc ttctaattgg    480

gagttatctt cagcacgagc ggcaaatatg attcaccatt taattgaagt gtataatgtg    540

gatgataaaa ggctagctgc ggtaggatat gcag                                574
```

<210> SEQ ID NO 43
<211> LENGTH: 659
<212> TYPE: DNA
<213> ORGANISM: Bacillus cereus

<400> SEQUENCE: 43

```
ccagtagcca agaatggcca gcaaccagca agtggattcc aaccgcctga tttcattagt     60

tctgacattt ctttttgata ctgcttttgt ttttcaaggt ctttgcttac atcaccgtac    120

tttttcttta gcttctgcag ttcaggttgc attttcttca ttttcgcttg actgcgatat    180

tgcgaaacag ctaatggaat cattgctgaa cgaataacga gcgtcataat aatgatggca    240

atcccaaagc tagctccagg tatatgatga gcgacaaatt gaatcataaa cgagattgga    300

tatacaaaat aatgatccca aatcccagta ctatgtgcat caattggggc tgcattactg    360

caaccagata aaacaaaaac aaataataat gataaactaa cgagcacagc tcggtatgat    420

tttaacatgt tcattcctcc aatgtttcgt aattatttag cgaaacattg gtgtatacgg    480

accgacctcg tcattctctt cacttgattc ttgtctgcgt acagaacgaa tcattccata    540

tttataaaaa atagaaaata gcggtacatt tcccgcacta tcttcacatg tatcaactag    600

cgcaaaagct ctttgtctac cgcttgatgc ttgttgacgc acaaagcggc gattattcc     659
```

<210> SEQ ID NO 44
<211> LENGTH: 738
<212> TYPE: DNA
<213> ORGANISM: Bacillus cereus

<400> SEQUENCE: 44

```
atgccgtacc gaaaatatag agaaaaaaaa tacgaaacaa aatatcgtga agcatttaaa     60

gtgtttcaag aaaagatagg tattacgttt acagatgaaa aattattgat tcaagcattt    120

acgcattcat cgtatgtgaa tgagcatcga aaaaaaccgc atgaagataa tgagcgtctt    180

gaatttcttg gagatgcagt attggaactt actgtatcgc agtatctgtt tcaaaaatat    240

ccgacaatga gcgaaggaga gttaacaaaa ctacgtgcag ctattgtatg tgagccatct    300

cttgttcgtt ttgcgaacga attgtcattt ggtagccttg ttttattagg aaaaggtgaa    360

gaaatgacag gtggacgtga acgaccagct ttattagcgg atgtctttga agcgtttatt    420

ggtgcccttt atcttgatca agggttagaa acagtttggg aattcttaaa agaaattgta    480

tatccgaaaa ttaatgaggg tgctttttct catgtgatgg attataagag tcagttacaa    540

gaattgattc agcgtgatgg tagtggcaat gttgagtatc aaattttgca agaaaaagga    600

ccagctcaca atcgagaatt tgtgtcacgt gttacgttaa ataacgtagc tttaggtctt    660

ggtagtggta agtcgaaaaa agaagcagag caacaagctg ctgcagaagc attgaaaaaa    720

ttaaaagaac aactataa                                                  738
```

<210> SEQ ID NO 45
<211> LENGTH: 70
<212> TYPE: DNA
<213> ORGANISM: Artificial Sequence -continued
<220> FEATURE:
<223> OTHER INFORMATION: 50 bp homologous sequences to the E. coli rnc gene and primers used for amplification of the Kanamycin resistance marker

<400> SEQUENCE: 45
atgaacccca tcgtaattaa tcggcttcaa cggaagctgg gctacacttt agcgattgtg 60
taggctggag 70

<210> SEQ ID NO 46
<211> LENGTH: 73
<212> TYPE: DNA
<213> ORGANISM: Artificial Sequence
<220> FEATURE:
<223> OTHER INFORMATION: 50 bp homologous sequences to the E. coli rnc gene and primers used for amplification of the Kanamycin resistance marker

<400> SEQUENCE: 46
ctgatcgtgc gcttcgccac gtacctggac taccagataa gtcggcagcg ttaacggctg 60
acatgggaat tag 73

<210> SEQ ID NO 47
<211> LENGTH: 25
<212> TYPE: DNA
<213> ORGANISM: Artificial Sequence
<220> FEATURE:
<223> OTHER INFORMATION: 50 bp homologous sequences to the E. coli rnc gene and primers used for amplification of the Kanamycin resistance marker

<400> SEQUENCE: 47
atgaacccca tcgtaattaa tcggc 25

<210> SEQ ID NO 48
<211> LENGTH: 17
<212> TYPE: DNA
<213> ORGANISM: Artificial Sequence
<220> FEATURE:
<223> OTHER INFORMATION: 50 bp homologous sequences to the E. coli rnc gene and primers used for amplification of the Kanamycin resistance marker

<400> SEQUENCE: 48
ctgatcgtgc gcttcgc 17

<210> SEQ ID NO 49
<211> LENGTH: 20
<212> TYPE: DNA
<213> ORGANISM: Artificial Sequence
<220> FEATURE:
<223> OTHER INFORMATION: 50 bp homologous sequences to the E. coli rnc gene and primers used for amplification of the Kanamycin resistance marker

<400> SEQUENCE: 49
accggtaaac tgaaactgca 20

<210> SEQ ID NO 50
<211> LENGTH: 19
<212> TYPE: DNA
<213> ORGANISM: Artificial Sequence
<220> FEATURE:
<223> OTHER INFORMATION: 50 bp homologous sequences to the E. coli rnc gene and primers used for amplification of the Kanamycin resistance marker

<400> SEQUENCE: 50
tggagatttt ctgccccag 19

<210> SEQ ID NO 51
<211> LENGTH: 22
<212> TYPE: DNA
<213> ORGANISM: Artificial Sequence
<220> FEATURE:
<223> OTHER INFORMATION: 50 bp homologous sequences to the E. coli rnc gene and primers used for amplification of the Kanamycin resistance marker

<400> SEQUENCE: 51
agcgattgtg taggctggag ct 22

<210> SEQ ID NO 52
<211> LENGTH: 24
<212> TYPE: DNA
<213> ORGANISM: Artificial Sequence
<220> FEATURE:
<223> OTHER INFORMATION: 50 bp homologous sequences to the E. coli rnc gene and primers used for amplification of the Kanamycin resistance marker

<400> SEQUENCE: 52
ttaacggctg acatgggaat tagc 24

<210> SEQ ID NO 53
<211> LENGTH: 20
<212> TYPE: DNA
<213> ORGANISM: Artificial Sequence
<220> FEATURE:
<223> OTHER INFORMATION: Primers used for identification and verification of Bacillus spp

<400> SEQUENCE: 53
agagtttgat cctggctcag 20

<210> SEQ ID NO 54
<211> LENGTH: 20
<212> TYPE: DNA
<213> ORGANISM: Artificial Sequence
<220> FEATURE:
<223> OTHER INFORMATION: Primers used for identification and verification of Bacillus spp

<400> SEQUENCE: 54
cggttacctt gttacgactt 20

<210> SEQ ID NO 55
<211> LENGTH: 19
<212> TYPE: DNA
<213> ORGANISM: Artificial Sequence
<220> FEATURE:
<223> OTHER INFORMATION: Primers used for identification and verification of Bacillus spp

<400> SEQUENCE: 55
agagtgcgta atagctcac 19

<210> SEQ ID NO 56
<211> LENGTH: 23
<212> TYPE: DNA
<213> ORGANISM: Artificial Sequence
<220> FEATURE:
<223> OTHER INFORMATION: Primers used for identification and verification of Bacillus spp

<400> SEQUENCE: 56
cggtctagaa cttaccgaca agg 23

<210> SEQ ID NO 57
<211> LENGTH: 20
<212> TYPE: DNA
<213> ORGANISM: Artificial Sequence
<220> FEATURE:
<223> OTHER INFORMATION: Primers used for identification and verification of Bacillus spp

<400> SEQUENCE: 57
atcgcctcgt tggatgacga 20

<210> SEQ ID NO 58
<211> LENGTH: 21
<212> TYPE: DNA
<213> ORGANISM: Artificial Sequence
<220> FEATURE:
<223> OTHER INFORMATION: Primers used for identification and verification of Bacillus spp

<400> SEQUENCE: 58
ctgcatatcc taccgcagct a 21

<210> SEQ ID NO 59
<211> LENGTH: 22
<212> TYPE: DNA
<213> ORGANISM: Artificial Sequence
<220> FEATURE:
<223> OTHER INFORMATION: Primers used for identification and verification of Bacillus spp

<400> SEQUENCE: 59
ccagtagcca agaatggcca gc 22

<210> SEQ ID NO 60
<211> LENGTH: 21
<212> TYPE: DNA
<213> ORGANISM: Artificial Sequence
<220> FEATURE:
<223> OTHER INFORMATION: Primers used for identification and verification of Bacillus spp

<400> SEQUENCE: 60
ggaataatcg ccgctttgtg c 21

<210> SEQ ID NO 61
<211> LENGTH: 25
<212> TYPE: DNA
<213> ORGANISM: Artificial Sequence
<220> FEATURE:
<223> OTHER INFORMATION: Primers used for identification and verification of Bacillus spp

<400> SEQUENCE: 61
atgagccctg tgatcaggaa gatcg 25

<210> SEQ ID NO 62
<211> LENGTH: 25
<212> TYPE: DNA
<213> ORGANISM: Artificial Sequence
<220> FEATURE:
<223> OTHER INFORMATION: Primers used for identification and verification of Bacillus spp -continued

```
<400> SEQUENCE: 62

acgatgagcc ttctcagcaa atgcg                                          25


<210> SEQ ID NO 63
<211> LENGTH: 20
<212> TYPE: DNA
<213> ORGANISM: Artificial
<220> FEATURE:
<223> OTHER INFORMATION: Primer for N. tabacum reference gene

<400> SEQUENCE: 63

cccctcacca cagagtctgc                                                20


<210> SEQ ID NO 64
<211> LENGTH: 24
<212> TYPE: DNA
<213> ORGANISM: Artificial
<220> FEATURE:
<223> OTHER INFORMATION: Primer for N. tabacum reference gene

<400> SEQUENCE: 64

aagggtgttg ttgtcctcaa tctt                                           24


<210> SEQ ID NO 65
<211> LENGTH: 21
<212> TYPE: DNA
<213> ORGANISM: Artificial
<220> FEATURE:
<223> OTHER INFORMATION: Primer for TMV-GFP-F2

<400> SEQUENCE: 65

gatgacggga actacaagac g                                              21


<210> SEQ ID NO 66
<211> LENGTH: 22
<212> TYPE: DNA
<213> ORGANISM: Artificial
<220> FEATURE:
<223> OTHER INFORMATION: Primer for TMV-GFP-F2

<400> SEQUENCE: 66

gtttgtgtcc gagaatgttt cc                                             22
```